(12) United States Patent
Panescu et al.

(10) Patent No.: US 11,179,197 B2
(45) Date of Patent: Nov. 23, 2021

(54) METHODS OF DETERMINING CATHETER ORIENTATION

(71) Applicant: EPIX THERAPEUTICS, INC., Santa Clara, CA (US)

(72) Inventors: Dorin Panescu, San Jose, CA (US); Josef Vincent Koblish, Santa Clara, CA (US); Donghoon Chun, Santa Clara, CA (US); Jessi E. Johnson, Santa Clara, CA (US); Eric Andrew Schultheis, Sunnyvale, CA (US)

(73) Assignee: Epix Therapeutics, Inc., Santa Clara, CA (US)

(*) Notice: Subject to any disclaimer, the term of this patent is extended or adjusted under 35 U.S.C. 154(b) by 574 days.

(21) Appl. No.: 16/003,576

(22) Filed: Jun. 8, 2018

(65) Prior Publication Data
US 2018/0289284 A1 Oct. 11, 2018

Related U.S. Application Data

(63) Continuation of application No. 15/782,714, filed on Oct. 12, 2017, now Pat. No. 9,993,178, which is a (Continued)

(51) Int. Cl.
*A61B 18/12* (2006.01)
*A61B 18/14* (2006.01)
(Continued)

(52) U.S. Cl.
CPC .......... *A61B 18/1492* (2013.01); *A61B 5/01* (2013.01); *A61B 5/0538* (2013.01); *A61B 5/061* (2013.01);
(Continued)

(58) Field of Classification Search
CPC . A61B 18/12; A61B 18/1206; A61B 18/1233; A61B 18/14; A61B 18/1402;
(Continued)

(56) References Cited

U.S. PATENT DOCUMENTS

| 4,190,053 A | 2/1980 | Sterzer |
| 4,197,860 A | 4/1980 | Sterzer |

(Continued)

FOREIGN PATENT DOCUMENTS

| CN | 101534736 A | 9/2009 |
| CN | 107148249 A | 9/2017 |

(Continued)

OTHER PUBLICATIONS

Anter et al, "High-Resolution Mapping of Scar-Related Atrial Arrhythmias Using Smaller Electrodes with Closer Interelectrode Spacing," Circ. Arrhythm. Electrophysiol. 8(3):537-45 (2015).
(Continued)

*Primary Examiner* — Thomas A Giuliani
(74) *Attorney, Agent, or Firm* — Christopher & Weisberg, P.A.

(57) ABSTRACT

Systems, devices and methods of determining orientation of a distal end of a medical instrument (e.g., electrode-tissue orientation of an RF ablation catheter) are described herein. One or more processors may be configured to receive temperature measurements from each of a plurality of temperature-measurement devices distributed along a length of the distal end of the medical instrument and determine the orientation from a group of two or more possible orientation options based on whether temperature measurement values or characteristics of temperature response determined from the temperature measurement values satisfy one or more orientation criteria.

11 Claims, 58 Drawing Sheets

Related U.S. Application Data continuation of application No. PCT/US2017/022264, filed on Mar. 14, 2017.

(60) Provisional application No. 62/418,057, filed on Nov. 4, 2016, provisional application No. 62/323,502, filed on Apr. 15, 2016, provisional application No. 62/315,661, filed on Mar. 30, 2016, provisional application No. 62/308,461, filed on Mar. 15, 2016.

(51) Int. Cl.

| | | |
|---|---|---|
| *A61B 5/01* | (2006.01) | |
| *A61B 17/00* | (2006.01) | |
| *A61B 5/0538* | (2021.01) | |
| *A61B 5/06* | (2006.01) | |
| *A61B 18/00* | (2006.01) | |
| *A61B 18/02* | (2006.01) | |
| *A61B 18/04* | (2006.01) | |
| *A61B 5/287* | (2021.01) | |
| *A61B 34/20* | (2016.01) | |
| *A61B 34/00* | (2016.01) | |
| *A61B 34/10* | (2016.01) | |
| *A61B 5/00* | (2006.01) | |
| *A61B 8/12* | (2006.01) | |
| *A61B 18/08* | (2006.01) | |

(52) U.S. Cl.
CPC .......... *A61B 5/065* (2013.01); *A61B 5/287* (2021.01); *A61B 17/00* (2013.01); *A61B 18/00* (2013.01); *A61B 18/02* (2013.01); *A61B 18/04* (2013.01); *A61B 18/12* (2013.01); *A61B 34/20* (2016.02); *A61B 34/25* (2016.02); *A61B 5/015* (2013.01); *A61B 5/6852* (2013.01); *A61B 8/12* (2013.01); *A61B 18/082* (2013.01); *A61B 18/1233* (2013.01); *A61B 2017/00053* (2013.01); *A61B 2017/00084* (2013.01); *A61B 2017/00115* (2013.01); *A61B 2018/00023* (2013.01); *A61B 2018/00029* (2013.01); *A61B 2018/0066* (2013.01); *A61B 2018/00083* (2013.01); *A61B 2018/00136* (2013.01); *A61B 2018/00178* (2013.01); *A61B 2018/00297* (2013.01); *A61B 2018/00577* (2013.01); *A61B 2018/00648* (2013.01); *A61B 2018/00678* (2013.01); *A61B 2018/00702* (2013.01); *A61B 2018/00714* (2013.01); *A61B 2018/00755* (2013.01); *A61B 2018/00791* (2013.01); *A61B 2018/00797* (2013.01); *A61B 2018/00821* (2013.01); *A61B 2018/00839* (2013.01); *A61B 2018/00875* (2013.01); *A61B 2018/00898* (2013.01); *A61B 2018/00904* (2013.01); *A61B 2018/00988* (2013.01); *A61B 2034/104* (2016.02); *A61B 2217/007* (2013.01); *A61B 2218/002* (2013.01)

(58) Field of Classification Search
CPC .......... A61B 18/082; A61B 18/1492; A61B 2018/00577; A61B 2018/00636; A61B 2018/00642; A61B 2018/00648; A61B 2018/00666; A61B 2018/0702; A61B 2018/00708; A61B 2018/00714; A61B 2018/00791; A61B 2018/00797; A61B 2018/00821; A61B 2017/00084; A61B 5/0422; A61B 5/01; A61B 5/0538; A61B 5/061; A61B 5/065; A61B 5/6852; A61B 5/015

USPC .......... 606/34, 38, 41, 42; 607/98, 99, 102, 607/113, 115, 116, 122
See application file for complete search history.

(56) References Cited

U.S. PATENT DOCUMENTS

| | | |
|---|---|---|
| 4,346,716 A | 8/1982 | Carr |
| 4,557,272 A | 12/1985 | Carr |
| 4,614,514 A | 9/1986 | Carr et al. |
| 4,632,127 A | 12/1986 | Sterzer |
| 4,647,281 A | 3/1987 | Carr |
| 4,686,498 A | 8/1987 | Carr et al. |
| 4,715,727 A | 12/1987 | Carr |
| 4,727,874 A | 3/1988 | Bowers et al. |
| 4,774,961 A | 10/1988 | Carr |
| 4,815,479 A | 3/1989 | Carr |
| 4,922,912 A | 5/1990 | Watanabe |
| 4,945,912 A | 8/1990 | Langberg |
| 4,955,382 A | 9/1990 | Franz et al. |
| 4,979,510 A | 12/1990 | Franz et al. |
| 5,073,167 A | 12/1991 | Carr et al. |
| RE33,791 E | 1/1992 | Carr |
| 5,105,808 A | 4/1992 | Neuwirth et al. |
| 5,149,198 A | 9/1992 | Sterzer |
| 5,176,146 A | 1/1993 | Chive et al. |
| 5,198,776 A | 3/1993 | Carr |
| 5,230,349 A | 7/1993 | Langberg |
| 5,282,840 A | 2/1994 | Hudrlik |
| 5,334,141 A | 8/1994 | Carr et al. |
| 5,334,193 A | 8/1994 | Nardella |
| 5,344,435 A | 9/1994 | Turner et al. |
| 5,354,325 A | 10/1994 | Chive et al. |
| 5,364,336 A | 11/1994 | Carr |
| 5,370,676 A | 12/1994 | Sozanski et al. |
| 5,383,874 A | 1/1995 | Jackson et al. |
| 5,385,146 A | 1/1995 | Goldreyer |
| 5,398,683 A | 3/1995 | Edwards et al. |
| 5,456,682 A | 10/1995 | Edwards et al. |
| 5,462,521 A | 10/1995 | Brucker et al. |
| 5,485,849 A | 1/1996 | Panescu et al. |
| 5,487,391 A | 1/1996 | Panescu |
| 5,494,042 A | 2/1996 | Panescu et al. |
| 5,514,130 A | 5/1996 | Baker |
| 5,522,815 A | 6/1996 | Durgin, Jr. et al. |
| 5,531,662 A | 7/1996 | Carr |
| 5,540,655 A | 7/1996 | Edwards et al. |
| 5,546,940 A | 8/1996 | Panescu et al. |
| 5,549,639 A | 8/1996 | Ross |
| 5,562,619 A | 10/1996 | Mirarchi et al. |
| 5,577,509 A | 11/1996 | Panescu et al. |
| 5,582,589 A | 12/1996 | Edwards et al. |
| 5,582,609 A | 12/1996 | Swanson et al. |
| 5,584,830 A | 12/1996 | Ladd et al. |
| 5,591,125 A | 1/1997 | Edwards et al. |
| 5,595,183 A | 1/1997 | Swanson et al. |
| 5,598,848 A | 2/1997 | Swanson et al. |
| 5,599,295 A | 2/1997 | Rosen et al. |
| 5,601,088 A | 2/1997 | Swanson et al. |
| 5,605,157 A | 2/1997 | Panescu et al. |
| 5,609,157 A | 3/1997 | Panescu et al. |
| 5,616,268 A | 4/1997 | Carr |
| 5,624,392 A | 4/1997 | Saab |
| 5,630,425 A | 5/1997 | Panescu et al. |
| 5,643,197 A | 7/1997 | Brucker et al. |
| 5,647,870 A | 7/1997 | Kordis et al. |
| 5,651,780 A | 7/1997 | Jackson et al. |
| 5,656,030 A | 8/1997 | Hunjan et al. |
| 5,658,278 A | 8/1997 | Imran et al. |
| 5,662,110 A | 9/1997 | Carr |
| 5,667,488 A | 9/1997 | Lundquist et al. |
| 5,672,174 A | 9/1997 | Gough et al. |
| 5,673,704 A | 10/1997 | Marchlinski et al. |
| 5,674,191 A | 10/1997 | Edwards et al. |
| 5,683,381 A | 11/1997 | Carr et al. |
| 5,683,382 A | 11/1997 | Lenihan et al. |
| 5,683,384 A | 11/1997 | Gough et al. |

(56) References Cited

U.S. PATENT DOCUMENTS

| | | |
|---|---|---|
| 5,685,839 A | 11/1997 | Edwards et al. |
| 5,685,878 A | 11/1997 | Falwell et al. |
| 5,688,050 A | 11/1997 | Sterzer et al. |
| 5,688,266 A | 11/1997 | Edwards et al. |
| 5,688,267 A | 11/1997 | Panescu et al. |
| 5,690,614 A | 11/1997 | Carr et al. |
| 5,702,386 A | 12/1997 | Stern et al. |
| 5,707,369 A | 1/1998 | Vaitekunas et al. |
| 5,711,305 A | 1/1998 | Swanson et al. |
| 5,712,047 A | 1/1998 | Aso et al. |
| 5,715,832 A | 2/1998 | Koblish et al. |
| 5,718,701 A | 2/1998 | Shai et al. |
| 5,722,402 A | 3/1998 | Swanson et al. |
| 5,722,403 A | 3/1998 | McGee et al. |
| 5,722,416 A | 3/1998 | Swanson et al. |
| 5,732,698 A | 3/1998 | Swanson et al. |
| 5,735,846 A | 4/1998 | Panescu et al. |
| 5,735,847 A | 4/1998 | Gough et al. |
| 5,740,808 A | 4/1998 | Panescu et al. |
| 5,743,903 A | 4/1998 | Stern et al. |
| 5,752,518 A | 5/1998 | McGee et al. |
| 5,755,715 A | 5/1998 | Stern et al. |
| 5,762,786 A | 6/1998 | Oelbermann |
| 5,769,846 A | 6/1998 | Edwards et al. |
| 5,769,847 A | 6/1998 | Panescu et al. |
| 5,779,635 A | 7/1998 | Carr |
| 5,779,646 A | 7/1998 | Koblish et al. |
| 5,782,827 A | 7/1998 | Gough et al. |
| 5,782,828 A | 7/1998 | Chen et al. |
| 5,782,897 A | 7/1998 | Carr |
| 5,792,064 A | 8/1998 | Panescu et al. |
| 5,792,140 A | 8/1998 | Tu et al. |
| 5,795,303 A | 8/1998 | Swanson et al. |
| 5,797,903 A | 8/1998 | Swanson et al. |
| 5,797,905 A | 8/1998 | Fleischman et al. |
| 5,800,378 A | 9/1998 | Edwards et al. |
| 5,800,432 A | 9/1998 | Swanson |
| 5,807,309 A | 9/1998 | Lundquist et al. |
| 5,807,395 A | 9/1998 | Mulier et al. |
| 5,810,802 A | 9/1998 | Panescu et al. |
| 5,810,804 A | 9/1998 | Gough et al. |
| 5,823,955 A | 10/1998 | Kuck et al. |
| 5,827,277 A | 10/1998 | Edwards |
| 5,830,213 A | 11/1998 | Panescu et al. |
| 5,833,621 A | 11/1998 | Panescu et al. |
| 5,833,688 A | 11/1998 | Sieben et al. |
| 5,836,874 A | 11/1998 | Swanson et al. |
| 5,836,947 A | 11/1998 | Fleischman et al. |
| 5,836,990 A | 11/1998 | Li |
| 5,837,001 A | 11/1998 | Mackey |
| 5,840,076 A | 11/1998 | Swanson et al. |
| 5,846,238 A | 12/1998 | Jackson et al. |
| 5,846,239 A | 12/1998 | Swanson et al. |
| 5,848,969 A | 12/1998 | Panescu et al. |
| 5,849,028 A | 12/1998 | Chen |
| 5,853,409 A | 12/1998 | Swanson et al. |
| 5,853,411 A | 12/1998 | Whayne et al. |
| 5,863,290 A | 1/1999 | Gough et al. |
| 5,865,800 A | 2/1999 | Mirarchi et al. |
| 5,868,736 A | 2/1999 | Swanson et al. |
| 5,868,743 A | 2/1999 | Saul et al. |
| 5,871,483 A | 2/1999 | Jackson et al. |
| 5,876,336 A | 3/1999 | Swanson et al. |
| 5,876,340 A | 3/1999 | Tu et al. |
| 5,879,348 A | 3/1999 | Owens et al. |
| 5,879,349 A | 3/1999 | Edwards |
| 5,891,136 A | 4/1999 | McGee et al. |
| 5,893,885 A | 4/1999 | Webster, Jr. |
| 5,897,552 A | 4/1999 | Edwards et al. |
| 5,904,651 A | 5/1999 | Swanson et al. |
| 5,904,680 A | 5/1999 | Kordis et al. |
| 5,904,709 A | 5/1999 | Arndt et al. |
| 5,906,590 A | 5/1999 | Hunjan et al. |
| 5,906,614 A | 5/1999 | Stern et al. |
| 5,908,445 A | 6/1999 | Whayne et al. |
| 5,910,129 A | 6/1999 | Koblish et al. |
| 5,911,739 A | 6/1999 | Kordis et al. |
| 5,913,856 A | 6/1999 | Chia et al. |
| 5,916,163 A | 6/1999 | Panescu et al. |
| 5,919,218 A | 7/1999 | Carr |
| 5,925,038 A | 7/1999 | Panescu et al. |
| 5,928,228 A | 7/1999 | Kordis et al. |
| 5,928,229 A | 7/1999 | Gough et al. |
| 5,933,672 A | 8/1999 | Huang |
| 5,935,063 A | 8/1999 | Nguyen |
| 5,935,079 A | 8/1999 | Swanson et al. |
| 5,935,124 A | 8/1999 | Klumb et al. |
| 5,938,658 A | 8/1999 | Tu |
| 5,938,659 A | 8/1999 | Tu et al. |
| 5,941,251 A | 8/1999 | Panescu et al. |
| 5,948,009 A | 9/1999 | Tu |
| 5,954,661 A | 9/1999 | Greenspon et al. |
| 5,954,662 A | 9/1999 | Swanson et al. |
| 5,954,719 A | 9/1999 | Chen et al. |
| 5,957,863 A | 9/1999 | Koblish et al. |
| 5,957,922 A | 9/1999 | Imran |
| 5,957,961 A | 9/1999 | Maguire et al. |
| 5,961,513 A | 10/1999 | Swanson et al. |
| 5,964,727 A | 10/1999 | Edwards et al. |
| 5,967,976 A | 10/1999 | Larsen et al. |
| 5,968,040 A | 10/1999 | Swanson et al. |
| 5,971,980 A | 10/1999 | Sherman |
| 5,974,343 A | 10/1999 | Brevard et al. |
| 5,980,517 A | 11/1999 | Gough |
| 5,983,124 A | 11/1999 | Carr |
| 5,991,650 A | 11/1999 | Swanson et al. |
| 5,992,419 A | 11/1999 | Sterzer et al. |
| 5,997,534 A | 12/1999 | Tu et al. |
| 6,006,123 A | 12/1999 | Nguyen et al. |
| 6,009,351 A | 12/1999 | Flachman |
| 6,014,581 A | 1/2000 | Whayne et al. |
| 6,014,590 A | 1/2000 | Whayne et al. |
| 6,022,346 A | 2/2000 | Panescu et al. |
| 6,030,379 A | 2/2000 | Panescu et al. |
| 6,030,382 A | 2/2000 | Fleischman et al. |
| 6,032,061 A | 2/2000 | Koblish |
| 6,035,226 A | 3/2000 | Panescu |
| 6,042,580 A | 3/2000 | Simpson |
| 6,047,218 A | 4/2000 | Whayne et al. |
| 6,048,329 A | 4/2000 | Thompson et al. |
| 6,049,732 A | 4/2000 | Panescu et al. |
| 6,053,912 A | 4/2000 | Panescu et al. |
| 6,056,745 A | 5/2000 | Panescu et al. |
| 6,059,780 A | 5/2000 | Gough et al. |
| 6,063,078 A | 5/2000 | Wittkampf |
| 6,070,094 A | 5/2000 | Swanson et al. |
| 6,071,278 A | 6/2000 | Panescu et al. |
| 6,076,012 A | 6/2000 | Swanson et al. |
| 6,080,150 A | 6/2000 | Gough |
| 6,083,222 A | 7/2000 | Klein et al. |
| 6,086,532 A | 7/2000 | Panescu et al. |
| 6,090,105 A | 7/2000 | Zepeda et al. |
| 6,095,150 A | 8/2000 | Panescu et al. |
| 6,097,976 A | 8/2000 | Yang et al. |
| 6,101,409 A | 8/2000 | Swanson et al. |
| 6,101,410 A | 8/2000 | Panescu et al. |
| 6,106,460 A | 8/2000 | Panescu et al. |
| 6,106,522 A | 8/2000 | Fleischman et al. |
| 6,113,591 A | 9/2000 | Whayne et al. |
| 6,113,593 A | 9/2000 | Tu et al. |
| 6,115,626 A | 9/2000 | Whayne et al. |
| 6,123,702 A | 9/2000 | Swanson et al. |
| 6,123,703 A | 9/2000 | Tu et al. |
| 6,129,669 A | 10/2000 | Panescu et al. |
| 6,129,724 A | 10/2000 | Fleischman et al. |
| 6,132,425 A | 10/2000 | Gough |
| 6,142,994 A | 11/2000 | Swanson et al. |
| 6,146,359 A | 11/2000 | Carr et al. |
| 6,162,184 A | 12/2000 | Swanson et al. |
| 6,165,169 A | 12/2000 | Panescu et al. |
| 6,171,275 B1 | 1/2001 | Webster, Jr. |
| 6,171,306 B1 | 1/2001 | Swanson et al. |
| 6,179,835 B1 | 1/2001 | Panescu et al. |
| 6,183,468 B1 | 2/2001 | Swanson et al. |

(56) References Cited

U.S. PATENT DOCUMENTS

| | | |
|---|---|---|
| 6,188,924 B1 | 2/2001 | Swanson et al. |
| 6,192,266 B1 | 2/2001 | Dupree et al. |
| 6,193,713 B1 | 2/2001 | Geistert et al. |
| 6,197,021 B1 | 3/2001 | Panescu et al. |
| 6,206,831 B1 | 3/2001 | Suorsa et al. |
| 6,210,367 B1 | 4/2001 | Carr |
| 6,210,406 B1 | 4/2001 | Webster |
| 6,216,043 B1 | 4/2001 | Swanson et al. |
| 6,217,528 B1 | 4/2001 | Koblish et al. |
| 6,217,573 B1 | 4/2001 | Webster |
| 6,217,574 B1 | 4/2001 | Webster |
| 6,217,576 B1 | 4/2001 | Tu et al. |
| 6,221,013 B1 | 4/2001 | Panescu et al. |
| 6,230,060 B1 | 5/2001 | Mawhinney |
| 6,235,022 B1 | 5/2001 | Hallock et al. |
| 6,235,023 B1 | 5/2001 | Lee et al. |
| 6,238,389 B1 | 5/2001 | Paddock et al. |
| 6,245,061 B1 | 6/2001 | Panescu et al. |
| 6,245,065 B1 | 6/2001 | Panescu et al. |
| 6,251,107 B1 | 6/2001 | Schaer |
| 6,256,525 B1 | 7/2001 | Yang et al. |
| 6,256,540 B1 | 7/2001 | Panescu et al. |
| 6,259,941 B1 | 7/2001 | Chia et al. |
| 6,264,653 B1 | 7/2001 | Falwell |
| 6,277,113 B1 | 8/2001 | Berube |
| 6,283,962 B1 | 9/2001 | Tu et al. |
| 6,289,239 B1 | 9/2001 | Panescu et al. |
| 6,293,943 B1 | 9/2001 | Panescu et al. |
| 6,309,385 B1 | 10/2001 | Simpson |
| 6,312,425 B1 | 11/2001 | Simpson et al. |
| 6,330,473 B1 | 12/2001 | Swanson et al. |
| 6,346,104 B2 | 2/2002 | Daly et al. |
| 6,350,262 B1 | 2/2002 | Ashley |
| 6,352,534 B1 | 3/2002 | Paddock et al. |
| 6,353,751 B1 | 3/2002 | Swanson et al. |
| 6,356,790 B1 | 3/2002 | Maguire et al. |
| 6,357,447 B1 | 3/2002 | Swanson et al. |
| 6,364,876 B1 | 4/2002 | Erb et al. |
| 6,370,435 B2 | 4/2002 | Panescu et al. |
| 6,371,955 B1 | 4/2002 | Fuimaono et al. |
| 6,389,311 B1 | 5/2002 | Whayne et al. |
| 6,391,024 B1 | 5/2002 | Sun et al. |
| 6,402,739 B1 | 6/2002 | Neev |
| 6,402,742 B1 | 6/2002 | Blewett et al. |
| 6,405,067 B1 | 6/2002 | Mest et al. |
| 6,423,057 B1 | 7/2002 | He et al. |
| 6,424,869 B1 | 7/2002 | Carr et al. |
| 6,425,895 B1 | 7/2002 | Swanson et al. |
| 6,428,536 B2 | 8/2002 | Panescu et al. |
| 6,440,129 B1 | 8/2002 | Simpson |
| 6,445,957 B1 | 9/2002 | Bolmsjo |
| 6,456,864 B1 | 9/2002 | Swanson et al. |
| 6,458,123 B1 | 10/2002 | Brucker et al. |
| 6,463,331 B1 | 10/2002 | Edwards |
| 6,464,700 B1 | 10/2002 | Koblish et al. |
| 6,468,272 B1 | 10/2002 | Koblish et al. |
| 6,470,219 B1 | 10/2002 | Edwards et al. |
| 6,471,693 B1 | 10/2002 | Carroll et al. |
| 6,471,699 B1 | 10/2002 | Fleischman et al. |
| 6,477,396 B1 | 11/2002 | Mest et al. |
| 6,477,426 B1 | 11/2002 | Fenn et al. |
| 6,482,203 B2 | 11/2002 | Paddock et al. |
| 6,487,441 B1 | 11/2002 | Swanson et al. |
| 6,488,679 B1 | 12/2002 | Swanson et al. |
| 6,490,488 B1 | 12/2002 | Rudie et al. |
| 6,494,880 B1 | 12/2002 | Swanson et al. |
| 6,496,738 B2 | 12/2002 | Carr |
| 6,500,172 B1 | 12/2002 | Panescu et al. |
| 6,500,175 B1 | 12/2002 | Gough et al. |
| 6,508,765 B2 | 1/2003 | Suorsa et al. |
| 6,511,478 B1 | 1/2003 | Burnside et al. |
| 6,514,249 B1 | 2/2003 | Maguire et al. |
| 6,514,250 B1 | 2/2003 | Jahns et al. |
| 6,516,807 B1 | 2/2003 | Panescu et al. |
| 6,522,913 B2 | 2/2003 | Swanson et al. |
| 6,522,930 B1 | 2/2003 | Schaer et al. |
| 6,522,931 B2 | 2/2003 | Manker et al. |
| 6,529,756 B1 | 3/2003 | Phan et al. |
| 6,537,272 B2 | 3/2003 | Christopherson et al. |
| 6,542,773 B2 | 4/2003 | Dupree et al. |
| 6,542,781 B1 | 4/2003 | Koblish et al. |
| 6,565,511 B2 | 5/2003 | Panescu et al. |
| 6,577,902 B1 | 6/2003 | Laufer et al. |
| 6,579,288 B1 | 6/2003 | Swanson et al. |
| 6,582,425 B2 | 6/2003 | Simpson |
| 6,584,360 B2 | 6/2003 | Francischelli et al. |
| 6,587,732 B1 | 7/2003 | Carr |
| 6,597,955 B2 | 7/2003 | Panescu et al. |
| 6,602,242 B1 | 8/2003 | Fung et al. |
| 6,605,087 B2 | 8/2003 | Swartz et al. |
| 6,607,505 B1 | 8/2003 | Thompson et al. |
| 6,610,055 B1 | 8/2003 | Swanson et al. |
| 6,611,699 B2 | 8/2003 | Messing |
| 6,613,046 B1 | 9/2003 | Jenkins et al. |
| 6,615,073 B1 | 9/2003 | Panescu et al. |
| 6,616,657 B2 | 9/2003 | Simpson et al. |
| 6,625,482 B1 | 9/2003 | Panescu et al. |
| 6,632,221 B1 | 10/2003 | Edwards et al. |
| 6,632,222 B1 | 10/2003 | Edwards et al. |
| 6,635,056 B2 | 10/2003 | Kadhiresan et al. |
| 6,645,200 B1 | 11/2003 | Koblish et al. |
| 6,652,513 B2 | 11/2003 | Panescu et al. |
| 6,652,516 B1 | 11/2003 | Gough |
| 6,658,279 B2 | 12/2003 | Swanson et al. |
| 6,668,198 B2 | 12/2003 | Swanson et al. |
| 6,669,692 B1 | 12/2003 | Nelson et al. |
| 6,685,702 B2 | 2/2004 | Quijano et al. |
| 6,689,127 B1 | 2/2004 | Gough et al. |
| 6,692,490 B1 | 2/2004 | Edwards |
| 6,699,241 B2 | 3/2004 | Rappaport et al. |
| 6,706,038 B2 | 3/2004 | Francischelli et al. |
| 6,711,444 B2 | 3/2004 | Koblish |
| 6,735,465 B2 | 5/2004 | Panescu |
| 6,736,811 B2 | 5/2004 | Panescu et al. |
| 6,740,040 B1 | 5/2004 | Mandrusov et al. |
| 6,740,083 B2 | 5/2004 | Messing |
| 6,743,197 B1 | 6/2004 | Edwards |
| 6,743,225 B2 | 6/2004 | Sanchez et al. |
| 6,745,080 B2 | 6/2004 | Koblish |
| 6,746,401 B2 | 6/2004 | Panescu |
| 6,752,804 B2 | 6/2004 | Simpson et al. |
| 6,752,805 B2 | 6/2004 | Maguire et al. |
| 6,770,070 B1 | 8/2004 | Balbierz |
| 6,773,433 B2 | 8/2004 | Stewart et al. |
| 6,786,905 B2 | 9/2004 | Swanson et al. |
| 6,788,969 B2 | 9/2004 | Dupree et al. |
| 6,788,977 B2 | 9/2004 | Fenn et al. |
| 6,790,206 B2 | 9/2004 | Panescu |
| 6,805,129 B1 | 10/2004 | Pless et al. |
| 6,814,730 B2 | 11/2004 | Li |
| 6,823,216 B1 | 11/2004 | Salomir et al. |
| 6,824,515 B2 | 11/2004 | Suorsa et al. |
| 6,827,715 B2 | 12/2004 | Francischelli et al. |
| 6,837,885 B2 | 1/2005 | Koblish et al. |
| 6,840,936 B2 | 1/2005 | Sliwa, Jr. et al. |
| 6,847,848 B2 | 1/2005 | Sterzer et al. |
| 6,849,073 B2 | 2/2005 | Hoey et al. |
| 6,852,120 B1 | 2/2005 | Fuimaono |
| 6,887,238 B2 | 5/2005 | Jahns et al. |
| 6,888,141 B2 | 5/2005 | Carr |
| 6,895,267 B2 | 5/2005 | Panescu et al. |
| 6,904,303 B2 | 6/2005 | Phan et al. |
| 6,905,495 B1 | 6/2005 | Fuimaono et al. |
| 6,917,834 B2 | 7/2005 | Koblish et al. |
| 6,932,776 B2 | 8/2005 | Carr |
| 6,932,813 B2 | 8/2005 | Thompson et al. |
| 6,936,047 B2 | 8/2005 | Nasab et al. |
| 6,942,661 B2 | 9/2005 | Swanson |
| 6,949,095 B2 | 9/2005 | Vaska et al. |
| 6,953,460 B2 | 10/2005 | Maguire et al. |
| 6,958,075 B2 | 10/2005 | Mon et al. |
| 6,960,205 B2 | 11/2005 | Jahns et al. |
| 6,960,207 B2 | 11/2005 | Vanney et al. |
| 6,974,455 B2 | 12/2005 | Garabedian et al. |

(56) References Cited

U.S. PATENT DOCUMENTS

| | | |
|---|---|---|
| 6,976,492 B2 | 12/2005 | Ingle et al. |
| 6,979,329 B2 | 12/2005 | Burnside et al. |
| 6,984,232 B2 | 1/2006 | Vanney et al. |
| 6,986,769 B2 | 1/2006 | Nelson et al. |
| 7,001,383 B2 | 2/2006 | Keidar |
| 7,008,417 B2 | 3/2006 | Eick |
| 7,029,470 B2 | 4/2006 | Francischelli et al. |
| 7,052,492 B2 | 5/2006 | Swanson et al. |
| 7,101,387 B2 | 9/2006 | Garabedian et al. |
| 7,150,744 B2 | 12/2006 | Edwards et al. |
| 7,151,964 B2 | 12/2006 | Desai et al. |
| 7,160,296 B2 | 1/2007 | Pearson et al. |
| 7,163,537 B2 | 1/2007 | Lee et al. |
| 7,166,075 B2 | 1/2007 | Varghese et al. |
| 7,175,619 B2 | 2/2007 | Koblish et al. |
| 7,175,734 B2 | 2/2007 | Stewart et al. |
| 7,184,811 B2 | 2/2007 | Phan et al. |
| 7,186,250 B2 | 3/2007 | Koblish et al. |
| 7,194,294 B2 | 3/2007 | Panescu et al. |
| 7,197,356 B2 | 3/2007 | Carr |
| 7,229,437 B2 | 6/2007 | Johnson et al. |
| 7,238,184 B2 | 7/2007 | Megerman et al. |
| 7,252,664 B2 | 8/2007 | Nasab et al. |
| 7,263,398 B2 | 8/2007 | Carr |
| 7,276,061 B2 | 10/2007 | Schaer et al. |
| 7,285,116 B2 | 10/2007 | de la Rama et al. |
| 7,303,558 B2 | 12/2007 | Swanson |
| 7,306,593 B2 | 12/2007 | Keidar et al. |
| 7,326,208 B2 | 2/2008 | Vanney et al. |
| 7,326,235 B2 | 2/2008 | Edwards |
| 7,331,960 B2 | 2/2008 | Schaer |
| 7,338,486 B2 | 3/2008 | Sliwa et al. |
| 7,344,533 B2 | 3/2008 | Pearson et al. |
| 7,364,546 B2 | 4/2008 | Panescu et al. |
| 7,364,578 B2 | 4/2008 | Francischelli et al. |
| 7,367,972 B2 | 5/2008 | Francischelli et al. |
| 7,371,233 B2 | 5/2008 | Swanson et al. |
| 7,371,235 B2 | 5/2008 | Thompson et al. |
| 7,435,248 B2 | 10/2008 | Taimisto et al. |
| 7,474,909 B2 | 1/2009 | Phan et al. |
| 7,565,208 B2 | 7/2009 | Harris et al. |
| 7,582,050 B2 | 9/2009 | Schlorff et al. |
| 7,582,084 B2 | 9/2009 | Swanson et al. |
| 7,588,568 B2 | 9/2009 | Fuimaono et al. |
| 7,588,658 B2 | 9/2009 | Yamamoto et al. |
| 7,623,899 B2 | 11/2009 | Worley et al. |
| 7,628,788 B2 | 12/2009 | Datta |
| 7,662,152 B2 | 2/2010 | Sharareh et al. |
| 7,669,309 B2 | 3/2010 | Johnson et al. |
| 7,676,264 B1 | 3/2010 | Pillai et al. |
| 7,678,104 B2 | 3/2010 | Keidar |
| 7,679,336 B2 | 3/2010 | Gale et al. |
| 7,699,829 B2 | 4/2010 | Harris et al. |
| 7,699,841 B2 | 4/2010 | Carr |
| 7,715,926 B2 | 5/2010 | Boser et al. |
| 7,727,230 B2 | 6/2010 | Fuimaono et al. |
| 7,734,330 B2 | 6/2010 | Carr |
| 7,761,148 B2 | 7/2010 | Fuimaono et al. |
| 7,764,994 B2 | 7/2010 | Fuimaono et al. |
| 7,766,693 B2 | 8/2010 | Sartor et al. |
| 7,766,907 B2 | 8/2010 | Dando et al. |
| 7,769,469 B2 | 8/2010 | Carr et al. |
| 7,771,418 B2 | 8/2010 | Chopra et al. |
| 7,771,420 B2 | 8/2010 | Butty et al. |
| 7,774,039 B2 | 8/2010 | Koblish |
| 7,776,034 B2 | 8/2010 | Kampa |
| 7,794,404 B1 | 9/2010 | Gutfinger et al. |
| 7,794,460 B2 | 9/2010 | Mulier et al. |
| 7,811,313 B2 | 10/2010 | Mon et al. |
| 7,815,635 B2 | 10/2010 | Wittkampf et al. |
| 7,819,862 B2 | 10/2010 | Panchon Mateos et al. |
| 7,819,866 B2 | 10/2010 | Bednarek |
| 7,824,399 B2 | 11/2010 | Francischelli et al. |
| 7,826,904 B2 | 11/2010 | Appling et al. |
| 7,833,220 B2 | 11/2010 | Mon et al. |
| 7,837,720 B2 | 11/2010 | Mon |
| 7,857,809 B2 | 12/2010 | Drysen |
| 7,857,810 B2 | 12/2010 | Wang et al. |
| 7,862,563 B1 | 1/2011 | Cosman et al. |
| 7,867,227 B2 | 1/2011 | Slater |
| 7,879,029 B2 | 2/2011 | Jimenez |
| 7,914,528 B2 | 3/2011 | Wang et al. |
| 7,918,850 B2 | 4/2011 | Govari et al. |
| 7,918,851 B2 | 4/2011 | Webster, Jr. et al. |
| 7,925,341 B2 | 4/2011 | Fuimaono |
| 7,925,349 B1 | 4/2011 | Wong et al. |
| 7,927,328 B2 | 4/2011 | Orszulak et al. |
| 7,933,660 B2 | 4/2011 | Carr |
| 7,938,828 B2 | 5/2011 | Koblish |
| 7,945,326 B1 | 5/2011 | Wong et al. |
| 7,946,995 B1 | 5/2011 | Koh et al. |
| 7,955,369 B2 | 6/2011 | Thompson et al. |
| 7,957,813 B1 | 6/2011 | Persson et al. |
| 7,959,628 B2 | 6/2011 | Schaer et al. |
| 7,959,630 B2 | 6/2011 | Taimisto et al. |
| 7,963,925 B1 | 6/2011 | Schecter |
| 7,967,817 B2 | 6/2011 | Anderson et al. |
| 7,976,537 B2 | 7/2011 | Lieber et al. |
| 7,989,741 B2 | 8/2011 | Carr |
| 7,996,078 B2 | 8/2011 | Paul et al. |
| 7,998,140 B2 | 8/2011 | McClurken et al. |
| 7,998,141 B2 | 8/2011 | Wittkampf et al. |
| 8,002,770 B2 | 8/2011 | Swanson et al. |
| 8,007,497 B2 | 8/2011 | Young et al. |
| 8,010,196 B1 | 8/2011 | Wong et al. |
| 8,011,055 B2 | 9/2011 | Lesley |
| 8,012,150 B2 | 9/2011 | Wham et al. |
| 8,019,419 B1 | 9/2011 | Panescu et al. |
| 8,032,218 B2 | 10/2011 | Wong et al. |
| 8,034,050 B2 | 10/2011 | Sharareh et al. |
| 8,034,052 B2 | 10/2011 | Podhajsky |
| 8,038,670 B2 | 10/2011 | McClurken |
| 8,048,070 B2 | 11/2011 | O'Brien et al. |
| 8,052,680 B2 | 11/2011 | Hassett et al. |
| 8,052,684 B2 | 11/2011 | Wang et al. |
| 8,062,228 B2 | 11/2011 | Carr |
| 8,065,005 B1 | 11/2011 | Wong et al. |
| 8,083,736 B2 | 12/2011 | McClurken et al. |
| 8,100,895 B2 | 1/2012 | Panos et al. |
| 8,104,956 B2 | 1/2012 | Blaha |
| 8,118,809 B2 | 2/2012 | Paul et al. |
| 8,123,745 B2 | 2/2012 | Beeckler et al. |
| 8,128,617 B2 | 3/2012 | Bencini et al. |
| 8,128,621 B2 | 3/2012 | Wang et al. |
| 8,133,220 B2 | 3/2012 | Lee et al. |
| 8,145,289 B2 | 3/2012 | Calabro' et al. |
| 8,152,801 B2 | 4/2012 | Goldberg et al. |
| 8,157,796 B2 | 4/2012 | Collins et al. |
| 8,160,693 B2 | 4/2012 | Fuimaono |
| 8,175,680 B2 | 5/2012 | Panescu |
| 8,192,424 B2 | 6/2012 | Woloszko |
| 8,202,224 B2 | 6/2012 | Gutfinger et al. |
| 8,206,380 B2 | 6/2012 | Lenihan et al. |
| 8,206,383 B2 | 6/2012 | Hauck et al. |
| 8,206,385 B2 | 6/2012 | Stangenes et al. |
| 8,208,999 B2 | 6/2012 | Wenzel et al. |
| 8,211,099 B2 | 7/2012 | Buysse et al. |
| 8,216,216 B2 | 7/2012 | Warnking et al. |
| 8,221,408 B2 | 7/2012 | Johnson et al. |
| 8,221,413 B2 | 7/2012 | Mon et al. |
| 8,221,414 B2 | 7/2012 | Mon et al. |
| 8,224,455 B2 | 7/2012 | Mon et al. |
| 8,226,645 B2 | 7/2012 | Harrington et al. |
| 8,229,538 B2 | 7/2012 | Koblish |
| 8,256,428 B2 | 9/2012 | Hindricks et al. |
| 8,262,652 B2 | 9/2012 | Podhajsky |
| 8,262,653 B2 | 9/2012 | Plaza |
| 8,265,745 B2 | 9/2012 | Hauck et al. |
| 8,265,747 B2 | 9/2012 | Rittman, III et al. |
| 8,267,926 B2 | 9/2012 | Paul et al. |
| 8,267,929 B2 | 9/2012 | Wham et al. |
| 8,267,932 B2 | 9/2012 | Baxter et al. |
| 8,273,082 B2 | 9/2012 | Wang et al. |
| 8,280,511 B2 | 10/2012 | Zhao et al. |

(56) References Cited

U.S. PATENT DOCUMENTS

| | | |
|---|---|---|
| 8,287,532 B2 | 10/2012 | Carroll et al. |
| 8,287,533 B2 | 10/2012 | Wittkampf et al. |
| 8,290,578 B2 | 10/2012 | Schneider |
| 8,298,223 B2 | 10/2012 | Wham et al. |
| 8,298,227 B2 | 10/2012 | Leo et al. |
| 8,303,172 B2 | 11/2012 | Zei et al. |
| 8,303,580 B2 | 11/2012 | Wham et al. |
| 8,306,623 B2 | 11/2012 | Wong et al. |
| 8,308,719 B2 | 11/2012 | Sliwa et al. |
| 8,317,783 B2 | 11/2012 | Cao et al. |
| 8,321,019 B2 | 11/2012 | Esch et al. |
| 8,333,759 B2 | 12/2012 | Podhajsky |
| 8,333,762 B2 | 12/2012 | Mest et al. |
| 8,348,937 B2 | 1/2013 | Wang et al. |
| 8,359,092 B2 | 1/2013 | Hayam et al. |
| 8,369,922 B2 | 2/2013 | Paul et al. |
| 8,372,066 B2 | 2/2013 | Manwaring et al. |
| 8,374,670 B2 | 2/2013 | Selkee |
| 8,374,702 B2 | 2/2013 | Mon et al. |
| 8,377,052 B2 | 2/2013 | Manwaring et al. |
| 8,377,054 B2 | 2/2013 | Gilbert |
| 8,380,275 B2 | 2/2013 | Kim et al. |
| 8,386,049 B2 | 2/2013 | Persson et al. |
| 8,394,093 B2 | 3/2013 | Wang et al. |
| 8,398,623 B2 | 3/2013 | Warnking et al. |
| 8,403,925 B2 | 3/2013 | Miller et al. |
| 8,406,866 B2 | 3/2013 | Deno et al. |
| 8,409,191 B2 | 4/2013 | Avitall et al. |
| 8,409,192 B2 | 4/2013 | Asirvatham et al. |
| 8,414,570 B2 | 4/2013 | Turner et al. |
| 8,414,579 B2 | 4/2013 | Kim et al. |
| 8,419,725 B2 | 4/2013 | Haemmerich et al. |
| 8,423,115 B2 | 4/2013 | Koblish |
| 8,440,949 B2 | 5/2013 | Carr |
| 8,442,613 B2 | 5/2013 | Kim et al. |
| 8,444,637 B2 | 5/2013 | Podmore et al. |
| 8,449,535 B2 | 5/2013 | Deno et al. |
| 8,449,537 B2 | 5/2013 | Cao et al. |
| 8,449,539 B2 | 5/2013 | Wang et al. |
| 8,460,285 B2 | 6/2013 | Wang et al. |
| 8,473,023 B2 | 6/2013 | Worley et al. |
| 8,475,448 B2 | 7/2013 | Sharareh et al. |
| 8,475,450 B2 | 7/2013 | Govari et al. |
| 8,480,663 B2 | 7/2013 | Ingle et al. |
| 8,480,666 B2 | 7/2013 | Buysse et al. |
| 8,486,065 B2 | 7/2013 | Lee et al. |
| 8,491,578 B2 | 7/2013 | Manwaring et al. |
| 8,504,152 B2 | 8/2013 | Wenzel et al. |
| 8,504,153 B2 | 8/2013 | Wenzel et al. |
| 8,515,554 B2 | 8/2013 | Carr |
| 8,517,999 B2 | 8/2013 | Pappone et al. |
| 8,523,851 B2 | 9/2013 | Manwaring et al. |
| 8,523,852 B2 | 9/2013 | Manwaring et al. |
| 8,535,303 B2 | 9/2013 | Avitall et al. |
| 8,545,409 B2 | 10/2013 | Sliwa et al. |
| 8,554,333 B2 | 10/2013 | Wu et al. |
| 8,556,893 B2 | 10/2013 | Potter |
| 8,560,086 B2 | 10/2013 | Just et al. |
| 8,562,600 B2 | 10/2013 | Kirkpatrick et al. |
| 8,568,402 B2 | 10/2013 | Buysse et al. |
| 8,574,166 B2 | 11/2013 | Carr |
| 8,600,472 B2 | 12/2013 | Govari et al. |
| 8,600,497 B1 | 12/2013 | Yang et al. |
| 8,603,084 B2 | 12/2013 | Fish et al. |
| 8,603,085 B2 | 12/2013 | Jimenez |
| 8,628,520 B2 | 1/2014 | Sharareh et al. |
| 8,632,533 B2 | 1/2014 | Greeley et al. |
| 8,636,729 B2 | 1/2014 | Esch et al. |
| 8,641,708 B2 | 2/2014 | Govari et al. |
| 8,657,814 B2 | 2/2014 | Werneth et al. |
| 8,663,122 B2 | 3/2014 | Schecter |
| 8,668,686 B2 | 3/2014 | Govari et al. |
| 8,672,936 B2 | 3/2014 | Thao et al. |
| 8,679,109 B2 | 3/2014 | Paul et al. |
| 8,690,870 B2 | 4/2014 | Wang et al. |
| 8,696,659 B2 | 4/2014 | Marion |
| 8,700,120 B2 | 4/2014 | Koblish |
| 8,702,690 B2 | 4/2014 | Paul et al. |
| 8,702,693 B2 | 4/2014 | Subramaniam et al. |
| 8,712,519 B1 | 4/2014 | Panescu et al. |
| 8,721,634 B2 | 5/2014 | Esch et al. |
| 8,721,636 B2 | 5/2014 | Vaska et al. |
| 8,725,228 B2 | 5/2014 | Koblish et al. |
| 8,728,074 B2 | 5/2014 | West et al. |
| 8,728,077 B2 | 5/2014 | Paul et al. |
| 8,731,631 B2 | 5/2014 | Kim et al. |
| 8,731,684 B2 | 5/2014 | Carr et al. |
| 8,734,442 B2 | 5/2014 | Cao et al. |
| 8,740,900 B2 | 6/2014 | Kim et al. |
| 8,755,860 B2 | 6/2014 | Paul et al. |
| 8,764,746 B2 | 7/2014 | Podmore et al. |
| 8,777,942 B2 | 7/2014 | Wu et al. |
| 8,784,414 B2 | 7/2014 | Avitall et al. |
| 8,792,958 B2 | 7/2014 | Kim et al. |
| 8,795,271 B2 | 8/2014 | Koblish et al. |
| 8,798,706 B2 | 8/2014 | Kim et al. |
| 8,814,824 B2 | 8/2014 | Kauphusman et al. |
| 8,814,857 B2 | 8/2014 | Christian |
| 8,834,388 B2 | 9/2014 | Sherman |
| 8,834,461 B2 | 9/2014 | Werneth et al. |
| 8,845,629 B2 | 9/2014 | Demarais et al. |
| 8,845,631 B2 | 9/2014 | Werneth et al. |
| 8,845,633 B2 | 9/2014 | Wang et al. |
| 8,858,548 B2 | 10/2014 | Asconeguy |
| 8,868,165 B1 | 10/2014 | Nabutovsky et al. |
| 8,876,817 B2 | 11/2014 | Avitall et al. |
| 8,876,819 B2 | 11/2014 | Tegg et al. |
| 8,882,755 B2 | 11/2014 | Leung et al. |
| 8,882,759 B2 | 11/2014 | Manley et al. |
| 8,882,761 B2 | 11/2014 | Desai |
| 8,894,642 B2 | 11/2014 | Gibson et al. |
| 8,900,225 B2 | 12/2014 | Bar-Tal et al. |
| 8,900,228 B2 | 12/2014 | Grunewald et al. |
| 8,906,010 B2 | 12/2014 | Edwards et al. |
| 8,920,415 B2 | 12/2014 | Govari |
| 8,926,605 B2 | 1/2015 | McCarthy et al. |
| 8,932,284 B2 | 1/2015 | McCarthy et al. |
| 8,934,953 B2 | 1/2015 | Carr et al. |
| 8,942,828 B1 | 1/2015 | Schecter |
| 8,945,015 B2 | 2/2015 | Rankin et al. |
| 8,945,117 B2 | 2/2015 | Bencini |
| 8,954,161 B2 | 2/2015 | McCarthy et al. |
| 8,956,304 B2 | 2/2015 | Schecter |
| 8,961,506 B2 | 2/2015 | McCarthy et al. |
| 8,968,299 B2 | 3/2015 | Kauphusman et al. |
| 8,974,454 B2 | 3/2015 | de La Rama et al. |
| 8,992,519 B2 | 3/2015 | Kim et al. |
| 8,998,890 B2 | 4/2015 | Paul et al. |
| 9,014,814 B2 | 4/2015 | McCarthy et al. |
| 9,023,030 B2 | 5/2015 | Koblish et al. |
| 9,050,069 B2 | 6/2015 | Lalonde et al. |
| 9,060,756 B2 | 6/2015 | Bencini et al. |
| 9,066,662 B2 | 6/2015 | Wenzel et al. |
| 9,066,725 B2 | 6/2015 | Christian |
| 9,089,339 B2 | 7/2015 | McDaniel |
| 9,089,340 B2 | 7/2015 | Hastings et al. |
| 9,095,349 B2 | 8/2015 | Fish et al. |
| 9,138,281 B2 | 9/2015 | Zarins et al. |
| 9,144,460 B2 | 9/2015 | Clark et al. |
| 9,173,586 B2 | 11/2015 | Deno et al. |
| 9,179,972 B2 | 11/2015 | Olson |
| 9,186,081 B2 | 11/2015 | Afonso et al. |
| 9,204,927 B2 | 12/2015 | Afonso et al. |
| 9,226,791 B2 | 1/2016 | McCarthy et al. |
| 9,226,793 B2 | 1/2016 | Jimenez |
| 9,254,163 B2 | 2/2016 | Paul et al. |
| 9,265,574 B2 | 2/2016 | Bar-Tal et al. |
| 9,271,782 B2 | 3/2016 | Paul et al. |
| 9,277,961 B2 | 3/2016 | Panescu et al. |
| 9,283,025 B2 | 3/2016 | Paul et al. |
| 9,283,026 B2 | 3/2016 | Paul et al. |
| 9,289,606 B2 | 3/2016 | Paul et al. |
| 9,339,325 B2 | 5/2016 | Miller et al. |
| 9,364,282 B2 | 6/2016 | Just et al. |

(56) References Cited

U.S. PATENT DOCUMENTS

| | | |
|---|---|---|
| 9,364,286 B2 | 6/2016 | Werneth et al. |
| 9,370,311 B2 | 6/2016 | Stewart et al. |
| 9,427,167 B2 | 8/2016 | Maskara et al. |
| 9,433,465 B2 | 9/2016 | Gliner et al. |
| 9,456,867 B2 | 10/2016 | Lawrence et al. |
| 9,474,458 B2 | 10/2016 | Clark et al. |
| 9,492,226 B2 | 11/2016 | Fish et al. |
| 9,510,893 B2 | 12/2016 | Jimenez |
| 9,510,894 B2 | 12/2016 | Clark et al. |
| 9,510,905 B2 | 12/2016 | Panescu et al. |
| 9,517,103 B2 | 12/2016 | Panescu et al. |
| 9,522,036 B2 | 12/2016 | Panescu et al. |
| 9,522,037 B2 | 12/2016 | Panescu et al. |
| 9,526,574 B2 | 12/2016 | Wang et al. |
| 9,545,285 B2 | 1/2017 | Ghaffari et al. |
| 9,592,092 B2 | 3/2017 | Panescu et al. |
| 9,610,119 B2 | 4/2017 | Fish et al. |
| 9,636,164 B2 | 5/2017 | Panescu et al. |
| 9,687,289 B2 | 6/2017 | Govari et al. |
| 9,993,178 B2 * | 6/2018 | Panescu ................ A61B 5/061 |
| 2001/0001830 A1 | 5/2001 | Dobak et al. |
| 2001/0007927 A1 | 7/2001 | Koblish et al. |
| 2002/0004631 A1 | 1/2002 | Jenkins et al. |
| 2002/0022829 A1 | 2/2002 | Nagase et al. |
| 2002/0022834 A1 | 2/2002 | Simpson et al. |
| 2002/0026185 A1 | 2/2002 | Gough |
| 2002/0040229 A1 | 4/2002 | Norman |
| 2002/0058870 A1 | 5/2002 | Panescu et al. |
| 2002/0065465 A1 | 5/2002 | Panescu et al. |
| 2002/0115941 A1 | 8/2002 | Whayne et al. |
| 2002/0128636 A1 | 9/2002 | Chin et al. |
| 2002/0128639 A1 | 9/2002 | Pless et al. |
| 2002/0128643 A1 | 9/2002 | Simpson et al. |
| 2002/0165529 A1 | 11/2002 | Danek |
| 2002/0169444 A1 | 11/2002 | Mest et al. |
| 2002/0183736 A1 | 12/2002 | Francischelli et al. |
| 2002/0193790 A1 | 12/2002 | Fleischman et al. |
| 2002/0198520 A1 | 12/2002 | Coen et al. |
| 2003/0014049 A1 | 1/2003 | Koblish et al. |
| 2003/0050557 A1 | 3/2003 | Susil et al. |
| 2003/0055470 A1 | 3/2003 | Mon et al. |
| 2003/0065322 A1 | 4/2003 | Panescu et al. |
| 2003/0069619 A1 | 4/2003 | Fenn et al. |
| 2003/0078509 A1 | 4/2003 | Panescu |
| 2003/0078573 A1 | 4/2003 | Truckai et al. |
| 2003/0088244 A1 | 5/2003 | Swanson et al. |
| 2003/0093067 A1 | 5/2003 | Panescu |
| 2003/0120171 A1 | 6/2003 | Diamantopoulos et al. |
| 2003/0153967 A1 | 8/2003 | Koblish et al. |
| 2003/0195406 A1 | 10/2003 | Jenkins et al. |
| 2003/0199817 A1 | 10/2003 | Thompson et al. |
| 2004/0054272 A1 | 3/2004 | Messing |
| 2004/0092806 A1 | 5/2004 | Sagon et al. |
| 2004/0097803 A1 | 5/2004 | Panescu |
| 2004/0138656 A1 | 7/2004 | Francischelli et al. |
| 2004/0147915 A1 | 7/2004 | Hasebe |
| 2004/0260278 A1 | 12/2004 | Anderson et al. |
| 2005/0015082 A1 | 1/2005 | O'Sullivan et al. |
| 2005/0033221 A1 | 2/2005 | Fiumaono |
| 2005/0059963 A1 | 3/2005 | Phan et al. |
| 2005/0143727 A1 | 6/2005 | Koblish et al. |
| 2005/0177151 A1 | 8/2005 | Coen et al. |
| 2005/0197657 A1 | 9/2005 | Goth et al. |
| 2005/0228370 A1 | 10/2005 | Sterzer et al. |
| 2005/0245949 A1 | 11/2005 | Goth et al. |
| 2005/0251125 A1 | 11/2005 | Pless et al. |
| 2006/0025758 A1 | 2/2006 | Strul et al. |
| 2006/0064083 A1 | 3/2006 | Khalaj et al. |
| 2006/0089688 A1 | 4/2006 | Panescu |
| 2006/0095032 A1 | 5/2006 | Jackson et al. |
| 2006/0135957 A1 | 6/2006 | Panescu |
| 2006/0167445 A1 | 7/2006 | Shafirstein |
| 2006/0184166 A1 | 8/2006 | Valle et al. |
| 2006/0184221 A1 | 8/2006 | Stewart et al. |
| 2006/0217701 A1 | 9/2006 | Young et al. |
| 2006/0247615 A1 | 11/2006 | McCullagh et al. |
| 2006/0253115 A1 | 11/2006 | Avitall et al. |
| 2006/0293731 A1 | 12/2006 | Rubinsky et al. |
| 2007/0032788 A1 | 2/2007 | Edwards et al. |
| 2007/0049925 A1 | 3/2007 | Phan et al. |
| 2007/0055227 A1 | 3/2007 | Khalaj et al. |
| 2007/0055326 A1 | 3/2007 | Farley et al. |
| 2007/0055328 A1 | 3/2007 | Mayse et al. |
| 2007/0066968 A1 | 3/2007 | Rahn |
| 2007/0066972 A1 | 3/2007 | Ormsby et al. |
| 2007/0073286 A1 | 3/2007 | Panescu et al. |
| 2007/0129720 A1 | 6/2007 | Demarais et al. |
| 2007/0135810 A1 | 6/2007 | Lee et al. |
| 2007/0149963 A1 | 6/2007 | Matsukuma et al. |
| 2007/0156048 A1 | 7/2007 | Panescu et al. |
| 2007/0156114 A1 | 7/2007 | Worley et al. |
| 2007/0179378 A1 | 8/2007 | Boese et al. |
| 2007/0185478 A1 | 8/2007 | Cosentino |
| 2007/0198007 A1 | 8/2007 | Govari et al. |
| 2007/0225697 A1 | 9/2007 | Shroff et al. |
| 2007/0244476 A1 | 10/2007 | Kochamba et al. |
| 2007/0244534 A1 | 10/2007 | Kochamba et al. |
| 2007/0299488 A1 | 12/2007 | Carr |
| 2008/0015562 A1 * | 1/2008 | Hong .................. A61B 5/7203 606/34 |
| 2008/0015563 A1 | 1/2008 | Hoey et al. |
| 2008/0015571 A1 | 1/2008 | Rubinsky et al. |
| 2008/0033300 A1 | 2/2008 | Hoang et al. |
| 2008/0077126 A1 | 3/2008 | Rashidi |
| 2008/0082091 A1 | 4/2008 | Rubtsov et al. |
| 2008/0161791 A1 | 7/2008 | Cao et al. |
| 2008/0161797 A1 * | 7/2008 | Wang ................ A61B 18/1492 606/41 |
| 2008/0172048 A1 | 7/2008 | Martin et al. |
| 2008/0177205 A1 | 7/2008 | Rama et al. |
| 2008/0243112 A1 | 10/2008 | De Neve |
| 2008/0243214 A1 | 10/2008 | Koblish |
| 2008/0249463 A1 | 10/2008 | Pappone et al. |
| 2008/0275440 A1 | 11/2008 | Kratoska et al. |
| 2008/0300589 A1 | 12/2008 | Paul et al. |
| 2008/0312521 A1 | 12/2008 | Solomon |
| 2009/0005768 A1 | 1/2009 | Sharareh et al. |
| 2009/0036882 A1 | 2/2009 | Webster et al. |
| 2009/0069808 A1 | 3/2009 | Pike, Jr. et al. |
| 2009/0076409 A1 | 3/2009 | Wu et al. |
| 2009/0093810 A1 | 4/2009 | Subramaniam et al. |
| 2009/0099560 A1 | 4/2009 | Rioux et al. |
| 2009/0118613 A1 | 5/2009 | Krugman et al. |
| 2009/0163916 A1 | 6/2009 | Paul et al. |
| 2009/0177111 A1 | 7/2009 | Miller et al. |
| 2009/0177193 A1 | 7/2009 | Wang et al. |
| 2009/0187183 A1 | 7/2009 | Epstein |
| 2009/0221999 A1 | 9/2009 | Shahidi |
| 2009/0248006 A1 | 10/2009 | Paulus et al. |
| 2009/0254083 A1 | 10/2009 | Wallace et al. |
| 2009/0275827 A1 | 11/2009 | Aiken et al. |
| 2009/0287201 A1 | 11/2009 | Lalonde et al. |
| 2009/0306641 A1 | 12/2009 | Govari et al. |
| 2009/0306643 A1 | 12/2009 | Pappone et al. |
| 2009/0312754 A1 | 12/2009 | Lenihan et al. |
| 2009/0312756 A1 | 12/2009 | Schlesinger et al. |
| 2010/0016848 A1 | 1/2010 | Desai |
| 2010/0023000 A1 | 1/2010 | Stevenson et al. |
| 2010/0030209 A1 | 2/2010 | Govari et al. |
| 2010/0049011 A1 | 2/2010 | Boese et al. |
| 2010/0057072 A1 | 3/2010 | Roman et al. |
| 2010/0057073 A1 | 3/2010 | Roman et al. |
| 2010/0057074 A1 | 3/2010 | Roman et al. |
| 2010/0057080 A1 | 3/2010 | West et al. |
| 2010/0076424 A1 | 3/2010 | Carr |
| 2010/0094271 A1 | 4/2010 | Ward et al. |
| 2010/0114087 A1 | 5/2010 | Edwards et al. |
| 2010/0114227 A1 | 5/2010 | Cholette |
| 2010/0137837 A1 | 6/2010 | Govari et al. |
| 2010/0137857 A1 | 6/2010 | Shroff et al. |
| 2010/0152724 A1 | 6/2010 | Marion et al. |
| 2010/0168557 A1 | 7/2010 | Deno et al. |
| 2010/0168570 A1 | 7/2010 | Sliwa et al. |
| 2010/0168571 A1 | 7/2010 | Savery et al. |

(56) References Cited

U.S. PATENT DOCUMENTS

| | | |
|---|---|---|
| 2010/0168620 A1 | 7/2010 | Klimovitch et al. |
| 2010/0174280 A1 | 7/2010 | Grimaldi |
| 2010/0185191 A1 | 7/2010 | Carr et al. |
| 2010/0198312 A1 | 8/2010 | Stevenson et al. |
| 2010/0204691 A1 | 8/2010 | Bencini |
| 2010/0211070 A1 | 8/2010 | Subramaniam et al. |
| 2010/0217255 A1 | 8/2010 | Greeley et al. |
| 2010/0222859 A1 | 9/2010 | Govari et al. |
| 2010/0286684 A1 | 11/2010 | Hata et al. |
| 2010/0286690 A1 | 11/2010 | Paul et al. |
| 2010/0298823 A1 | 11/2010 | Cao et al. |
| 2010/0331838 A1 | 12/2010 | Ibrahim et al. |
| 2011/0009857 A1 | 1/2011 | Subramaniam et al. |
| 2011/0022041 A1 | 1/2011 | Ingle et al. |
| 2011/0028821 A1 | 2/2011 | Bojovic et al. |
| 2011/0066147 A1 | 3/2011 | He et al. |
| 2011/0077498 A1 | 3/2011 | McDaniel |
| 2011/0105928 A1 | 5/2011 | Bojovic et al. |
| 2011/0112413 A1 | 5/2011 | Panescu et al. |
| 2011/0112414 A1 | 5/2011 | Panescu et al. |
| 2011/0112415 A1 | 5/2011 | Bojovic et al. |
| 2011/0118726 A1 | 5/2011 | de La Rama et al. |
| 2011/0144479 A1 | 6/2011 | Hastings et al. |
| 2011/0144524 A1 | 6/2011 | Fish et al. |
| 2011/0144639 A1 | 6/2011 | Govari |
| 2011/0152853 A1 | 6/2011 | Manley et al. |
| 2011/0160726 A1 | 6/2011 | Ingle |
| 2011/0166472 A1 | 7/2011 | Björling et al. |
| 2011/0172658 A1 | 7/2011 | Gelbart et al. |
| 2011/0184300 A1 | 7/2011 | Shvilkin et al. |
| 2011/0184313 A1 | 7/2011 | Gianchandani et al. |
| 2011/0213356 A1 | 9/2011 | Wright et al. |
| 2011/0224573 A1 | 9/2011 | Bar-Tal et al. |
| 2011/0224664 A1 | 9/2011 | Bar-Tal et al. |
| 2011/0224667 A1 | 9/2011 | Koblish et al. |
| 2011/0257645 A1 | 10/2011 | Thompson et al. |
| 2011/0264000 A1 | 10/2011 | Paul et al. |
| 2011/0264011 A1 | 10/2011 | Wu et al. |
| 2011/0264089 A1 | 10/2011 | Zirkle et al. |
| 2011/0270244 A1 | 11/2011 | Clark et al. |
| 2011/0270246 A1 | 11/2011 | Clark et al. |
| 2011/0270247 A1 | 11/2011 | Sherman |
| 2011/0282250 A1 | 11/2011 | Fung et al. |
| 2011/0282342 A1 | 11/2011 | Leo et al. |
| 2011/0288544 A1 | 11/2011 | Verin et al. |
| 2011/0295247 A1 | 12/2011 | Schlesinger et al. |
| 2011/0319748 A1 | 12/2011 | Bronskill et al. |
| 2012/0029504 A1 | 2/2012 | Afonson et al. |
| 2012/0029511 A1 | 2/2012 | Smith et al. |
| 2012/0029512 A1 | 2/2012 | Willard et al. |
| 2012/0035603 A1 | 2/2012 | Lenihan |
| 2012/0059368 A1 | 3/2012 | Takaoka et al. |
| 2012/0071870 A1 | 3/2012 | Salahieh et al. |
| 2012/0078138 A1 | 3/2012 | Leo et al. |
| 2012/0089123 A1 | 4/2012 | Organ et al. |
| 2012/0101538 A1 | 4/2012 | Ballakur et al. |
| 2012/0116382 A1 | 5/2012 | Ku et al. |
| 2012/0116392 A1 | 5/2012 | Willard |
| 2012/0123411 A1 | 5/2012 | Ibrahim et al. |
| 2012/0130364 A1 | 5/2012 | Besch et al. |
| 2012/0136346 A1 | 5/2012 | Condie et al. |
| 2012/0143097 A1 | 6/2012 | Pike, Jr. |
| 2012/0150170 A1 | 6/2012 | Buysse et al. |
| 2012/0157890 A1 | 6/2012 | Govari et al. |
| 2012/0157990 A1 | 6/2012 | Christian |
| 2012/0165809 A1 | 6/2012 | Christian et al. |
| 2012/0172859 A1 | 7/2012 | Condie et al. |
| 2012/0179068 A1 | 7/2012 | Leo et al. |
| 2012/0189998 A1 | 7/2012 | Kruecker et al. |
| 2012/0197243 A1 | 8/2012 | Sherman et al. |
| 2012/0239019 A1 | 9/2012 | Asconeguy |
| 2012/0245577 A1 | 9/2012 | Mihalik et al. |
| 2012/0265076 A1 | 10/2012 | Schecter |
| 2012/0265137 A1 | 10/2012 | Mon |
| 2012/0265190 A1 | 10/2012 | Curley et al. |
| 2012/0271306 A1 | 10/2012 | Buysse et al. |
| 2012/0277574 A1 | 11/2012 | Panescu |
| 2012/0277737 A1 | 11/2012 | Curley |
| 2012/0283534 A1 | 11/2012 | Carr et al. |
| 2012/0283722 A1 | 11/2012 | Asconeguy |
| 2012/0302877 A1 | 11/2012 | Harks et al. |
| 2012/0303103 A1 | 11/2012 | Mon et al. |
| 2013/0006139 A1 | 1/2013 | Tiano |
| 2013/0006238 A1 | 1/2013 | Ditter et al. |
| 2013/0030385 A1 | 1/2013 | Schultz et al. |
| 2013/0030426 A1 | 1/2013 | Gallardo et al. |
| 2013/0030427 A1 | 1/2013 | Betts et al. |
| 2013/0060245 A1 | 3/2013 | Grunewald et al. |
| 2013/0066312 A1 | 3/2013 | Subramaniam et al. |
| 2013/0066315 A1 | 3/2013 | Subramaniam et al. |
| 2013/0079768 A1 | 3/2013 | De Luca et al. |
| 2013/0096447 A1 | 4/2013 | Dhawan et al. |
| 2013/0103064 A1 | 4/2013 | Arenson et al. |
| 2013/0110104 A1 | 5/2013 | Corvi et al. |
| 2013/0123775 A1 | 5/2013 | Grunewald et al. |
| 2013/0137999 A1 | 5/2013 | Wenzel et al. |
| 2013/0158536 A1 | 6/2013 | Bloom |
| 2013/0158548 A1* | 6/2013 | Govari ............... A61B 18/1492 606/41 |
| 2013/0172742 A1 | 7/2013 | Rankin et al. |
| 2013/0172873 A1 | 7/2013 | Govari et al. |
| 2013/0172879 A1 | 7/2013 | Sutermeister et al. |
| 2013/0184549 A1 | 7/2013 | Avitall et al. |
| 2013/0190747 A1 | 7/2013 | Koblish et al. |
| 2013/0197504 A1 | 8/2013 | Cronin et al. |
| 2013/0197507 A1 | 8/2013 | Kim et al. |
| 2013/0204124 A1 | 8/2013 | Duindam et al. |
| 2013/0204240 A1 | 8/2013 | McCarthy et al. |
| 2013/0226169 A1 | 8/2013 | Miller et al. |
| 2013/0237977 A1 | 9/2013 | McCarthy et al. |
| 2013/0237979 A1 | 9/2013 | Shikhman et al. |
| 2013/0253504 A1 | 9/2013 | Fang |
| 2013/0253505 A1 | 9/2013 | Schultz |
| 2013/0272339 A1 | 10/2013 | Tofighi |
| 2013/0281851 A1 | 10/2013 | Carr et al. |
| 2013/0289550 A1 | 10/2013 | Ingle et al. |
| 2013/0296840 A1 | 11/2013 | Condie et al. |
| 2013/0303892 A1 | 11/2013 | Zhao et al. |
| 2013/0303945 A1 | 11/2013 | Blumenkranz et al. |
| 2013/0310674 A1 | 11/2013 | Deno et al. |
| 2013/0324993 A1 | 12/2013 | McCarthy et al. |
| 2013/0338664 A1 | 12/2013 | Wang et al. |
| 2013/0345692 A1 | 12/2013 | Brannan |
| 2014/0012132 A1 | 1/2014 | Carr et al. |
| 2014/0018697 A1 | 1/2014 | Allison |
| 2014/0018793 A1 | 1/2014 | Sharonov |
| 2014/0025056 A1 | 1/2014 | Dowlatshahi |
| 2014/0025057 A1 | 1/2014 | Hoey et al. |
| 2014/0031785 A1 | 1/2014 | Schwagten et al. |
| 2014/0051959 A1 | 2/2014 | Gliner et al. |
| 2014/0058244 A1 | 2/2014 | Krocak |
| 2014/0058375 A1 | 2/2014 | Koblish |
| 2014/0081111 A1 | 3/2014 | Tun et al. |
| 2014/0081112 A1 | 3/2014 | Kim et al. |
| 2014/0081262 A1 | 3/2014 | Koblish et al. |
| 2014/0094794 A1 | 4/2014 | Orszulak |
| 2014/0142561 A1 | 5/2014 | Reu et al. |
| 2014/0171821 A1 | 6/2014 | Govari et al. |
| 2014/0171936 A1 | 6/2014 | Govari et al. |
| 2014/0180077 A1 | 6/2014 | Huennekens et al. |
| 2014/0187949 A1 | 7/2014 | Zhao et al. |
| 2014/0188440 A1 | 7/2014 | Donhowe et al. |
| 2014/0194867 A1 | 7/2014 | Fish et al. |
| 2014/0207010 A1 | 7/2014 | Schecter |
| 2014/0214017 A1 | 7/2014 | Brannan |
| 2014/0214110 A1 | 7/2014 | Yang et al. |
| 2014/0243813 A1 | 8/2014 | Paul et al. |
| 2014/0249510 A1 | 9/2014 | Koblish et al. |
| 2014/0249521 A1 | 9/2014 | McCarthy et al. |
| 2014/0257261 A1 | 9/2014 | Kim et al. |
| 2014/0276716 A1 | 9/2014 | Melsheimer |
| 2014/0276755 A1 | 9/2014 | Cao et al. |
| 2014/0276811 A1 | 9/2014 | Koblish et al. |
| 2014/0288548 A1 | 9/2014 | Kim et al. |

(56) References Cited

U.S. PATENT DOCUMENTS

| | | | |
|---|---|---|---|
| 2014/0336638 A1 | 11/2014 | Deem et al. | |
| 2014/0343416 A1 | 11/2014 | Panescu et al. | |
| 2014/0378956 A1 | 12/2014 | Shafirstein | |
| 2015/0011995 A1 | 1/2015 | Avitall et al. | |
| 2015/0094710 A1 | 4/2015 | Edwards et al. | |
| 2015/0105645 A1 | 4/2015 | Subramaniam et al. | |
| 2015/0126995 A1* | 5/2015 | Govari | A61B 18/1492 606/40 |
| 2015/0133914 A1 | 5/2015 | Koblish | |
| 2015/0133920 A1 | 5/2015 | Rankin et al. | |
| 2015/0141978 A1 | 5/2015 | Subramaniam et al. | |
| 2015/0265341 A1 | 9/2015 | Koblish | |
| 2015/0265348 A1 | 9/2015 | Avitall et al. | |
| 2015/0272652 A1 | 10/2015 | Ghaffari et al. | |
| 2015/0272667 A1 | 10/2015 | Govari et al. | |
| 2015/0342676 A1 | 12/2015 | McCarthy et al. | |
| 2016/0038229 A1 | 2/2016 | McCarthy et al. | |
| 2016/0058505 A1 | 3/2016 | Condie et al. | |
| 2016/0095642 A1 | 4/2016 | Deno et al. | |
| 2016/0128770 A1 | 5/2016 | Afonso et al. | |
| 2016/0199131 A1 | 7/2016 | Allison et al. | |
| 2016/0213282 A1 | 7/2016 | Leo et al. | |
| 2016/0220307 A1 | 8/2016 | Miller et al. | |
| 2016/0256682 A1 | 9/2016 | Paul et al. | |
| 2016/0278842 A1 | 9/2016 | Panescu et al. | |
| 2016/0278856 A1* | 9/2016 | Panescu | A61B 5/068 |
| 2016/0287136 A1 | 10/2016 | Condie et al. | |
| 2016/0287137 A1 | 10/2016 | Condie et al. | |
| 2016/0317210 A1 | 11/2016 | McCarthy et al. | |
| 2016/0324567 A1 | 11/2016 | Panescu et al. | |
| 2016/0324568 A1 | 11/2016 | Panescu et al. | |
| 2016/0331267 A1 | 11/2016 | Maskara et al. | |
| 2017/0042613 A1 | 2/2017 | Panescu et al. | |
| 2017/0065348 A1 | 3/2017 | Fish et al. | |
| 2017/0079545 A1 | 3/2017 | Panescu et al. | |
| 2017/0112405 A1 | 4/2017 | Sterrett et al. | |
| 2017/0143415 A1 | 5/2017 | Laughner et al. | |
| 2017/0189105 A1 | 7/2017 | Panescu et al. | |
| 2017/0340377 A1 | 11/2017 | Panescu et al. | |
| 2017/0354475 A1 | 12/2017 | Allison et al. | |

FOREIGN PATENT DOCUMENTS

| | | |
|---|---|---|
| EP | 0746372 | 5/2003 |
| EP | 1008327 | 10/2008 |
| EP | 2008602 | 12/2008 |
| EP | 1803407 | 11/2010 |
| EP | 2294490 | 3/2011 |
| EP | 2338431 A1 | 6/2011 |
| EP | 1962710 | 8/2015 |
| EP | 1962708 | 9/2015 |
| JP | H06-503028 | 4/1994 |
| JP | H06-510450 | 11/1994 |
| JP | T-2002-523127 | 7/2002 |
| JP | 2003-52736 | 2/2003 |
| JP | T-2004-500935 | 1/2004 |
| JP | T-2006-500103 | 1/2006 |
| WO | WO 1993/02747 | 2/1993 |
| WO | WO 1993/04727 | 3/1993 |
| WO | WO 1999/003535 | 1/1999 |
| WO | WO 1999/044523 | 9/1999 |
| WO | WO 2000/010472 | 3/2000 |
| WO | WO 2000/036987 | 6/2000 |
| WO | WO 2001/098764 | 12/2001 |
| WO | WO 2003/028572 | 4/2003 |
| WO | WO 2003/047446 | 6/2003 |
| WO | WO 2003/070298 | 8/2003 |
| WO | WO 2004/026098 | 4/2004 |
| WO | WO 2004/073505 | 9/2004 |
| WO | WO 2004/084748 | 10/2004 |
| WO | WO 2004/107974 | 12/2004 |
| WO | WO 2005/007000 | 1/2005 |
| WO | WO 2006/074571 | 7/2006 |
| WO | WO 2007/019876 | 2/2007 |
| WO | WO 2008/002517 | 1/2008 |
| WO | WO 2010/090701 | 8/2010 |
| WO | WO 2012/120498 | 9/2012 |
| WO | WO 2013/009977 | 1/2013 |
| WO | WO 2013/019544 | 2/2013 |
| WO | WO 2013/034629 | 3/2013 |
| WO | WO 2013/119620 | 8/2013 |
| WO | WO 2013/123020 | 8/2013 |
| WO | WO 2013/138262 | 9/2013 |
| WO | WO 2014/097300 | 6/2014 |
| WO | WO 2015/033317 | 3/2015 |
| WO | WO 2015/042173 | 3/2015 |
| WO | WO 2015/104672 | 7/2015 |
| WO | WO 2015/200518 | 12/2015 |
| WO | 2016081650 A1 | 5/2016 |
| WO | WO 2016/081598 | 5/2016 |
| WO | WO 2016/081602 | 5/2016 |
| WO | WO 2016/081606 | 5/2016 |
| WO | WO 2016/081611 | 5/2016 |
| WO | WO 2016/081650 | 5/2016 |

OTHER PUBLICATIONS

Arunachalam et al., "Characterization of a digital microwave radiometry system for noninvasive thermometry using temperature controlled homogeneous test load," Phys. Med. Biol. 53(14): 3883-3901, Jul. 21, 2008.

Calkins, "Breaking News! When It Comes to Complications of Catheter Ablation of Atrial Fibrillation, Experience Matters," Circulation, 2013; 128: 2099-2100 (Sep. 2013).

Carr, "Thermography: Radiometric sensing in medicine," New Frontiers in Medical Device Technology, Edited by Rosen et al., pp. 311-342, 1995.

Chierchia et al., "An Initial Clinical Experience with a Novel Microwave Radiometry Sensing Technology used in Irrigated RF Ablation for Flutter" (datE:Jan. 1, 2011).

ConstellationTM , Full Contact Mapping Catheter, Boston Scientific Corporation Brochure, Dec. 2014.

El-Sharkawy et al., "Absolute temperature monitoring using RF radiometry in the MRI scanner," IEEE Trans Circuits Syst I Regul Pap. 53(11): 2396-2404, Nov. 2006.

Ikeda et al., "Microwave Volumetric Temperature Sensor Improves Control of Radiofrequency Lesion Formation and Steam Pop," Presentation Abstract, May 2012.

Ikeda et al., "Novel Irrigated Radiofrequency Ablation Catheter With Microwave Volumetric Temperature Sensor Predicts Lesion Size and Incidence of Steam Pop in Canine Beating Heart," Presentation Abstract, May 2012.

Jacobsen et al., "Dual-mode antenna design for microwave heating and noninvasive thermometry of superficial tissue disease," IEEE Transactions on Biomedical Engineering 47(11): 1500-1509, Nov. 2000.

Johnson et al., "Automatic Temperature Controller for Multielement Array Hyperthermia Systems", IEEE Transactions on Biomedical Engeineering, vol. 53, No. 6, 1006-1015, Jun. 2016.

Koruth et al., "Occurrence of Steam Pops During Irrigated RF Ablation: Novel Insights from Microwave Radiometry," J. Cardiovasc, Electrophysiol., vol. 24, Issue 11, pp. 1271-1277, Nov. 2013.

Koruth et al,, "Tissue Temperature Sensing During Irrigated Radiofrequency Ablation: A Novel Strategy to Predict Steam Pops," Presentation Abstract, May 2012.

Lantis et al, "Microwave Applications in Clinical Medicine," Surgical Endoscopy, vol. 12, Issue 2, pp. 170-176, Feb. 1998.

Panescu et al., Three-Dimensional Finite Element Analysis of Current Density and Temperature Distributions During Radio-Frequency Ablation, IEEE Transactions on Biomedical Engineering (1995) 42(9):879-889.

Price et al., "Novel Ablation Catheter Technology that Improves Mapping Resolution and Monitoring of Lesion Maturation", The Journal of Innovations in Cardiac Rhythm Management, vol. 3, 599-609, Jan. 2012.

Rozen et al., "Prediction of radiofrequency ablation lesion formation using a novel temperature sensing technology incorporated in a force sensing catheter", Heart Rhythm, vol. 14, No. 2, pp. 248-254, Feb. 2017.

(56) References Cited

OTHER PUBLICATIONS

Schecter et al., "Palpation of Intra-cardiac Blood Flow, Pressure, Contact Force and Motor Reaction Time of Subjects Using a Novel Haptic Feedback System", Poster Contributions, JACC vol. 65, Issue 10S, Mar. 17, 2015.
Schecter et al., "Tactile Feedback Provides Real Time in Vivo TissuE:Catheter Contact Force Information During Cardiac Radiofrequency Ablation" —Abstract, Journal of Cardiovascular Electrophysiology, vol. 27, No. 5, p. 649, May 2016.
Stevenson, "Irrigated RF ablation: Power titration and fluid management for optimal safety and efficacy," Biosense Webster, Inc., 4 pages, 2005.
Tokmakoff et al, "Thermal Diffusivity Measurements of Natural and Isotopically Enriched Diamond by Picosecond Infrared Transient Grating Experiments," Appl. Phys., A56, pp. 87-90 (1993).
Tungjitkusolmun et al., "Finite element analyses of uniform current density electrodes for radio-frequency cardiac ablation," in IEEE Transactions on Biomedical Engineering, vol. 47, No. 1, pp. 32-40, Jan. 2000.
Tungjitkusolmun et al., "Three-dimensional finite-element analyses for radio-frequency hepatic tumor ablation," in IEEE Transactions on Biomedical Engineering, vol. 49, No. 1, pp. 3-9, Jan. 2002.
Vandekerckhove et al., "Flutter Ablation with an Irrigated Catheter Using Microwave Radiometry Sensing Technology: first report in men" (datE:Jan. 1, 2011).
Wang et al., "Microwave Radiometric Thermometry and its Potential Applicability to Ablative Therapy," Journal of Interventional Cardiac Electrophysiology, vol. 4, pp. 295-300, Apr. 2000.
Wang et al., "Tissue Dielectric Measurement Using an Interstitial Dipole Antenna," IEEE Trans Biomed. Eng., vol. 59, No. 1, 115-121, Jan. 2012.
Yazdandoost et al., "Theoretical study of the power distributions for interstitial microwave hyperthermia," Proceedings of the 2002 WSEAS International Conferences, Cadiz, Spain, pp. 1021-1025, Jun. 12-16, 2002.
Supplementary European Search Report dated Oct. 10, 2019 for corresponding European Application No. EP 17 76 7316; 6 pages.
China National Intellectual Property Administration, Notice on the Second Office Action and Search Report for corresponding Application No. 201780027973.6, dated Aug. 25, 2021, 37 pages.

\* cited by examiner

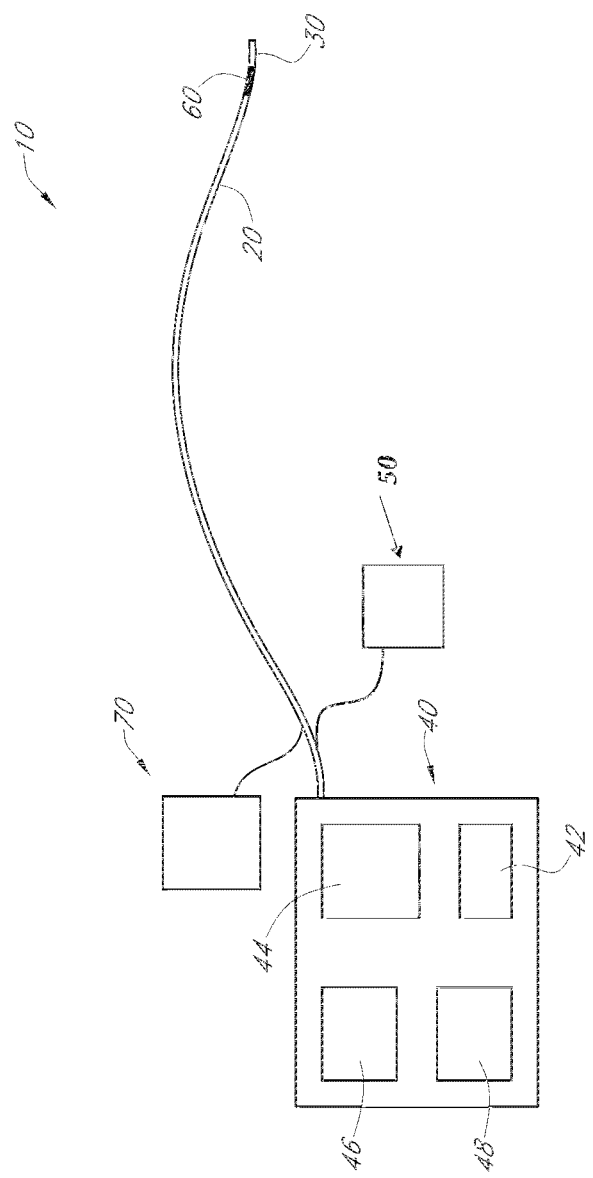

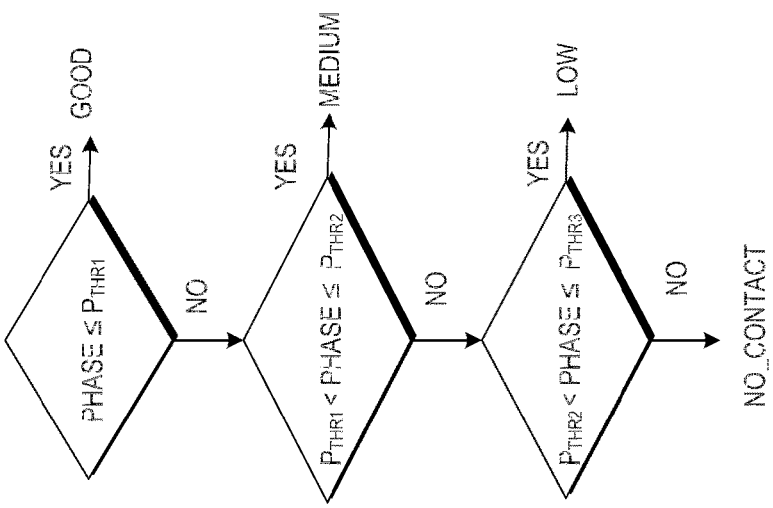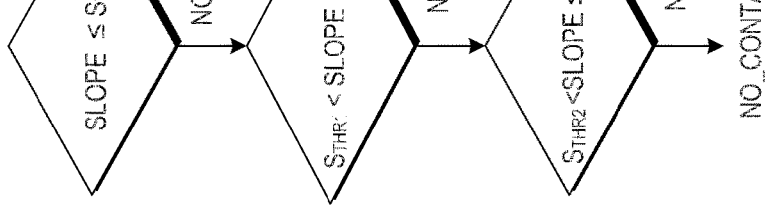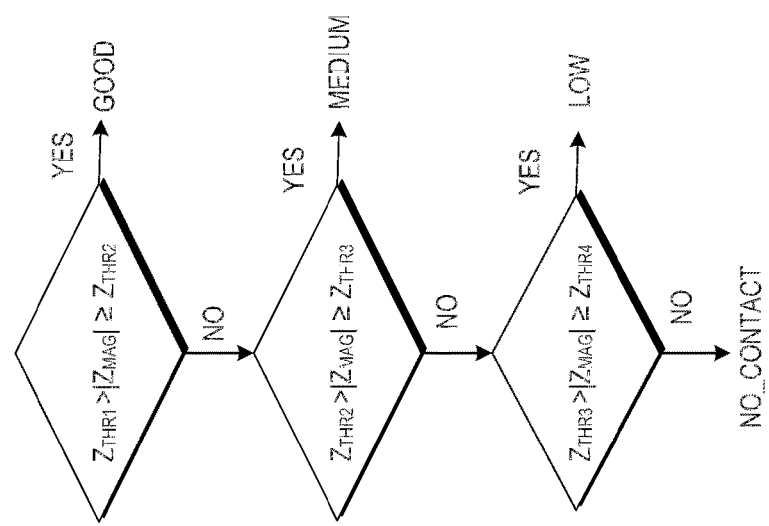
FIG. 32A

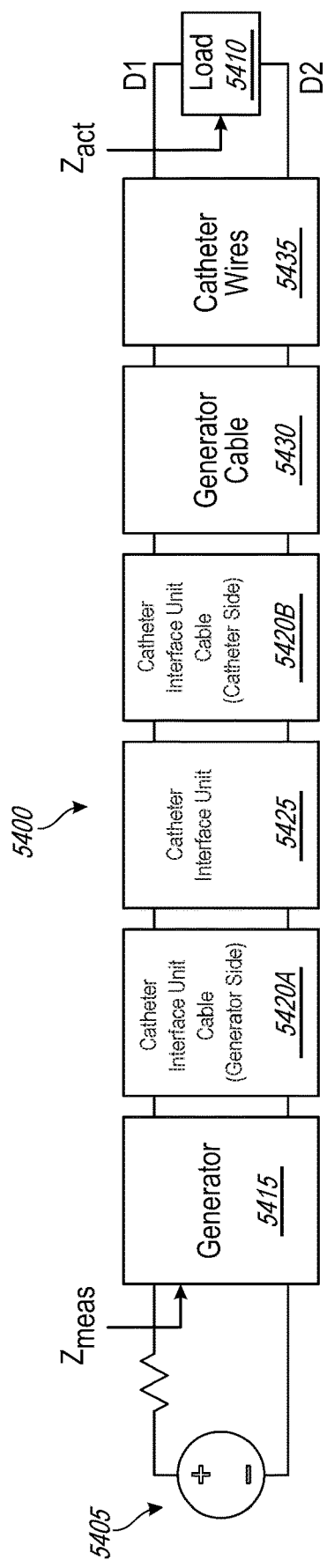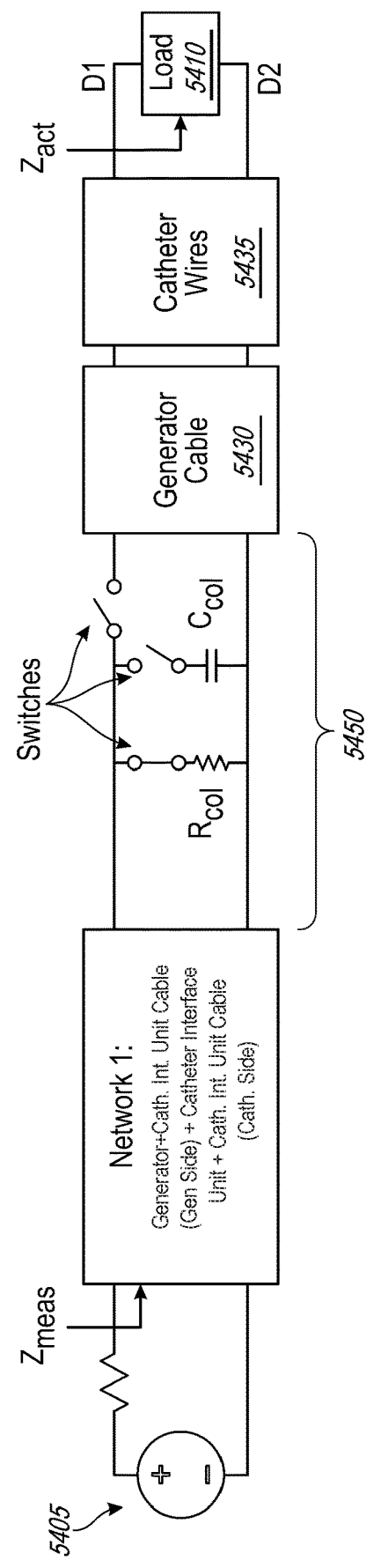
FIG. 34A
FIG. 34B

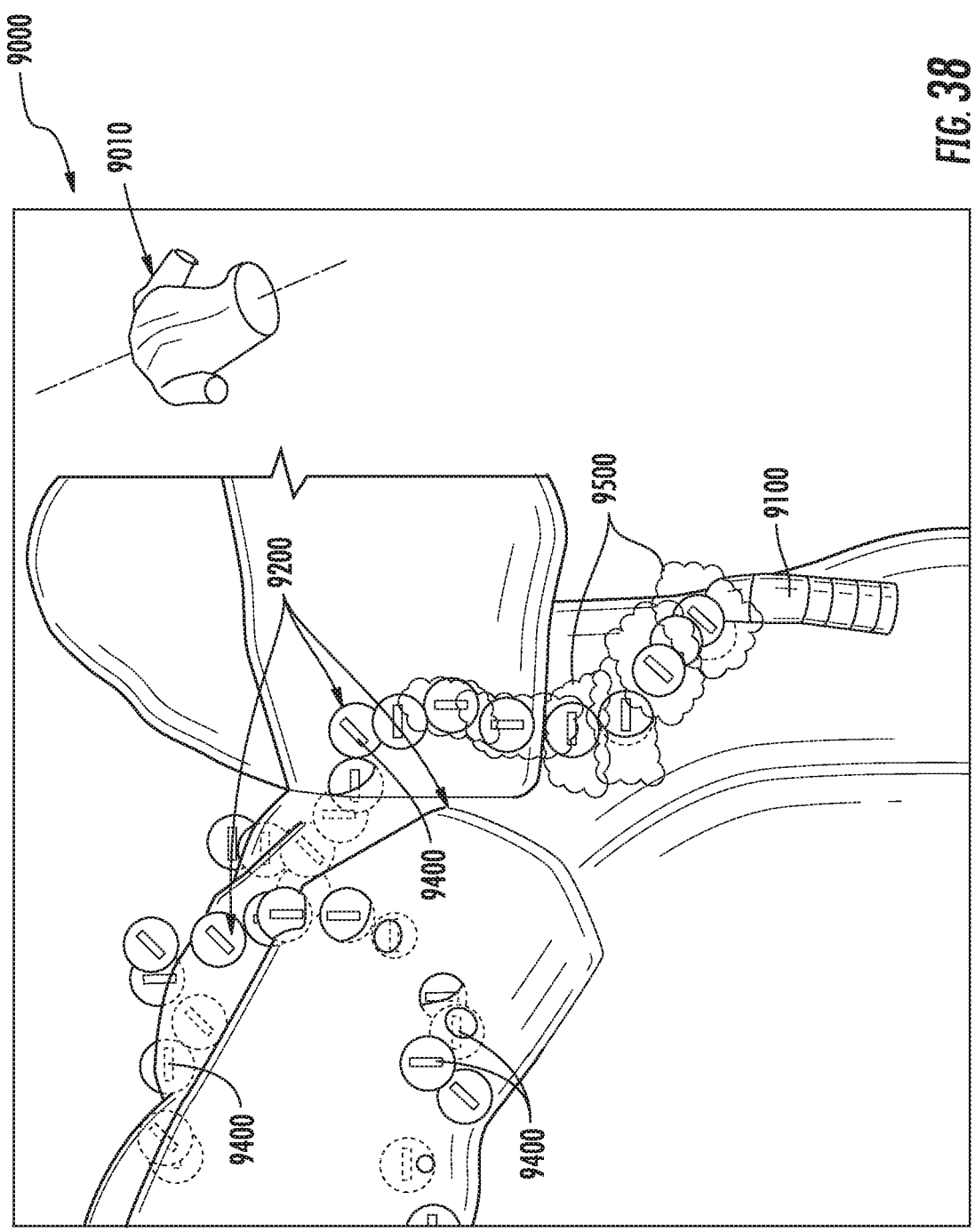

METHODS OF DETERMINING CATHETER ORIENTATION

INCORPORATION BY REFERENCE TO ANY PRIORITY APPLICATIONS

This application is a continuation of U.S. patent application Ser. No. 15/782,714, filed Oct. 12, 2017, now U.S. Pat. No. 9,993,178 issued Jun. 12, 2018, which is a continuation of International PCT Application No. PCT/US2017/022264, filed Mar. 14, 2017, which claims priority to U.S. Provisional Application No. 62/308,461, filed Mar. 15, 2016, to U.S. Provisional Application No. 62/315,661, filed Mar. 30, 2016, to U.S. Provisional Application No. 62/323,502, filed Apr. 15, 2016, and to U.S. Provisional Application No. 62/418,057, filed Nov. 4, 2016, the entire contents of each of which are incorporated herein by reference in their entirety.

BACKGROUND

Tissue ablation may be used to treat a variety of clinical disorders. For example, tissue ablation may be used to treat cardiac arrhythmias by at least partially destroying (e.g., at least partially or completely ablating, interrupting, inhibiting, terminating conduction of, otherwise affecting, etc.) aberrant pathways that would otherwise conduct abnormal electrical signals to the heart muscle. Several ablation techniques have been developed, including cryoablation, microwave ablation, radio frequency (RF) ablation, and high frequency ultrasound ablation. For cardiac applications, such techniques are typically performed by a clinician who introduces a catheter having an ablative tip to the endocardium via the venous vasculature, positions the ablative tip adjacent to what the clinician believes to be an appropriate region of the endocardium based on tactile feedback, mapping electrocardiogram (ECG) signals, anatomy, and/or fluoroscopic imaging, actuates flow of an irrigant to cool the surface of the selected region, and then actuates the ablative tip for a period of time and at a power believed sufficient to destroy tissue in the selected region. In ablation procedures involving radiofrequency energy delivery using one or more electrodes, the clinician strives to establish stable and uniform contact between the electrode(s) and the tissue to be ablated.

Successful electrophysiology procedures require precise knowledge about the anatomic substrate. Additionally, ablation procedures may be evaluated within a short period of time after their completion. Cardiac ablation catheters typically carry only regular mapping electrodes. Cardiac ablation catheters may incorporate high-resolution mapping electrodes. Such high-resolution mapping electrodes provide more accurate and more detailed information about the anatomic substrate and about the outcome of ablation procedures. High-resolution mapping electrodes can allow the electrophysiology to evaluate precisely the morphology of electrograms, their amplitude and width and to determine changes in pacing thresholds. Morphology, amplitude and pacing threshold are accepted and reliable electrophysiology (EP) markers that provide useful information about the outcome of ablation.

SUMMARY

According to some embodiments, an ablation device comprises an elongate body comprising a distal end, an electrode positioned at the distal end of the elongate body, at least one thermal shunt member placing a heat absorption element in thermal communication with the electrode to selectively remove heat from at least one of the electrode and tissue being treated by the electrode when the electrode is activated, wherein the at least one thermal shunt member extends through an interior of the electrode to dissipate and remove heat from the electrode during use, and wherein the at least one thermal shunt member comprises at least one layer or coating such that the at least one thermal shunt member does not extend to an exterior of the elongate body, and at least one fluid conduit extending at least partially through an interior of the elongate body and at least partially through an interior of the at least one thermal shunt member, wherein the at least one thermal shunt member is in thermal communication with the at least one fluid conduit, the at least one fluid conduit being configured to place the electrode in fluid communication with a fluid source to selectively remove heat from the electrode or tissue.

According to some embodiments, the at least one thermal shunt member comprises a thermal diffusivity greater than 1.5 $cm^2/sec$, wherein the electrode comprises a composite electrode, wherein the composite electrode comprises a first electrode portion and at least a second electrode portion, wherein an electrically insulating gap is located between the first electrode portion and the at least a second electrode portion to facilitate high-resolution mapping along a targeted anatomical area, and wherein the at least one fluid conduit comprises at least one opening.

According to some embodiments, an ablation device comprises an elongate body (e.g., catheter, other medical instrument, etc.) comprising a distal end, an ablation member positioned at the distal end of the elongate body, at least one thermal shunt member placing a heat shunting element in thermal communication with the ablation member to selectively remove heat from at least a portion of the ablation member or tissue being treated by the ablation member when the ablation member is activated, wherein the heat shunting element of the at least one thermal shunt extends at least partially through an interior of the ablation member to help remove and dissipate heat generated by the ablation member during use, at least one layer or coating positioned at least partially along an outer surface of the at least one thermal shunt member, and at least one fluid conduit extending at least partially through an interior of the elongate body, wherein the at least one thermal shunt member is in thermal communication with the at least one fluid conduit.

According to some embodiments, the at least one layer or coating is electrically insulative, the at least one fluid conduit extends at least partially through an interior of the at least one thermal shunt member; wherein the at least one fluid conduit comprises at least one opening, and wherein the at least one thermal shunt member comprises a thermal diffusivity greater than 1.5 $cm^2/sec$.

According to some embodiments, a method of heat removal from an ablation member during a tissue treatment procedure comprises activating an ablation system, the system comprising an elongate body comprising a distal end, an ablation member positioned at the distal end of the elongate body, wherein the elongate body of the ablation system comprises at least one thermal shunt member along its distal end, wherein the at least one thermal shunt member extends at least partially through an interior of the ablation member, wherein at least one layer or coating is positioned at least partially along an outer surface of the at least one thermal shunt member, at least partially removing heat generated by the ablation member along the distal end of the elongate body via the at least one thermal shunt member so as to reduce the likelihood of localized hot spots along the distal end of the elongate body, wherein the elongate body further comprises at least one fluid conduit or passage extending at least partially through an interior of the elongate body, and delivering fluid through the at least one fluid conduit or passage to selectively remove heat away from the ablation member when the ablation member is activated.

According to some embodiments, the at least one layer or coating is electrically insulative. In some embodiments, the at least one layer or coating comprises an electrical resistivity of greater than 1000 Ωcm at 20° C. In some embodiments, the at least one layer or coating is thermally insulative. In some embodiments, the at least one layer or coating comprises a thermal conductivity of less than 0.001 W/(cm K) at 20° C. In some arrangements, the at least one layer or coating comprises a polymeric material (e.g., thermoset polymers, polyimide, PEEK, polyester, polyethylene, polyurethane, pebax, nylon, hydratable polymers and/or the like). In some embodiments, the at least one layer or coating comprises a thickness between 1 and 50 µm. In some embodiments, the at least one layer or coating comprises a thickness less than 100 µm. In some arrangements, the at least one layer or coating comprises a single layer or coating. In other embodiments, the at least one layer or coating comprises more than one layer or coating. In some embodiments, the at least one layer or coating is directly positioned along a surface of the at least one shunt member. In some embodiments, the at least one layer or coating is not directly positioned along a surface of the at least one shunt member. In some embodiments, at least one intermediate member or structure is positioned between the at least one shunt member and the at least one layer or coating. In some embodiments, the at least one layer or coating is secured to the at least one heat shunt member using an adhesive. In some embodiments, the at least one layer or coating is secured to the at least one heat shunt member using a press fit connection, dip molding or other molding technology.

According to some embodiments, the at least one thermal shunt member comprises a thermal diffusivity greater than 1.5 cm$^2$/sec. In some embodiments, the at least one thermal shunt member comprises a diamond (e.g., an industrial diamond). In some embodiments, the at least one thermal shunt member comprises Graphene or another carbon-based material.

According to some embodiments, the electrode comprises a composite electrode, wherein the composite electrode comprises a first electrode portion and at least a second electrode portion, wherein an electrically insulating gap is located between the first electrode portion and the at least a second electrode portion. In some embodiments, the at least one fluid conduit is in direct thermal communication with the at least one thermal shunt member. In some embodiments, the at least one fluid conduit is in indirect thermal communication with the at least one thermal shunt member. In some arrangements, the at least one fluid conduit comprises at least one opening, wherein the at least one opening places irrigation fluid passing through the at least one fluid conduit in direct physical contact with at least a portion of the at least one thermal shunt member.

According to some embodiments, a mapping system configured to process data related to a targeted anatomical location being treated comprises at least one processor, wherein the processor is configured to, upon execution of specific instructions stored on a computer-readable medium, receive and process mapping data of the targeted anatomical location and to create a three-dimensional model of the targeted anatomical location, and at least one output device for displaying the three-dimensional model of the targeted anatomical location to a user, wherein the processor is configured to be operatively coupled to at least one component of a separate ablation system, wherein the separate ablation system is configured to selectively ablate at least a portion of the targeted anatomical location, the separate ablation system comprising at least one electrode positioned along a distal end of a catheter, the at least one processor being configured to receive ablation data from the separate ablation system, wherein the ablation data relate to at least one ablation performed along a tissue of the targeted anatomical location, wherein the mapping system is configured to determine a real-time location of the at least one electrode relative to the three-dimensional model of the targeted anatomical location to assist a user in ablating the tissue of the targeted anatomical location, and wherein the at least one processor is configured to generate a representation on the at least one output device, the representation comprising the three-dimensional model of the targeted anatomical location, the real-time location of the at least one electrode and at least a portion of the ablation data received from the separate ablation system.

According to some embodiments, a mapping system configured to process data related to a targeted anatomical location being treated comprises at least one processor, wherein the processor is configured to, upon execution of specific instructions stored on a computer-readable medium, receive and process mapping data of the targeted anatomical location and to create a three-dimensional model of the targeted anatomical location, wherein the at least one processor is configured to be operatively coupled to at least one output device for displaying the three-dimensional model of the targeted anatomical location to a user, wherein the processor is configured to be operatively coupled to at least one component of a separate ablation system, wherein the separate ablation system is configured to selectively ablate at least a portion of the targeted anatomical location, the separate ablation system comprising at least one electrode positioned along a distal end of a catheter, the at least one processor being configured to receive ablation data from the separate ablation system, wherein the ablation data relate to at least one ablation performed along a tissue of the targeted anatomical location, wherein the mapping system is configured to determine a real-time location of the at least one electrode relative to the three-dimensional model of the targeted anatomical location to assist a user in ablating the tissue of the targeted anatomical location, and wherein the at least one processor is configured to generate a representation on the at least one output device, the representation comprising the three-dimensional model of the targeted anatomical location, the real-time location of the at least one electrode and at least a portion of the ablation data received from the separate ablation system.

According to some embodiments, the separate ablation system is integrated into a single system with the mapping system. In some embodiments, the at least one processor of the mapping system is configured to be operatively coupled to at least one separate mapping system, wherein the at least one separate mapping system is configured to obtain and process EGM or other electrical activity data of the targeted anatomical location. In one embodiment, the at least one separate mapping system comprises multiple mapping electrodes. In some embodiments, the at least one separate mapping system is integrated with the mapping system.

According to some embodiments, a system of any of the preceding claims, wherein the ablation data comprises one or more of the following: electrode orientation, temperature data related to tissue being treated, temperature data of one or more sensors included within the system, qualitative or quantitative contact information, impedance information, a length or a width of a lesion created by the ablation system, a volume of a lesion created by the ablation system, a subject's heart rate data, a subject's blood pressure data, and the like.

According to some embodiments, the representation on the at least one output device further comprises EGM data, rotor map data and/or other electrical activity data. In some embodiments, the EGM data, rotor map data and/or other electrical activity data is received by the at least one processor via a separate mapping system that is operatively coupled to the mapping system.

According to some embodiments, the data in the representation on the at least one output device is provided textually and/or graphically. In some embodiments, at least a portion of the ablation data is displayed on the at least one output device along or near a corresponding ablation location.

According to some embodiments, at least a portion of the ablation data is configured to be intermittently displayed on the representation of the at least one output device. In some embodiments, at least a portion of the ablation data is displayed on the representation of the at least one output device when selected by a user. In some embodiments, at least a portion of the ablation data is configured to be displayed on the representation by using a selection device to select a specific treatment location. In one embodiment, the selection device comprises a mouse, a touchpad, a dial or another type of manipulatable controller. In several arrangements, the selection device comprises a touchscreen, wherein the user is able to make a selection on the touchscreen using his or her finger.

According to some embodiments, the system further comprises the ablation system (e.g., an ablation system comprising a catheter with at least one distal electrode or other energy delivery member, a generator and/or the like). In some embodiments, the ablation system comprises a radiofrequency ablation system.

According to some embodiments, the processor is part of the mapping system. In some embodiments, the processor is not part of the mapping system, but is operatively coupled to the mapping system. In some embodiments, the processor is part of the separate ablation system. In one embodiment, the processor is part of a stand-alone interface unit that is coupled to the mapping system.

According to some embodiments, a method of integrating data from an ablation device with mapping data comprises generating a three-dimensional map of a targeted anatomical location using a mapping system, receiving ablation data from an ablation system, and displaying the three-dimensional map and at least a portion of the ablation data on a single output device (e.g., monitor, screen, etc.).

According to some embodiments, the mapping system comprises an electroanatomical navigation system. In some embodiments, the mapping system and the ablation system are integrated into a single system. In other embodiments, the mapping system and the ablation system are separate from each other. In some embodiments, the method additionally comprises receiving electrical activity data from a second mapping system. In some embodiments, the electrical activity data comprise EGM activity data, rotor mapping data and/or any other electrical data.

According to some embodiments, the ablation data comprises one or more of the following: electrode orientation, temperature data related to tissue being treated, temperature data of one or more sensors included within the system, qualitative or quantitative contact information, impedance information, a length or a width of a lesion created by the ablation system, a volume of a lesion created by the ablation system, a subject's heart rate data, a subject's blood pressure data, and the like.

According to some embodiments, the ablation data is provided textually and/or graphically on the output device. In some embodiments, at least a portion of the ablation data is displayed on the output device along or near a corresponding ablation location. In some embodiments, at least a portion of the ablation data is configured to be intermittently displayed on the output device.

According to some embodiments, at least a portion of the ablation data is displayed on the output device when selected by a user. In some embodiments, at least a portion of the ablation data is configured to be displayed by using a selection device to select a specific treatment location. In several arrangements, the selection device comprises a mouse, a touchpad, a dial or another type of manipulatable controller. In some embodiments, the selection device comprises a touchscreen, wherein the user is able to make a selection on the touchscreen using his or her finger.

According to some embodiments, the method further comprises alerting a user of potential gaps along a targeted anatomical location. In one embodiment, alerting a user comprises highlighting gaps on the output device.

According to some embodiments, a device for ablation and high-resolution of cardiac tissue comprises an elongate body (e.g., catheter, other medical instrument, etc.) comprising a distal end and an electrode assembly positioned along the distal end of the elongate body, wherein the electrode assembly comprises a first electrode portion, at least a second electrode portion positioned adjacent the first electrode portion, the first electrode portion and the second electrode portion being configured to contact tissue of a subject and deliver radiofrequency energy sufficient to at least partially ablate the tissue, at least one electrically insulating gap positioned between the first electrode portion and the second electrode portion, the at least one electrically insulating gap comprising a gap width separating the first and second electrode portions, and at least one separator positioned within the at least one electrically insulating gap, wherein the at least one separator contacts a proximal end of the first electrode portion and the distal end of the second electrode portion. The device additionally comprises at least one conductor configured to electrically couple an energy delivery module to at least one of the first and second electrode portions, wherein the at least one conductor is electrically coupled to an energy delivery module and wherein a frequency of energy provided to the first and second electrodes is in the radiofrequency range.

According to some embodiments, the device further comprises a filtering element electrically coupling the first electrode portion to the second electrode portion and configured to present a low impedance (e.g., effectively shorting the two electrode portions) at a frequency used for delivering ablative energy via the first and second electrode portions, wherein the filtering element comprises a capacitor, wherein the capacitor comprises a capacitance of 50 to 300 nF (e.g., 100 nF, 50-100, 100-150, 150-200, 200-250, 250-300 nF, values between the foregoing ranges, etc.), wherein the elongate body comprises at least one irrigation passage, said at least one irrigation passage extending to the first electrode portion, wherein the first electrode portion comprises at least one outlet port in fluid communication with the at least one irrigation passage, wherein the gap width is approximately 0.2 to 1.0 mm (e.g., 0.2, 0.2-0.3, 0.3-0.4, 0.4-0.5, 0.5-0.6, 0.6-0.7, 0.7-0.8, 0.8-0.9, 0.9-1.0 mm, values between the foregoing ranges, less than 0.2 mm, greater than 1 mm, etc.), wherein a series impedance of lower than about 3 ohms ($\Omega$) (e.g., 0-1, 1-2, 2-3 ohms, values between the foregoing ranges, etc.) is introduced across the first and second electrode portions in the operating RF frequency range, and wherein the operating RF frequency range is 200 kHz to 10 MHz (e.g., 200-300, 300-400, 400-500, 500-600, 600-700, 700-800, 800-900, 900-1000 kHz, up to 10 MHz or higher frequencies between the foregoing ranges, etc.). Electrode portions or sections can be used interchangeably with electrodes herein.

According to some embodiments, the device further comprises a first plurality of temperature-measurement devices positioned within separate apertures formed in a distal end of the electrode assembly, the first plurality of temperature-measurement devices (e.g., thermocouples, other temperature sensors, etc.) being thermally insulated from the electrode assembly, and a second plurality of temperature-measurement devices (e.g., thermocouples, other temperature sensors, etc.) positioned within separate apertures located in relation to the proximal end of the electrode assembly, the second plurality of temperature-measurement devices being thermally insulated from the electrode assembly, wherein temperature measurements determined from the first plurality of temperature-measurement devices and the second plurality of temperature-measurement devices facilitate determination of orientation of the electrode assembly with respect to tissue being treated, and at least one thermal shunt member placing a heat absorption element in thermal communication with the electrode assembly to selectively remove heat from at least one of the electrode assembly and tissue being treated by the electrode assembly when the electrode assembly is activated, a contact sensing subsystem comprising a signal source configured to deliver a range of frequencies to the electrode assembly, and a processing device configured to obtain impedance measurements while different frequencies within the range of frequencies are being applied to the electrode assembly by the signal source, process the impedance measurements obtained at the different frequencies, and determine whether the electrode assembly is in contact with tissue based on said processing of the impedance measurements, wherein the elongate body comprises at least one irrigation passage, said at least one irrigation passage extending to the first electrode portion.

According to some embodiments, the device further comprises a first plurality of temperature-measurement devices (e.g., thermocouples, other temperature sensors, etc.) positioned within separate apertures formed in a distal end of the electrode assembly, the first plurality of temperature-measurement devices being thermally insulated from the electrode assembly, and a second plurality of temperature-measurement devices (e.g., thermocouples, other temperature sensors, etc.) positioned within separate apertures located in relation to the proximal end of the electrode assembly, the second plurality of temperature-measurement devices being thermally insulated from the electrode assembly, wherein temperature measurements determined from the first plurality of temperature-measurement devices and the second plurality of temperature-measurement devices facilitate determination of orientation of the electrode assembly with respect to tissue being treated.

According to some embodiments, the device further comprises at least one thermal shunt member placing a heat absorption element in thermal communication with the electrode assembly to selectively remove heat from at least one of the electrode assembly and tissue being treated by the electrode assembly when the electrode assembly is activated.

According to some embodiments, the device further comprises a contact sensing subsystem comprising a signal source configured to deliver a range of frequencies to the electrode assembly, and a processing device configured to obtain impedance measurements while different frequencies within the range of frequencies are being applied to the electrode assembly by the signal source, process the impedance measurements obtained at the different frequencies, and determine whether the electrode assembly is in contact with tissue based on said processing of the impedance measurements.

According to some embodiments, the filtering element comprises a capacitor. In some embodiments, the capacitor comprises a capacitance of 50 to 300 nF (e.g., 100 nF, 50-100, 100-150, 150-200, 200-250, 250-300 nF, values between the foregoing ranges, etc.).

According to some embodiments, the at least one thermal shunt member is in thermal communication with at least one fluid conduit (e.g., internal passageway) extending at least partially through an interior of the elongate body, the at least one fluid conduit being configured to place the electrode in fluid communication with a fluid source to selectively remove heat from the electrode assembly and/or tissue of a subject located adjacent the electrode assembly.

According to some embodiments, the at least one thermal shunt member comprises a thermal diffusivity greater than 1.5 cm$^2$/sec. In some embodiments, the at least one thermal shunt member comprises diamond (e.g., industrial-grade diamond).

According to some embodiments, the second plurality of temperature-measurement devices is positioned along a plane that is substantially perpendicular to a longitudinal axis of the distal end of the elongate body and spaced proximal to the first plurality of temperature-measurement devices. In some embodiments, each of the temperature-measurement devices comprises a thermocouple, a thermistor and/or any other type of temperature sensor or temperature measuring device or component. In some embodiments, the first plurality of temperature-measurement devices comprises at least three (e.g., 3, 4, 5, 6, more than 6, etc.) temperature sensors, and wherein the second plurality of temperature-measurement devices comprises at least three (e.g., 3, 4, 5, 6, more than 6, etc.) temperature sensors.

According to some embodiments, the device further comprises a means for facilitating high-resolution mapping. In some embodiments, electrically separating the first and second electrode portions facilitates high-resolution mapping along a targeted anatomical area. In some embodiments, the device further comprises at least one separator positioned within the at least one electrically insulating gap. In one embodiment, the at least one separator contacts a proximal end of the first electrode and the distal end of the second electrode portion.

According to some embodiments, the device further comprises at least one conductor configured to electrically couple an energy delivery module to at least one of the first and second electrodes. In some embodiments, the at least one conductor is electrically coupled to an energy delivery module.

According to some embodiments, a frequency of energy provided to the first and second electrodes is in the radiofrequency range. In some embodiments, a series impedance introduced across the first and second electrodes is lower than: (i) an impedance of a conductor that electrically couples the electrodes to an energy delivery module, and (ii) an impedance of a tissue being treated. In some embodiments, the gap width is approximately 0.2 to 1.0 mm (e.g., 0.5 mm, 0.2-0.3, 0.3-0.4, 0.4-0.5, 0.5-0.6, 0.6-0.7, 0.7-0.8, 0.8-0.9, 0.9-1.0 mm, values between the foregoing ranges, less than 0.2 mm, greater than 1 mm, etc.). In some embodiments, the elongate body (e.g., catheter) comprises at least one irrigation passage, said at least one irrigation passage extending to the first electrode.

According to some embodiments, the at least a second electrode comprises a second electrode and a third electrode portion, the second electrode portion positioned axially between the first and third electrode portions, wherein an electrically insulating gap separates the second and third electrode portions. In some embodiments, gaps are included between the first and second electrode portions and between the second and third electrode portions to increase a ratio of mapped tissue surface to ablated tissue surface. In some embodiments, the ratio is between 0.2 and 0.8 (e.g., 0.2-0.3, 0.3-0.4, 0.4-0.5, 0.5-0.6, 0.6-0.7, 0.7-0.8, ratios between the foregoing, etc.). In some embodiments, the device further comprises a separator positioned within the gap between the second and third electrode portions.

According to some embodiments, a device for mapping and ablating tissue comprises an elongate body (e.g., a catheter, other medical instrument, etc.) including a proximal end and a distal end, a first electrode (or electrode portion or section) positioned on the elongate body, at least a second electrode (or electrode portion or section) positioned adjacent the first electrode, the first electrode (or electrode portion or section) and the second electrode (or electrode portion or section) being configured to contact tissue of a subject and deliver radiofrequency energy sufficient to at least partially ablate the tissue, at least one electrically insulating gap positioned between the first electrode (or electrode portion or section) and the second electrode (or electrode portion or section), the at least one electrically insulating gap comprising a gap width separating the first and second electrodes (or electrode portions or sections), and a filtering element electrically coupling the first electrode (or electrode portion or section) to the second electrode (or electrode portion or section) and configured to present a low impedance (e.g., effectively shorting the two electrodes, portions or sections) at a frequency used for delivering ablative energy via the first and second electrodes (or electrode portions or sections).

According to some embodiments, the device further comprises a means for facilitating high-resolution mapping. In some embodiments, electrically separating the first and second electrodes (or electrode portions or sections) facilitates high-resolution mapping along a targeted anatomical area (e.g., cardiac tissue). In some embodiments, the device further comprises at least one separator positioned within the at least one electrically insulating gap. In one embodiment, the at least one separator contacts a proximal end of the first electrode (or electrode portion or section) and the distal end of the second electrode (or electrode portion or section). In some embodiments, the device further comprises at least one conductor configured to electrically couple an energy delivery module to at least one of the first and second electrodes (or electrode portions or sections). In some embodiments, the at least one conductor is electrically coupled to an energy delivery module.

According to some embodiments, a frequency of energy provided to the first and second electrodes is in the radiofrequency range. In some embodiments, the filtering element comprises a capacitor. In some embodiments, the capacitor comprises a capacitance of 50 to 300 nF (e.g., 100 nF, 50-100, 100-150, 150-200, 200-250, 250-300 nF, values between the foregoing ranges, etc.). In some embodiments, the capacitor comprises a capacitance of 100 nF. In some embodiments, a series impedance of lower than about 3 ohms ($\Omega$) (e.g., 0-1, 1-2, 2-3 ohms, values between the foregoing ranges, etc.) is introduced across the first and second electrodes in the operating RF frequency range. In some embodiments, the operating RF frequency range is 200 kHz to 10 MHz (e.g., 200-300, 300-400, 400-500, 500-600, 600-700, 700-800, 800-900, 900-1000 kHz, up to 10 MHz or higher frequencies between the foregoing ranges, etc.).

According to some embodiments, a series impedance introduced across the first and second electrodes is lower than: (i) an impedance of a conductor that electrically couples the electrodes to an energy delivery module, and (ii) an impedance of a tissue being treated. In some embodiments, the gap width is approximately 0.2 to 1.0 mm (e.g., 0.2, 0.2-0.3, 0.3-0.4, 0.4-0.5, 0.5-0.6, 0.6-0.7, 0.7-0.8, 0.8-0.9, 0.9-1.0 mm, values between the foregoing ranges, less than 0.2 mm, greater than 1 mm, etc.). In some embodiments, the gap width is 0.5 mm.

According to some embodiments, the elongate body comprises at least one irrigation passage, the at least one irrigation passage extending to the first electrode. In some embodiments, the first electrode (or electrode portion or section) comprises at least one outlet port in fluid communication with the at least one irrigation passage.

According to some embodiments, the at least a second electrode (or electrode portion or section) comprises a second electrode (or electrode portion or section) and a third electrode (or electrode portion or section), the second electrode (or electrode portion or section) being positioned axially between the first and third electrodes (or electrode portions or sections), wherein an electrically insulating gap separates the second and third electrodes (or electrode portions or sections). In some embodiments, gaps are included between the first and second electrodes (or electrode portions or sections) and between the second and third electrodes (or electrode portions or sections) to increase a ratio of mapped tissue surface to ablated tissue surface. In some embodiments, the ratio is between 0.2 and 0.8 (e.g., 0.2-0.3, 0.3-0.4, 0.4-0.5, 0.5-0.6, 0.6-0.7, 0.7-0.8, ratios between the foregoing, etc.). In some embodiments, the device further comprising a separator positioned within the gap between the second and third electrodes (or electrode portions or sections).

According to some embodiments, an ablation device comprises a first electrode (or electrode portion or section) positioned at a distal end of a catheter, at least a second electrode (or electrode portion or section) positioned at a location proximal to the first electrode (or electrode portion or section), the first electrode (or electrode portion or section) and the second electrode (or electrode portion or section) being configured to contact tissue (e.g., cardiac tissue, other targeted anatomical tissue, etc.) of a subject and deliver energy sufficient to at least partially ablate the tissue, an electrically insulating gap positioned between the first electrode (or electrode portion or section) and the second electrode (or electrode portion or section), the electrically insulating gap comprising a gap width separating the first and second electrodes (or electrode portions or sections), and a filtering element electrically coupling the first electrode (or electrode portion or section) to the second electrode (or electrode portion or section).

According to some embodiments, electrically separating the first and second electrodes (or electrode portions or sections) facilitates high-resolution mapping along a targeted anatomical area. In some embodiments, the device further comprises at least one separator positioned within the at least one electrically insulating gap. In several embodiments, the at least one separator contacts a proximal end of the first electrode (or electrode portion or section) and the distal end of the second electrode (or electrode portion or section).

According to some embodiments, the device additionally comprises at least one conductor configured to energize at least one of the first and second electrodes (or electrode portions or sections). In one embodiment, the at least one conductor is electrically coupled to an energy delivery module (e.g., a RF generator).

According to some embodiments, the device further comprises means for connectivity to an electrophysiology recorder. In some embodiments, the device is configured to connect to an electrophysiology recorder.

According to some embodiments, a frequency of energy provided to the first and second electrodes is in the radiofrequency (RF) range. In some embodiments, the operating RF frequency range is 200 kHz to 10 MHz (e.g., 200-300, 300-400, 400-500, 500-600, 600-700, 700-800, 800-900, 900-1000 kHz, up to 10 MHz or higher frequencies between the foregoing ranges, etc.). In some embodiments, the filtering element comprises a capacitor. In some embodiments, the capacitor comprises a capacitance of 50 to 300 nF (e.g., 100 nF, 50-100, 100-150, 150-200, 200-250, 250-300 nF, values between the foregoing ranges, etc.). In some embodiments, a series impedance of less than 3 ohms ($\Omega$) (e.g., 0-1, 1-2, 2-3 ohms, values between the foregoing ranges, etc.) is introduced across the first and second electrodes (or electrode portions or sections) at 500 kHz.

According to some embodiments, a series impedance introduced across the first and second electrodes is lower than: (i) an impedance of a conductor that electrically couples the electrodes to an energy delivery module, and (ii) an impedance of a tissue being treated. In some embodiments, the gap width is approximately 0.2 to 1.0 mm (e.g., 0.2, 0.2-0.3, 0.3-0.4, 0.4-0.5, 0.5-0.6, 0.6-0.7, 0.7-0.8, 0.8-0.9, 0.9-1.0 mm, values between the foregoing ranges, less than 0.2 mm, greater than 1 mm, etc.). In one embodiment, the gap width is 0.5 mm.

According to some embodiments, the at least a second electrode (or electrode portion or section) comprises a second electrode (or electrode portion or section) and a third electrode (or electrode portion or section), the second electrode (or electrode portion or section) being positioned axially between the first and third electrodes (or electrode portions or sections), wherein an electrically insulating gap separates the second and third electrodes (or electrode portions or sections). In some embodiments, a separator is positioned within the gap between the second and third electrodes (or electrode portions or sections). In some embodiments, gaps are included between the first and second electrodes (or electrode portions or sections) and between the second and third electrodes (or electrode portions or sections) to increase a ratio of mapped tissue surface to ablated tissue surface. In some embodiments, the ratio is between 0.2 and 0.8 (e.g., 0.2-0.3, 0.3-0.4, 0.4-0.5, 0.5-0.6, 0.6-0.7, 0.7-0.8, ratios between the foregoing, etc.).

According to some embodiments, the system further comprises means for connectivity to an electrophysiology recorder. In some embodiments, the system is configured to connect to an electrophysiology recorder. In some embodiments, the system comprises an ablation device, and at least one of (i) a generator for selectively energizing the device, and (ii) an electrophysiology recorder.

According to some embodiments, a method of delivering energy to an ablation device comprises energizing a split tip or split section electrode positioned on a catheter (or other medical instrument), the split tip or split section electrode comprising a first electrode and a second electrode (or electrode portions or sections), the first electrode and the second electrode being configured to contact tissue of a subject and deliver energy sufficient to at least partially ablate the tissue, wherein an electrically insulating gap is positioned between the first electrode and the second electrode, the electrically insulating gap comprising a gap width separating the first and second electrodes, wherein a filtering element electrically couples the first electrode to the second electrode, and wherein electrically separating the first and second electrodes facilitates high-resolution mapping along a targeted anatomical area.

According to some embodiments, the method additionally includes receiving high-resolution mapping data from the first and second electrodes (or electrode portions or sections), the high-resolution mapping data relating to tissue of a subject adjacent the first and second electrodes (or electrode portions or sections). In some embodiments, receiving high-resolution mapping data occurs prior to, during or after energizing a split tip electrode positioned on a catheter.

According to some embodiments, a method of mapping tissue of a subject includes receiving high-resolution mapping data using a composite tip electrode (e.g., split-tip or split-section electrode), said composite tip electrode comprising first and second electrodes or electrode portions located on a catheter and separated by an electrically insulating gap, wherein a filtering element electrically couples the first electrode to the second electrode in the operating RF range, and wherein electrically insulating the first and second electrodes facilitates high-resolution mapping along a targeted anatomical area.

According to some embodiments, the method additionally includes energizing at least one of the first and second electrodes to deliver energy sufficient to at least partially ablate the tissue of the subject. In some embodiments, the high-resolution mapping data relates to tissue of a subject adjacent the first and second electrodes. In some embodiments, receiving high-resolution mapping data occurs prior to, during or after energizing a split tip or a split section electrode positioned on a catheter.

According to some embodiments, a separator is positioned within the at least one electrically insulating gap. In some embodiments, the at least one separator contacts a proximal end of the first electrode and the distal end of the second electrode. In some embodiments, the first and second electrodes are selectively energized using at least one conductor electrically coupled to an energy delivery module. In some embodiments, the mapping data is provided to an electrophysiology recorder.

According to some embodiments, a frequency of energy provided to the first and second electrodes is in the radiofrequency (RF) range. In some embodiments, the filtering element comprises a capacitor.

In some embodiments, the operating RF frequency range is 200 kHz to 10 MHz (e.g., 200-300, 300-400, 400-500, 500-600, 400-600, 600-700, 700-800, 800-900, 900-1000 kHz, up to 10 MHz or higher frequencies between the foregoing ranges, etc.). In some embodiments, the filtering element comprises a capacitor. In some embodiments, the capacitor comprises a capacitance of 50 to 300 nF (e.g., 100 nF, 50-100, 100-150, 150-200, 200-250, 250-300 nF, values between the foregoing ranges, etc.). In some embodiments, a series impedance of less than 3 ohms (Ω) (e.g., 0-1, 1-2, 2-3 ohms, values between the foregoing ranges, etc.) is introduced across the first and second electrodes (or electrode portions or sections) at 500 kHz.

According to some embodiments, a series impedance introduced across the first and second electrodes is lower than: (i) an impedance of a conductor that electrically couples the electrodes to an energy delivery module, and (ii) an impedance of a tissue being treated. In some embodiments, the gap width is approximately 0.2 to 1.0 mm (e.g., 0.2, 0.2-0.3, 0.3-0.4, 0.4-0.5, 0.5-0.6, 0.6-0.7, 0.7-0.8, 0.8-0.9, 0.9-1.0 mm, values between the foregoing ranges, less than 0.2 mm, greater than 1 mm, etc.). In one embodiment, the gap width is 0.5 mm.

According to some embodiments, a kit for ablation and high-resolution mapping of cardiac tissue, comprising a device for high-resolution mapping, the device further being configured to provide ablative energy to targeted tissue, the device comprising an elongate body (e.g., catheter, other medical instrument, etc.) comprising a proximal end and a distal end, the elongate body comprising an electrode assembly, the electrode assembly comprising a first and second high-resolution portions, the first high-resolution electrode portion positioned on the elongate body, the second electrode portion being positioned adjacent the first electrode portion, the first and second electrode portions being configured to contact tissue of a subject, and at least one electrically insulating gap positioned between the first electrode portion and the second electrode portion, the at least one electrically insulating gap comprising a gap width separating the first and second electrode portions, wherein the first electrode portion is configured to electrically couple to the second electrode portion using a filtering element, wherein the filtering element is configured to present a low impedance at a frequency used for delivering ablative energy via the first and second electrode portions, and wherein the device is configured to be positioned within targeted tissue of the subject to obtain high-resolution mapping data related to said tissue when ablative energy is not delivered to the first and second electrode portions. The kit further comprises an energy delivery module configured to generate energy for delivery to the electrode assembly, and a processor configured to regulate the delivery of energy from the energy delivery module to the electrode assembly.

According to some embodiments, a kit for ablation and high-resolution mapping of cardiac tissue comprises an ablation device, an energy delivery module (e.g., a generator) configured to generate energy for delivery to the electrode assembly, and a processor configured to regulate the delivery of energy from the energy delivery module to the electrode assembly. In some embodiments, the energy delivery module comprises a RF generator. In some embodiments, the energy delivery module is configured to couple to the device.

According to some embodiments, a generator for selectively delivering energy to an ablation device comprises an energy delivery module configured to generate ablative energy for delivery to an ablation device, and a processor configured to regulate the delivery of energy from the energy delivery module to the ablation device.

According to some embodiments, an ablation device comprises an elongate body (e.g., catheter, other medical instrument, etc.) comprising a distal end, an electrode positioned at the distal end of the elongate body, and at least one thermal shunt member placing a heat absorption element in thermal communication with the electrode to selectively remove heat from at least one of the electrode and tissue being treated by the electrode when the electrode is activated, wherein the at least one thermal shunt member extends at least partially through an interior of the electrode to dissipate and remove heat from the electrode during use.

According to some embodiments, the at least one thermal shunt member is in thermal communication with at least one fluid conduit extending at least partially through an interior of the elongate body, the at least one fluid conduit being configured to place the electrode in fluid communication with a fluid source to selectively remove heat from the electrode and/or tissue of a subject located adjacent the electrode. In some embodiments, a fluid conduit or passage extends at least partially through an interior of the elongate body. In some embodiments, the fluid conduit or passage extends at least partially through the at least one thermal shunt member. In several configurations, the at least one thermal shunt member is at least partially in thermal communication with a thermally convective fluid. In some embodiments, a flow rate of the thermally convective fluid is less than 15 ml/min in order to maintain a desired temperature along the electrode during an ablation procedure. In some embodiments, a flow rate of the thermally convective fluid is approximately less than 10 ml/min in order to maintain a desired temperature along the electrode during an ablation procedure. In some embodiments, a flow rate of the thermally convective fluid is approximately less than 5 ml/min in order to maintain a desired temperature along the electrode during an ablation procedure. In some embodiments, the desired temperature along the electrode during an ablation procedure is 60 degrees C. In some embodiments, the thermally convective fluid comprises blood and/or another bodily fluid.

According to some embodiments, the at least one fluid conduit is in direct thermal communication with the at least one thermal shunt member. In some embodiments, the at least one fluid conduit is not in direct thermal communication with the at least one thermal shunt member. In some embodiments, the at least one fluid conduit comprises at least one opening, wherein the at least one opening places irrigation fluid passing through the at least one fluid conduit in direct physical contact with at least a portion of the at least one thermal shunt member. In some embodiments, the at least one opening is located along a perforated portion of the at least one conduit, wherein the perforated portion of the at least one conduit is located distally to the electrode. In some embodiments, the at least one fluid conduit is in fluid communication only with exit ports located along the distal end of the elongate body. In several configurations, the at least one fluid conduit directly contacts the at least one thermal shunt member. In some embodiments, the at least one fluid conduit does not contact the at least one thermal shunt member.

According to some embodiments, the at least one thermal shunt member comprises a thermal diffusivity greater than 1.5 $cm^2$/sec. In some embodiments, the at least one thermal shunt member comprises diamond (e.g., an industrial-grade diamond). In other embodiments, the at least one thermal shunt member comprises a carbon-based material (e.g., Graphene, silica, etc.). In some embodiments, a temperature of the at least one thermal shunt member does not exceed 60 to 62 degrees Celsius while maintaining a desired temperature along the electrode during an ablation procedure. In some embodiments, the desired temperature along the electrode during an ablation procedure is 60 degrees C.

According to some embodiments, the electrode comprises a radiofrequency (RF) electrode. In some embodiments, the electrode comprises a composite electrode (e.g., split-tip or split-section electrode). In several configurations, the composite electrode comprises a first electrode portion and at least a second electrode portion, wherein an electrically insulating gap is located between the first electrode portion and the at least a second electrode portion to facilitate high-resolution mapping along a targeted anatomical area.

According to some embodiments, at least a portion of the at least one thermal shunt member extends to an exterior of the catheter adjacent the proximal end of the electrode. In some embodiments, at least a portion of the at least one thermal shunt member extends to an exterior of the catheter adjacent the distal end of the electrode. In some embodiments, at least a portion of the at least one thermal shunt member extends proximally relative to the proximal end of the electrode. In some embodiments, the at least one thermal shunt member comprises a disk or other cylindrically-shaped member. In some embodiments, the at least one thermal shunt member comprises at least one extension member extending outwardly from a base member.

According to some embodiments, the at least one fluid conduit comprises at least one fluid delivery conduit and at least one fluid return conduit, wherein the fluid is at least partially circulated through an interior of the elongate body via the at least one fluid delivery conduit and the at least one fluid return conduit, wherein the at least one fluid conduit is part of a closed-loop or non-open cooling system. In some embodiments, the elongate body comprises a cooling chamber along a distal end of the elongate body, wherein the cooling chamber is configured to be in fluid communication with the at least one fluid conduit. In some embodiments, the at least one fluid conduit comprises a metallic material, an alloy and/or the like. In some embodiments, the elongate body does not comprise a fluid conduit. In some embodiments, an interior of a distal end of the elongate body comprises an interior member generally along a location of the electrode. In some embodiments, the interior member comprises at least one thermally conductive material configured to dissipate and/or transfer heat generated by the electrode.

According to some embodiments, an ablation device comprises an elongate body (e.g., catheter, other medical instrument, etc.) including a distal end, an ablation member positioned at the distal end of the elongate body, and at least one thermal shunt member placing a heat shunting element in thermal communication with the electrode to selectively remove heat from at least a portion of the electrode and/or tissue being treated by the electrode when the electrode is activated, wherein the heat shunting element of the at least one thermal shunt extends at least partially through an interior of the ablation member to help remove and dissipate heat generated by the ablation member during use.

According to several embodiments, the at least one thermal shunt member is in thermal communication with at least one fluid conduit or passage extending at least partially through an interior of the elongate body, the at least one fluid conduit or passage being configured to place the ablation member in fluid communication with a fluid source to selectively remove heat from the ablation member and/or tissue of a subject located adjacent the ablation member. In some embodiments, the at least one thermal shunt member comprises at least one fluid conduit or passage extending at least partially through an interior of the elongate body. In some embodiments, the at least one thermal shunt member does not comprise a fluid conduit or passage extending at least partially through an interior of the elongate body. In some embodiments, an interior of the distal end of the elongate body comprises an interior member generally along a location of the ablation member. In several configurations, the interior member comprises at least one thermally conductive material configured to dissipate and/or transfer heat generated by the ablation member.

According to some embodiments, the ablation member comprises a radiofrequency (RF) electrode. In some embodiments, the ablation member comprises one of a microwave emitter, an ultrasound transducer and a cryoablation member.

According to some embodiments, the at least one thermal shunt member comprises a thermal diffusivity greater than 1.5 cm$^2$/sec (e.g., greater than 1.5 cm$^2$/sec or 5 cm$^2$/sec (e.g., 1.5-2, 2-2.5, 2.5-3, 3-4, 4-5, 5-6, 6-7, 7-8, 8-9, 9-10, 10-11, 11-12, 12-13, 13-14, 14-15, 15-20 cm$^2$/sec, values between the foregoing ranges, greater than 20 cm$^2$/sec). In some arrangements, the at least one thermal shunt member comprises a thermal diffusivity greater than 5 cm$^2$/sec. In some embodiments, the at least one thermal shunt member comprises a diamond (e.g., an industrial-grade diamond). In some embodiments, the at least one thermal shunt member comprises a carbon-based material (e.g., Graphene, silica, etc.). In some embodiments, the radiofrequency (RF) electrode comprises a composite electrode (e.g., a split-tip RF electrode or other high-resolution electrode).

According to some embodiments, the at least one fluid conduit or passage is in direct thermal communication with the at least one thermal shunt member. In some embodiments, the at least one irrigation conduit is not in direct thermal communication with the at least one thermal shunt member. In some arrangements, the at least one fluid conduit or passage directly contacts the at least one thermal shunt member. In some embodiments, the at least one fluid conduit or passage does not contact the at least one thermal shunt member. In some embodiments, the at least one fluid conduit or passage comprises at least one opening, wherein the at least one opening places irrigation fluid passing through the at least one fluid conduit or passage in direct physical contact with at least a portion of the at least one thermal shunt member. In some embodiments, the at least one opening is located along a perforated portion of the at least one conduit or passage, wherein the perforated portion of the at least one conduit or passage is located distally to the electrode.

According to some embodiments, at least a portion of the at least one thermal shunt member extends to an exterior of the catheter adjacent the proximal end of the ablation member. In some embodiments, at least a portion of the at least one thermal shunt member extends to an exterior of the catheter adjacent the distal end of the ablation member. In some embodiments, at least a portion of the at least one thermal shunt member extends proximally relative to the proximal end of the ablation member. In some embodiments, the at least one thermal shunt member comprises a disk or other cylindrically-shaped member. In several configurations, the at least one thermal shunt member comprises at least one extension member extending outwardly from a base member. In some embodiments, the at least one extension member comprises at least one of a fin, a pin or a wing. In some embodiments, the at least one fluid conduit or passage comprises a metallic material.

According to some embodiments, a method of heat removal from an ablation member during a tissue treatment procedure includes activating an ablation system, the system comprising an elongate body (e.g., catheter, other medical instrument, etc.) comprising a distal end, an ablation member positioned at the distal end of the elongate body, wherein the elongate body of the ablation system comprises at least one thermal shunt member along its distal end, wherein the at least one thermal shunt member extends at least partially through an interior of the ablation member, and at least partially removing heat generated by the ablation member along the distal end of the elongate body via the at least one thermal shunt member so as to reduce the likelihood of localized hot spots along the distal end of the elongate body.

According to some embodiments, the elongate body further comprises at least one fluid conduit or passage extending at least partially through an interior of the elongate body, wherein the method further comprises delivering fluid through the at least one fluid conduit or passage, wherein the at least one thermal shunt member places the at least one fluid conduit or passage in thermal communication with a proximal portion of the ablation member to selectively remove heat from the proximal portion of the ablation member when the electrode is activated, wherein the at least one fluid conduit or passage is configured to place the ablation member in fluid communication with a fluid source to selectively remove heat from the ablation member and/or tissue of a subject located adjacent the ablation member.

According to some embodiments, the elongate body is advanced to a target anatomical location of the subject through a bodily lumen of the subject. In some embodiments, the bodily lumen of the subject comprises a blood vessel, an airway or another lumen of the respiratory tract, a lumen of the digestive tract, a urinary lumen or another bodily lumen. In some embodiments, the ablation member comprises a radiofrequency (RF) electrode. In other arrangements, the ablation member comprises one of a microwave emitter, an ultrasound transducer and a cryoablation member.

According to some embodiments, the at least one thermal shunt member comprises a thermal diffusivity greater than 1.5 $cm^2$/sec (e.g., greater than 1.5 $cm^2$/sec or 5 $cm^2$/sec (e.g., 1.5-2, 2-2.5, 2.5-3, 3-4, 4-5, 5-6, 6-7, 7-8, 8-9, 9-10, 10-11, 11-12, 12-13, 13-14, 14-15, 15-20 $cm^2$/sec, values between the foregoing ranges, greater than 20 $cm^2$/sec). In some arrangements, the at least one thermal shunt member comprises a thermal diffusivity greater than 5 $cm^2$/sec. In some embodiments, the at least one thermal shunt member comprises a diamond (e.g., an industrial-grade diamond). In some embodiments, the at least one thermal shunt member comprises a carbon-based material (e.g., Graphene, silica, etc.). In some embodiments, the radiofrequency (RF) electrode comprises a composite electrode (e.g., split-tip RF electrode or other high-resolution electrode). In some embodiments, the method additionally includes obtaining at least one high-resolution image of the target anatomical locations of the subject adjacent the ablation member.

According to some embodiments, the at least one fluid conduit or passage is in direct thermal communication with the at least one thermal shunt member. In some embodiments, the at least one irrigation conduit is not in direct thermal communication with the at least one thermal shunt member. According to some embodiments, the at least one fluid conduit or passage directly contacts the at least one thermal shunt member. In some embodiments, the at least one fluid conduit or passage does not contact the at least one thermal shunt member. In some embodiments, delivering fluid through the at least one fluid conduit or passage comprises delivering fluid to and through the distal end of the catheter in an open irrigation system. In several configurations, delivering fluid through the at least one fluid conduit or passage includes circulating fluid through the distal end of the catheter adjacent the ablation member in a closed fluid cooling system.

According to some embodiments, the elongate body of the ablation system does not comprise any fluid conduits or passages. In one embodiment, the elongate body comprises an interior member. In some embodiments, the interior member comprises a thermally conductive material that is in thermal communication with the at least one thermal shunt member to help dissipate and distribute heat generated by the ablation member during use. In some embodiments, at least a portion of the at least one thermal shunt member extends to an exterior of the catheter adjacent the proximal end of the ablation member. In some embodiments, at least a portion of the at least one thermal shunt member extends proximally to the proximal end of the ablation member. In some embodiments, at least a portion of the at least one thermal shunt member extends distally to the proximal end of the ablation member such that at least a portion of the at least one thermal shunt member is located along a length of the ablation member. In several configurations, the at least one thermal shunt member comprises a disk or other cylindrically-shaped member. In some arrangements, the at least one thermal shunt member comprises at least one extension member extending outwardly from a base member. In some embodiments, the at least one extension member comprises at least one of a fin, a pin, a wing and/or the like.

According to some embodiments, a system comprises means for connectivity to an electrophysiology recorder. In some embodiments, the system is configured to connect to an electrophysiology recorder. In some embodiments, the system further comprises at least one of (i) a generator for selectively energizing the device, and (ii) an electrophysiology recorder. In some embodiments, the system further comprises both (i) a generator for selectively energizing the device, and (ii) an electrophysiology recorder.

According to some embodiments, a system for delivering energy to targeted tissue of a subject includes a catheter having a high-resolution electrode (e.g., a composite electrode such as a split-tip or split-section electrode). The composite electrode can include two or more electrodes or electrode portions that are separated by an electrically-insulating gap. A filtering element can electrically couple the first and second electrodes or electrode portions, or any adjacent electrode sections (e.g., in a circumferential or radial arrangement) and can be configured to present a low impedance (e.g., effectively shorting the two electrodes, portions or sections) at a frequency used for delivering ablative energy via the first and second electrodes or electrode portions. In some embodiments, electrically separating the first and second electrodes, or electrode portions (e.g., in a circumferential or radial arrangement), facilitates high-resolution mapping along a targeted anatomical area. The catheter can further include a plurality of temperatures sensors (e.g., thermocouples) that are thermally insulated from the electrode and are configured to detect tissue temperature at a depth. The catheter can also include one or more thermal shunt members and/or components for transferring heat away from the electrode and/or the tissue being treated. In some embodiments, such thermal shunt members and/or components include diamond (e.g., industrial diamond) and/or other materials with favorable thermal diffusivity characteristics. Further, the system can be configured to detect whether and to what extent contact has been achieved between the electrode and targeted tissue.

According to some embodiments, an energy delivery device (e.g., ablation device) comprises an elongate body (e.g., a catheter) comprising a proximal end and a distal end, a first electrode (e.g., radiofrequency electrode) positioned at the distal end of the elongate body, and one or more second electrodes (e.g., radiofrequency electrodes) positioned at a location proximal to the first electrode, the first electrode and the second electrode being configured to contact tissue of a subject and deliver radiofrequency energy sufficient to at least partially ablate the tissue. In alternative embodiments, the electrodes are distributed or otherwise located circumferentially around the catheter (e.g., along four quadrant sections distributed around the catheter shaft circumference separated by gaps). In other embodiments, the catheter may have additional support structures and may employ multiple electrodes distributed on the support structures. The device further comprises at least one electrically insulating gap positioned between the first electrode and the second electrode or the sections of circumferential electrodes, the at least one electrically insulating gap comprising a gap width separating the first and second electrodes, and a band-pass filtering element electrically coupling the first electrode to the second electrode, or any adjacent electrode sections (e.g., in a circumferential or radial arrangement), and configured to present a low impedance (e.g., effectively shorting the two electrodes or sections) at a frequency used for delivering ablative energy via the first and second electrodes. In some embodiments, electrically separating the first and second electrodes, or electrode sections (e.g., in a circumferential or radial arrangement), facilitates high-resolution mapping along a targeted anatomical area. In some embodiments, the ratio of ablated tissue surface to that of mapped tissue is enhanced (e.g., optimized).

Several embodiments disclosed in the present application are particularly advantageous because they include one, more or all of the following benefits: a system configured to deliver energy (e.g., ablative or other type of energy) to anatomical tissue of a subject and configured for high-resolution mapping; a system configured to deliver energy to anatomical tissue of a subject and configured to detect the effectiveness of the resulting treatment procedure using its high-resolution mapping capabilities and functions; a composite tip design (e.g., split-tip or split-section design) can be configured to be energized as a unitary tip or section to more uniformly provide energy to targeted anatomical tissue of a subject and/or the like.

According to some embodiments, the device further comprises a separator positioned within the at least one electrically insulating gap. In some embodiments, the at least one separator contacts a proximal end of the first electrode and the distal end of the second electrode. In some embodiments, the separator contacts, at least partially, a side of one electrode section and an opposing side of the adjacent electrode section. In one embodiment, the first and second electrodes and the separator are cylindrical. In one embodiment, the outer diameter of the electrodes and the separator are equal. In some embodiments, the first and second electrodes include quadrants or other sections that are circumferentially distributed on the catheter shaft. In some embodiments, the first and second electrodes comprise other geometries that make suitable for distribution on a catheter shaft and also be separated by a narrow non-conductive gap. In some embodiments, the device further comprises at least one conductor (e.g., wire, cable, etc.) configured to electrically couple an energy delivery module (e.g., a RF or other generator) to at least one of the first and second electrodes. In some embodiments, the device further comprises one or more additional conductors connected to each of the first and second electrodes for distributing signals (e.g., cardiac signals) picked up by said electrodes to an electrophysiology (EP) recorder.

According to some embodiments, a device additionally includes an electrophysiology recorder. In some embodiments, a frequency of energy provided to the first and second electrodes is in an operating radiofrequency (RF) range (e.g., approximately 300 kHz to 10 MHz).

According to some embodiments, the band-pass filtering element comprises a capacitor. In some embodiments, the capacitor comprises a capacitance of 50 to 300 nF (e.g., 100 nF, 50-100, 100-150, 150-200, 200-250, 250-300 nF, values between the foregoing ranges, etc.), depending, e.g., on the operating frequency used to deliver ablative energy. In some embodiments, a series impedance of about 3 ohms (0) or less than about 3 ohms (e.g., 0-1, 1-2, 2-3 ohms, values between the foregoing ranges, etc.) is introduced between the first and second electrodes in the operating RF frequency range (e.g., 300 kHz to 10 MHz). For example, a lower capacitance value (e.g. 5-10 nF) may be used at a higher frequency range (e.g. 10 MHz). In some embodiments, a 100 nF capacitance value may be well-suited for applications in the 500 kHz frequency range. In some embodiments, a series impedance introduced across the first and second electrodes is lower than: (i) an impedance of a conductor that electrically couples the electrodes to an energy delivery module, and (ii) an impedance of a tissue being treated. In some embodiments, the device further comprises a band-pass filtering element electrically coupling the second electrode to the third electrode, or any adjacent electrode sections (e.g., in a circumferential or radial arrangement), and configured to present a low impedance at a frequency used for delivering ablative energy via the second and third electrodes.

According to some embodiments, the gap width between the first and second electrodes is approximately 0.2 to 1.0 mm (e.g., 0.5 mm). In some embodiments, the elongate body comprises at least one irrigation passage, said at least one irrigation passage extending to the first electrode. In one embodiment, the first electrode comprises at least one outlet port in fluid communication with the at least one irrigation passage.

According to some embodiments, the device further comprises a third electrode, wherein the second electrode is positioned axially between the first and third electrodes, wherein an electrically insulating gap separates the second and third electrodes. In some embodiments, the device further comprises a separator positioned within the gap between the second and third electrodes.

According to some embodiments, a system comprises an ablation device according to any of the embodiments disclosed herein. In some embodiments, the system additionally comprises means for connectivity to an electrophysiology recorder. In some embodiments, the system is configured to connect to an electrophysiology recorder. In some embodiments, the system further comprises at least one of (i) a generator for selectively energizing the device, and (ii) an electrophysiology recorder.

According to some embodiments, a method of simultaneously delivering energy to an ablation device and mapping tissue of a subject comprises energizing a composite electrode (e.g., split-tip electrode, split-section electrode, etc.) being separated by a non-conductive gap from the first electrode and a second electrode, the second electrode positioned at a location proximal to the first electrode, the first electrode and the second electrode being configured to contact tissue of a subject to deliver energy sufficient to at least partially ablate the tissue and to receive high-resolution mapping data, the high-resolution mapping data relating to tissue of a subject adjacent the first and second electrodes. In some embodiments, an electrically insulating gap is positioned between the first electrode and the second electrode, the electrically insulating gap comprising a gap width separating the first and second electrodes. In some embodiments, a filtering element electrically couples the first electrode to the second electrode only in the operating RF frequency range. In one embodiment, electrically separating the first and second electrodes facilitates high-resolution mapping along a targeted anatomical area.

According to some embodiments, a separator is positioned within the at least one electrically insulating gap. In one embodiment, the at least one separator contacts a proximal end of the first electrode and the distal end of the second electrode.

According to some embodiments, the mapping data is provided to an electrophysiology recorder. In some embodiments, a frequency of energy provided to the first and second electrodes is in the radiofrequency range.

According to some embodiments, the filtering element comprises a capacitor. In one embodiment, the capacitor comprises a capacitance of 50 to 300 nF (e.g., 100 nF), depending on, e.g., the operating frequency used for ablative energy. In some embodiments, a series impedance of about 3 ohms ($\Omega$) is introduced across the first and second electrodes at 500 kHz. In some embodiments, a series impedance introduced across the first and second electrodes is lower than: (i) an impedance of a conductor that electrically couples the electrodes to an energy delivery module, and (ii) an impedance of a tissue being treated.

According to some embodiments, the gap width is approximately 0.2 to 1.0 mm. In one embodiment, the gap width is 0.5 mm.

According to some embodiments, an ablation device comprises an elongate body (e.g., catheter, other medical instrument, etc.) comprising a distal end, an electrode positioned at the distal end of the elongate body and at least one thermal shunt member placing a heat absorption element in thermal communication with the electrode to selectively remove heat from at least one of the electrode and tissue being treated by the electrode when the electrode is activated, wherein the at least one thermal shunt member extends at least partially through an interior of the electrode to dissipate and remove heat from the electrode during use. In some embodiments, the at least one thermal shunt member is in thermal communication with at least one fluid conduit extending at least partially through an interior of the elongate body, the at least one fluid conduit being configured to place the electrode in fluid communication with a fluid source to selectively remove heat from the electrode and/or tissue of a subject located adjacent the electrode. In some embodiments, a fluid conduit or passage extends at least partially through an interior of the elongate body. In one embodiment, the fluid conduit or passage extends at least partially through the at least one thermal shunt member. In some embodiments, the at least one thermal shunt member is at least partially in thermal communication with a thermally convective fluid. In some embodiments, the thermally convective fluid comprises blood and/or another bodily fluid.

According to some embodiments, a flow rate of the thermally convective fluid is less than 15 ml/min in order to maintain a desired temperature along the electrode during an ablation procedure. In some embodiments, a flow rate of the thermally convective fluid is approximately less than 10 ml/min in order to maintain a desired temperature along the electrode during an ablation procedure. In some embodiments, a flow rate of the thermally convective fluid is approximately less than 5 ml/min in order to maintain a desired temperature along the electrode during an ablation procedure. According to some embodiments, the desired temperature along the electrode during an ablation procedure is 60 degrees C.

According to some embodiments, the at least one thermal shunt member comprises a thermal diffusivity greater than 1.5 $cm^2$/sec or 5 $cm^2$/sec (e.g., 1.5-2, 2-2.5, 2.5-3, 3-4, 4-5, 5-6, 6-7, 7-8, 8-9, 9-10, 10-11, 11-12, 12-13, 13-14, 14-15, 15-20 $cm^2$/sec, values between the foregoing ranges, greater than 20 $cm^2$/sec). In some embodiments, the at least one thermal shunt member comprises diamond (e.g., an industrial-grade diamond). In some embodiments, the at least one thermal shunt member comprises a carbon-based material. In some embodiments, the at least one thermal shunt member comprises at least one of Graphene and silica.

According to some embodiments, a temperature of the at least one thermal shunt member does not exceed 60 to 62 degrees Celsius while maintaining a desired temperature along the electrode during an ablation procedure. In some embodiments, the desired temperature along the electrode during an ablation procedure is 60 degrees C.

According to some embodiments, the electrode comprises a radiofrequency (RF) electrode. In some embodiments, the electrode comprises a composite electrode (e.g., split-tip electrode). In some embodiments, the composite electrode comprises a first electrode portion and at least a second electrode portion, wherein an electrically insulating gap is located between the first electrode portion and the at least a second electrode portion to facilitate high-resolution mapping along a targeted anatomical area.

According to some embodiments, the at least one fluid conduit is in direct thermal communication with the at least one thermal shunt member. In some embodiments, the at least one fluid conduit is not in direct thermal communication with the at least one thermal shunt member. In some embodiments, the at least one fluid conduit comprises at least one opening, wherein the at least one opening places irrigation fluid passing through the at least one fluid conduit in direct physical contact with at least a portion of the at least one thermal shunt member. In some embodiments, the at least one opening is located along a perforated portion of the at least one conduit, wherein the perforated portion of the at least one conduit is located distally to the electrode. In one embodiment, the at least one fluid conduit is in fluid communication only with exit ports located along the distal end of the elongate body. In some embodiments, the at least one fluid conduit directly contacts the at least one thermal shunt member. In some embodiments, the at least one fluid conduit does not contact the at least one thermal shunt member. In some embodiments, at least a portion of the at least one thermal shunt member extends to an exterior of the catheter adjacent the proximal end of the electrode. In one embodiment, at least a portion of the at least one thermal shunt member extends to an exterior of the catheter adjacent the distal end of the electrode. In certain embodiments, at least a portion of the at least one thermal shunt member extends proximally relative to the proximal end of the electrode. In some embodiments, the at least one thermal shunt member comprises a disk or other cylindrically-shaped member.

According to some embodiments, an ablation device comprises an elongate body (e.g., catheter, other medical instrument, etc.) comprising a distal end, an ablation member positioned at the distal end of the elongate body and at least one thermal shunt member placing a heat shunting element in thermal communication with the electrode to selectively remove heat from at least a portion of the electrode and/or tissue being treated by the electrode when the electrode is activated, wherein the heat shunting element of the at least one thermal shunt extends at least partially through an interior of the ablation member to help remove and dissipate heat generated by the ablation member during use. In some embodiments, the at least one thermal shunt member is in thermal communication with at least one fluid conduit or passage extending at least partially through an interior of the elongate body, the at least one fluid conduit or passage being configured to place the ablation member in fluid communication with a fluid source to selectively remove heat from the ablation member and/or tissue of a subject located adjacent the ablation member.

According to some embodiments, the at least one thermal shunt member comprises at least one fluid conduit or passage extending at least partially through an interior of the elongate body. In some embodiments, the at least one thermal shunt member does not comprise a fluid conduit or passage extending at least partially through an interior of the elongate body. In some embodiments, an interior of the distal end of the elongate body comprises an interior member generally along a location of the ablation member. In one embodiment, the interior member comprises at least one thermally conductive material configured to dissipate and/or transfer heat generated by the ablation member.

According to some embodiments, the ablation member comprises a radiofrequency (RF) electrode. In some embodiments, the ablation member comprises one of a microwave emitter, an ultrasound transducer and a cryoablation member.

According to some embodiments, the at least one thermal shunt member comprises at least one extension member extending outwardly from a base member. In some embodiments, the at least one fluid conduit comprises at least one fluid delivery conduit and at least one fluid return conduit, wherein the fluid is at least partially circulated through an interior of the elongate body via the at least one fluid delivery conduit and the at least one fluid return conduit, wherein the at least one fluid conduit is part of a closed-loop or non-open cooling system. In some embodiments, the elongate body comprises a cooling chamber along a distal end of the elongate body, wherein the cooling chamber is configured to be in fluid communication with the at least one fluid conduit. In some embodiments, the at least one fluid conduit comprises at least one of a metallic material and an alloy. In some embodiments, the elongate body does not comprise a fluid conduit. In one embodiment, an interior of a distal end of the elongate body comprises an interior member generally along a location of the electrode. In some embodiments, the interior member comprises at least one thermally conductive material configured to dissipate and/or transfer heat generated by the electrode.

According to some embodiments, a method of heat removal from an ablation member during a tissue treatment procedure comprises activating an ablation system, the system comprising an elongate body comprising a distal end, an ablation member positioned at the distal end of the elongate body, wherein the elongate body of the ablation system comprises at least one thermal shunt member along its distal end, wherein the at least one thermal shunt member extends at least partially through an interior of the ablation member, and at least partially removing heat generated by the ablation member along the distal end of the elongate body via the at least one thermal shunt member so as to reduce the likelihood of localized hot spots along the distal end of the elongate body.

According to some embodiments, the elongate body (e.g., catheter, medical instrument, etc.) further comprises at least one fluid conduit or passage extending at least partially through an interior of the elongate body, the method further comprising delivering fluid through the at least one fluid conduit or passage, wherein the at least one thermal shunt member places the at least one fluid conduit or passage in thermal communication with a proximal portion of the ablation member to selectively remove heat from the proximal portion of the ablation member when the electrode is activated, wherein the at least one fluid conduit or passage is configured to place the ablation member in fluid communication with a fluid source to selectively remove heat from the ablation member and/or tissue of a subject located adjacent the ablation member.

According to some embodiments, the elongate body is advanced to a target anatomical location of the subject through a bodily lumen of the subject. In some embodiments, the bodily lumen of the subject comprises a blood vessel, an airway or another lumen of the respiratory tract, a lumen of the digestive tract, a urinary lumen or another bodily lumen. In some embodiments, the ablation member comprises a radiofrequency (RF) electrode. In some embodiments, the ablation member comprises one of a microwave emitter, an ultrasound transducer and a cryoablation member. In some embodiments, the at least one thermal shunt member comprises a thermal diffusivity greater than 1.5 $cm^2$/sec or 5 $cm^2$/sec (e.g., 1.5-2, 2-2.5, 2.5-3, 3-4, 4-5, 5-6, 6-7, 7-8, 8-9, 9-10, 10-11, 11-12, 12-13, 13-14, 14-15, 15-20 $cm^2$/sec, values between the foregoing ranges, greater than 20 $cm^2$/sec). In some embodiments, the at least one thermal shunt member comprises diamond (e.g., an industrial-grade diamond). In some embodiments, the at least one thermal shunt member comprises a carbon-based material. In some embodiments, the at least one thermal shunt member comprises at least one of Graphene and silica.

According to some embodiments, the radiofrequency (RF) electrode comprises a composite RF electrode (e.g., split-tip RF electrode). In some embodiments, the method further comprises obtaining at least one high-resolution image of the target anatomical locations of the subject adjacent the ablation member. In some embodiments, the at least one fluid conduit or passage is in direct thermal communication with the at least one thermal shunt member. In some embodiments, the at least one irrigation conduit is not in direct thermal communication with the at least one thermal shunt member. In some embodiments, the at least one fluid conduit or passage directly contacts the at least one thermal shunt member. In one embodiment, the at least one fluid conduit or passage does not contact the at least one thermal shunt member. In certain embodiments, delivering fluid through the at least one fluid conduit or passage comprises delivering fluid to and through the distal end of the catheter in an open irrigation system. In some embodiments, delivering fluid through the at least one fluid conduit or passage comprises circulating fluid through the distal end of the catheter adjacent the ablation member in a closed fluid cooling system.

According to some embodiments, the elongate body (e.g., catheter, medical instrument, etc.) of the ablation system does not comprise any fluid conduits or passages. In some embodiments, the distal end of the elongate body comprises an interior member. In some embodiments, the interior member comprises a thermally conductive material that is in thermal communication with the at least one thermal shunt member to help dissipate and distribute heat generated by the ablation member during use. In some embodiments, at least a portion of the at least one thermal shunt member extends to an exterior of the catheter adjacent the proximal end of the ablation member. In one embodiment, at least a portion of the at least one thermal shunt member extends proximally to the proximal end of the ablation member. In some embodiments, at least a portion of the at least one thermal shunt member extends distally to the proximal end of the ablation member such that at least a portion of the at least one thermal shunt member is located along a length of the ablation member. In some embodiments, the at least one thermal shunt member comprises a disk or other cylindrically-shaped member. In one embodiment, the at least one thermal shunt member comprises at least one extension member extending outwardly from a base member. In some embodiments, the at least one extension member comprises at least one of a fin, a pin or a wing.

According to some embodiments, a system comprising a device in accordance with the present application further comprises means for connectivity to an electrophysiology recorder. In some embodiments, the system is configured to connect to an electrophysiology recorder. In some embodiments, the system further comprises at least one of (i) a generator for selectively energizing the device, and (ii) an electrophysiology recorder.

According to some embodiments, an ablation device comprises an elongate body (e.g., a catheter) having a distal end, an electrode (e.g., a RF electrode, composite electrode, etc.) positioned at the distal end of the elongate body, at least one irrigation conduit extending at least partially through an interior of the elongate body, the at least one irrigation conduit configured to place the electrode in fluid communication with a fluid source to selectively remove heat from the electrode and/or tissue of a subject located adjacent the electrode and at least one heat transfer member placing the at least one irrigation conduit in thermal communication with a proximal portion of the electrode to selectively remove heat from the proximal portion of the electrode when the electrode is activated.

According to some embodiments, an ablation device comprises an elongate body (e.g., a catheter, other medical instrument, etc.) comprising a distal end, an ablation member positioned at the distal end of the elongate body, at least one irrigation conduit extending at least partially through an interior of the elongate body, the at least one irrigation conduit configured to place the ablation member in fluid communication with a fluid source and at least one thermal transfer member placing the at least one irrigation conduit in thermal communication with a proximal portion of the ablation member to selectively remove heat from the proximal portion of the ablation member when the electrode is activated. In some embodiments, the ablation member comprises a radiofrequency (RF) electrode, a microwave emitter, an ultrasound transducer, a cryoablation member and/or any other member.

According to some embodiments, the at least one thermal transfer member comprises a thermal conductance greater than 300 W/m/° C. (e.g., 300-350, 350-400, 400-450, 450-500 W/m/° C., ranges between the foregoing, etc.). In other embodiments, the at least one thermal transfer member comprises a thermal conductance greater than 500 W/m/° C. (e.g., 500-550, 550-600, 600-650, 650-700, 700-800, 800-900, 900-1000 W/m/° C., ranges between the foregoing, greater than 1000 W/m/° C., etc.).

According to some embodiments, the at least one thermal transfer member comprises a diamond (e.g., industrial-grade diamond). In some embodiments, the at least one thermal transfer member comprises at least one of a metal and an alloy (e.g., copper, beryllium, brass, etc.).

According to some embodiments, the electrode comprises a radiofrequency (RF) electrode. In one embodiment, the electrode comprises a composite electrode (e.g., a split-tip electrode). In some embodiments, the composite electrode comprises a first electrode portion and at least a second electrode portion, wherein an electrically insulating gap is located between the first electrode portion and the at least a second electrode portion to facilitate high-resolution mapping along a targeted anatomical area.

According to some embodiments, the device further comprises a radiometer. In some embodiments, the radiometer is located in the catheter (e.g., at or near the electrode or other ablation member). In other embodiments, however, the radiometer is located in the handle of the device and/or at another location of the device and/or accompanying system. In embodiments of the device that comprise a radiometer, the catheter comprises one or more antennas (e.g., at or near the electrode) configured to detect microwave signals emitted by tissue. In some embodiments, the device does not comprise a radiometer or does not incorporate radiometry technology (e.g., for measuring temperature of tissue). As discussed herein, other types of temperature-measurement devices (e.g., thermocouples, thermistors, other temperature sensors, etc.) can be incorporate into a device or system.

According to some embodiments, an ablation device consists essentially of a catheter, an ablation member (e.g., a RF electrode, a composite electrode, etc.), an irrigation conduit extending through an interior of the catheter to or near the ablation member, at least one electrical conductor (e.g., wire, cable, etc.) to selectively activate the ablation member and at least one heat transfer member that places at least a portion of the ablation member (e.g., a proximal portion of the ablation member) in thermal communication with the irrigation conduit.

According to some embodiments, an ablation device consists essentially of a catheter, an ablation member (e.g., a RF electrode, a composite electrode, etc.), an irrigation conduit extending through an interior of the catheter to or near the ablation member, at least one electrical conductor (e.g., wire, cable, etc.) to selectively activate the ablation member, an antenna configured to receive microwave signals emitted by tissue of a subject, a radiometer and at least one heat transfer member that places at least a portion of the ablation member (e.g., a proximal portion of the ablation member) in thermal communication with the irrigation conduit.

According to some embodiments, the at least one irrigation conduit is in direct thermal communication with the at least one thermal transfer member. In some embodiments, the at least one irrigation conduit is not in direct thermal communication with the at least one thermal transfer member. In some embodiments, the irrigation conduit is fluid communication only with exit ports located along the distal end of the elongate body. In some embodiments, the catheter only comprises irrigation exit openings along a distal end of the catheter (e.g., along a distal end or the electrode). In some embodiments, the system does not comprise any irrigation openings along the heat transfer members.

According to some embodiments, the at least one irrigation conduit directly contacts the at least one thermal transfer member. In some embodiments, the at least one irrigation conduit does not contact the at least one thermal transfer member. In one embodiment, at least a portion of the heat transfer member extends to an exterior of the catheter adjacent the proximal end of the electrode. In some embodiments, at least a portion of the heat transfer member extends proximally to the proximal end of the electrode. In certain embodiments, at least a portion of the heat transfer member extends distally to the proximal end of the electrode such that at least a portion of the heat transfer member is located along a length of the electrode. According to some embodiments, the at least one irrigation conduit comprises a metallic material and/or other thermally conductive materials.

According to some embodiments, the heat transfer member comprises a disk or other cylindrically-shaped member. In some embodiments, the heat transfer member comprises at least one extension member extending outwardly from a base member.

According to some embodiments, the device further comprises a radiometer to enable the device and/or accompanying system to detect a temperature to tissue of the subject at a depth. In some embodiments, the radiometer is included, at least in part, in the catheter. In other embodiments, the radiometer is located, at least in part, in the handle of the system and/or in a portion of the device and/or accompanying system external to the catheter.

According to some embodiments, a method of heat removal from an ablation member during an ablation procedure comprises activating an ablation system, the system comprising an elongate body comprising a distal end, an ablation member positioned at the distal end of the elongate body, at least one irrigation conduit extending at least partially through an interior of the elongate body, and at least one thermal transfer member, wherein the at least one irrigation conduit configured to place the ablation member in fluid communication with a fluid source to selectively remove heat from the ablation member and/or tissue of a subject located adjacent the ablation member, and delivering fluid through the at least one irrigation conduit, wherein the at least one thermal transfer member places the at least one irrigation conduit in thermal communication with a proximal portion of the ablation member to selectively remove heat from the proximal portion of the ablation member when the electrode is activated.

According to some embodiments, the elongate body is advanced to a target anatomical location of the subject through a bodily lumen of the subject. In some embodiments, the bodily lumen of the subject comprises a blood vessel, an airway or another lumen of the respiratory tract, a lumen of the digestive tract, a urinary lumen or another bodily lumen.

According to some embodiments, the ablation member comprises a radiofrequency (RF) electrode, a microwave emitter, an ultrasound transducer, a cryoablation member and/or the like. In some embodiments, the at least one thermal transfer member comprises a thermal conductance greater than 300 W/m/° C. In one embodiment, the at least one thermal transfer member comprises a thermal conductance greater than 500 W/m/° C.

According to some embodiments, the at least one thermal transfer member comprises a diamond (e.g., industrial-grade diamond). In some embodiments, the at least one thermal transfer member comprises at least one of a metal and an alloy (e.g., copper, beryllium, brass, etc.).

According to some embodiments, a system comprises an ablation device according to any of the embodiments disclosed herein. In some embodiments, the system additionally comprises means for connectivity to an electrophysiology recorder. In some embodiments, the system is configured to connect to an electrophysiology recorder. In some embodiments, the system further comprises at least one of (i) a generator for selectively energizing the device, and (ii) an electrophysiology recorder.

According to one embodiment, a medical instrument (e.g., ablation catheter) includes an elongate body having a proximal end and a distal end. The medical instrument also includes an energy delivery member positioned at the distal end of the elongate body that is configured to deliver energy to the targeted tissue. The medical instrument further includes a first plurality of temperature-measurement devices positioned within the energy delivery member and being thermally insulated from the energy delivery member and a second plurality of temperature-measurement devices positioned along the elongate body and spaced apart axially from the first plurality of temperature-measurement devices, the second plurality of temperature-measurement devices also being thermally insulated from the energy delivery member. The energy delivery member may optionally be configured to contact the tissue. The first plurality of temperature-measurement devices may optionally be positioned along a first plane that is substantially perpendicular to a longitudinal axis of the elongate body. The second plurality of temperature-measurement devices may optionally be positioned along a second plane that is substantially perpendicular to a longitudinal axis of the elongate body and spaced apart axially along the longitudinal axis proximal to the first plane. The energy delivery member may optionally comprise one or more electrode portions, one or more ultrasound transducers, one or more laser elements, or one or more microwave emitters.

According to one embodiment, a medical instrument (e.g., an ablation catheter or other device) comprises an elongate body having a proximal end and a distal end. The medical instrument comprises at least one energy delivery member (e.g., a tip electrode or multiple electrode portions) positioned at the distal end of the elongate body. In this embodiment, the at least one energy delivery member is configured to deliver energy (e.g., radiofrequency energy, acoustic energy, microwave power, laser energy) to the targeted tissue with or without contacting the tissue. In one embodiment, the energy is sufficient to generate a lesion at a depth from a surface of the targeted tissue. The embodiment of the medical instrument comprises a first plurality of temperature-measurement devices carried by, or positioned within separate apertures, recesses or other openings formed in a distal end (e.g., a distal-most surface) of the at least one energy delivery member. The first plurality of temperature-measurement devices are thermally insulated from the energy delivery member. The embodiment of the medical instrument comprises a second plurality of temperature-measurement devices positioned adjacent to (e.g., within 1 mm of) a proximal end of the at least one energy delivery member (e.g., carried by or within the energy delivery member or carried by or within the elongate body proximal of the proximal end of the energy delivery member), the second plurality of temperature-measurement devices being thermally insulated from the at least one energy delivery member. The second plurality of temperature-measurement devices may be positioned just proximal or just distal of the proximal end of the at least one energy delivery member. If the medical instrument comprises two or more energy delivery members, then the second plurality of temperature-measurement devices may be positioned adjacent the proximal edge of the proximal-most energy delivery member and the first plurality of temperature-measurement devices may be positioned within the distal-most energy delivery member. In some embodiments, the second plurality of temperature-measurement devices are positioned along a thermal shunt member (e.g., thermal transfer member) proximal of the at least one energy delivery member. In some embodiments, the second plurality of temperature-measurement devices is positioned along a plane that is perpendicular or substantially perpendicular to a longitudinal axis of the distal end of the elongate body and spaced proximal to the first plurality of temperature-measurement devices.

In some embodiments, each of the temperature-measurement devices comprises a thermocouple or a thermistor (e.g., Type K or Type T thermocouples). In some embodiments, the first plurality of temperature-measurement devices comprises at least three temperature-measurement devices and the second plurality of temperature-measurement devices comprises at least three temperature-measurement devices. In one embodiment, the first plurality of temperature-measurement devices consists of only three temperature-measurement devices and the second plurality of temperature-measurement devices consists of only three temperature-measurement devices. Each of the first plurality of temperature-measurement devices and each of the second plurality of temperature-measurement devices may be spaced apart (equidistantly or non-equally spaced) from each of the other temperature-measurement devices of its respective group (e.g., circumferentially or radially around an outer surface of the elongate body or otherwise arranged). For example, where three temperature-measurement devices are included in each plurality, group or set, the temperature-measurement devices may be spaced apart by about 120 degrees. In some embodiments, the first plurality of temperature-measurement devices and the second plurality of temperature-measurement devices protrude or otherwise extend beyond an outer surface of the elongate body to facilitate increased depth of insertion (e.g., burying) within the targeted tissue. In one embodiment the elongate body is cylindrical or substantially cylindrical. The distal ends of the temperature-measurement devices may comprise a generally rounded casing or shell to reduce the likelihood of penetration or scraping of the targeted tissue.

In accordance with one embodiment, a medical instrument (e.g., ablation device) comprises an elongate body having a proximal end and a distal end and a combination or high-resolution electrode assembly (e.g., a composite electrode assembly, such as a split-tip electrode assembly) positioned at the distal end of the elongate body. The composite electrode assembly or other high-resolution electrode assembly comprises a first electrode member positioned at a distal terminus of the distal end of the elongate body, a second electrode member positioned proximal to the first electrode member and spaced apart from the first electrode member, and an electrically-insulating gap between the first electrode member and the second electrode member. The first electrode member and the second electrode member may be configured to contact tissue of a subject and to deliver radiofrequency energy to the tissue. In some embodiments, the energy may be sufficient to ablate the tissue. The electrically-insulating gap may comprise a gap width separating the first electrode member and the second electrode member. The embodiment of the medical instrument comprises a first plurality of temperature sensors positioned within separate openings, apertures, slits, slots, grooves or bores formed in the first electrode member and spaced apart (e.g., circumferentially, radially or otherwise) and a second plurality of temperature sensors positioned at a region proximal to the second electrode member (e.g., adjacent to (just proximal or just distal, within less than 1 mm from) a proximal edge of the second electrode member). Positioning within 1 mm of the proximal edge may advantageously provide more useful or important temperature measurements because typically the hottest spots form at the proximal edge of an electrode. The second plurality of temperature sensors are thermally insulated from the second electrode member. In some embodiments, the second plurality of temperature sensors is spaced apart circumferentially or radially around an outer circumferential surface of the elongate body. The first plurality of temperature sensors may be thermally insulated from the first electrode member and may extend beyond an outer surface (e.g., distal-most surface) of the first electrode member. In one embodiment, at least a portion of each of the second plurality of temperature sensors extends beyond the outer circumferential surface of the elongate body.

In some embodiments, the medical instrument comprises a heat exchange chamber (e.g., irrigation conduit) extending at least partially through an interior of the elongate body. The medical instrument may be coupled to a fluid source configured to supply cooling fluid to the heat exchange chamber and a pump configured to control delivery of the cooling fluid to the heat exchange chamber from the fluid source through one or more internal lumens within the heat exchange chamber. In one embodiment, the first electrode member comprises a plurality of irrigation exit ports in fluid communication with the heat exchange chamber such that the cooling fluid supplied by the fluid source exits from the irrigation exit ports, thereby providing cooling to the composite electrode assembly or other high resolution electrode assembly, blood and/or tissue being heated.

For open irrigation arrangements, the medical instrument (e.g., ablation device) may comprise a fluid delivery lumen having a diameter or other cross-sectional dimension smaller than the lumen of the heat exchange chamber (e.g., irrigation conduit) to facilitate increased velocity to expel the saline or other fluid out of the irrigation exit ports at a regular flow rate. For closed irrigation arrangements, the medical instrument may comprise an inlet lumen (e.g., fluid delivery lumen) extending between the heat exchange chamber and the fluid source and an outlet lumen (e.g., return lumen) extending between the heat exchange chamber (e.g., irrigation conduit) and a return reservoir external to the medical instrument. In one embodiment, a distal end (e.g., outlet) of the inlet lumen is spaced distally from the distal end (e.g., inlet) of the outlet lumen so as to induce turbulence or other circulation within the heat exchange chamber. In various embodiments, an irrigation flow rate is 10 mL/min or less (e.g., 9 mL/min or less, 8 mL/min or less, 7 mL/min or less, 6 mL/min or less, 5 m/min or less). In some embodiments, the medical instruments are not irrigated.

According to one embodiment, a medical instrument (e.g., ablation device) comprises an elongate body (e.g., a catheter, wire, probe, etc.) comprising a proximal end and a distal end and a longitudinal axis extending from the proximal end to the distal end. The medical instrument comprises a combination or high-resolution electrode assembly (e.g., composite electrode assembly, such as a split-tip electrode assembly). In the embodiment, the composite electrode assembly comprises a first electrode member positioned at a distal terminus of the distal end of the elongate body and a second electrode member positioned proximal to the first electrode member and spaced apart from the first electrode member. The first electrode member and the second electrode member are configured to contact tissue of a subject and to deliver radiofrequency energy to the tissue. The energy delivered may be sufficient to at least partially ablate or otherwise heat the tissue. The composite electrode assembly also comprises an electrically-insulating gap comprising a gap width separating the first electrode member and the second electrode member. The embodiment of the ablation device further comprises at least one thermal transfer member in thermal communication with the first and second electrode members to selectively remove or dissipate heat from the first and second electrode members, a first plurality of temperature-measurement devices positioned within the first electrode member and spaced apart (e.g., circumferentially, radially) and a second plurality of temperature-measurement devices positioned within a portion of the at least one thermal heat shunt member (e.g., heat transfer member) proximal to the second electrode member. The first plurality of temperature-measurement devices is thermally insulated from the first electrode member and may extend beyond an outer surface of the first electrode member in a direction that is at least substantially parallel to the longitudinal axis of the elongate body. The second plurality of thermocouples is thermally insulated from the second electrode member and may extend beyond an outer surface of the at least one thermal heat shunt member in a direction that is at least substantially perpendicular to the longitudinal axis of the elongate body.

In some embodiments, the medical instrument comprises a heat exchange chamber (e.g., irrigation conduit) extending at least partially through an interior of the elongate body. The medical instrument may be fluidly coupled to a fluid source configured to supply cooling fluid to the heat exchange chamber and a pump configured to control delivery of the cooling fluid. In one embodiment, the first electrode member comprises a plurality of irrigation exit ports in fluid communication with the heat exchange chamber such that the cooling fluid supplied by the fluid source is expelled from the irrigation exit ports, thereby providing cooling to the composite electrode assembly (e.g., split-tip electrode assembly). In some embodiments, at least an inner surface or layer of the heat exchange chamber comprises a biocompatible material, such as stainless steel.

In some embodiments, the at least one thermal shunt member (e.g., heat shunt network or heat transfer member(s)) comprises a thermal conductance greater than 300 W/m/° C. (e.g., 300-350, 350-400, 400-450, 450-500 W/m/° C., ranges between the foregoing, etc.). In other embodiments, the at least one thermal transfer member comprises a thermal conductance greater than 500 W/m/° C. (e.g., 500-550, 550-600, 600-650, 650-700, 700-800, 800-900, 900-1000 W/m/° C., ranges between the foregoing, greater than 1000 W/m/° C., etc.). According to some embodiments, the at least one thermal transfer member comprises a diamond (e.g., industrial-grade diamond).

The electrode member(s) may comprise platinum in any of the embodiments. The temperature-measurement devices may comprise one of more of the following types of thermocouples: nickel alloy, platinum/rhodium alloy, tungsten/rhenium alloy, gold/iron alloy, noble metal alloy, platinum/molybdenum alloy, iridium/rhodium alloy, pure noble metal, Type K, Type T, Type E, Type J, Type M, Type N, Type B, Type R, Type S, Type C, Type D, Type G, and/or Type P.

According to some embodiments, the medical instrument comprises at least one separator positioned within the at least one electrically-insulating gap. In one embodiment, the at least one separator comprises a portion of the at least one thermal transfer member. For example, the at least one separator may comprise industrial grade diamond.

According to some embodiments, the medical instrument comprises at least one conductor configured to conduct current from an energy source to the composite electrode assembly (e.g., split-tip electrode assembly) or other ablation members. In some embodiments, the first plurality of thermocouples or other temperature-measurement devices and the second plurality of thermocouples or other temperature-measurement devices extend up to 1 mm beyond the outer surface of the first electrode member and the at least one thermal transfer member, respectively.

According to some embodiments, an outer diameter of a portion of the at least one thermal heat transfer member comprising the second plurality of temperature-measurement devices is greater than the outer diameter of the elongate body so as to facilitate greater insertion depth within the tissue, thereby increasing isolation of the thermocouples or other temperature-measurement devices from the thermal effects of the electrode member(s).

In accordance with several embodiments, a treatment system comprises a medical instrument (e.g., an ablation catheter), a processor, and an energy source. The medical instrument comprises an elongate body having a proximal end and a distal end, an energy delivery member (e.g., electrode) positioned at the distal end of the elongate body, a first plurality of temperature-measurement devices carried by or positioned along or within the energy delivery member, and a second plurality of temperature-measurement devices positioned proximal of the electrode along the elongate body. The energy delivery member may be configured to contact tissue of a subject and to deliver energy generated by the energy source to the tissue. In some embodiments, the energy is sufficient to at least partially ablate the tissue. In some embodiments, the first plurality of temperature-measurement devices are thermally insulated from the energy delivery member and the second plurality of temperature-measurement devices are thermally insulated from the energy delivery member. In one embodiment, the second plurality of temperature-measurement devices is spaced apart around an outer surface of the elongate body. The energy source of the embodiment of the system may be configured to provide the energy to the energy delivery member through one or more conductors (e.g., wires, cables, etc.) extending from the energy source to the energy delivery member.

The processor of the embodiment of the system may be programmed or otherwise configured (e.g., by execution of instructions stored on a non-transitory computer-readable storage medium) to receive signals from each of the temperature-measurement devices indicative of temperature and determine an orientation of the distal end of the elongate body of the ablation catheter with respect to the tissue based on the received signals. In some embodiments, the processor may be configured to adjust one or more treatment parameters based on the determined orientation. The one or more treatment parameters may include, among other things, duration of treatment, power of energy, target or setpoint temperature, and maximum temperature.

In some embodiments, the processor is configured to cause an identification of the determined orientation to be output to a display. The output may comprise textual information (such as a word, phrase, letter or number). In some embodiments, the display comprises a graphical user interface and the output comprises one or more graphical images indicative of the determined orientation.

In some embodiments, the determination of the orientation of the distal end of the elongate body of the medical instrument with respect to the tissue is based on a comparison of tissue measurements determined from received signals with respect to each other. The orientation may be selected from one of three orientation options: perpendicular, parallel and angled or oblique. In one embodiment, the processor is configured to generate an output to terminate delivery of energy if the determined orientation changes during energy delivery (e.g., an alarm to cause a user to manually terminate energy delivery or a signal to automatically cause termination of energy delivery. In some embodiments, the processor may be configured to adjust one or more treatment parameters based on the determined orientation. The one or more treatment parameters may include, among other things, duration of treatment, power of energy, target or setpoint temperature, and maximum temperature.

According to some embodiments, a treatment system comprises a medical instrument (e.g., an ablation catheter) and a processor. The medical instrument may comprise an elongate body having a proximal end and a distal end, an energy delivery member positioned at the distal end of the elongate body, the energy delivery member being configured to contact tissue of a subject and to deliver energy (e.g., ablative energy) to the tissue, a first plurality of temperature-measurement devices positioned within the energy delivery member, and a second plurality of temperature-measurement devices positioned proximal to the energy delivery member along the elongate body. The first plurality of temperature-measurement devices may be thermally insulated from the energy delivery member and may be spaced apart from each other and the second plurality of temperature-measurement devices may be thermally insulated from the energy delivery member and may be spaced apart around an outer surface of the elongate body.

A processor of the embodiment of the treatment system may be programmed or otherwise configured (e.g., by execution of instructions stored on a non-transitory computer-readable storage medium) to receive signals from each of the temperature-measurement devices, and calculate a peak temperature of the tissue at a depth based on the received signals. The peak temperature may comprise an extreme temperature (e.g., a peak or a valley/trough temperature, a hot or a cold temperature, a positive peak or a negative peak).

According to some embodiments, the processor is configured to calculate the peak temperature of the tissue at a depth by comparing individual temperature measurements determined from the received signals to each other. In some embodiments, the processor is configured to adjust one or more treatment parameters based on the calculated peak temperature, including duration of treatment, power of energy, target temperature, and maximum temperature.

According to some embodiments, the processor is configured to generate an output to automatically terminate delivery of energy if the calculated peak temperature exceeds a threshold temperature or to generate an alert to cause a user to manually terminate energy delivery. In some embodiments, the processor is configured to cause an identification of the calculated peak temperature to be output to a display (e.g., using a color, textual information, and/or numerical information).

In accordance with several embodiments, a treatment system comprises a medical instrument (e.g., ablation catheter) comprising an elongate body comprising a proximal end and a distal end, an energy delivery member positioned at the distal end of the elongate body. In one embodiment, the energy delivery member (e.g., electrode) is configured to contact tissue of a subject and to deliver energy (e.g., ablative energy) to the tissue. The medical instrument comprises a first plurality of temperature-measurement devices positioned within separate openings or apertures formed in the energy delivery member, and a second plurality of temperature-measurement devices positioned proximal to the energy delivery member along the elongate body. The first plurality of temperature-measurement devices may be thermally insulated from the electrode and spaced apart from each other and the second plurality of temperature-measurement devices may be thermally insulated from the electrode. In one embodiment, the second plurality of temperature-measurement devices is spaced apart around an outer surface of the elongate body. The treatment system may also comprise a processor that is programmed or otherwise configured (e.g., by execution of instructions stored on a non-transitory computer-readable storage medium) to receive signals from each of the temperature-measurement devices and determine an estimated location of a peak temperature zone at a depth within the tissue based, at least in part, on the received signals. In some embodiments, the processor determines individual temperature measurements based on the received signals and compares them to determine the estimated location of the peak temperature. The processor may be configured to adjust one or more treatment parameters based on the estimated location, including duration, power, target temperature, and maximum temperature. The processor may also be configured to cause an identification of the estimated location to be output to a display. The output may comprise alphanumeric information and/or one or more graphical images indicative of the estimated location of the peak temperature zone.

In accordance with several embodiments, a method of determining a peak temperature of tissue being ablated at a depth from a surface of the tissue may comprise receiving signals indicative of temperature from a first plurality of temperature sensors positioned at a distal end of an ablation catheter. In one embodiment, each of the first plurality of temperature sensors is spaced apart around the distal end of the ablation catheter. The method also comprises receiving signals indicative of temperature from a second plurality of temperature sensors positioned at a distance proximal to the first plurality of temperature sensors. The method further comprises determining temperature measurements from the signals received from the first plurality of temperature sensors and the second plurality of temperature sensors and comparing the determined temperature measurements to each other. In some embodiments, the method comprises applying one or more correction factors to one or more of the determined temperature measurements based, at least in part, on the comparison to determine the peak temperature. In one embodiment, the method comprises outputting the determined peak temperature on a display textually, visually and/or graphically. In one embodiment, the method comprises adjusting one or more treatment (e.g., ablation) parameters and/or terminating ablation based on the determined hotspot temperature. The second plurality of temperature sensors may be spaced apart around a circumference of the ablation catheter or other medical instrument.

According to some embodiments, a method of determining a location of a peak temperature zone within tissue being ablated comprises receiving signals indicative of temperature from a first plurality of temperature sensors positioned at a distal end of an ablation catheter. In one embodiment, each of the first plurality of temperature sensors is spaced apart around the distal end of the ablation catheter. The method comprises receiving signals indicative of temperature from a second plurality of temperature sensors positioned at a distance proximal to the first plurality of temperature sensors. The method further comprises determining temperature measurements from the signals received from the first plurality of temperature sensors and the second plurality of temperature sensors and, comparing the determined temperature measurements to each other. The method may comprise determining a location of a peak temperature zone of a thermal lesion based, at least in part, on the comparison. In one embodiment, the method comprises outputting the determined peak location on a display, textually, visually and/or graphically. In one embodiment, each of the second plurality of temperature sensors is spaced apart around a circumference of the ablation catheter.

According to some embodiments, a method of determining an orientation of a distal tip of an ablation catheter with respect to tissue in contact with the distal tip comprises receiving signals indicative of temperature from a first plurality of temperature sensors positioned at a distal end of an ablation catheter and receiving signals indicative of temperature from a second plurality of temperature sensors positioned at a distance proximal to the first plurality of temperature sensors. The method further comprises determining temperature measurements from the signals received from the first plurality of temperature sensors and the second plurality of temperature sensors and comparing each of the determined temperature measurements with each other. The method further comprises determining an orientation of a distal tip of an ablation catheter with respect to tissue in contact with the distal tip based, at least in part, on the comparison. In one embodiment, the method comprises outputting the determined orientation on a display. The output may comprise textual information or one or more graphical images. The embodiments of the methods may also comprise terminating energy delivery or generating an output (e.g., an alert) to signal to a user that energy delivery should be terminated. In some embodiments, each of the first plurality of temperature sensors is spaced apart around a distal end of the ablation catheter and each of the second plurality of temperature sensors is spaced apart around a circumference of the ablation catheter.

In accordance with several embodiments, a system for quickly determining an orientation of an ablation catheter with respect to a target region comprises an ablation catheter comprising an elongate body having a plurality of temperature-measurement devices distributed along a distal end of the elongate body and at least one electrode member positioned at the distal end of the elongate body, an energy source configured to apply ablative energy to the electrode member sufficient to ablate target tissue and at least one processing device. The at least one processing device is configured to, upon execution of specific instructions stored on a computer-readable medium, determine an orientation of a contact surface of the at least one electrode member with respect to the target tissue based on a first set of orientation criteria at a plurality of time points over a first time period.

The contact surface of the at least one electrode member may be an outer distal surface of the at least one electrode member (for example a tip electrode member having a planar or rounded outer distal surface). In some embodiments, the at least one electrode member is a distal electrode member of a combination electrode assembly configured for high-resolution mapping and radiofrequency energy delivery, the combination electrode assembly comprising the distal electrode member and a proximal electrode member separated by a gap, such as the combination electrode assemblies described herein. In some embodiments, the at least one processing device is configured to determine the orientation of the contact surface of the at least one electrode member with respect to the target tissue based on a second set of orientation criteria at a plurality of time points over a second time period starting after an end of the first time period. The second set of orientation criteria may be different than the first orientation criteria. In embodiments involving two sets of orientation criteria, the first time period may correspond to a temperature rise phase where temperatures are rising and the second time period corresponds to a steady state phase where temperatures remain at a steady peak temperature without significant deviation. For example, the first time period may be between 1 and 20 seconds, between 5 and 20 seconds, between 5 and 13 seconds, between 3 and 15 seconds, or between 5 and 10 seconds after initial application of ablative energy, as well as overlapping ranges thereof or any value within the ranges. In some embodiments, the plurality of time points over the first time period and the second time period occur every second; however other frequencies are possible for both time periods (e.g., every 100 ms, every 500 ms, every 1500 ms, every 2 seconds, every 3 seconds, every 4 seconds, every 5 seconds). In some embodiments, the frequency of the time points over the second period is longer than the frequency of the time points over the first period.

In some embodiments, the first set of orientation criteria comprises time-dependent conditions and/or static conditions and the second set of orientation criteria consists only of static conditions. The first set of orientation criteria in the temperature rise phase may comprise comparisons of time-based characteristics of temperature responses of at least two of the plurality of temperature-measurement devices (for example, rate of change of temperature over a period of time or the time that it takes to rise to a certain temperature from a starting temperature). For example, the comparisons of time-based characteristics of temperature responses may include different comparisons between time-based characteristics of temperature responses of a proximal group of temperature-measurement devices and time-based characteristics of temperature responses of a distal group of temperature-measurement devices. The at least one processing device may be configured to determine an orientation from a plurality of orientation, or alignment, candidates or options based on the comparisons. For example, if the average proximal temperature rise is greater than the average distal temperature rise by a certain factor, this may be an indicator that the electrode-tissue orientation is oblique. As another example, time-dependent thresholds may be used to help determine orientation during the temperature rise phase. For example, the maximum proximal temperature rise can be subtracted from the minimum distal temperature rise and this value can be compared to a time-dependent threshold. If the threshold is exceeded, that may be an indicator that the orientation is oblique. The second set of orientation criteria may comprise comparisons of temperature measurement values of at least two of the plurality of temperature-measurement devices.

The first set of orientation criteria and the second set of orientation criteria may both involve first testing for a first orientation and if the orientation for the first orientation are not satisfied then testing for a second orientation. If the orientation criteria for the second orientation are not met, then the at least one processing device may determine that the ablation catheter is in a third orientation by default if there are only three orientation options. The first set of orientation criteria and the second set of orientation criteria may both involve testing for the orientations in the same order (e.g., oblique, then parallel, then perpendicular) or different orders. The orientation criteria can vary depending on the order of testing of the orientation options. In some embodiments, temperatures may constantly increase during a desired time period and so only one set of orientation criteria are used.

In accordance with several embodiments, a system for determining an orientation of an ablation catheter with respect to a target region comprises an ablation catheter comprising an elongate body having a plurality of temperature-measurement devices distributed along a distal end of the elongate body, an energy source configured to apply ablative energy sufficient to ablate target tissue to at least one energy delivery member positioned along the distal end of the ablation catheter; and at least one processing device. The at least one processing device is configured to, upon execution of specific instructions stored on a computer-readable medium: obtain temperature measurements from each of the plurality of temperature-measurement devices at a plurality of time points; at each time point, determine a time-based characteristic of a temperature response for each of the plurality of temperature-measurement devices from the obtained temperature measurements; and at each time point, determine an orientation of the distal end of the elongate body from one of a plurality of orientation options based, at least in part, on a comparison of the time-based characteristics of the temperature responses for at least two of the plurality of temperature-measurement devices.

The time-based characteristic of the temperature response may be a rate of change of temperature measurement values between a current time point and a previous time point or the time elapsed between a starting temperature value and a predefined or predetermined increased temperature value. In some embodiments, time-based characteristic of the temperature response is a difference between temperature measurement values at a current time point and a previous time point. In some embodiments, the plurality of time points are spaced apart at regular time intervals (e.g., every second). The temperature measurement values may be moving average values. In some embodiments, the temperature measurement value at a previous time point is a starting temperature value obtained within five seconds after the ablative energy is initially applied by the energy source; however times other than five seconds may be used (e.g., within ten seconds, within eight seconds, within six seconds, within four seconds, within three seconds, within two seconds, at or within one second). The starting temperature value may be an average of temperature values obtained over a period of time (for example, an average of temperature values obtained every 100 ms from 0 to 1 second after initiation of energy delivery).

In various embodiments, the plurality of temperature-measurement devices consists of two spaced-apart groups of temperature-measurement devices. In one embodiment, the temperature-measurement devices consists of six thermocouples. The six thermocouples may comprise a first group of three co-planar thermocouples and a second group of three co-planar thermocouples spaced proximal to the first group of three thermocouples. Other numbers of temperature-measurement devices may be used as desired and/or required.

In several embodiments, an initial orientation is advantageously determined quickly after application of ablative energy by the energy source (e.g., less than 20 seconds, less than 15 seconds, less than 10 seconds, less than 5 seconds). In accordance with several embodiments, the orientation may be determined quickly because the comparisons of the temperature responses of the temperature-measurement devices are based on rate of change rather than the spread or differences in values after reaching a steady state. The plurality of orientation options may comprise two or three orientations. If two orientation options are possible, the options may consist of a parallel orientation and a perpendicular orientation. If three orientation options are possible, the options may consist of a parallel orientation, a perpendicular orientation and an oblique (or angled) orientation. In embodiments involving three orientation options, the at least one processing device is configured to first determine whether the orientation is an oblique orientation based on orientation criteria defined for the oblique orientation. If the oblique orientation criteria are satisfied, the orientation is determined to be oblique. If the oblique orientation criteria are not satisfied, then the at least one processing device is then configured to determine whether the orientation is in a parallel orientation based on orientation criteria defined for the parallel orientation. If the parallel orientation criteria are satisfied, the orientation is determined to be parallel. If the parallel orientation criteria are not met, then the at least one processing device determines that the ablation catheter must be in a perpendicular orientation by default. Other orders may be used. For example, a perpendicular or parallel condition could be tested for first if only two orientation options are possible.

In accordance with several embodiments, the at least one processing device is configured to generate an output indicative of the determined orientation The output may comprise a graphical icon of an electrode in the determined orientation and/or other visual indicator identifying the determined orientation from the plurality of orientation options. For example, the output may comprise a graphical user interface that includes three radio buttons, each accompanied by a textual label of a respective one of the plurality of orientation options and the visual indicator may indicate or mark the radio button corresponding to the determined orientation.

The orientation criteria may comprise one or more of the following: a comparison of a relationship between an average rate of change of temperature measurement values of the first plurality of temperature-measurement devices and an average rate of change of temperature measurement values of the second plurality of temperature-measurement devices, a comparison of a relationship between a maximum rate of change of temperature measurement values of the first plurality of temperature-measurement devices and a maximum rate of change of temperature measurement values of the second plurality of temperature-measurement devices, a comparison of a relationship between a maximum rate of change of temperature measurement values of the first plurality of temperature-measurement devices and a minimum rate of change of temperature measurement values of the second plurality of temperature-measurement devices, a comparison of a relationship between a minimum rate of change of temperature measurement values of the first plurality of temperature-measurement devices and a maximum rate of change of temperature measurement values of the second plurality of temperature-measurement devices, a comparison of a rate of change of temperature measurement values from a previous time point until the current time point between at least two of the first plurality of temperature-measurement devices, and/or a comparison of a rate of change of temperature measurement values from a previous time point until the current time point between at least two of the second plurality of temperature-measurement devices.

In accordance with several embodiments, a method of determining an orientation of a distal end of an ablation catheter with respect to a target region comprises receiving signals indicative of temperature from a plurality of temperature sensors distributed along a distal end of an ablation catheter at a plurality of time points over a period of time, determining temperature measurement values at each of the plurality of time points for each of the plurality of temperature sensors, calculating a rate of change between the determined temperature values at each of the plurality of time points and a starting temperature value for each of the plurality of temperature sensors, and, at each time point of the plurality of time points, determining an orientation of the distal end of the ablation catheter relative to a target surface based on a comparison of the calculated rate of change of at least two of the plurality of temperature sensors.

Determining temperature measurement values at each of the plurality of time points for each of the plurality of temperature sensors comprises calculating a moving average value at each of the plurality of time points based on a current temperature measurement value and one or more previous temperature measurement values in some embodiments. Calculating the rate of change between the determined temperature values at each of the plurality of time points and the starting temperature value for each of the plurality of temperature sensors may comprise subtracting the starting temperature value from the moving average value and dividing by the time elapsed from the start of the period of time to the current time point. In some embodiments, the starting temperature value may be determined by receiving signals indicative of temperature from a plurality of temperature sensors distributed along a distal end of an ablation catheter at a first plurality of time points in a first period of time, determining temperature measurement values at each of the first plurality of time points for each of the plurality of temperature sensors and then calculating a starting temperature value for each of the plurality of temperature sensors based on the determined temperature measurement values.

In some embodiments, the plurality of temperature sensors comprises a first plurality of temperature sensors (e.g., a first co-planar group of three thermocouples or thermistors) positioned at a distal tip of the ablation catheter and a second plurality of temperature sensors (e.g., a second co-planar group of three thermocouples or thermistors) positioned at a distance proximal to the first plurality of temperature sensors. In some embodiments, determining the orientation of the distal end of the ablation catheter relative to the target surface based on a comparison of the calculated rates of change of at least two of the plurality of temperature sensors comprises determining whether the calculated rates of change satisfy one or more orientation criteria of a respective orientation (e.g., oblique, parallel or perpendicular). The orientation criteria may be different for each of the orientation options. At least some of the orientation criteria are time-dependent. In accordance with several embodiments, the orientation criteria are empirically determined based on previous data.

In accordance with several embodiments, a method of determining an orientation of a distal end of an ablation catheter with respect to a target region comprises receiving signals indicative of temperature from a plurality of temperature sensors distributed along a distal end of an ablation catheter at a plurality of time points over a period of time, determining temperature measurement values at each of the plurality of time points for each of the plurality of temperature sensors, determining a characteristic of a temperature response at each of the plurality of time points for each of the plurality of temperature sensors, and, at each time point of the plurality of time points, determining an orientation of the distal end of the ablation catheter relative to a target surface based on a comparison of the characteristics of the temperature responses of at least two of the plurality of temperature sensors. The characteristic of the temperature response may be a rate of change of the temperature or a difference between a temperature measurement value obtained at a current time point and a temperature measurement value obtained at a previous time point or the time it takes to rise from a starting temperature value to a predetermined increased temperature value.

In accordance with several embodiments, a method of determining an orientation of a distal end of an ablation catheter with respect to a target region comprises receiving signals indicative of temperature from a plurality of temperature sensors distributed along a distal end of an ablation catheter at a first plurality of time points over a first period of time; determining temperature measurement values at each of the first plurality of time points for each of the plurality of temperature sensors; at each time point of the first plurality of time points, determining an orientation of the distal end of the ablation catheter relative to a target surface based on a first set of orientation criteria applied to the determined temperature measurement values; receiving signals indicative of temperature from the plurality of temperature sensors at a second plurality of time points over a second period of time after the first period of time; determining temperature measurement values at each of the second plurality of time points for each of the plurality of temperature sensors; and, at each time point of the second plurality of time points, determining an orientation of the distal end of the ablation catheter relative to a target surface based on a second set of orientation criteria applied to the determined temperature measurement values. In several embodiments, the second set of orientation criteria is different than the first set of orientation criteria. For example, the first set of orientation criteria may comprise comparisons of time-based characteristics of temperature responses of at least two of the plurality of temperature sensors and the second set of orientation criteria comprises comparisons of temperature measurement values of at least two of the plurality of temperature sensors. The first period of time may correspond to a temperature rise phase and the second period of time may correspond to a steady state phase. The first set of orientation criteria and the second set of orientation criteria may be empirically determined.

In accordance with several embodiments, a method of determining an orientation of a distal end of an ablation catheter with respect to a target region comprises receiving signals indicative of temperature from a plurality of temperature sensors distributed along a distal end of an ablation catheter at a first plurality of time points in a first period of time; determining temperature measurement values at each of the first plurality of time points for each of the plurality of temperature sensors; calculating a starting temperature value for each of the plurality of temperature sensors based on the determined temperature measurement values; receiving signals indicative of temperature from the plurality of temperature sensors at a second plurality of time points in a second period of time after the first period of time; determining temperature measurement values at each of the second plurality of time points for each of the plurality of temperature sensors; calculating a rate of change between the determined temperature values at each of the second plurality of time points and a starting temperature value for each of the plurality of temperature sensors; and, at each time point of the second plurality of time points, determining an orientation of the distal end of the ablation catheter relative to a target surface based on a comparison of the calculated rate of change of at least two of the plurality of temperature sensors. In some embodiments, the method further comprises receiving signals indicative of temperature from the plurality of temperature sensors during a third period of time after the second period of time, determining temperature measurement values for each of the plurality of temperature sensors and determining an orientation of the distal end of the ablation catheter relative to the target surface based on a comparison of the temperature measurement values of at least two of the plurality of temperature sensors.

In accordance with several embodiments, a system comprises at least one signal source configured to deliver at least a first frequency and a second frequency to a pair of electrodes or electrode portions of a combination electrode or electrode assembly. The system also comprises a processing device configured to: obtain impedance measurements while the first frequency and the second frequency are being applied to the pair of electrodes by the signal source, process the electrical (e.g., voltage, current, impedance) measurements obtained at the first frequency and the second frequency, and determine whether the pair of electrodes is in contact with tissue based on said processing of the electrical (e.g., impedance) measurements. The pair of electrodes may be positioned along a medical instrument (e.g., at a distal end portion of an ablation catheter). The pair of electrodes may comprise radiofrequency electrodes and the at least one signal source may comprise one, two or more sources of radiofrequency energy.

The signal source may comprise a first signal source configured to generate, deliver or apply signals to the pair of electrodes having a frequency configured for tissue ablation and a second signal source configured to generate, deliver or apply signals to the pair of electrodes having frequencies adapted for contact sensing and/or tissue type determination (e.g., whether the tissue is ablated or still viable). The first and second signal sources may be integrated within an energy delivery module (e.g., RF generator) or within an elongate body or handle of a medical instrument (e.g., ablation catheter). In some embodiments, the second signal source is within a contact sensing subsystem, which may be a distinct and separate component from the energy delivery module and medical instrument or integrated within the energy delivery module or medical instrument. In one embodiment, only one signal source capable of applying signals having frequencies adapted for ablation or other treatment and signals having frequencies adapted for contact sensing or tissue type determination functions is used. The frequencies adapted for contact sensing or tissue type determination may be within the treatment frequency range or outside the treatment frequency range. By way of example, in one non-limiting embodiment, the system comprises an energy source configured to generate, deliver or apply signals to at least a pair of electrode members (and also to a ground pad or reference electrode) to deliver energy having a frequency configured for tissue ablation or other treatment and a signal source configured to generate, deliver or apply signals to the pair of electrode members (and not to a ground pad or reference electrode) having frequencies adapted for contact sensing and/or tissue type determination (e.g., whether the tissue is ablated or still viable). The signals generated by the signal source may comprise constant current AC excitation signals or AC voltage excitation signals. The excitation signals may advantageously be outside the frequency range of the ablative frequencies and/or electrogram mapping frequencies. The energy source and the signal source may both be integrated within an energy delivery module (e.g., RF generator) or one of the sources (e.g., the signal source) may be incorporated within an elongate body or handle of a medical instrument (e.g., ablation catheter). In some embodiments, the signal source is within a contact sensing subsystem, which may be a distinct and separate component from the energy delivery module and medical instrument or integrated within the energy delivery module or medical instrument. In some embodiments, a single source configured for applying signals having frequencies adapted for ablation or other treatment and configured for applying signals having frequencies adapted for contact sensing or tissue type determination functions is used. Signals having the treatment frequencies (for example, frequencies adapted for ablation of cardiac tissue) may also be delivered to a ground pad or reference electrode.

In some embodiments, the system consists essentially of or comprises a medical instrument (e.g., an energy delivery device), one or more energy sources, one or more signal sources and one or more processing devices. The medical instrument (e.g., energy delivery catheter) may comprise an elongate body having a proximal end and a distal end and a pair of electrodes or electrode portions (e.g., a combination, or composite, such as a split-tip, electrode assembly) positioned at the distal end of the elongate body. In one embodiment, the pair of electrodes comprises or consists essentially of a first electrode positioned on the elongate body and a second electrode positioned adjacent (e.g., proximal of) the first electrode. The first electrode and the second electrode may be configured to contact tissue of a subject and provide energy to the tissue to heat (e.g., ablate or otherwise treat) the tissue at a depth from the surface of the tissue. In one embodiment, the pair of electrodes comprises an electrically insulating gap positioned between the first electrode and the second electrode, the electrically insulating gap comprising a gap width separating the first and second electrodes. A separator (e.g., a capacitor or insulation material) may be positioned within the electrically insulating gap.

The one or more signal sources may be configured to deliver signals over a range of frequencies (e.g., frequencies within a radiofrequency range). In some embodiments, the processing device is configured to execute specific program instructions stored on a non-transitory computer-readable storage medium to: obtain impedance or other electrical measurements while different frequencies of energy within the range of frequencies are being applied to the pair of electrodes by a signal source, process the impedance or other electrical measurements obtained at the first frequency and the second frequency, and determine whether at least one of (e.g., the distal-most electrode) the pair of electrodes is in contact with tissue based on said processing of the impedance or other electrical measurements. In accordance with several embodiments, the impedance measurements constitute bipolar contact impedance between the pair of electrodes or between the electrode members of a combination electrode assembly and not the impedance between an electrode and target tissue. In accordance with several embodiments, the impedance or other electrical measurements do not involve passing current to one or more patch or reference electrodes positioned at a location external to the medical instrument or at a location remote from the target tissue (for example, at a location on the skin of a patient at the neck, torso and/or leg).

In some embodiments, the medical instrument consists essentially of or comprises a radiofrequency ablation catheter and the first and second electrodes or electrode portions comprise radiofrequency electrodes. The signal source(s)

may comprise a radiofrequency (RF) generator. In one embodiment, the range of frequencies that is delivered by the signal source(s) (e.g., of a contact sensing subsystem) comprises at least a range between 1 kHz and 5 MHz (e.g., between 5 kHz and 1000 kHz, between 10 kHz and 500 kHz, between 5 kHz and 800 kHz, between 20 kHz and 800 kHz, between 50 kHz and 5 MHz, between 100 kHz and 1000 kHz, and overlapping ranges thereof). The signal source(s) may also be configured to deliver frequencies below and above this range. The frequencies may be at least greater than five times or at least greater than ten times the electrogram mapping frequencies so as not to interfere with high-resolution mapping images or functions obtained by the first and second electrodes or electrode portions. In one embodiment, the different frequencies at which impedance measurements are obtained consists only of two discrete frequencies. In another embodiment, the different frequencies comprise two or more discrete frequencies. In some embodiments, the processing device is configured to obtain impedance measurements while a full sweep of frequencies from a minimum frequency to a maximum frequency of the range of frequencies is applied to the pair of electrodes or electrode portions. As one example, the range of frequencies is between 5 kHz and 1000 kHz. The second frequency may be different from (e.g., higher or lower than) the first frequency. In accordance with several embodiments, the frequencies used for contact sensing or determination are outside (for example, below) the frequency range of the ablative frequencies.

The system may comprise an ablative energy source (e.g., signal source such as an RF generator) configured to deliver signals to the pair of electrodes (and possibly also to a ground pad or reference electrode) to generate energy sufficient to ablate or otherwise treat tissue (such as cardiac tissue). In one embodiment, the processing device is configured to adjust one or more energy delivery parameters of the ablative energy based on a determination of whether at least one of the pair of electrodes is in contact with tissue and/or is configured to terminate energy delivery based on a determination of whether at least one of the pair of electrodes is in contact with tissue or that contact has been lost. In some embodiments, the ablative energy source and the at least one signal source comprise a single source. In other embodiments, the signal source comprises a first source and the ablative energy source comprises a second source that is separate and distinct from the first source. In some embodiments, the processing is performed in the time domain. In some embodiments, the processing is performed in the frequency domain. Portions of the processing may be performed in both the time domain and the frequency domain.

In some embodiments, the processing device is configured to execute specific program instructions stored on a non-transitory computer-readable storage medium to generate an output indicative of contact. The processing device may be configured to cause the generated output to be displayed on a display (for example an LCD or LED monitor) in communication with the processing device. In various embodiments, the output comprises textual information, quantitative information (e.g., numeric information, binary assessment of whether contact exists or not) and/or a qualitative information (e.g., color or other information indicative of a level of contact).

In accordance with several embodiments, a system comprises a signal source configured to deliver signals having a range of frequencies and a processing device configured to execute specific program instructions stored on a non-transitory computer-readable storage medium to: obtain impedance (e.g., bipolar contact impedance) or other electrical measurements while different frequencies of energy are being applied to a pair of electrodes (e.g., combination electrode, or composite (such as a split-tip), electrode assembly) by the signal source, compare the impedance measurements obtained at the different frequencies of energy; and determine whether or not tissue in contact with at least one of the pair of electrodes has been ablated. In some embodiments, the range of frequencies over which contact determination is made is between 5 kHz and 1000 kHz. The different frequencies consist of two discrete frequencies in one embodiment or may comprise two or more discrete frequencies in other embodiments. The processing device may be configured to obtain impedance measurements while a full sweep of frequencies from a minimum frequency to a maximum frequency of the range of frequencies (e.g., 5 kHz to 1000 kHz) is applied to the pair of electrodes. In some embodiments, one component of an impedance measurement (e.g., impedance magnitude) is obtained at a first frequency and a second component of a different impedance measurement (e.g., phase angle) is obtained at a second frequency. A comparison (e.g., derivative of impedance versus frequency, delta or slope of impedance vs. frequency) of impedance magnitude measurements between the pair of electrodes at two or more different frequencies may also be obtained. A weighted combination of various impedance measurements at two or more different frequencies may be calculated by the processing device and used by the processing device to determine an overall contact level or state. The impedance measurements may be obtained directly or may be calculated based on electrical parameter measurements, such as voltage and/or current measurements. In accordance with several embodiments, the impedance measurements comprise bipolar impedance measurements.

In some embodiments, the processing device is configured to execute specific program instructions stored on a non-transitory computer-readable storage medium to generate an output indicative of tissue type based on the determination of whether or not tissue in contact with at least one of the pair of electrodes has been ablated. The processing device may be configured to cause the generated output to be displayed on a display in communication with the processing device. The output may comprise one or more of textual information, a color or other qualitative information, and numerical information. In various embodiments, the processing device is configured to adjust one or more energy delivery parameters based on the determination of whether the tissue in contact with the pair of electrodes has been ablated and/or is configured to terminate energy delivery based on the determination of whether tissue in contact with the pair of electrodes has been ablated.

In accordance with several embodiments, a system for determining whether a medical instrument is in contact with tissue based, at least in part, on impedance measurements comprises a signal source configured to deliver signals having different frequencies to a pair of electrodes of a medical instrument and a processing device configured to process a resulting waveform that formulates across the pair of electrodes to obtain impedance measurements at a first frequency and a second frequency and determine a ratio between the magnitude of the impedance at the second frequency and the first frequency. If the determined ratio is below a predetermined threshold indicative of contact, the processing device is configured, upon execution of stored instructions on a computer-readable medium, to generate a first output indicative of contact. If the determined ratio is above the predetermined threshold, the processing device is configured to, upon execution of stored instructions on a computer-readable medium, generate a second output indicative of no contact. In one embodiment, the signal source comprises a radiofrequency energy source. The first and second frequencies may be between 5 kHz and 1000 kHz. In some embodiments, the signal source is configured to generate signals having a frequency adapted for tissue ablation. In other embodiments, the system comprises a second signal source (or an ablative energy source) configured to generate signals having a frequency adapted for tissue ablation. The frequency adapted for tissue ablation may be between 400 kHz and 600 kHz (e.g., 400 kHz, 450 kHz, 460 kHz, 480 kHz, 500 kHz, 550 kHz, 600 kHz, 400 kHz-500 kHz, 450 kHz-550 kHz, 500 kHz-600 kHz, or overlapping ranges thereof). In various embodiments, the predetermined threshold is a value between 0.5 and 0.9. Processing the waveforms may comprise obtaining voltage and/or current measurements and calculating impedance measurements based on the voltage and/or current measurements or directly obtaining impedance measurements.

A method of determining whether a medical instrument is in contact with a target region (e.g., tissue) based, at least in part, on electrical measurements (e.g., impedance measurements), may comprise applying signals having a first frequency and a second frequency to a pair of electrodes or electrode portions of the medical instrument, processing a resulting waveform to obtain impedance measurements at the first frequency and the second frequency, and determining a ratio between the magnitude of the impedance at the second frequency and the first frequency. If the determined ratio is below a predetermined threshold indicative of contact, the method comprises generating a first output indicative of contact. If the determined ratio is above the predetermined threshold, the method comprises generating a second output indicative of no contact. The method may further comprise applying a signal adapted to cause ablative energy to be delivered by the pair of electrodes or electrode portions sufficient to ablate the target region (for example, cardiac tissue or other body tissue).

In accordance with several embodiments, a system for determining a contact state of a distal end portion of a medical instrument with a target region (e.g., tissue) based, at least in part, on electrical measurements comprises a signal source configured to generate at least one signal having a first frequency and a second frequency to be applied to a pair of electrode members of a combination electrode assembly. The signal source may be a component of a contact sensing or detection subsystem or an energy delivery module, such as a radiofrequency generator. The system also comprises a processor or other computing device configured to, upon execution of specific program instructions stored in memory or a non-transitory computer-readable storage medium, cause the signal source to generate and apply the at least one signal to the pair of electrode members. The signal may be a single multi-tone waveform or signal or multiple waveforms or signals having a single frequency.

The processor may be configured to process a resulting waveform that formulates across the pair of electrode members to obtain a first electrical measurement at the first frequency and to process the resulting waveform that formulates across the pair of electrode members to obtain a second electrical measurement at the second frequency of the plurality of frequencies. The processor is further configured to: determine an impedance magnitude based on the first electrical measurement (e.g., voltage and/or current measurement), determine an impedance magnitude and a phase based on the second electrical measurement, and calculate a contact indication value indicative of a state of contact between the distal end portion of the medical instrument and the target region based on a criterion combining the impedance magnitude based on the first electrical measurement, a ratio of the impedance magnitudes based on the first electrical measurement and the second electrical measurement, and the phase based on the second electrical measurement. The first and second electrical measurements may comprise voltage and/or current measurements or direct impedance measurements between the pair of electrode members. In some embodiments, the first and second electrical measurements do not comprise direct measurements of electrical parameters or a degree of coupling between an electrode and tissue but are measurements between two electrode members. Impedance measurements may be calculated based on the voltage and/or current measurements or may be directly obtained or measured by an instrument or device configured to output impedance measurements. The impedance measurements may comprise complex impedance measurements composed of real and imaginary components (for example, impedance magnitude and phase angle measurements or resistance and reactance measurements). In accordance with several embodiments, the impedance measurements comprise bipolar contact impedance measurements between the two electrode members.

In some embodiments, the criterion comprises a weighted combination of the impedance magnitude based on the first electrical measurement, a ratio of the impedance magnitudes based on the first and second electrical measurements, and the phase based on the second electrical measurement. In some embodiments, the criterion comprises an if-then case conditional criterion, such as described in connection with FIGS. 11 and 11A. In various embodiments, only one impedance measurement or calculation (e.g., only impedance magnitude, only slope between impedance magnitude values, or only phase) or only two types of impedance measurements or calculations are used to determine the contact state.

In accordance with several embodiments, a system for determining whether a medical instrument is in contact with a target region (e.g., tissue) based, at least in part, on impedance measurements consists essentially of or comprises a signal source configured to generate one or more signals having a first frequency and a second frequency to a pair of electrodes (e.g., positioned at a distal end of a medical instrument, catheter or probe) and a processing device configured to execute specific program instructions stored on a non-transitory computer-readable storage medium to process a resulting waveform that formulates across the pair of electrodes to obtain impedance measurements at the first frequency and the second frequency. If the impedance magnitude at the first and/or second frequency is above a predetermined threshold indicative of contact, the processing device is configured to, upon execution of stored instructions on the computer-readable storage medium, generate a first output indicative of contact. If the impedance magnitude at the first and/or second frequency is below a predetermined threshold indicative of no contact, the processing device is configured to, upon execution of stored instructions on the computer-readable storage medium, generate a second output indicative of no contact. Processing the waveforms may comprise obtaining voltage and/or current measurements and calculating impedance measurements based on the voltage and/or current measurements or directly obtaining impedance measurements.

A method of determining whether a medical instrument is in contact with a target region (e.g., tissue) based, at least in part, on impedance measurements comprises delivering at least one signal having a first frequency and a second frequency (e.g., a multi-tonal waveform) to a pair of electrodes or electrode portions and processing a resulting waveform that formulates across the pair of electrodes to obtain impedance measurements at the first frequency and the second frequency. If the impedance magnitude at the first frequency and/or second frequency is above a predetermined threshold indicative of contact, the method comprises generating a first output indicative of contact. If the impedance magnitude at the first frequency and/or second frequency is below a predetermined threshold indicative of no contact, the method comprises generating a second output indicative of no contact. The method may further comprise applying a signal adapted to cause ablative energy to be delivered by the pair of electrodes or electrode portions sufficient to ablate or otherwise treat cardiac or other body tissue.

A method of determining whether a medical instrument is in contact with a target region (e.g., tissue) based, at least in part, on impedance measurements may comprise applying a signal comprising a multi-tone waveform having a first frequency and a second frequency to a pair of electrodes, processing the resulting waveform to obtain impedance measurements at the first frequency and the second frequency, comparing values of the impedance measurements at the first frequency and the second frequency to a known impedance of blood or a blood and saline mixture (or other known tissue impedance), comparing values of the impedance measurements at the first and second frequency to each other; and generating an output indicative of whether or not the medical instrument is in contact with tissue based on said comparisons. A system for determining whether a medical instrument is in contact with tissue based, at least in part, on impedance measurements may comprise a signal source configured to generate a multi-tone waveform or signal having a first frequency and a second frequency to a pair of electrodes (e.g., at a distal end of a combination electrode (such as a split-tip electrode) catheter); and a processing device. The processing device may be configured to, upon execution of stored instructions on a computer-readable storage medium, process the resulting waveform to obtain impedance measurements at the first frequency and the second frequency, compare values of the impedance measurements at the first frequency and the second frequency to a known impedance of blood or a blood and saline mixture, compare values of the impedance measurements at the first and second frequency to each other and/or generate an output indicative of whether or not the medical instrument is in contact with tissue based on said comparisons. The method may further comprise applying a signal adapted to cause ablative energy to be delivered by the pair of electrodes or electrode portions sufficient to ablate or otherwise treat cardiac or other body tissue.

In accordance with several embodiments, a method of determining whether a medical instrument comprising a pair of electrodes or electrode portions is in contact with a target region (e.g., tissue) based, at least in part, on impedance measurements comprises applying at least one signal having a plurality of frequencies (e.g., a multi-tonal waveform) to a pair of electrodes of a medical instrument, and processing a resulting waveform that formulates across the pair of electrodes to obtain impedance measurements at a first frequency and a second frequency of the plurality of frequencies. If a variation of the impedance measurements across the range of frequencies has a model whose parameter values are indicative of contact, the method comprises generating a first output indicative of contact. If the variation of the impedance measurements across the range of frequencies has a model whose parameter values are indicative of no contact, the method comprises generating a second output indicative of no contact. The model may comprise a fitting function or a circuit model such as shown in FIG. 5B. The method may further comprise applying a signal adapted to cause ablative energy to be delivered by the pair of electrodes or electrode portions sufficient to ablate or otherwise treat cardiac or other body tissue.

A system for determining whether a medical instrument is in contact with tissue based, at least in part, on impedance measurements comprises a signal source configured to generate at least one signal having a first frequency and a second frequency to a pair of electrodes and a processing device. The processing device may be configured to, upon execution of stored instructions on a computer-readable storage medium, apply at least one signal having a plurality of frequencies to a pair of electrodes of a medical instrument and process a resulting waveform that formulates across the pair of electrodes to obtain impedance measurements at a first frequency and a second frequency of the plurality of frequencies. If a variation of the impedance measurements across the range of frequencies follows a model whose parameter values are indicative of contact the processor is configured to generate a first output indicative of contact. If the variation of the impedance measurements across the range of frequencies follows a model whose parameter values are indicative of no contact, the processor is configured to generate a second output indicative of no contact. Processing the waveforms to obtain impedance measurements may comprise obtaining voltage and/or current measurements and calculating impedance measurements based on the voltage and/or current measurements or directly obtaining impedance measurements.

In accordance with several embodiments, a method of determining whether tissue has been ablated by an ablation catheter comprising a pair of electrodes is provided. The method comprises applying one or more signals having a first frequency and a second frequency (e.g., a multi-tonal waveform) to a pair of electrodes along the ablation catheter and processing a resulting waveform that formulates across the pair of electrodes to obtain impedance measurements at the first frequency and the second frequency. The method may comprise assessing absolute change in the impedance as well as the slope or ratio between impedance. If the first impedance measurement at the first and/or second frequency is greater than a known impedance level of blood and if a ratio of the second impedance measurement to the first impedance measurement is above a predetermined threshold, the method comprises generating a first output indicative of ablated tissue. If the first impedance measurement at the first and/or second frequency is greater than a known impedance level of blood and if a ratio of the second impedance measurement to the first impedance measurement is below a predetermined threshold, the method comprises generating a second output indicative of viable tissue. Processing the waveforms to obtain impedance measurements may comprise obtaining voltage and/or current measurements and calculating impedance measurements based on the voltage and/or current measurements or directly obtaining impedance measurements. The method may further comprise applying a signal adapted to cause ablative energy to be delivered by the pair of electrodes or electrode portions sufficient to ablate or otherwise treat cardiac or other body tissue.

In some embodiments, a phase of the impedance measurements at the first frequency and/or second frequency is compared to a known phase response for blood or a blood and saline mixture and utilized in conjunction with the magnitude values of the impedance measurements to generate an output indicative of whether or not the medical instrument is in contact with tissue. A system for determining whether tissue has been ablated by an ablation catheter comprising a pair of electrodes or electrode portions may comprise a signal source configured to generate at least one signal having a first frequency and a second frequency to a pair of electrodes along the ablation catheter and a processing device. The processing device may be configured to, upon execution of stored instructions on a computer-readable storage medium, process a resulting waveform that formulates across the pair of electrodes to obtain impedance measurements at the first frequency and the second frequency. If the first impedance measurement at the first and/or second frequency is greater than a known impedance level of blood and if a ratio of the second impedance measurement to the first impedance measurement is above a predetermined threshold, the processing device is configured to generate a first output indicative of ablated tissue. If a ratio of the second impedance measurement to the first impedance measurement is below a predetermined threshold, the processor is configured to generate a second output indicative of viable (e.g., unablated) tissue. Processing the waveforms to obtain impedance measurements may comprise obtaining voltage and/or current measurements and calculating impedance measurements based on the voltage and/or current measurements or directly obtaining impedance measurements.

Processing the resulting waveform may comprise applying a transform (e.g., a Fourier transform) to the waveform to obtain the impedance measurements. In some embodiments, the first frequency and the second frequency are within a range between 5 kHz and 1000 kHz. In one embodiment, the second frequency is higher than the first frequency. The impedance measurements may be obtained simultaneously or sequentially. The second frequency may be at least 20 kHz higher than the first frequency. In one embodiment, the first frequency is between 10 kHz and 100 kHz (e.g., between 10 KHz and 30 kHz, between 15 kHz and 40 kHz, between 20 kHz and 50 kHz, between 30 kHz and 60 kHz, between 40 kHz and 80 kHz, between 50 kHz and 90 kHz, between 60 kHz and 100 kHz, overlapping ranges thereof, 20 kHz or any values from 10 kHz and 100 kHz) and the second frequency is between 400 kHz and 1000 kHz (e.g., between 400 kHz and 600 kHz, between 450 kHz and 750 kHz, between 500 kHz and 800 kHz, between 600 kHz and 850 kHz, between 700 kHz and 900 kHz, between 800 kHz and 1000 kHz, overlapping ranges thereof, 800 kHz, or any values from 400 kHz to 1000 kHz). The predetermined threshold may have a value between 0.5 and 0.9. In some embodiments, generating a first output and generating a second output further comprises causing the first output or the second output to be displayed on a display (for example via one or more display drivers). The output may comprise textual information, quantitative measurements and/or qualitative assessments indicative of contact state. In some embodiments, the output includes an amount of contact force corresponding to the level of contact (e.g., grams of force).

A method of determining whether a medical instrument having a pair of electrodes or electrode portions is in contact with a target region (e.g., tissue) based, at least in part, on impedance measurements may comprise obtaining a first impedance measurement at a first frequency within a range of frequencies, obtaining a second impedance measurement at a second frequency within the range of frequencies and obtaining a third impedance measurement at a third frequency within the range of frequencies. If a variation of the impedance measurements across the range of frequencies is above a predetermined threshold indicative of contact, the method comprises generating a first output indicative of contact. If the variation of the impedance measurements across the range of frequencies is below the predetermined threshold, the method comprises generating a second output indicative of no contact. The impedance measurements may be calculated based on voltage and/or current measurements or may be directly-measured impedance measurements. The method may further comprise applying a signal adapted to cause ablative energy to be delivered by the pair of electrodes or electrode portions sufficient to ablate or otherwise treat cardiac or other body tissue.

The range of frequencies may be between 5 kHz and 5 MHz (e.g., between 5 kHz and 1000 kHz, between 1 MHz and 3 MHz, between 2.5 MHz and 5 MHz, or overlapping ranges thereof). In one embodiment, the first frequency is between 10 kHz and 100 kHz (e.g., between 10 KHz and 30 kHz, between 15 kHz and 40 kHz, between 20 kHz and 50 kHz, between 30 kHz and 60 kHz, between 40 kHz and 80 kHz, between 50 kHz and 90 kHz, between 60 kHz and 100 kHz, overlapping ranges thereof, 20 kHz or any values from 10 kHz and 100 kHz) and the second frequency is between 400 kHz and 1000 kHz (e.g., between 400 kHz and 600 kHz, between 450 kHz and 750 kHz, between 500 kHz and 800 kHz, between 600 kHz and 850 kHz, between 700 kHz and 900 kHz, between 800 kHz and 1000 kHz, overlapping ranges thereof, 800 kHz, or any values from 400 kHz to 1000 kHz) and the third frequency is between 20 kHz and 800 kHz. The predetermined threshold may be a value between 0.5 and 0.9. In some embodiments, generating a first output and generating a second output comprises causing the first output or the second output to be displayed on a display. The output may comprise textual information indicative of contact. In one embodiment, the output comprises a quantitative measurement and/or qualitative assessment of contact.

In some embodiments, the distal end portion of the medical instrument comprises a high-resolution electrode assembly comprising a first electrode portion and second electrode portion spaced apart and insulated from the first electrode portion (e.g., a composite electrode assembly or combination radiofrequency electrode). The control unit may comprise a contact detection subsystem or module configured to receive signals from the high-resolution electrode assembly and the control unit (e.g., processor) of the contact detection subsystem or module or a separate processor may be configured (e.g., specifically programmed with instructions stored in or on a non-transitory computer-readable medium) to determine a level of contact or a contact state with tissue (e.g., cardiac tissue) based on the received signals from the high-resolution electrode assembly and to modulate the opposition force provided by the opposition force motor based, at least in part, on the determined level of contact, or the contact state. The control unit may further comprise a power delivery module configured to apply radiofrequency power to the high-resolution electrode assembly at a level sufficient to effect ablation of tissue in contact with at least a portion of the distal end portion of the medical instrument.

In some embodiments, the control unit (e.g., processor) is configured to generate output indicative of the level of contact for display on a display coupled to the control unit (e.g., via one or more display drivers). In various embodiments, the output is based on a contact function determined based on one or more criteria combining multiple electrical parameter measurements (such as voltage measurements, current measurements or impedance measurements). In one embodiment, the contact function is determined by summing a weighted combination of impedance (e.g., bipolar impedance) measurements that are directly measured or that are calculated based on voltage and/or current measurements. In one embodiment, the contact function is based on one or more if-then case conditional criteria. In one embodiment, the impedance measurements comprise one or more of an impedance magnitude determined by the contact detection subsystem at a first frequency, a ratio of impedance magnitudes at the first frequency and a second frequency and a phase of a complex impedance measurement at the second frequency. The second frequency may be higher than the first frequency (e.g., at least 20 kHz higher than the first frequency). In some embodiments, the first frequency and the second frequency are between 5 kHz and 1000 kHz. In one embodiment, the first frequency is between 10 kHz and 100 kHz (e.g., between 10 KHz and 30 kHz, between 15 kHz and 40 kHz, between 20 kHz and 50 kHz, between 30 kHz and 60 kHz, between 40 kHz and 80 kHz, between 50 kHz and 90 kHz, between 60 kHz and 100 kHz, overlapping ranges thereof, 20 kHz or any values from 10 kHz and 100 kHz) and the second frequency is between 400 kHz and 1000 kHz (e.g., between 400 kHz and 600 kHz, between 450 kHz and 750 kHz, between 500 kHz and 800 kHz, between 600 kHz and 850 kHz, between 700 kHz and 900 kHz, between 800 kHz and 1000 kHz, overlapping ranges thereof, 800 kHz, or any values from 400 kHz to 1000 kHz); however, other frequencies may be used as desired and/or required. In some embodiments, the frequencies at which impedance measurements are obtained are outside treatment (e.g., ablation) frequency ranges. In some embodiments, filters (such as bandpass filters) are used to isolate the treatment frequency ranges from the impedance measurement frequency ranges.

In some embodiments, the handle of the medical instrument further comprises a motion detection element (e.g., at least one of an accelerometer and a gyroscope). In some embodiments, the first motor is configured to be actuated only when the motion detection element is detecting motion of the handle.

In accordance with several embodiments, a method of determining a contact state of a distal end portion of a medical instrument with a target region, for example, tissue, comprises applying at least one signal having a plurality of frequencies to a pair of electrodes or electrode portions of a combination electrode assembly positioned along a distal end portion of a medical instrument. The method comprises processing a resulting waveform that formulates across the pair of electrodes to obtain a first impedance measurement at a first frequency of the plurality of frequencies and processing the resulting waveform that formulates across the pair of electrodes to obtain a second impedance measurement at a second frequency of the plurality of frequencies. The method further comprises determining a magnitude of the first impedance measurement, determining a magnitude and a phase of the second impedance measurement and applying a contact function (e.g., via execution of a computer program stored on a non-transitory computer storage medium) to calculate a contact indication value indicative of a state of contact between the distal end portion of the medical instrument and the target region (e.g., cardiac tissue). The contact function may be determined by summing a weighted combination of the magnitude of the first impedance measurement, a ratio of the magnitudes of the first impedance measurement and the second impedance measurement, and the phase of the second impedance measurement. In various embodiments, the first frequency and the second frequency are different. In one embodiment, the second frequency is higher than the first frequency.

The method may further comprise generating output corresponding to the contact indication value for display on a display monitor (e.g., via one or more display drivers). In some embodiments, the output comprises a qualitative and/or a quantitative output. The output may comprise a numerical value between 0 and 1 or between 0 and 1.5, with values above 1 indicating excessive contact. In some embodiments, the output comprises a percentage value or a number corresponding to an amount of contact force (e.g., grams of contact force). The output may comprise a color and/or pattern indicative of the contact state and/or one or more of a gauge, a bar, or a scale. The method may further comprise applying a signal adapted to cause ablative energy to be delivered by the pair of electrodes or electrode portions sufficient to ablate or otherwise treat cardiac or other body tissue.

In accordance with several embodiments, a system for determining a contact state of a distal end portion of a medical instrument with a target region (e.g., tissue, based, at least in part, on electrical parameter measurements consists essentially of or comprises a signal source configured to generate at least one signal having a first frequency and a second frequency to be applied to a pair of electrode members of a combination electrode assembly (e.g., two electrode members separated by a gap). The system also consists essentially of or comprises a processing device configured to (a) cause the signal source to generate and apply the at least one signal to the pair of electrode members, (b) process a resulting waveform that formulates across the pair of electrode members to obtain a first electrical measurement at the first frequency, (c) process the resulting waveform that formulates across the pair of electrode members to obtain a second electrical measurement at the second frequency of the plurality of frequencies, (d) determine an impedance magnitude based on the first electrical measurement, (e) determine an impedance magnitude and a phase based on the second electrical measurement, and (f) calculate a contact indication value indicative of a state of contact between the distal end portion of the medical instrument and the target region based on a criterion combining the impedance magnitude based on the first electrical measurement, a ratio of the impedance magnitudes based on the first and second electrical measurements, and the phase based on the second electrical measurement. The electrical measurements may comprise voltage, current, and/or other electrical parameter measurements from which impedance measurements (such as impedance magnitude or phase) may be calculated or may comprise directly-obtained impedance measurements. The criterion may comprise a weighted combination of the impedance magnitude based on the first electrical measurement, a ratio of the impedance magnitudes based on the first and second electrical measurements, and the phase based on the second electrical measurement or the criterion may comprise an if-then case conditional criterion.

In some embodiments, the system further comprises the medical instrument, which may be a radiofrequency ablation catheter. The first frequency and the second frequency may be different. In some embodiments, the second frequency is higher than the first frequency. In other embodiments, the second frequency is lower than the first frequency. In some embodiments, the first frequency and the second frequency are between 5 kHz and 1000 kHz (e.g., between 5 kHz and 50 kHz, between 10 kHz and 100 kHz, between 50 kHz and 200 kHz, between 100 kHz and 500 kHz, between 200 kHz and 800 kHz, between 400 kHz and 1000 kHz, or overlapping ranges thereof). In various embodiments, the two frequencies are at least 20 kHz apart in frequency.

In some embodiments, the processor is further configured to generate output corresponding to the contact indication value for display on a display monitor, upon execution of specific instructions stored in or on a computer-readable medium. In some embodiments, the output comprises a numerical value between 0 and 1. In some embodiments, the output comprises a qualitative output (such as a color and/or pattern indicative of the contact state). In some embodiments, the output comprises one or more of a gauge, a bar, a meter or a scale. In one embodiment, the output comprises a virtual gauge having a plurality of regions (e.g., two, three, four, five or more than five regions or segments) indicative of varying levels of contact, or contact states. The plurality of regions may be represented in different colors. Each of the plurality of regions may correspond to a different range of numerical values indicative of varying levels of contact.

In accordance with several embodiments, a system for displaying a contact state of a distal tip of a medical instrument with a target region (e.g., body tissue) on a patient monitor comprises a processor configured to generate output for display on the patient monitor. The output may be generated on a graphical user interface on the patient monitor. In one embodiment, the output comprises a graph that displays a contact function indicative of a contact state between a distal tip of a medical instrument and body tissue calculated by a processing device based, at least in part, on impedance measurements obtained by the medical instrument. The graph may be a scrolling waveform. The output also comprises a gauge separate from the graph that indicates a real-time state of contact corresponding to a real-time numerical value of the contact function displayed by the graph. The gauge includes a plurality of regions indicative of varying contact states. In some embodiments, each one of the plurality of regions is optionally displayed in a different color or graduation to provide a qualitative indication of the real-time state of contact. In one embodiment, the gauge consists of three regions or segments. The three regions may be colored red, yellow and green. In another embodiment, the gauge consists of four regions or segments. The four regions may be colored red, orange, yellow and green. Each of the plurality of regions may correspond to a different range of numerical values indicative of the current contact state. The gauge may comprise a pointer that indicates a level on the gauge corresponding to the real-time numerical value of the contact function. The real-time numerical value may range between 0 and 1 or between 0 and 1.25 or between 0 and 1.5. Values above 1 may generate a "contact alert" to the clinician to prevent excessive contact, which could result in perforation of tissue. By way of example, the gauge may comprise a contact indicator of the quality of tissue-electrode contact calculated based on bipolar impedance magnitude, bipolar impedance-frequency slope and bipolar impedance phase.

The output may also comprise other graphs or waveforms of individual components of impedance measurements (e.g., impedance magnitude and phase) at multiple frequencies or of comparisons (e.g., a slope) between two impedance measurements (e.g., impedance magnitude at two different frequencies).

In some embodiments, the contact function is calculated based on a weighted combination of a magnitude of a first impedance measurement at a first frequency, a ratio of the magnitudes of the first impedance measurement and a second impedance measurement at a second frequency different from the first frequency, and the phase of the second impedance measurement at the second frequency. In one embodiment, the second frequency is higher than the first frequency. In another embodiment, the second frequency is lower than the first frequency. The first frequency and the second frequency may be between 5 kHz and 1000 kHz. In some embodiments, the system further comprises the patient monitor.

In accordance with several embodiments, a system for assessing a level of contact between a distal end portion of an ablation catheter having a pair of spaced-apart electrode members of a combination electrode assembly and target region, e.g., tissue, comprises a signal source configured to generate signals having at least a first frequency and a second frequency to be applied to the pair of spaced-apart electrode members. The system also comprises a processor configured to, upon execution of specific program instructions stored on a computer-readable storage medium, measure network parameters at an input of a network measurement circuit comprising a plurality of hardware components between the signal source and the pair of spaced-apart electrode members. The processor may also be configured (e.g., specifically programmed, constructed or designed) to determine an aggregate effect on a measured network parameter value caused by the hardware components of the network measurement circuit, remove the aggregate effect to result in a corrected network parameter value between the pair of spaced-apart electrode members, and determine a level of contact based, at least in part, on the corrected network parameter value.

In some embodiments, the processor is configured to generate an output indicative of the level of contact for display. The signal source may be located within a radiofrequency generator or within the ablation catheter. The processor may be configured to measure network parameters at at least two frequencies (e.g., two frequencies, three frequencies, four frequencies or more than four frequencies). In some embodiments, the frequencies are between 5 kHz and 1000 kHz. In embodiments involving two frequencies, the second frequency may be at least 20 kHz higher than the first frequency. For example, the first frequency may be between 10 kHz and 100 kHz and the second frequency is between 400 kHz and 1000 kHz. A third frequency may be higher than the first frequency and lower than the second frequency (e.g., the third frequency may be between 20 kHz and 120 kHz.).

The network parameters may comprise scattering parameters or other electrical parameters (such as voltage, current, impedance). The network parameter values may comprise, for example, voltage and current values or impedance values either directly measured or determined from voltage and/or current values. Impedance values may comprise impedance magnitude values and impedance phase values. The impedance magnitude values may be obtained at two or more frequencies and slopes may be determined between magnitude values at different frequencies. The impedance phase values may be obtained at one or more frequencies.

In accordance with several embodiments, a method of assessing a level of contact determination of a distal end portion of an ablation catheter having a pair of spaced-apart electrode members comprises measuring network parameters at an input of a network parameter circuit of hardware components between a signal source and the pair of spaced-apart electrode members. The method also comprises determining an aggregate effect on a measured network parameter value determined from the network parameters caused by the hardware components, removing the aggregate effect to result in a corrected network parameter value between the pair of spaced-apart electrode members, and determining a level of contact based, at least in part, on the corrected network parameter value.

Measuring network parameters may comprise measuring network parameters at a plurality of frequencies. In some embodiments, determining an aggregate effect on the measured network parameter value caused by the hardware components of the network parameter circuit comprises measuring network parameters associated with each individual hardware component. In some embodiments, determining an aggregate effect on the measured network parameter value caused by the hardware components of the network parameter circuit comprises combining the network parameters of the individual hardware components into total network parameters at a plurality of frequencies. Removing the aggregate effect so as to isolate an actual network parameter value between the pair of spaced-apart electrode members may comprise de-embedding the total network parameters from a measured input reflection coefficient to result in an actual reflection coefficient corresponding to the actual network parameter value. In some embodiments, the method is performed automatically by a processor. The method may further comprise applying a signal adapted to cause ablative energy to be delivered by the pair of spaced-apart electrode members sufficient to ablate or otherwise treat cardiac or other body tissue.

In accordance with several embodiments, a system comprises a signal source (for example, a source of radiofrequency energy or excitation signals) configured to deliver signals having at least a first frequency and a second frequency to a pair of electrode members of a combination electrode assembly (for example, spaced-apart bipolar pair of electrode members) positioned along a distal end portion of a medical instrument (for example, radiofrequency ablation catheter). The embodiment of the system also comprises a processing device (for example, specific-purpose processor) configured to, upon execution of specific program instructions stored on a computer-readable storage medium: cause the signal source to generate and apply the signals to the pair of electrode members, obtain electrical measurements (for example, bipolar contact impedance measurements that are directly measured or that are calculated or otherwise determined from voltage and/or current measurements) between the pair of electrode members while signals having at least the first frequency and the second frequency are being applied to the pair of electrode members, process the electrical measurements obtained at the first frequency and the second frequency, and determine whether the combination electrode assembly is in contact with tissue based on said processing of the electrical measurements. The processing device is configured to generate an output indicative of contact. The output may comprise any type of output described herein (for example, visual, audible) and may be output on a display in communication with the processing device. The embodiment of the system may comprise a contact sensing subsystem including the signal source and the processing device. The system may also comprise an ablative energy source configured to generate and apply power to the combination electrode assembly for ablating the target region, as described herein. The processing device may be configured (for example, specifically programmed) to adjust one or more energy delivery parameters of the ablative energy based on a determination of whether the combination electrode assembly is in contact with tissue and/or to terminate energy delivery based on a determination of whether the combination electrode assembly is in contact with tissue. In some embodiments, the ablative energy source and the signal source comprise a single source. In some embodiments, the signal source comprises a first source and the ablative energy source comprises a second source that is separate and distinct from the first source. In some embodiments, the contact sensing subsystem is located within the energy delivery device. In some embodiments where the signal source and the ablative energy source are separate sources, the contact sensing subsystem is located within a housing that also houses the ablative energy source.

The embodiment of the system optionally comprises the medical instrument itself. The medical instrument may consist essentially of or comprise an ablation catheter comprising an elongate body having a proximal end and a distal end and wherein the energy delivery device comprises the combination electrode assembly. The combination electrode assembly includes a first electrode member positioned along the elongate body (for example, at a distal terminus) and a second electrode member positioned adjacent the first electrode member (for example, spaced apart by a gap sufficient to electrically insulate the two electrode members). The two electrode members may be positioned, shaped, sized and/or designed (for example, configured) to contact tissue of a subject. The combination electrode assembly also includes an electrically insulating gap positioned between the first electrode member and the second electrode member, the electrically insulating gap comprising a gap width separating the first and second electrode members.

In some embodiments, the processing device of the system is configured to determine an impedance magnitude value based on a first electrical measurement obtained from the signal at the first frequency and to determine an impedance magnitude value and an impedance phase angle value based on a second electrical measurement obtained from the signal at the second frequency. In some embodiments, the processing device is configured to calculate a contact indication value indicative of a state of contact between the distal end portion of the medical instrument and the target region based on a criterion combining the impedance magnitude value based on the first electrical measurement, a ratio of the impedance magnitude values based on the first electrical measurement and the second electrical measurement, and the impedance phase based on the second electrical measurement. The criterion may comprise a weighted combination of the impedance magnitude based on the first electrical measurement, a ratio of the impedance magnitude values based on the first and second electrical measurements, and the impedance phase value based on the second electrical measurement or the criterion may comprise an if-then conditional criterion. In some embodiments, the signals generated and applied to the pair of electrode members do not travel to a patch electrode remote from the target region so as to facilitate bipolar contact measurements between the two electrode members.

As described herein, the processing device of the embodiment of the system may be configured to measure network parameters at an input of a network measurement circuit comprising a plurality of hardware components between the signal source and the pair of electrode members, determine an aggregate effect on a measured network parameter value caused by the hardware components of the network measurement circuit, remove the aggregate effect to result in a corrected network parameter value between the pair of electrode members, and determine a level of contact between the pair of electrode members and tissue based, at least in part, on the corrected network parameter value. The first applied frequency may be between 10 kHz and 100 kHz and the second applied frequency may be between 400 kHz and 1000 kHz. In some embodiments, the signal source is further configured to generate a signal having a third frequency to be applied to the pair of spaced-apart electrode members and the processing device is further configured to measure network parameters at the third frequency. In some embodiments, the third frequency is higher than the first frequency and lower than the second frequency. In various embodiments, the third frequency is between 20 kHz and 120 kHz. The network parameters may be scattering parameters or impedance parameters. The network parameter values may be impedance values comprised of bipolar impedance magnitude values, bipolar impedance phase values and/or bipolar slope values between impedance magnitude values at different frequencies.

In accordance with several embodiments, a kit comprises a radiofrequency generator comprising an ablative energy source, an ablation catheter comprising a pair of electrode members separated by a gap positioned along a distal end portion of the ablation catheter; and a contact sensing subsystem comprising a signal source configured to generate and apply signals having at least two different frequencies to the pair of electrode members and a processor configured to determine a level of contact between the pair of electrode members and target tissue based, at least in part, on electrical measurements between the pair of electrode members while the signals having the at least two different frequencies are being applied.

The contact sensing subsystem of the kit may be housed within the radiofrequency generator or may be a separate component from the radiofrequency generator. The kit may optionally comprise electrical cables for connecting the ablation catheter to the radiofrequency generator and/or for connecting the ablation catheter to the contact sensing subsystem. The radiofrequency generator may include an integrated display and the contact sensing subsystem may be configured to generate an output indicative of the level of contact to the display.

According to some embodiments, an ablation system consists essentially of a catheter, an ablation member (e.g., a RF electrode, a composite (e.g., split-tip) electrode, another type of high-resolution electrode, etc.), an irrigation conduit extending through an interior of the catheter to or near the ablation member, at least one electrical conductor (e.g., wire, cable, etc.) to selectively activate the ablation member and at least one heat transfer member that places at least a portion of the ablation member (e.g., a proximal portion of the ablation member) in thermal communication with the irrigation conduit, at least one heat shunt member configured to effectively transfer heat away from the electrode and/or tissue being treated and a plurality of temperature sensors (e.g., thermocouples) located along two different longitudinal locations of the catheter, wherein the temperature sensors are thermally isolated from the electrode and configured to detect temperature of tissue at a depth.

In accordance with several embodiments, a system for compensating for drift in electrode-tissue contact impedance values over time caused by changes in blood impedance comprises or consists essentially of a signal source configured to deliver signals to a first set of electrodes positioned along a distal end portion of a medical instrument (e.g., RF ablation catheter) that is configured to be positioned in contact with target body tissue (e.g., cardiac tissue) and at least one processing device. The at least one processing device is communicatively coupled to the signal source.

In some embodiments, the at least one processing device is configured to, upon execution of specific program instructions stored on a non-transitory computer-readable storage medium: determine reference impedance values (e.g., bipolar impedance values) while signals having the least one frequency (e.g., a single frequency or two frequencies) are applied to a second set of electrodes not in contact with the target body tissue, adjust contact impedance values (e.g., bipolar impedance values) obtained while signals having the at least one frequency are applied to the first set of electrodes based on the reference impedance values, and calculate contact indication values indicative of a level of contact (e.g., no contact, poor contact, medium contact, good contact) between the distal end portion of the medical instrument and the target body tissue using the adjusted contact impedance values.

In some embodiments, the signal source is configured to deliver signals having at least a first frequency to a first set of electrode members positioned along a distal end portion of a medical instrument that is configured to be positioned in contact with target body tissue and to a second set of electrodes that is not likely to be in contact with target body tissue and the at least one processing device is configured to, upon execution of specific program instructions stored on a non-transitory computer-readable storage medium: cause the signal source to generate and apply the signals to the second set of electrodes, determine at least one reference impedance value between the second set of electrodes while signals having at least the first frequency are being applied to the second set of electrodes, cause the signal source to generate and apply the signals to the first set of electrodes, determine at least one contact impedance value between the first set of electrodes, adjust the at least one contact impedance value based on the at least one reference impedance value and calculate a contact indication value indicative of a level of contact between the distal end portion of the medical instrument and the target body tissue using the at least one adjusted actual impedance value.

The first set of electrodes may comprise a bipolar pair of electrodes. The bipolar pair of electrodes may be a proximal and distal electrode member of a combination electrode assembly configured for both high-resolution mapping and tissue ablation. The second set of electrodes may comprise a pair of reference electrodes (or three, four or more electrodes) positioned along the medical instrument at a location proximal to the first set of electrodes. For example, the pair of electrodes may comprise a pair of spaced-apart ring electrodes that are used for mapping in addition to being used for reference measurements to correct for drift. In some embodiments, the second set of electrodes comprises a pair of reference electrodes or other measurement devices on a separate device from the medical instrument. The signals delivered by the signal source may have at least one frequency (e.g., one frequency, two different frequencies, three different frequencies) configured to facilitate electrical measurements (e.g., direct impedance measurements or impedance values obtained from voltage and/or current measurements) that are in turn used to facilitate electrode-tissue contact assessment (e.g., whether in contact or not or a qualitative assessment of contact state or level).

In some embodiments, the reference impedance values (e.g., bipolar impedance values) are calculated from one or more electrical measurements (e.g., at least one voltage measurement and at least one current measurement) obtained using the pair of electrodes not in contact with the target body tissue. In some embodiments, the second set of electrodes is the same set of electrodes as the first set of electrodes but reference measurements or values are obtained at a time when the first set of electrodes are not in contact with the target body tissue. In some embodiments involving a pair of spaced-apart ring electrodes as the second set of electrodes, a distal one of the ring electrodes is separated from a proximal one of the first set of electrodes by a distance between 2 mm and 5 mm and a distance between a proximal edge of the distal one of the ring electrodes and a distal edge of a proximal one of the ring electrodes is between 1 mm and 3 mm.

In some embodiments, the reference impedance values comprise a first reference bipolar impedance value for an impedance magnitude at the first frequency, a second reference bipolar impedance value for a slope between the impedance magnitude at the first frequency and an impedance magnitude at a second frequency, and a third reference bipolar impedance value for a phase at the second frequency. In such embodiments, the at least one processing device may be configured to adjust the first bipolar contact impedance value based on the first reference bipolar impedance value, adjust the second bipolar contact impedance value based on the second reference bipolar impedance value, and adjust the third bipolar contact impedance value based on the third reference bipolar impedance value. The at least one processing device may also be configured to calculate the contact indication values using the adjusted first, second and third bipolar contact impedance values.

In some embodiments, the first set of electrodes comprises a pair of electrode members of a combination electrode assembly. The combination electrode assembly may comprise a first electrode member positioned along an elongate body and a second electrode member positioned adjacent the first electrode member, with the first electrode member and the second electrode member being configured to contact tissue of a subject. An electrically insulating gap is positioned between the first electrode member and the second electrode member, the electrically insulating gap comprising a gap width separating the first and second electrode members. A filtering element (e.g., a capacitor) may be positioned within the gap width.

The signal source may comprises a source of radiofrequency energy configured to generate signals having a single frequency or signals at multiple different frequencies (e.g., a first frequency and a second frequency). The first and second frequencies may be between 5 kHz and 1000 kHz. In some embodiments, the second frequency is greater than the first frequency.

In some embodiments, the system for correcting, or accounting for, drift comprises an ablative energy source configured to generate and apply power to the first set of electrodes (e.g., a combination electrode assembly) for ablating the target body tissue. The at least one processing device may be further configured to generate an output indicative of a level of contact based on the calculated contact indication value and to cause the output to be displayed on a display in communication with the at least one processing device. The ablative energy source and the signal source may consist of a single source or may be separate and distinct sources. In some embodiments, the system comprises a contact sensing subsystem that includes (e.g., resides within or is communicatively coupled to) the signal source, and/or the at least one processing device. In some embodiments, the contact sensing subsystem is housed within a housing of a radiofrequency energy generator.

In accordance with several embodiments, a method of compensating for (e.g., correcting for or accounting for) drift in electrode-tissue contact impedance values over time caused by changes in blood impedance (e.g., due to introduction of liquids during an ablation procedure) comprises or consists essentially of determining reference impedance values based on electrical measurements obtained using a pair of electrode members positioned along a medical instrument when the electrode members are in contact with blood, determining bipolar contact impedance values using the pair of electrode members when the electrode members are positioned in contact with target tissue at a target tissue ablation site, and adjusting the bipolar contact impedance values based on the determined reference impedance values, thereby resulting in adjusted bipolar contact impedance values that compensate for drift in the bipolar contact impedance values caused by changes in blood impedance over time. The method may further comprise determining that the one or more measurement devices are not in contact with tissue. In some embodiments, the step of adjusting the contact impedance values comprises determining proportionality (or other relationship) between the determined reference impedance values or the drift in the determined reference impedance values and the bipolar contact impedance values or the drift in the bipolar contact impedance values, and applying a correction factor, or scaling value, based on the determined proportionality (or other relationship).

In accordance with several embodiments, a method of compensating for drift in electrode-tissue contact impedance values over time caused by changes in blood impedance comprises or consists essentially of determining reference impedance values (e.g., bipolar impedance values) based on electrical measurements obtained using one or more measurement devices in contact with blood, determining contact impedance values (e.g., bipolar impedance values) using a pair of electrode members positioned at a distal end portion of a medical instrument in contact with target tissue at the target tissue ablation site, and adjusting the contact impedance values based on the determined reference impedance values, thereby resulting in adjusted contact impedance values that compensate for drift in the contact impedance values caused by changes in blood impedance and/or resistivity over time. The step of determining reference impedance values may comprise determining that the pair of electrode members is not in contact with tissue. In some embodiments, the step of adjusting the contact impedance values comprises determining proportionality or other relationship between the determined reference impedance values and the contact impedance values and applying a correction factor based on the determined proportionality or other relationship.

In accordance with several embodiments, a method of compensating for drift in electrode-tissue contact impedance values over time caused by changes in blood impedance comprises or consists essentially of determining reference impedance values based on electrical measurements obtained using one or more measurement devices in contact with blood but not in contact with tissue, determining contact impedance values (e.g., bipolar impedance values) using a pair of electrode members of a combination electrode assembly positioned at a distal end portion of a medical instrument in contact with target tissue at the target tissue ablation site, and adjusting the contact impedance values based on the determined reference impedance values, thereby resulting in adjusted contact impedance values that compensate for drift in the contact impedance values caused by changes in blood impedance and/or resistivity over time. The electrical measurements comprise at least one voltage measurement and at least one current measurement. The step of determining reference impedance values based on electrical measurements obtained using one or more measurement devices in contact with blood adjacent to a target tissue ablation site but not in contact with tissue may comprise positioning the pair of electrode members of the combination electrode assembly at a location so as not to be in contact with tissue and determining reference impedance values based on electrical measurements obtained using the pair of electrode members of the combination electrode assembly. In some implementations, the one or more measurement devices comprise two spaced-apart ring electrodes positioned along the medical instrument at a location proximal to the pair of electrode members of the combination electrode assembly. The method may further comprise calculating contact indication values indicative of a qualitative assessment of contact using the adjusted contact impedance values.

In accordance with several embodiments, a method of compensating for drift in electrode-tissue contact impedance values (e.g., bipolar impedance values) over time caused by changes in blood impedance comprises or consists essentially of determining reference impedance values (e.g., bipolar impedance values) using a pair of reference electrodes at a time when the pair of reference electrodes is in contact with blood but not in contact with tissue, determining contact impedance values (e.g., bipolar impedance values) using a pair of electrode members of a combination electrode assembly positioned at a distal end portion of a medical instrument in contact with target tissue at a target tissue ablation site, and adjusting the contact impedance values based on the determined reference impedance values, thereby resulting in adjusted contact impedance values that compensate for drift in the contact impedance values caused by changes in blood resistivity or impedance over time.

In some embodiments, the step of determining reference impedance values comprises calculating reference impedance values (e.g., bipolar impedance values) from one or more electrical measurements (e.g., at least one voltage measurement and at least one current measurement) obtained using the pair of reference electrodes. The pair of reference electrodes may comprise two spaced-apart ring electrodes positioned along the medical instrument at a location proximal to the pair of electrode members of the combination electrode assembly. A distal one of the ring electrodes may be separated from a proximal one of the pair of electrode members of the combination electrode assembly by a distance between 2 mm and 5 mm. A distance between a proximal edge of the distal one of the ring electrodes and a distal edge of a proximal one of the ring electrodes may be between 1 mm and 3 mm.

In some embodiments, the step of determining reference impedance values comprises determining a first reference bipolar impedance value for an impedance magnitude while a signal having a first frequency is being applied to the pair of reference electrodes, determining a second reference bipolar impedance value for a slope between the impedance magnitude while the signal having the first frequency is being applied to the pair of reference electrodes and an impedance magnitude while a signal having a second frequency is being applied to the pair of reference electrodes, and determining a third reference bipolar impedance value for a phase while the signal having the second frequency is being applied to the pair of reference electrodes. In some embodiments, the step of determining bipolar contact impedance values comprises determining a first bipolar contact impedance value for an impedance magnitude while the signal having the first frequency is being applied to the combination electrode assembly, determining a second bipolar contact impedance value for a slope between the impedance magnitude while the signal having the first frequency is being applied to the combination electrode assembly and an impedance magnitude while the signal having the second frequency is being applied to the combination electrode assembly, and determining a third bipolar contact impedance value for a phase while the signal having the second frequency is being applied to the combination electrode assembly. In some embodiments, the step of adjusting the bipolar contact impedance values comprises adjusting the first bipolar contact impedance value based on the first reference bipolar impedance value, adjusting the second bipolar contact impedance value based on the second reference bipolar impedance value, and adjusting the third bipolar contact impedance value based on the third reference bipolar impedance value. The method may further comprise calculating a contact indication value using the adjusted first, second and third bipolar contact impedance values or calculating contact indication values indicative of a qualitative assessment of contact using the adjusted bipolar contact impedance values.

Any of the methods or portions thereof described in the Summary section above or in the Detailed Description below may be performed by one or more processing devices even if only a single processor is described. Any of the drift correction methods described herein may be automatically performed by at least one processing device of a contact sensing subsystem of an energy delivery system. The processing device(s) (e.g., processor or controller) may be configured to perform operations recited herein upon execution of instructions stored within memory or a non-transitory storage medium. The terms "processor," "processing device" and "controller" may be replaced with the plural forms of the words and should not be limited to a single device but could include multiple processors, processing devices or controllers in communication with each other (e.g., operating in parallel). The methods summarized above and set forth in further detail below may describe certain actions taken by a practitioner; however, it should be understood that they can also include the instruction of those actions by another party. For example, actions such as "terminating energy delivery" include "instructing the terminating of energy delivery." Further aspects of embodiments of the invention will be discussed in the following portions of the specification. With respect to the drawings, elements from one figure may be combined with elements from the other figures.

BRIEF DESCRIPTION OF THE DRAWINGS

These and other features, aspects and advantages of the present application are described with reference to drawings of certain embodiments, which are intended to illustrate, but not to limit, the concepts disclosed herein. The attached drawings are provided for the purpose of illustrating concepts of at least some of the embodiments disclosed herein and may not be to scale.

FIG. 1 schematically illustrates one embodiment of an energy delivery system configured to selectively ablate or otherwise heat targeted tissue of a subject;

FIGS. 23F-1, 23F-2 and 23F-3 illustrate example embodiments of output indicative of a determined orientation;

FIG. 32A illustrates an embodiment of a sub-process of the contact criterion process of FIG. 32;

FIG. 34A illustrates a schematic representation of possible hardware components of a network measurement circuit;

FIG. 34B illustrates a schematic representation of an embodiment of an auto-calibration circuit configured to calibrate (e.g., automatically) the network measurement circuit so as to remove the effects of one or more hardware components present in the circuit;

FIGS. 38 and 39 illustrates another embodiment of a graphical representation that is configured to provide data and/or information regarding specific ablations along targeted portions of a subject's anatomy;

DETAILED DESCRIPTION

Figure 2:
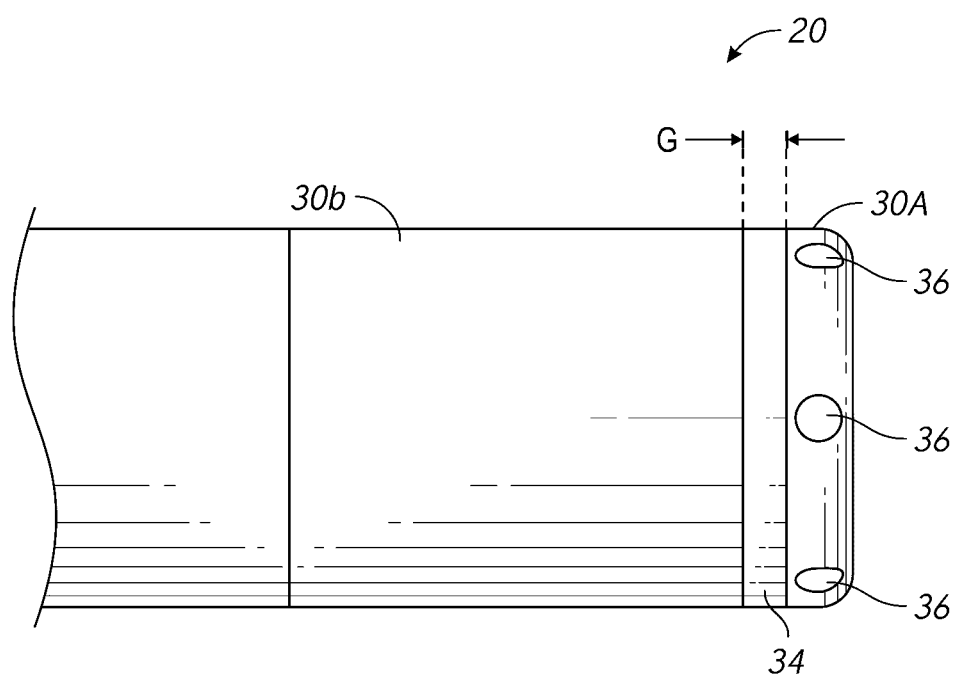
FIG. 2 illustrates a side view of a system's catheter comprising a high-resolution-tip design according to one embodiment.

According to some embodiments, successful electrophysiology procedures require precise knowledge about the anatomic substrate being targeted. Additionally, it may be desirable to evaluate the outcome of an ablation procedure within a short period of time after the execution of the procedure (e.g., to confirm that the desired clinical outcome was achieved). Typically, ablation catheters include only regular mapping electrodes (e.g., ECG electrodes). However, in some embodiments, it may be desirable for such catheters to incorporate high-resolution mapping capabilities. In some embodiments, high-resolution mapping electrodes can provide more accurate and more detailed information about the anatomic substrate and about the outcome of ablation procedures. For example, such high-resolution mapping electrodes can allow the electrophysiology (EP) practitioner to evaluate the morphology of electrograms, their amplitude and width and/or to determine changes in pacing thresholds. According to some arrangements, morphology, amplitude and/or pacing threshold are accepted as reliable EP markers that provide useful information about the outcome of ablation. Thus, high-resolution electrodes are defined as any electrode(s) capable of delivering ablative or other energy to tissue capable of transferring heat to/from such tissue, while being capable of obtaining accurate mapping data of adjacent tissue, and include, without limitation, composite (e.g., split-tip) RF electrodes, other closely oriented electrodes or electrode portions and/or the like.

According to some embodiments, the present application discloses devices, systems and/or methods that include one or more of the following features: a high-resolution electrode (e.g., split tip electrode), heat shunting concepts to help dissipate heat away from the electrode and/or the tissue of the subject being treated, multiple temperature sensors located along the exterior of the device to determine, among other things, temperature of the subject at a depth and contact sensing features that help determine if and to what extent the device is contacting targeted tissue.

Several embodiments of the invention are particularly advantageous because they include one, several or all of the following benefits: (i) provides the ability to obtain accurate tissue mapping data using the same electrode that delivers the ablative energy, (ii) reduces proximal edge heating, (iii) reduces likelihood of char or thrombus formation, (iv) provides feedback that may be used to adjust ablation procedures in real time, (v) provides noninvasive temperature measurements, (vi) does not require use of radiometry; (vii) provides tissue temperature monitoring and feedback during irrigated or non-irrigated ablation; (viii) provides multiple forms of output or feedback to a user; (ix) provides safer and more reliable ablation procedures, (x) confirmation of actual tissue contact that is easily ascertainable; (xi) confirmation of contact with ablated vs. unablated (viable) tissue that is easily ascertainable; (xii) low cost, as the invention does not require any specialized sensor; and/or does not require use of remote patch electrode(s) for tissue contact sensing or detection; and/or (xiii) more reliable contact indication or assessment.

High-Resolution Electrode

According to some embodiments, various implementations of electrodes (e.g., radiofrequency or RF electrodes) that can be used for high-resolution mapping are disclosed herein. For example, as discussed in greater detail herein, an ablation or other energy delivery system can comprise a high-resolution-tip design, wherein the energy delivery member (e.g., radiofrequency electrode) comprises two or more separate electrodes or electrode portions. As also discussed herein, in some embodiments, such separate electrodes or electrode portions can be advantageously electrically coupled to each other (e.g., to collectively create the desired heating or ablation of targeted tissue).

Figure 23A:
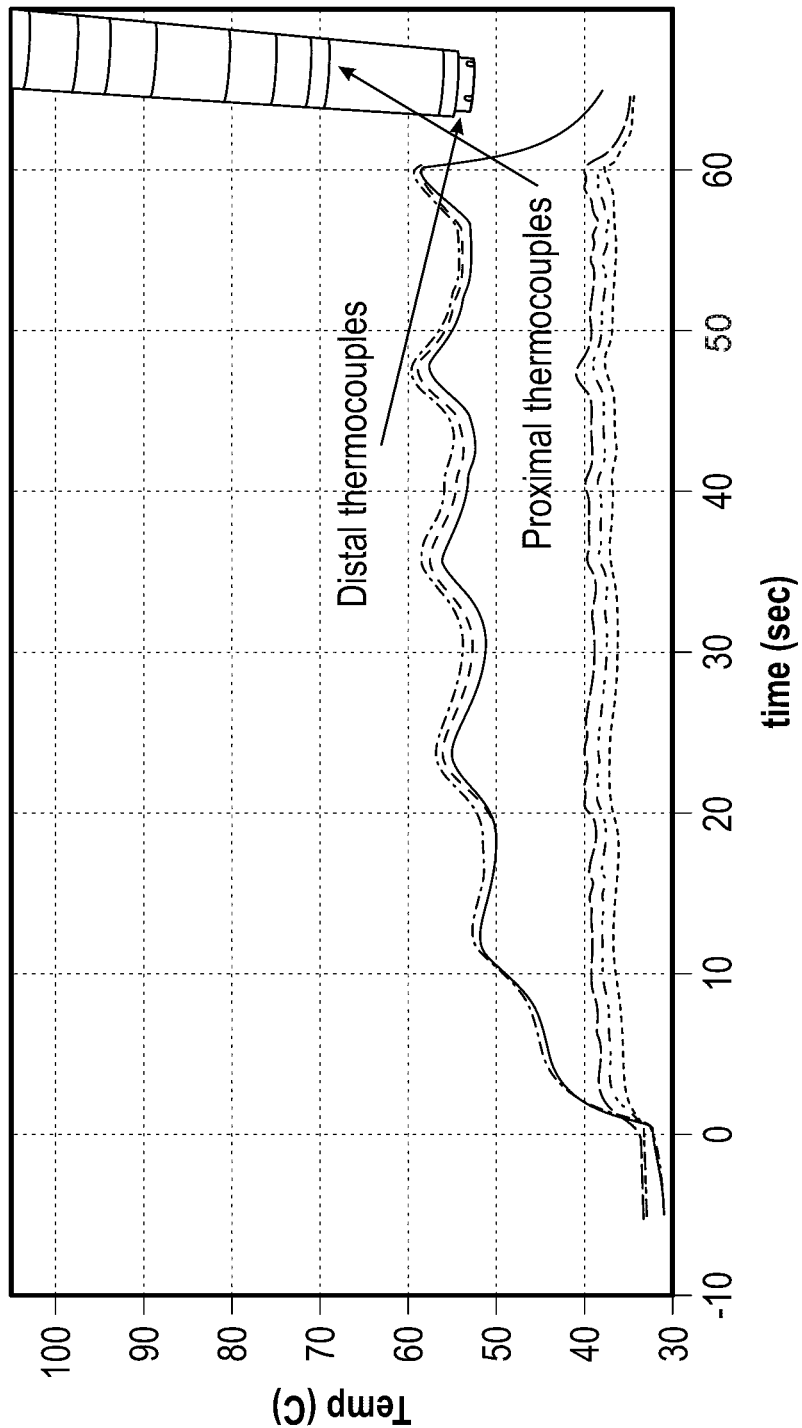
FIGS. 23A and 23B illustrate plots showing temperature measurements obtained by the multiple temperature-measurement devices of an embodiment of an ablation catheter for a parallel orientation and an oblique orientation, respectively.
Figure 23B:
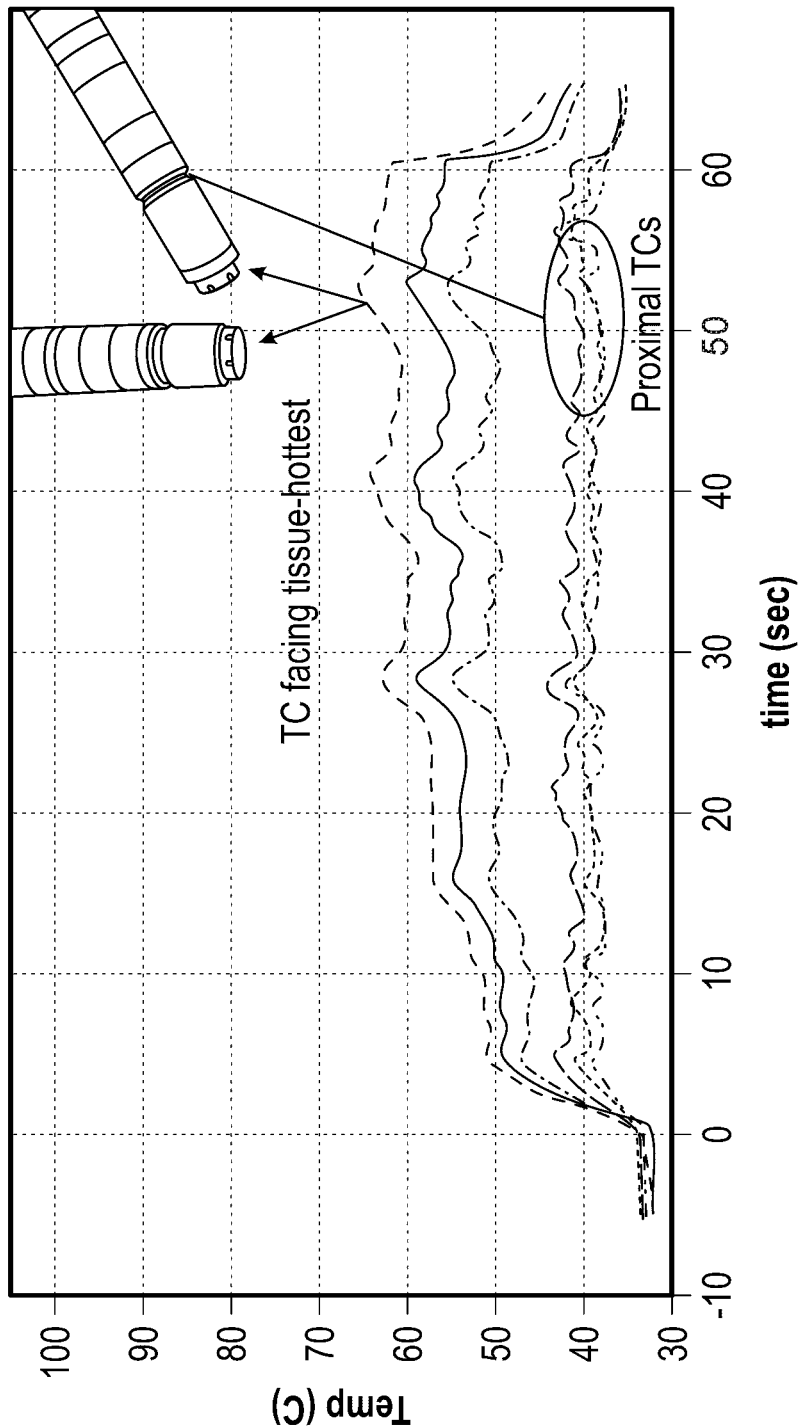
Figure 23C:
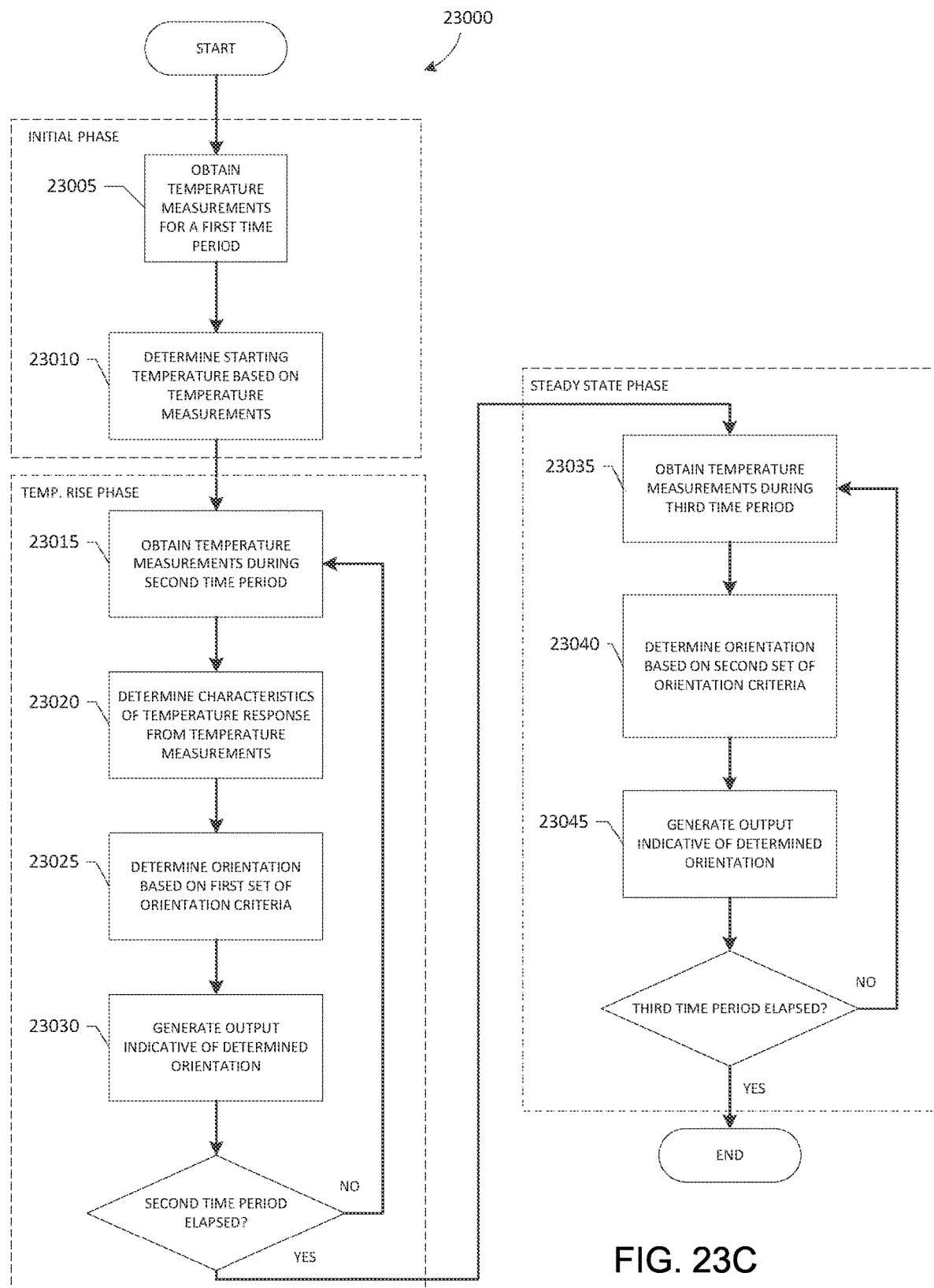
FIG. 23C illustrates an embodiment of a process for determining orientation of a distal end of an ablation catheter based, at least in part, on temperature measurements obtained by the multiple temperature-measurement devices of an embodiment of the ablation catheter.
Figures 23D, 23E:
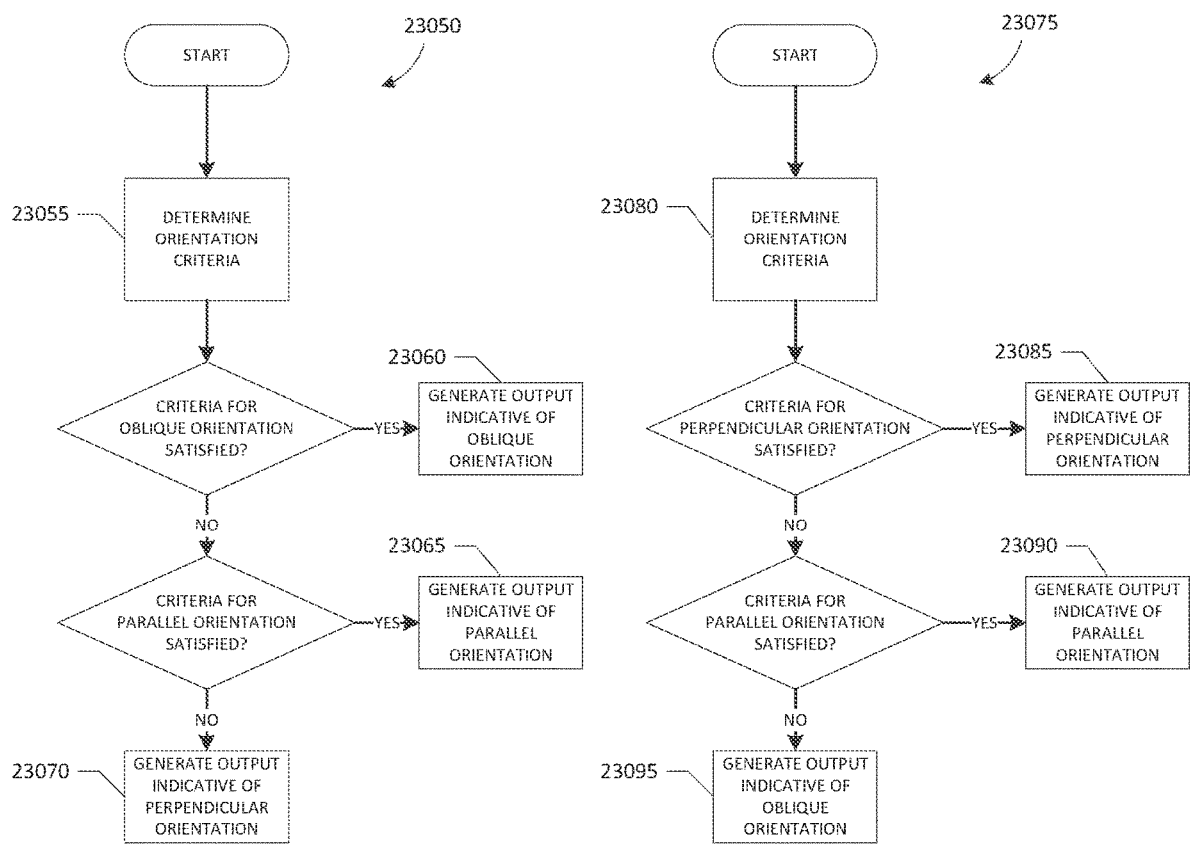
FIGS. 23D and 23E illustrate embodiments of flow processes for determining orientation of a distal end of an ablation catheter.
Figures 1, 23F:
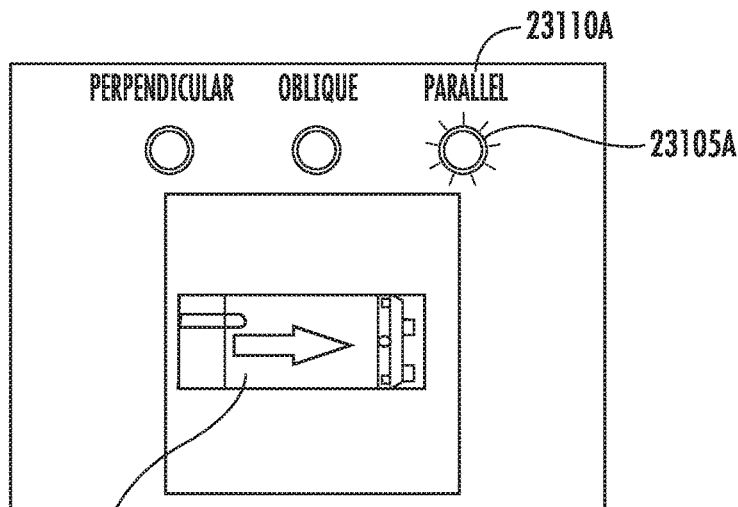
Figures 2, 23F:
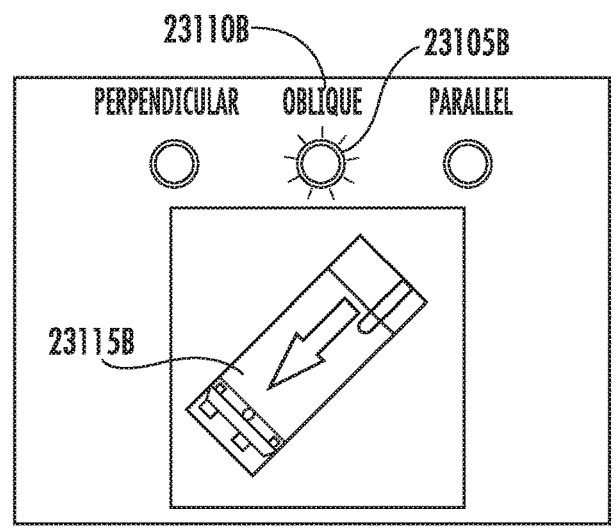
Figures 3, 23F:
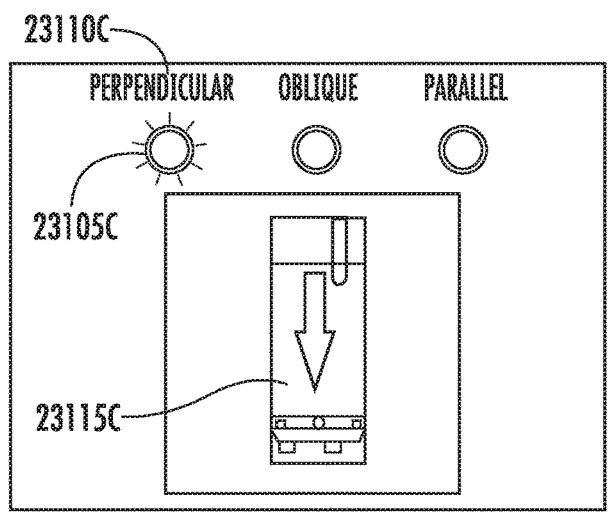

FIG. 1 schematically illustrates one embodiment of a treatment (e.g., energy delivery) system 10 that is configured to selectively ablate, stimulate, modulate and/or otherwise heat or treat targeted tissue (e.g., cardiac tissue, pulmonary vein, other vessels or organs, etc.). Although certain embodiments disclosed herein are described with reference to ablation systems and methods, any of the systems and methods can be used to stimulate, modulate, heat and/or otherwise affect tissue, with or without partial or complete ablation, as desired or required. As shown, the system 10 can include a medical instrument 20 (e.g., catheter) comprising one or more energy delivery members 30 (e.g., radiofrequency electrodes) along a distal end of the medical instrument 20. The medical instrument can be sized, shaped and/or otherwise configured to be passed intraluminally (e.g., intravascularly) through a subject being treated. In various embodiments, the medical instrument 20 comprises a catheter, a shaft, a wire, and/or other elongate instrument. In other embodiments, the medical instrument is not positioned intravascularly but is positioned extravascularly via laparoscopic or open surgical procedures. In various embodiments, the medical instrument 20 comprises a catheter, a shaft, a wire, and/or other elongate instrument. In some embodiments, one or more temperature sensing devices or systems 60 (e.g., thermocouples, thermistors, radiometers, etc.) may be included at the distal end of the medical instrument 20, or along its elongate shaft or in its handle. The term "distal end" does not necessarily mean the distal terminus or distal end. Distal end could mean the distal terminus or a location spaced from the distal terminus but generally at a distal end portion of the medical instrument 20. The medical instrument 20 may optionally include mapping electrodes (e.g., proximal ring electrodes).

In some embodiments, the medical instrument 20 is operatively coupled to one or more devices or components. For example, as depicted in FIG. 1, the medical instrument 20 can be coupled to a delivery module 40 (such as an energy delivery module). According to some arrangements, the energy delivery module 40 includes an energy generation device 42 that is configured to selectively energize and/or otherwise activate the energy delivery member(s) 30 (e.g., radiofrequency electrodes) located along the medical instrument 20. In some embodiments, for instance, the energy generation device 42 comprises one or more signal sources, such as a radiofrequency generator, an ultrasound energy source, a microwave energy source, a laser/light source, another type of energy source or generator, and the like, and combinations thereof. In other embodiments, energy generation device 42 is substituted with or used in addition to a source of fluid, such as a cryogenic fluid or other fluid that modulates temperature. Likewise, the delivery module (e.g., delivery module 40), as used herein, can also be a cryogenic device or other device that is configured for thermal modulation.

With continued reference to the schematic of FIG. 1, the energy delivery module 40 can include one or more input/output devices or components 44, such as, for example, a touchscreen device, a screen or other display, a controller (e.g., button, knob, switch, dial, etc.), keypad, mouse, joystick, trackpad, or other input device and/or the like. Such devices can permit a physician or other user to enter information into and/or receive information from the system 10. In some embodiments, the output device 44 can include a touchscreen or other display that provides tissue temperature information, contact information, other measurement information and/or other data or indicators that can be useful for regulating a particular treatment procedure (for example, on one or more graphical user interfaces generated by the processor 46). The input/output devices or components 44 may include an electrophysiology monitor and/or mapping or navigation systems. In some embodiments, the input devices or components are integrated into the output devices or components. For example, a touchscreen input interface or input keypads or knobs or switches may be integrated into a display monitor or the energy delivery module 40 (for example, generator or control unit).

According to some embodiments, the energy delivery module 40 includes a processor 46 (e.g., a processing or control device) that is configured to regulate one or more aspects of the treatment system 10. The delivery module 40 can also comprise a memory unit or other storage device 48 (e.g., non-transitory computer readable medium) that can be used to store operational parameters and/or other data related to the operation of the system 10. In some embodiments, the processor 46 comprises or is in communication with a contact sensing and/or a tissue type detection module or subsystem. The contact sensing subsystem or module may be adapted to determine whether or not the energy delivery member(s) 30 of the medical instrument 20 are in contact with tissue (for example, contact sufficient to provide effective energy delivery). In some embodiments, the processor 46 is configured to determine whether the tissue in contact with the one or more energy delivery member(s) 30 has been ablated or otherwise treated. In some embodiments, the system 10 comprises a contact sensing subsystem 50. The contact sensing subsystem 50 may be communicatively coupled to the processor 46 and/or comprises a separate controller or processor and memory or other storage media. The contact sensing subsystem 50 may perform both contact sensing and tissue type determination functions. The contact sensing subsystem 50 may be a discrete, standalone sub-component of the system (as shown schematically in FIG. 1) or may be integrated into the energy delivery module 40 or the medical instrument 20. Additional details regarding a contact sensing subsystem are provided below. The tissue type detection module or subsystem may be adapted to determine whether tissue is viable or ablated. In some embodiments, the processor 46 is configured to automatically regulate the delivery of energy from the energy generation device 42 to the energy delivery member 30 of the medical instrument 20 based on one or more operational schemes. For example, energy provided to the energy delivery member 30 (and thus, the amount of heat transferred to or from the targeted tissue) can be regulated based on, among other things, the detected temperature of the tissue being treated, whether the tissue is determined to have been ablated, or whether the energy delivery member 30 is determined to be in contact "sufficient" contact, or contact above a threshold level) with the tissue to be treated.

According to some embodiments, the energy delivery system 10 can include one or more temperature detection devices, such as, for example, reference temperature devices (e.g., thermocouples, thermistors, radiometers, etc.) and/or the like. For example, in some embodiments, the device further comprises a one or more temperature sensors or other temperature-measuring devices to help determine (e.g., detect) a peak (e.g., high or peak, low or trough, etc.) temperature of tissue being treated (e.g., at a depth (e.g., relative to a tissue surface)), to detect orientation of a treatment or monitoring portion of a medical instrument (for example, a distal end portion of a catheter comprising a high-resolution electrode assembly). In some embodiments, the temperature sensors (e.g., thermocouples) located at, along and/or near the ablation member (e.g., RF electrode) can help with the determination of whether contact is being made between the ablation member and targeted tissue (and/or to what degree such contact is being made). In some embodiments, such peak temperature is determined without the use of radiometry. Additional details regarding the use of temperature sensors (e.g., thermocouples) to determine peak tissue temperature and/or to confirm or evaluate tissue contact are provided herein.

With reference to FIG. 1, the energy delivery system 10 comprises (or is in configured to be placed in fluid communication with) an irrigation fluid system 70. In some embodiments, as schematically illustrated in FIG. 1, such a fluid system 70 is at least partially separate from the energy delivery module 40 and/or other components of the system 10. However, in other embodiments, the irrigation fluid system 70 is incorporated, at least partially, into the energy delivery module 40. The irrigation fluid system 70 can include one or more pumps or other fluid transfer devices that are configured to selectively move fluid (e.g., biocompatible fluid such as saline) through one or more lumens or other passages of the catheter 20. Such fluid can be used to selectively cool (e.g., transfer heat away from) the energy delivery member 30 during use. In other embodiments, the system 10 does not comprise an irrigation fluid system 70.

FIG. 2 illustrates one embodiment of a distal end of a medical instrument (e.g., catheter or other elongate member) 20. As shown, the medical instrument (e.g., catheter) 20 can include a high-resolution, combination electrode (e.g., split tip) design, such that there are two adjacent electrodes or two adjacent electrode members or portions 30A, 30B separated by a gap G. According to some embodiments, as depicted in the configuration of FIG. 2, the relative length of the different electrodes or electrode portions 30A, 30B can vary. For example, the length of the proximal electrode 30B can be between 1 to 20 times (e.g., 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, values between the foregoing ranges, etc.) the length of the distal electrode 30A, as desired or required. In other embodiments, the length of the proximal electrode 30B can be greater than 20 times (e.g., 20-25, 25-30, more than 30 times, etc.) the length of the distal electrode 30A. In yet other embodiments, the lengths of the distal and proximal electrodes 30A, 30B are about equal. In some embodiments, the distal electrode 30A is longer than the proximal electrode 30B (e.g., by 1 to 20 times, such as, for example, 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, values between the foregoing ranges, etc.).

In some embodiments, the distal electrode or electrode portion 30A is 0.5 mm-0.9 mm long. In some embodiments, the distal electrode or electrode portion 30A is between 0.1 mm and 1.51 mm long (e.g., 0.1-1.0, 0.1-0.2, 0.2-0.3, 0.3-0.4, 0.4-0.5, 0.5-0.6, 0.6-0.7, 07.0-0.8, 0.8-0.9, 0.9-1.0, 1.0-1.1, 1.1-1.2, 1.2-1.3, 1.3-1.4, 1.4-1.51 mm, values between the foregoing ranges, etc.). In other embodiments, the distal electrode or electrode portion 30A is greater than 1 mm or 1.51 mm in length, as desired or required. In some embodiments, the proximal electrode or electrode portion 30B is 2 to 4 mm long (e.g., 2-2.5, 2.5-3, 3-3.5, 3.5-4 mm, lengths between the foregoing, etc.). However, in other embodiments, the proximal electrode portion 30B is greater than 4 mm (e.g., 4-5, 5-6, 6-7, 7-8, 8-9, 9-10 mm, greater than 10 mm, etc.) or smaller than 1 mm (e.g., 0.1-0.5 0.5-1, 1-1.5, 1.5-2 mm, lengths between the foregoing ranges, etc.), as desired or required. In embodiments where the high-resolution electrodes or portions are located on catheter shafts, the length of the electrodes can be 1 to 5 mm (e.g., 1-2, 2-3, 3-4, 4-5 mm, lengths between the foregoing, etc.). However, in other embodiments, the electrodes or electrode portions can be longer than 5 mm (e.g., 5-6, 6-7, 7-8, 8-9, 9-10, 10-15, 15-20 mm, lengths between the foregoing, lengths greater than 20 mm, etc.), as desired or required.

In accordance with several embodiments, the use of a high-resolution, combination electrode, or composite tip (e.g., split-tip) design can permit a user to simultaneously ablate or otherwise thermally treat targeted tissue and map (e.g., using high-resolution mapping) in a single configuration. Thus, such systems can advantageously permit precise high-resolution mapping (e.g., to confirm that a desired level of treatment occurred) during a procedure. In some embodiments, the high-resolution tip design that includes two electrodes or electrode portions 30A, 30B can be used to record a high-resolution bipolar electrogram. For such purposes, the two electrodes or electrode portions 30A,30B can be connected to the inputs of an EP recorder. In some embodiments, a relatively small separation distance (e.g., gap G) between the electrodes or electrode portions 30A, 30B enables high-resolution mapping.

In some embodiments, a medical instrument (e.g., a catheter) 20 can include three or more electrodes or electrode portions (e.g., separated by gaps), as desired or required. Additional details regarding such arrangements are provided below. According to some embodiments, regardless of how many electrodes or electrode portions are positioned along a catheter tip, the electrodes or electrode portions 30A, 30B are radiofrequency electrodes and comprise one or more metals, such as, for example, stainless steel, platinum, platinum-iridium, gold, gold-plated alloys and/or the like.

According to some embodiments, as illustrated in FIG. 2, the electrodes or electrode portions 30A, 30B are spaced apart from each other (e.g., longitudinally or axially) using a gap (e.g., an electrically insulating gap). In some embodiments, the length of the gap G (or the separation distance between adjacent electrodes or electrode portions) is 0.5 mm. In other embodiments, the gap G or separation distance is greater or smaller than 0.5 mm, such as, for example, 0.1-1 mm (e.g., 0.1-0.2, 0.2-0.3, 0.3-0.4, 0.4-0.5, 0.5-0.6, 0.6-0.7, 0.7-0.8, 0.8-0.9, 0.9-1.0 mm, values between the foregoing ranges, less than 0.1 mm, greater than 1 mm, etc.), as desired or required.

According to some embodiments, a separator 34 is positioned within the gap G, between the adjacent electrodes or electrode portions 30A, 30B, as depicted in FIG. 2. The separator can comprise one or more electrically insulating materials, such as, for example, Teflon, polyetheretherketone (PEEK), polyetherimide resins (e.g., ULTEM™), diamond (e.g., industrial grade diamond), ceramic materials, polyimide and the like.

As noted above with respect to the gap G separating the adjacent electrodes or electrode portion, the insulating separator 34 can be 0.5 mm long. In other embodiments, the length of the separator 34 can be greater or smaller than 0.5 mm (e.g., 0.1-0.2, 0.2-0.3, 0.3-0.4, 0.4-0.5, 0.5-0.6, 0.6-0.7, 0.7-0.8, 0.8-0.9, 0.9-1.0 mm, values between the foregoing ranges, less than 0.1 mm, greater than 1 mm, etc.), as desired or required.

According to some embodiments, as discussed in greater detail herein, to ablate or otherwise heat or treat targeted tissue of a subject successfully with the high-resolution tip electrode design, such as the one depicted in FIG. 2, the two electrodes or electrode portions 30A, 30B are electrically coupled to each other at the RF treatment (e.g., ablation) frequency or range of RF treatment frequencies. Thus, the two electrodes or electrode portions can advantageously function as (e.g., behave like) a single longer electrode at the RF treatment frequency or range of treatment frequencies (e.g., frequencies between 400 kHz and 600 kHz) whereas the two electrodes or electrode portions behave as separate electrodes at frequencies used for mapping purposes (e.g., frequencies less than 1 kHz). For clarity, a filtering element such as described below, may have a value such that at ablative or other treatment frequencies, the filtering element effectively shorts the two electrodes or electrode portions such that the two electrodes or electrode portions behave as a single composite tip electrode during ablation or treatment and the filtering element effectively presents an open circuit between the two electrodes or electrode portions such that they behave as electrically separated distinct electrodes for mapping purposes (e.g., EGM mapping or recording). As shown, one of the electrode portions (for example, the distal electrode) 30A can be electrically coupled to an energy delivery module 40 (for example, an RF generator). As discussed herein, the module 40 can comprise one or more components or features, such as, for example, an energy generation device that is configured to selectively energize and/or otherwise activate the energy members (for example, RF electrodes), one or more input/output devices or components, a processor (for example, a processing or control device) that is configured to regulate one or more aspects of the treatment system, a memory and/or the like.

Figure 3:
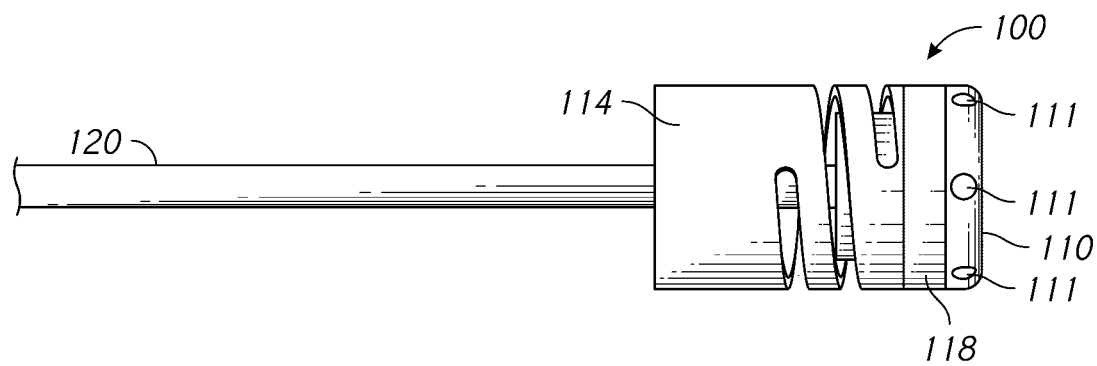
FIG. 3 illustrates a side view of a system's catheter comprising a high-resolution-tip design according to another embodiment.
Figure 4:
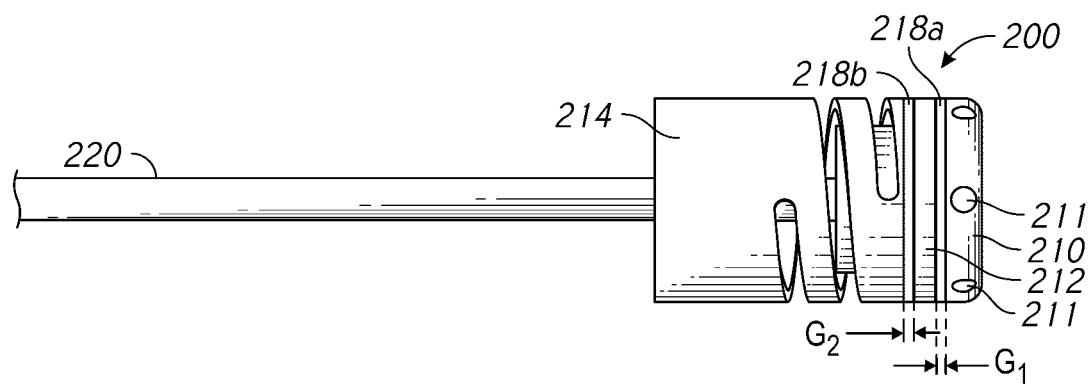
FIG. 4 illustrates a side view of a system's catheter comprising a high-resolution-tip design according to yet another embodiment.

FIGS. 3 and 4 illustrate different embodiments of catheter systems 100, 200 that incorporate a high-resolution tip design. For example, in FIG. 3, the electrode (e.g., radiofrequency electrode) along the distal end of the electrode comprises a first or distal electrode or electrode portion 110 and a second or proximal electrode or electrode portion 114. As shown and discussed in greater detail herein with reference to other configurations, the high-resolution tip design 100 includes a gap G between the first and second electrodes or electrode portions 110, 114. In some configurations, the second or proximal electrode or electrode portion 114 is generally longer than the first or distal electrode or electrode portion 110. For instance, the length of the proximal electrode 114 can be between 1 to 20 times (e.g., 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, values between the foregoing ranges, etc.) the length of the distal electrode 110, as desired or required. In other embodiments, the length of the proximal electrode can be greater than 20 times (e.g., 20-25, 25-30, more than 30 times, etc.) the length of the distal electrode. In yet other embodiments, the lengths of the distal and proximal electrodes are about the same. However, in some embodiments, the distal electrode 110 is longer than the proximal electrode 114 (e.g., by 1 to 20 times, such as, for example, 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, values between the foregoing ranges, etc.).

As shown in FIG. 3 and noted above, regardless of their exact design, relative length diameter, orientation and/or other characteristics, the electrodes or electrode portions 110, 114 can be separated by a gap G. The gap G can comprise a relatively small electrically insulating gap or space. In some embodiments, an electrically insulating separator 118 can be snugly positioned between the first and second electrodes or electrode portions 110, 114. In certain embodiments, the separator 118 can have a length of about 0.5 mm. In other embodiments, however, the length of the separator 118 can be greater or smaller than 0.5 mm (e.g., 0.1-0.2, 0.2-0.3, 0.3-0.4, 0.4-0.5, 0.5-0.6, 0.6-0.7, 0.7-0.8, 0.8-0.9, 0.9-1.0 mm, values between the foregoing ranges, less than 0.1 mm, greater than 1 mm, etc.), as desired or required. The separator can include one or more electrically insulating materials (e.g., materials that have an electrical conductivity less than about 1000 or less (e.g., 500-600, 600-700, 700-800, 800-900, 900-1000, 1000-1100, 1100-1200, 1200-1300, 1300-1400, 1400-1500, values between the foregoing, less than 500, greater than 1500, etc.) than the electrical conductivity of metals or alloys). The separator can comprise one or more electrically insulating materials, such as, for example, Teflon, polyetheretherketone (PEEK), polyoxymethylene, acetal resins or polymers and the like.

As shown in FIG. 3, the separator 118 can be cylindrical in shape and can have the identical or similar diameter and configuration as the adjacent electrodes or electrode portions 110, 114. Thus, in some embodiments, the outer surface formed by the electrodes or electrode portions 110, 114 and the separator 118 can be generally uniform or smooth. However, in other embodiments, the shape, size (e.g., diameter) and/or other characteristics of the separator 118 can be different than one or more of the adjacent electrodes or electrode portions 110, 114, as desired or required for a particular application or use.

FIG. 4 illustrates an embodiment of a system 200 having three or more electrodes or electrode portions 210, 212, 214 separated by corresponding gaps G1, G2. The use of such additional gaps, and thus, additional electrodes or electrode portions 210, 212, 214 that are physically separated (e.g., by gaps) yet in close proximity to each other, can provide additional benefits to the high-resolution mapping capabilities of the system. For example, the use of two (or more) gaps can provide more accurate high-resolution mapping data related to the tissue being treated. Such multiple gaps can provide information about the directionality of cardiac signal propagation. In addition, high-resolution mapping with high-resolution electrode portions involving multiple gaps can provide a more extended view of lesion progression during the ablation process and higher confidence that viable tissue strands are not left behind within the targeted therapeutic volume. In some embodiments, high-resolution electrodes with multiple gaps can optimize the ratio of mapped tissue surface to ablated tissue surface. Preferably, such ratio is in the range of 0.2 to 0.8 (e.g., 0.2-0.3, 0.3-0.4, 0.4-0.5, 0.5-0.6, 0.6-0.7, 0.7-0.8, ratios between the foregoing, etc.). Although FIG. 4 illustrates an embodiment having a total of three electrodes or electrode portions 210, 212, 214 (and thus, two gaps G1, G2), a system can be designed or otherwise modified to comprise additional electrodes or electrode portions, and thus, additional gaps. For example, in some embodiments, an ablation or other treatment system can include 4 or more (e.g., 5, 6, 7, 8, more than 8, etc.) electrodes or electrode portions (and thus, 3 or more gaps, e.g., 3, 4, 5, 6, 7 gaps, more than 7 gaps, etc.), as desired or required. In such configurations, a gap (and/or an electrical separator 218a, 218b) can be positioned between adjacent electrodes or electrode portions, in accordance with the embodiments illustrated in FIGS. 2 to 4.

As depicted in FIGS. 3 and 4, an irrigation tube 120, 220 can be routed within an interior of the catheter (not shown for clarity). In some embodiments, the irrigation tube 120, 220 can extend from a proximal portion of the catheter (e.g., where it can be placed in fluid communication with a fluid pump) to the distal end of the system. For example, in some arrangements, as illustrated in the side views of FIGS. 3 and 4, the irrigation tube 120, 220 extends and is in fluid communication with one or more fluid ports 211 that extend radially outwardly through the distal electrode 110, 210. Thus, in some embodiments, the treatment system comprises an open irrigation design, wherein saline and/or other fluid is selectively delivered through the catheter (e.g., within the fluid tube 120, 220) and radially outwardly through one or more outlet ports 111, 211 of an electrode 110, 210. The delivery of such saline or other fluid can help remove heat away from the electrodes and/or the tissue being treated. In some embodiments, such an open irrigation system can help prevent overheating of targeted tissue, especially along the tissue that is contacted by the electrodes. An open irrigation design is also incorporated in the system that is schematically illustrated in FIG. 2. For instance, as depicted in FIG. 2, the distal electrode or electrode portion 34 can include a plurality of outlet ports 36 through which saline or other irrigation fluid can exit.

Figure 5:
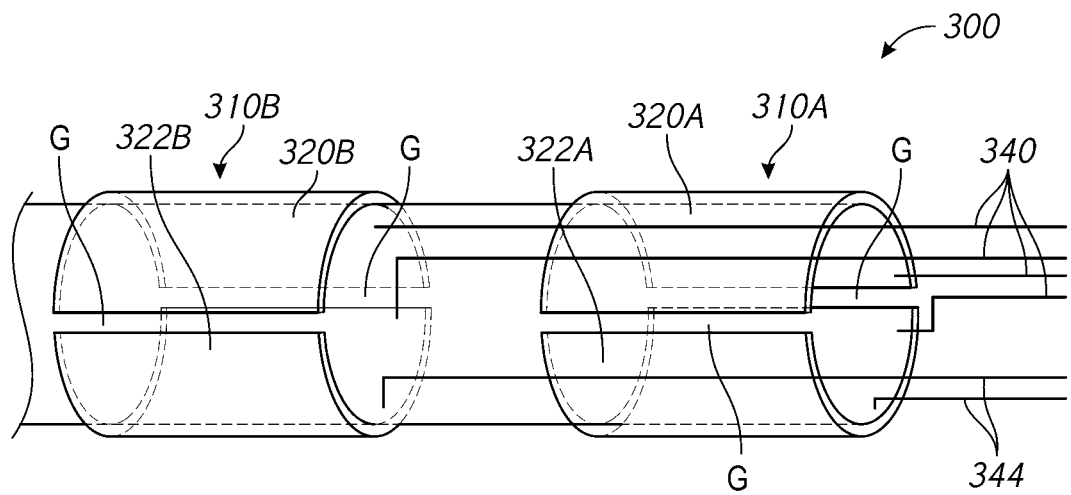
FIG. 5 illustrates an embodiment of a system's catheter comprising two high-resolution-section electrodes each consisting of separate sections circumferentially distributed on the catheter shaft.

According to some embodiments, a catheter can include a high-resolution-tip electrode design that includes one or more gaps in the circumferential direction (e.g., radially), either in addition to or in lieu of gaps in the longitudinal direction. One embodiment of a system 300 comprising one or more electrodes 310A, 310B is illustrated in FIG. 5. As shown, in arrangements where two or more electrodes are included, the electrodes 310A, 310B can be longitudinally or axially offset from each other. For example, in some embodiments, the electrodes 310A, 310B are located along or near the distal end of a catheter. In some embodiments, the electrodes 310A, 310B are located along an exterior portion of a catheter or other medical instrument. However, in other configurations, one or more of the electrodes can be positioned along a different portion of the catheter or other medical instrument (e.g., along at least an interior portion of a catheter), as desired or required.

With continued reference to FIG. 5, each electrode 310A, 310B can comprises two or more sections 320A, 322A and/or 320B, 322B. As shown, in some embodiments, the each section 320A, 322A and/or 320B, 322B can extend half-way around (e.g., 180 degrees) the diameter of the catheter. However, in other embodiments, the circumferential extent of each section can be less than 180 degrees. For example, each section can extend between 0 and 180 degrees (e.g., 15, 30, 45, 60, 75, 90, 105, 120 degrees, degrees between the foregoing, etc.) around the circumference of the catheter along which it is mounted. Thus, in some embodiments, an electrode can include 2, 3, 4, 5, 6 or more circumferential sections, as desired or required.

Regardless of how the circumferential electrode sections are designed and oriented, electrically insulating gaps G can be provided between adjacent sections to facilitate the ability to use the electrode to conduct high-resolution mapping, in accordance with the various embodiments disclosed herein. Further, as illustrated in the embodiment of FIG. 5, two or more (e.g., 3, 4, 5, more than 5, etc.) electrodes 310A, 310B having two or more circumferential or radial sections can be included in a particular system 300, as desired or required.

In alternative embodiments, the various embodiments of a high-resolution tip design disclosed herein, or variations thereof, can be used with a non-irrigated system or a closed-irrigation system (e.g., one in which saline and/or other fluid is circulated through or within one or more electrodes to selectively remove heat therefrom). Thus, in some arrangements, a catheter can include two or more irrigation tubes or conduits. For example, one tube or other conduit can be used to deliver fluid toward or near the electrodes, while a second tube or other conduit can be used to return the fluid in the reverse direction through the catheter.

According to some embodiments, a high-resolution tip electrode is designed to balance the current load between the various electrodes or electrode portions. For example, if a treatment system is not carefully configured, the electrical load may be delivered predominantly to one or more of the electrodes or electrode portions of the high-resolution tip system (e.g., the shorter or smaller distal electrode or electrode portion). This can lead to undesirable uneven heating of the electrode, and thus, uneven heating (e.g., ablation) of the adjacent tissue of the subject. Thus, in some embodiments, one or more load balancing configurations can be used to help ensure that the heating along the various electrodes or electrode portions of the system will be generally balanced. As a result, the high-resolution tip design can advantageously function more like a longer, single electrode, as opposed to two or more electrodes that receive an unequal electrical load (and thus, deliver an unequal amount of heat or level of treatment to the subject's targeted tissue).

Figure 6:
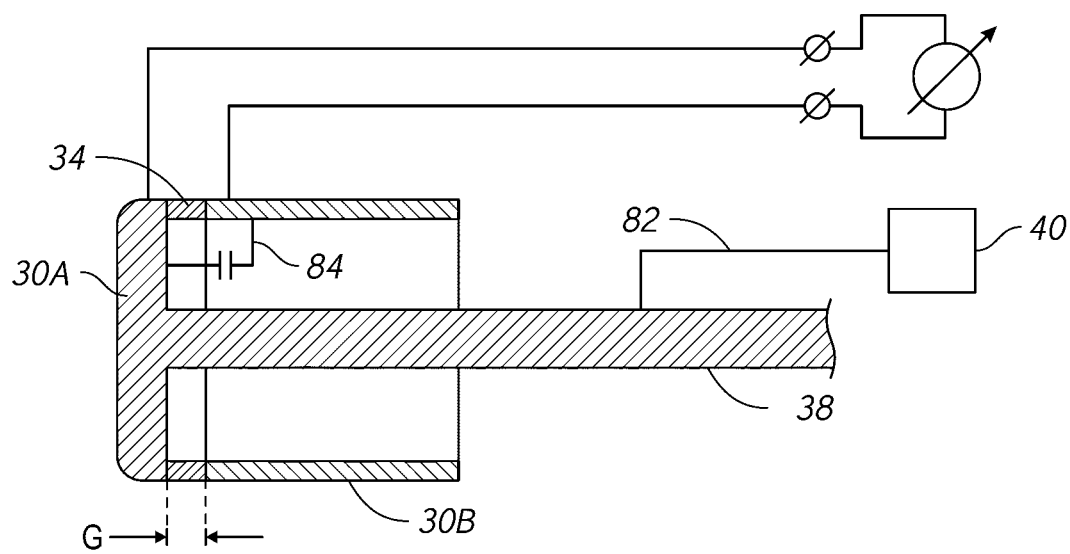
FIG. 6 schematically illustrates one embodiment of a high-pass filtering element consisting of a coupling capacitor. The filtering element can be incorporated into a system's catheter that comprises a high-resolution-tip design.

One embodiment of a configuration that can be used to balance the electrical current load delivered to each of the electrodes or electrode portions in a high-resolution tip design is schematically illustrated in FIG. 6. As shown, one of the electrodes (e.g., the distal electrode) 30A can be electrically coupled to an energy delivery module 40 (e.g., a RF generator). As discussed herein, the module 40 can comprise one or more components or features, such as, for example, an energy generation device that is configured to selectively energize and/or otherwise activate the energy members (e.g., RF electrodes), one or more input/output devices or components, a processor (e.g., a processing or control unit) that is configured to regulate one or more aspects of the treatment system, a memory and/or the like. Further, such a module can be configured to be operated manually or automatically, as desired or required.

In the embodiment that is schematically depicted in FIG. 6, the distal electrode 30A is energized using one or more conductors 82 (e.g., wires, cables, etc.). For example, in some arrangements, the exterior of the irrigation tube 38 comprises and/or is otherwise coated with one or more electrically conductive materials (e.g., copper, other metal, etc.). Thus, as shown in FIG. 6, the one or more conductors 82 can be placed in contact with such a conductive surface or portion of the irrigation tube 38 to electrically couple the electrode or electrode portion 30A to an energy delivery module (e.g., energy delivery module 40 of FIG. 1). However, one or more other devices and/or methods of placing the electrode or electrode portion 30A in electrical communication with an energy delivery module can be used. For example, one or more wires, cables and/or other conductors can directly or indirectly couple to the electrodes, without the use of the irrigation tube.

With continued reference to FIG. 6, the first or distal electrode or electrode portion 30A can be electrically coupled to the second or proximal electrode or electrode portion 30B using one more band-pass filtering elements 84, such as a capacitor, a filter circuit (see, e.g., FIG. 16), etc. For instance, in some embodiments, the band-pass filtering element 84 comprises a capacitor that electrically couples the two electrodes or electrode portions 30A, 30B when radiofrequency current is applied to the system (e.g., radiofrequency current or power having a frequency adapted for ablation or other treatment of tissue). In one embodiment, the capacitor 84 comprises a 100 nF capacitor that introduces a series impedance lower than about 3Ω at 500 kHz, which, according to some arrangements, is a target frequency for RF ablation. However, in other embodiments, the capacitance of the capacitor(s) or other band-pass filtering elements 84 that are incorporated into the system can be greater or less than 100 nF, for example, 5 nF to 300 nF, according to the operating RF frequency, as desired or required. In some embodiments, the capacitance of the filtering element 84 is selected based on a target impedance at a particular frequency or frequency range. For example, in some embodiments, the system can be operated at a frequency of 200 kHz to 10 MHz (e.g., 200-300, 300-400, 400-500, 500-600, 400-600, 600-700, 700-800, 800-900, 900-1000 kHz, up to 10 MHz or higher frequencies between the foregoing ranges, etc.). Thus, the capacitor that couples adjacent electrodes or electrode portions to each other can be selected based on the target impedance for a particular frequency. For example, a 100 nF capacitor provides about 3Ω of coupling impedance at an operating ablation frequency of 500 kHz.

In some embodiments, a series impedance of 3Ω across the electrodes or electrode portions 30A, 30B is sufficiently low when compared to the impedance of the conductor 82 (e.g., wire, cable, etc.), which can be about 5-10Ω, and the impedance of tissue, which can be about 100Ω, such that the resulting tissue heating profile is not negatively impacted when the system is in use. Thus, in some embodiments, a filtering element is selected so that the series impedance across the electrodes or electrode portions is lower than the impedance of the conductor that supplies RF energy to the electrodes. For example, in some embodiments, the insertion impedance of the filtering element is 50% of the conductor 82 impedance, or lower, or 10% of the equivalent tissue impedance, or lower.

In some embodiments, a filtering element (e.g., capacitor a filter circuit such as the one described herein with reference to FIG. 16, etc.) can be located at a variety of locations of the device or accompanying system. For example, in some embodiments, the filtering element is located on or within a catheter (e.g., near the distal end of the catheter, adjacent the electrode, etc.). In other embodiments, however, the filtering element is separate of the catheter. For instance, the filtering element can be positioned within or along a handle to which the catheter is secured, within the generator or other energy delivery module, within a separate processor or other computing device or component and/or the like).

Figure 7:
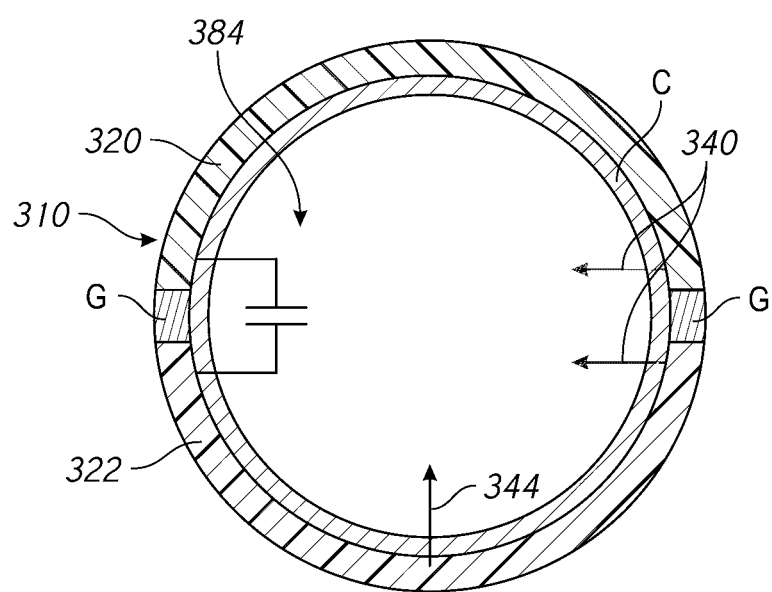
FIG. 7 schematically illustrates one embodiment of four high-pass filtering elements comprising coupling capacitors. The filtering elements can operatively couple, in the operating RF frequency range, the separate electrode sections of a system's catheter electrodes, e.g., those illustrated in FIG. 5.

Similarly, with reference to the schematic of FIG. 7, a filtering element 384 can be included in an electrode 310 comprising circumferentially-arranged portions 320, 322. In FIG. 7, the filtering element 384 permits the entire electrode 310 to be energized within RF frequency range (e.g., when the electrode is activated to ablate). One or more RF wires or other conductors 344 can be used to deliver power to the electrode from a generator or source. In addition, separate conductors 340 can be used to electrically couple the electrode 310 for mapping purposes.

In embodiments where the high-resolution-tip design (e.g., FIG. 4) comprises three or more electrodes or electrode portions, additional filtering elements (e.g., capacitors) can be used to electrically couple the electrodes or electrode portions to each other. Such capacitors or other filtering elements can be selected to create a generally uniform heating profile along the entire length of the high-resolution tip electrode. As noted in greater detail herein, for any of the embodiments disclosed herein or variations thereof, the filtering element can include something other than a capacitor. For example, in some arrangements, the filtering element comprises a LC circuit (e.g., a resonant circuit, a tank circuit, a tuned circuit, etc.). Such embodiments can be configured to permit simultaneous application of RF energy and measurement of EGM recordings.

As discussed above, the relatively small gap G between the adjacent electrodes or electrode portions 30A, 30B can be used to facilitate high-resolution mapping of the targeted tissue. For example, with continued reference to the schematic of FIG. 6, the separate electrodes or electrode portions 30A, 30B can be used to generate an electrogram that accurately reflects the localized electrical potential of the tissue being treated. Thus, a physician or other practitioner using the treatment system can more accurately detect the impact of the energy delivery to the targeted tissue before, during and/or after a procedure. For example, the more accurate electrogram data that result from such configurations can enable the physician to detect any gaps or portions of the targeted anatomical region that was not properly ablated or otherwise treated. Specifically, the use of a high-resolution tip design can enable a cardiac electrophysiologist to more accurately evaluate the morphology of resulting electrograms, their amplitude and width and/or to determine pacing thresholds. In some embodiments, morphology, amplitude and pacing threshold are accepted and reliable EP markers that provide useful information about the outcome of an ablation or other heat treatment procedure.

Figure 8:
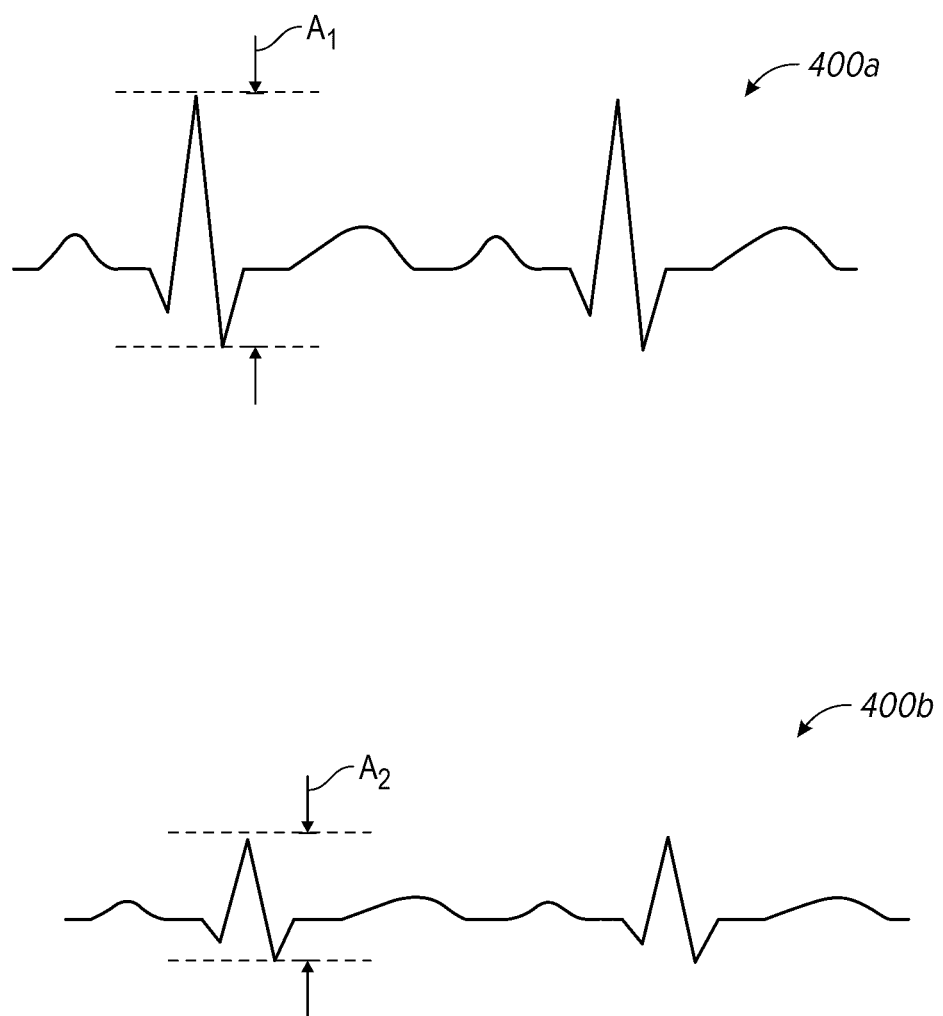
FIG. 8 illustrates embodiments of EKGs obtained from a high-resolution-tip electrode systems disclosed herein configured to detect whether an ablation procedure has been adequately performed.

According to some arrangements, the high-resolution-tip electrode embodiments disclosed herein are configured to provide localized high-resolution electrogram. For example, the electrogram that is obtained using a high-resolution-tip electrode, in accordance with embodiments disclosed herein, can provide electrogram data (e.g., graphical output) 400a, 400b as illustrated in FIG. 8. As depicted in FIG. 8, the localized electrograms 400a, 400b generated using the high-resolution-tip electrode embodiments disclosed herein include an amplitude A1, A2.

With continued reference to FIG. 8, the amplitude of the electrograms 400a, 400b obtained using high-resolution-tip electrode systems can be used to determine whether targeted tissue adjacent the high-resolution-tip electrode has been adequately ablated or otherwise treated. For example, according to some embodiments, the amplitude A1 of an electrogram 400*a* in untreated tissue (e.g., tissue that has not been ablated or otherwise heated) is greater that the amplitude A2 of an electrogram 400*b* that has already been ablated or otherwise treated. In some embodiments, therefore, the amplitude of the electrogram can be measured to determine whether tissue has been treated. For example, the electrogram amplitude A1 of untreated tissue in a subject can be recorded and used as a baseline. Future electrogram amplitude measurements can be obtained and compared against such a baseline amplitude in an effort to determine whether tissue has been ablated or otherwise treated to an adequate or desired degree.

In some embodiments, a comparison is made between such a baseline amplitude (A1) relative to an electrogram amplitude (A2) at a tissue location being tested or evaluated. A ratio of A1 to A2 can be used to provide a quantitative measure for assessing the likelihood that ablation has been completed. In some arrangements, if the ratio (i.e., A1/A2) is above a certain minimum threshold, then the user can be informed that the tissue where the A2 amplitude was obtained has been properly ablated. For example, in some embodiments, adequate ablation or treatment can be confirmed when the A1/A2 ratio is greater than 1.5 (e.g., 1.5-1.6, 1.6-1.7, 1.7-1.8, 1.8-1.9, 1.9-2.0, 2.0-2.5, 2.5-3.0, values between the foregoing, greater than 3, etc.). However, in other embodiments, confirmation of ablation can be obtained when the ratio of A1/A2 is less than 1.5 (e.g., 1-1.1, 1.1-1.2, 1.2-1.3, 1.3-1.4, 1.4-1.5, values between the foregoing, etc.).

For any of the embodiments disclosed herein, a catheter or other minimally-invasive medical instrument can be delivered to the target anatomical location of a subject (e.g., atrium, pulmonary veins, other cardiac location, renal artery, other vessel or lumen, etc.) using one or more imaging technologies. Accordingly, any of the ablation systems disclosed herein can be configured to be used with (e.g., separately from or at least partially integrated with) an imaging device or system, such as, for example, fluoroscopy technologies, intracardiac echocardiography (ICE) technologies and/or the like.

Thermal Shunting

Figure 9:
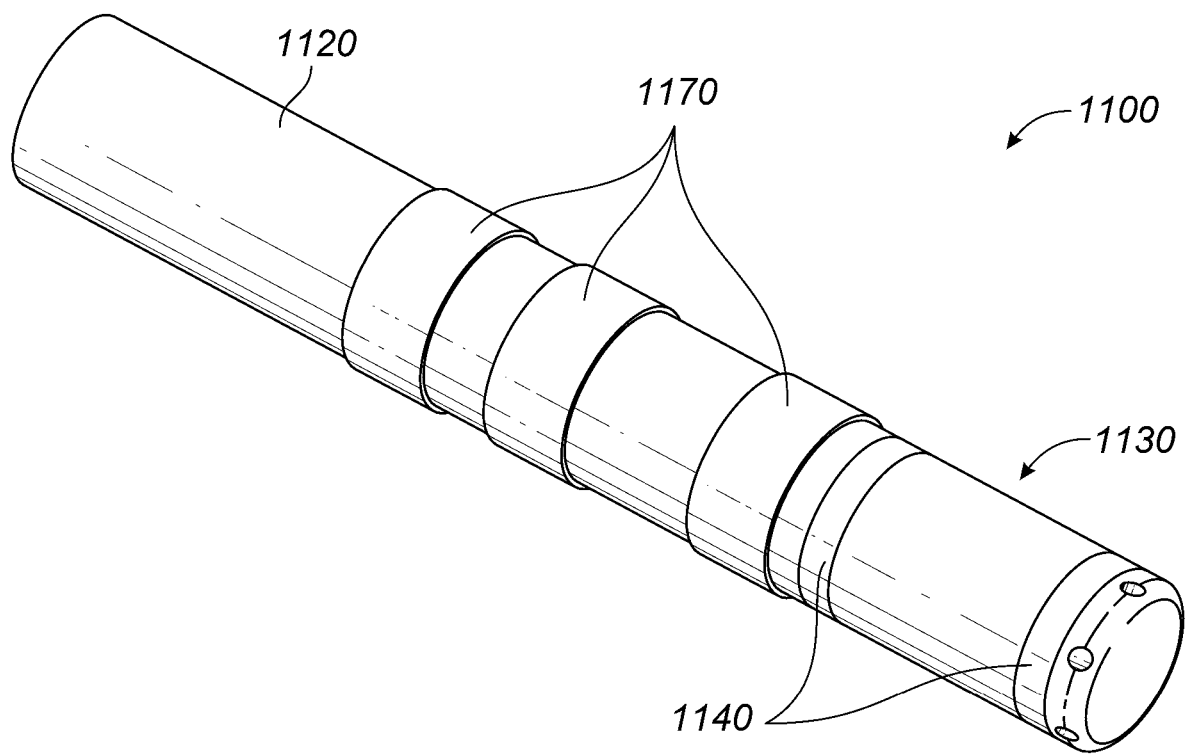
FIG. 9 illustrates a perspective view of an ablation system's catheter comprising an electrode and heat shunt network to facilitate the transfer of heat to an irrigation conduit during use, according to one embodiment.

FIG. 9 illustrates one embodiment of a system 1100 comprising an electrode 1130 (e.g., a unitary RF electrode, a composite (e.g., split-tip) electrode having two, three or more portions, other types of electrodes, etc.) located at or near the distal end of a catheter 1120. In addition, as with any other embodiments disclosed herein, the system can further include a plurality of ring electrodes 1170 to assist with the execution of a treatment procedure (e.g., mapping of tissue adjacent the treatment site, monitoring of the subject, etc.). Although the embodiments of the various systems and related methods disclosed herein are described in the context of radiofrequency (RF) based ablation, the heat transfer concepts (including heat shunting embodiments), either alone or in conjunction with other embodiments described herein (e.g., composite electrode concepts, temperature sensing concepts, etc.), can be implemented in other types of ablation systems as well, such as those, for example, that use microwave emitters, ultrasound transducers, cryoablation members and/or the like to target tissue of a subject.

Figure 10:
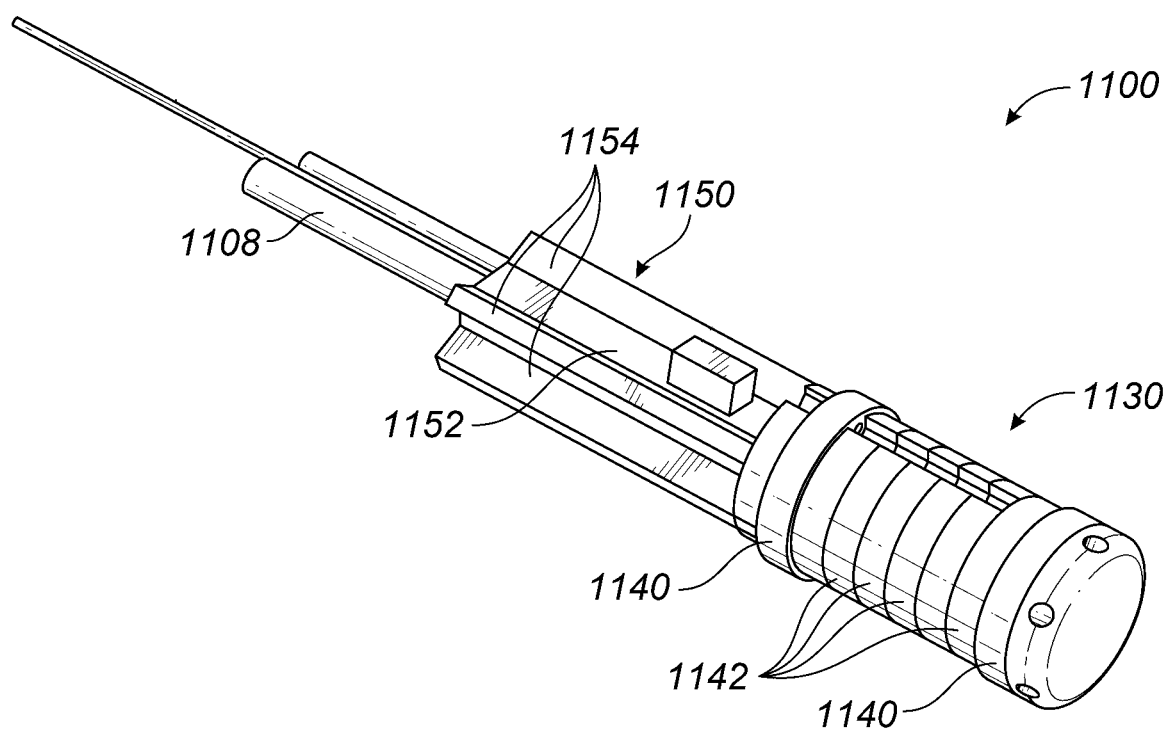
FIG. 10 illustrates a partially exposed view of the system of FIG. 9.
Figure 11:
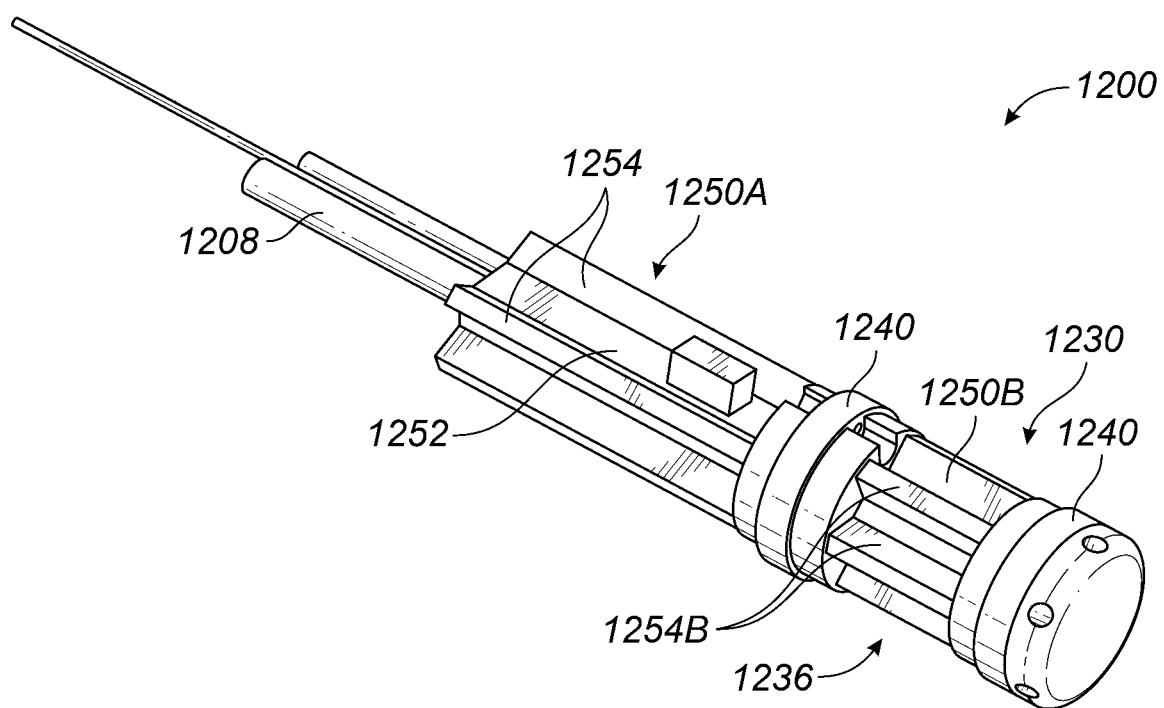
FIG. 11 illustrates a perspective view of an ablation system's catheter comprising an electrode and heat shunt network to facilitate the transfer of heat to an irrigation conduit during use, according to another embodiment.

With reference to FIG. 9 and the corresponding partially-exposed view of the distal end of the catheter illustrated in FIG. 10, one or more heat transfer members or other heat transfer components or features, including any of the heat shunting embodiments disclosed herein, can be used to facilitate the heat transfer from or near the electrode to the irrigation conduit 1108 that extends through the interior of the catheter 1120. For example, in some embodiments, as depicted in FIG. 10, one or more heat transfer disks or members 1140, 1142 (e.g., heat shunt disks or members) can be positioned along the length of the electrode 1130. In some arrangements, the disks or other heat transfer members 1140, 1142 (including any of the heat shunting embodiments disclosed herein) comprise separate components that may or may not contact each other. In other embodiments, however, the heat transfer disks or other heat transfer members 1140, 1142 comprise a unitary or monolithic structure, as desired or required. The disks 1140, 1142 can be in direct or indirect thermal communication with the irrigation conduit 1108 that passes, at least partially, through an interior portion (e.g., along the longitudinal centerline) of the catheter. For example, the disks 1140, 1142 can extend to and make contact with an exterior surface of the irrigation conduit and/or another interior portion of the catheter (e.g., non-irrigation component or portion for embodiments that do not include active cooling using open or closed irrigation). However, in other embodiments, as illustrated in FIG. 11, the disks 1140, 1142 can be in thermal communication (e.g., directly via contact or indirectly) with one or more other heat exchange components or members, including any heat shunting components or members, located between the disks and the irrigation conduit.

A heat sink includes both (i) a heat retention transfer in which heat is localized to/retained by a certain component, and (ii) a heat shunt (which can also be called a heat transfer member) that is used to shunt or transfer heat from, e.g., an electrode to an irrigation passageway. In one embodiment, a heat retention sink is used to retain heat for some period of time. Preferably, a heat shunt (heat transfer member) is used rather than a heat retention sink. A heat shunt (heat transfer member), in some embodiments, provides more efficient dissipation of heat and improved cooling, thus, for example, offering a protective effect to tissue that is considered non-target tissue. For any of the embodiments disclosed herein, one or more heat shunting components can be used to effectively and safely transfer heat away from an electrode and/or the tissue being heated. In some embodiments, a device or system can be configured to adequately transfer heat away from the electrode without any additional components or features (e.g., solely using the heat shunting configurations disclosed herein).

In any of the embodiments disclosed herein, the ablation system can include one or more irrigation conduits that extend at least partially along (e.g., through an interior portion of) a catheter or other medical instrument configured for placement within a subject. The irrigation conduit(s) can be part of an open irrigation system, in which fluid exits through one or more exit ports or openings along the distal end of the catheter (e.g., at or near the electrode) to cool the electrode and/or the adjacent targeted tissue. Alternatively, however, the irrigation conduit(s) can be part of a closed irrigation system, in which irrigation fluid is circulated at least partially through (e.g., as opposed to being expelled from) the catheter (e.g., in the vicinity of the electrode or other ablation member to selectively cool the electrode and/or the adjacent tissue of the subject. For example, in some arrangements, the catheter comprises at least two internal fluid conduits (e.g., a delivery conduit and a return conduit) to circulate irrigation fluid to and perform the desired or necessary heat transfer with the distal end of the catheter, as desired or required. Further, in some embodiments, in order to facilitate the heat transfer between the heat transfer members or components included in the ablation system (e.g., heat shunting members or components), the system can comprise an irrigation conduit that comprises one or more metallic and/or other favorable heat transfer materials (e.g., copper, stainless steel, other metals or alloys, ceramics, polymeric and/or other materials with relatively favorable heat transfer properties, etc.). In yet other embodiments, the catheter or other medical instrument of the ablation system does not include any active fluid cooling system (e.g., open or closed irrigation passage or other components extending through it), as desired or required. As discussed in greater detail herein, such embodiments that do not include active cooling using fluid passage through the catheter can take advantage of enhanced heat transfer components and/or designs to advantageously dissipate and/or distribute heat away from the electrode(s) and/or the tissue being treated.

In some embodiments, the irrigation conduit is fluid communication only with exit ports located along the distal end of the elongate body. In some embodiments, the catheter only comprises irrigation exit openings along a distal end of the catheter (e.g., along a distal end or the electrode). In some embodiments, the system does not comprise any irrigation openings along the heat transfer members (e.g., heat shunt members), and/or, as discussed herein, the system does not comprise an active irrigation system at all. Thus, in such embodiments, the use of heat transfer members along the catheter (e.g., at or near the electrode or other ablation member) help more evenly distribute the heat generated by the electrode or other ablation member and/or assist in heat transfer with the surrounding environment (e.g., blood or other fluid passing along an exterior of the ablation member and/or catheter).

With continued reference to FIG. 10, the proximal end 1132 of the electrode 1130 comprises one or more additional heat transfer members 1150, including any heat shunt embodiments disclosed herein. For example, according to some embodiments, such additional heat transfer members 1150 (e.g., heat shunt members) comprise one or more fins, pins and/or other members that are in thermal communication with the irrigation conduit 108 extending through an interior of the catheter of the system. Accordingly, as with the heat transfer disks or other heat transfer members 1140 positioned along the length of the electrode 1130, including heat shunting members, heat can be transferred and thus removed, from the electrode, the adjacent portions of the catheter and/or the adjacent tissue of the subject, when the electrode is activated, via these heat transfer members 1150.

In any of the embodiments disclosed herein or variations thereof, the heat transfer members 1140, 1150 of the system 1100 that are placed in thermal communication with the irrigation conduit 1108 can comprise one or more materials that include favorable heat transfer properties, including, but not limited to, favorable heat shunting properties. For example, in some embodiments, the thermal conductivity of the material(s) included in the heat transfer members and/or of the overall heat transfer assembly (e.g., when viewed as a unitary member or structure) is greater than 300 W/m/° C. (e.g., 300-350, 350-400, 400-450, 450-500, 500-600, 600-700 W/m/° C., ranges between the foregoing, greater than 700 W/m/° C., etc. Possible materials with favorable thermal conductivity properties include, but are not limited to, copper, brass, beryllium, other metals and/or alloys, aluminal ceramics, other ceramics, industrial diamond (e.g., chemical vapor deposit industrial diamond) and/or other metallic and/or non-metallic materials.

According to certain embodiments where the heat transfer members comprise heat shunting members, the thermal diffusivity of the material(s) included in the heat shunt members and/or of the overall heat shunt assembly (e.g., when viewed as a unitary member or structure) is greater than 1.5 cm$^2$/sec (e.g., 1.5-2, 2-2.5, 2.5-3, 3-4, 4-5, 5-6, 6-7, 7-8, 8-9, 9-10, 10-11, 11-12, 12-13, 13-14, 14-15, 15-20 cm$^2$/sec, values between the foregoing ranges, greater than 20 cm$^2$/sec). Thermal diffusivity measures the ability of a material to conduct thermal energy relative to its ability to store thermal energy. Thus, even though a material can be efficient as transferring heat (e.g., can have a relatively high thermal conductivity), it may not have favorable thermal diffusivity properties, because of its heat storage properties. Heat shunting, unlike heat transferring, requires the use of materials that possess high thermal conductance properties (e.g., to quickly transfer heat through a mass or volume) and a low heat capacity (e.g., to not store heat). Possible materials with favorable thermal diffusivity, and thus favorable heat shunting properties, include, but are not limited to, industrial diamond (e.g., chemical vapor deposit industrial diamond), Graphene, silica, other carbon-based materials and/or the like.

The use of materials with favorable thermal diffusivity properties can help ensure that heat can be efficiently transferred away from the electrode and/or the adjacent tissue during a treatment procedure. In contrast, materials that have favorable thermal conductivity properties, but not favorable thermal diffusivity properties, such as, e.g., copper, other metals or alloys, thermally conductive polypropylene or other polymers, etc., will tend to retain heat. As a result, the use of such materials that store heat may cause the temperature along the electrode and/or the tissue being treated to be maintained at an undesirably elevated level (e.g., over 75 degrees C.) especially over the course of a relatively long ablation procedure, which may result in charring, thrombus formation and/or other heat-related problems.

Industrial diamond (e.g., chemical vapor deposition industrial diamond) and other materials with the requisite thermal diffusivity properties for use in a thermal shunting network, as disclosed in the various embodiments herein, comprise favorable thermal conduction characteristics. Such favorable thermal conduction aspects emanate from a relatively high thermal conductance value (k) and the manner in which the heat shunt members of a network are arranged with respect to each other within the tip and with respect to the tissue. For example, in some embodiments, as RF energy is emitted from the tip and the ohmic heating within the tissue generates heat, the exposed distal most shunt member (e.g., located 0.5 mm from the distal most end of the tip) can actively extract heat from the lesion site. The thermal energy can advantageously transfer through the shunting network in a relatively rapid manner and dissipate through the shunt residing beneath the RF electrode surface the heat shunt network, through a proximal shunt member and/or into the ambient surroundings. Heat that is shunting through an interior shunt member can be quickly transferred to an irrigation conduit extending through an interior of the catheter or other medical instrument. In other embodiments, heat generated by an ablation procedure can be shunted through both proximal and distal shunt members (e.g., shunt members that are exposed to an exterior of the catheter or other medical instrument, such as shown in many of the embodiments herein).

Further, as noted above, the materials with favorable thermal diffusivity properties for use in a heat shunt network not only have the requisite thermal conductivity properties but also have sufficiently low heat capacity values (c). This helps ensure that the thermal energy is dissipated very quickly from the tip to tissue interface as well as the hot spots on the electrode, without heat retention in the heat shunting network. The thermal conduction constitutes the primary heat dissipation mechanism that ensures quick and efficient cooling of the tissue surface and of the RF electrode surface. Conversely a heat transfer (e.g., with relatively high thermal conductivity characteristics but also relatively high heat capacity characteristics) will store thermal energy. Over the course of a long ablation procedure, such stored heat may exceed 75 degrees C. Under such circumstances, thrombus and/or char formation can undesirably occur.

The thermal convection aspects of the various embodiments disclosed herein two-fold. First, an irrigation lumen of the catheter can absorb thermal energy which is transferred to it through the shunt network. Such thermal energy can then be flushed out of the distal end of the RF tip via the irrigation ports. In closed irrigation systems, however, such thermal energy can be transferred back to a proximal end of the catheter where it can be removed. Second, the exposed shunt surfaces along an exterior of the catheter or other medical instrument can further assist with the dissipation of heat from the electrode and/or the tissue being treated. For example, such heat dissipation can be accomplished via the inherent convective cooling aspects of the blood flowing over the surfaces of the electrode.

Accordingly, the use of materials in a heat shunting network with favorable thermal diffusivity properties, such as industrial diamond (e.g., chemical vapor deposition industrial diamond), can help ensure that heat is quickly and efficiently transferred away from the electrode and treated tissue, while maintaining the heat shunting network cool (e.g., due to its low heat capacity properties). This can create a safer ablation catheter and related treatment method, as potentially dangerous heat will not be introduced into the procedure via the heat shunting network itself.

For example, in some embodiments, during the course of an ablation procedure that attempts to maintain the subject's tissue at a desired temperature of about 60 degrees C., the temperature of the electrode is approximately 60 degrees Celsius. Further, the temperature of traditional heat transferring members positioned adjacent the electrode (e.g., copper, other metals or alloys, thermally-conductive polymers, etc.) during the procedure is approximately 70 to 75 degrees Celsius. In contrast, the temperature of the various portions or members of the heat shunting network for systems disclosed herein can be approximately 60 to 62 degrees Celsius (e.g., 10% to 30% less than comparable heat transferring systems) for the same desired level of treatment of tissue.

In some embodiments, the heat shunt members disclosed herein draw out heat from the tissue being ablated and shunt it into the irrigation channel. Similarly, heat is drawn away from the potential hot spots that form at the edges of RF electrodes and are shunted through the heat shunt network into the irrigation channel. From the irrigation channel, via convective cooling, heat can be advantageously released into the blood stream and dissipated away. In closed irrigation systems, heat can be removed from the system without expelling irrigation fluid into the subject.

According to some embodiments, the various heat shunting systems disclosed herein rely on heat conduction as the primary cooling mechanism. Therefore, such embodiments do not require a vast majority of the heat shunting network to extend to an external surface of the catheter or other medical instrument (e.g., for direct exposure to blood flow). In fact, in some embodiments, the entire shunt network can reside within an interior of the catheter tip (i.e., with no portion of the heat shut network extending to an exterior of the catheter or other medical instrument). Further, the various embodiments disclosed herein do not require electrical isolation of the heat shunts from the RF electrode or from the irrigation channel.

According to some embodiments, the heat transfer disks and/or other heat transfer members 1140, 1150, 1250A included in a particular system, including heat shunting members or components, can continuously and/or intermittently or partially extend to the irrigation conduit 108, as desired or required for a particular design or configuration. For instance, as illustrated in the embodiment of FIG. 10, the proximal heat transfer member 1150 (e.g., heat shunt members) can comprise one or more (e.g., 2, 3, 4, 5, more than 5, etc.) wings or portions 1154, 1254 that extend radially outwardly from a base or inner member 1152, 1252. In some embodiments, such wings or radially-extending portion 1154, 1254 are equally spaced from each other to more evenly transfer heat toward the irrigation conduit 1108 with which the heat transfer member 1150, 1250A is in thermal communication. Alternatively, however, the heat transfer member 1150, 1250A, including, but not limited to, a heat shunt member, can include a generally solid or continuous structure between the irrigation conduit 1108 and a radially exterior portion or region of the catheter.

According to some embodiments, heat transfer members (e.g., fins) 1150 can extend proximally to the proximal end of the electrode(s) included along the distal end of a catheter. For example, as illustrated in FIG. 10, the heat transfer members 1150 (e.g., heat shunt members) can extend to, near or beyond the proximal end of the electrode 1130. In some embodiments, the heat transfer members 1150 terminate at or near the proximal end 1132 of the electrode 1130. However, in other arrangements, the heat transfer members 1150, including, without limitation, heat shunt members, extend beyond the proximal end 1132 of the electrode 1130, and in some embodiments, contact and/or are otherwise in direct or indirect thermal communication with distally-located heat transfer members (e.g., heat transfer disks or other heat transfer members located along or near the length of the electrode 1130), including heat shunt members, as desired or required. In yet other embodiments, proximal heat transfer members (e.g., heat shunt members) terminate proximally to the proximal end 1132 of the electrode or other ablation member.

In any of the embodiments disclosed herein, including the systems comprising the enhanced heat transfer (e.g., heat shunting) properties discussed in connection with FIGS. 9-12, the system can include one or more temperature sensors or temperature detection components (e.g., thermocouples) for the detection of tissue temperature at a depth. For example, in the embodiments illustrated in FIGS. 9 and 10, the electrode and/or other portion of the distal end of the catheter can include one or more sensors (e.g., thermocouples, thermistors, etc.) and/or the like. Thus, signals received by sensors and/or other temperature-measurement components can be advantageously used to determine or approximate the extent to which the targeted tissue is being treated (e.g., heated, cooled, etc.). Temperature measurements can be used to control an ablation procedure (e.g., module power provided to the ablation member, terminate an ablation procedure, etc.), in accordance with a desired or required protocol.

In some embodiments, the device further comprises a one or more temperature sensors or other temperature-measuring devices to help determine a peak (e.g., high or peak, low or trough, etc.) temperature of tissue being treated. In some embodiments, the temperature sensors (e.g., thermocouples) located at, along and/or near the ablation member (e.g., RF electrode) can help with the determination of whether contact is being made between the ablation member and targeted tissue (and/or to what degree such contact is being made). In some embodiments, such peak temperature is determined without the use of radiometry. Additional details regarding the use of temperature sensors (e.g., thermocouples) to determine peak tissue temperature and/or to confirm or evaluate tissue contact are provided herein.

In some embodiments, for any of the systems disclosed herein (including but not limited to those illustrated herein) or variations thereof, one or more of the heat transfer members, including, but not limited to, heat shunt members, that facilitate the heat transfer to an irrigation conduit of the catheter are in direct contact with the electrode and/or the irrigation conduit. However, in other embodiments, one or more of the heat transfer members (e.g., heat shunt members) do not contact the electrode and/or the irrigation conduit. Thus, in such embodiments, the heat transfer members are in thermal communication with the electrode and/or irrigation conduit, but not in physical contact with such components. For example, in some embodiments, one or more intermediate components, layers, coatings and/or other members are positioned between a heat transfer member (e.g., a heat shunt member) and the electrode (or other ablation member) and/or the irrigation conduit.

FIG. 11 illustrates another embodiment of an ablation system 1200 comprising an electrode (e.g., a RF electrode, a composite (e.g., split-tip) electrode, etc.) or other ablation member 1230 located along or near the distal end of a catheter or other elongated member. In some embodiments, an interior portion 1236 of the electrode or other ablation member (not shown in FIG. 11, for clarity) can include a separate, internal heat transfer member 1250B, including any heat shunt embodiments disclosed herein. Such a heat transfer member 1250B can be in addition to or in lieu of any other heat transfer members located at, within and/or near the electrode or other ablation member. For example, in the depicted embodiment, in the vicinity of the electrode 1230, the system 1200 comprises both an internal heat transfer member 1250B and one or more disk-shaped or cylindrical heat transfer members 1240 (e.g., heat shunting members).

For any of the embodiments disclosed herein, at least a portion of heat transfer member, including a heat shunt member, that is in thermal communication with the irrigation conduit extends to an exterior surface of the catheter, adjacent to (and, in some embodiments, in physical and/or thermal contact with) the electrode or other ablation member. Such a configuration, can further enhance the cooling of the electrode or other ablation member when the system is activated, especially at or near the proximal end of the electrode or ablation member, where heat may otherwise tend to be more concentrated (e.g., relative to other portions of the electrode or other ablation member). According to some embodiments, thermal conductive grease and/or any other thermally conductive material (e.g., thermally-conductive liquid or other fluid, layer, member, coating and/or portion) can be used to place the thermal transfer, such as, for example, a heat shunt member or heat shunt network, in thermal communication with the irrigation conduit, as desired or required. In such embodiments, such a thermally conductive material places the electrode in thermal communication, at least partially, with the irrigation conduit.

With continued reference to FIG. 11, the heat transfer member (e.g., heat shunt member) 1250B located along an interior portion of the electrode 1230 can include one or more fins, wings, pins and/or other extension members 1254B. Such members 1254B can help enhance heat transfer with the (e.g., heat shunting to, for heat shunting embodiments) irrigation conduit 1208, can help reduce the overall size of the heat transfer member 1254B and/or provide one or more additional advantages or benefits to the system 1200.

Figure 12:
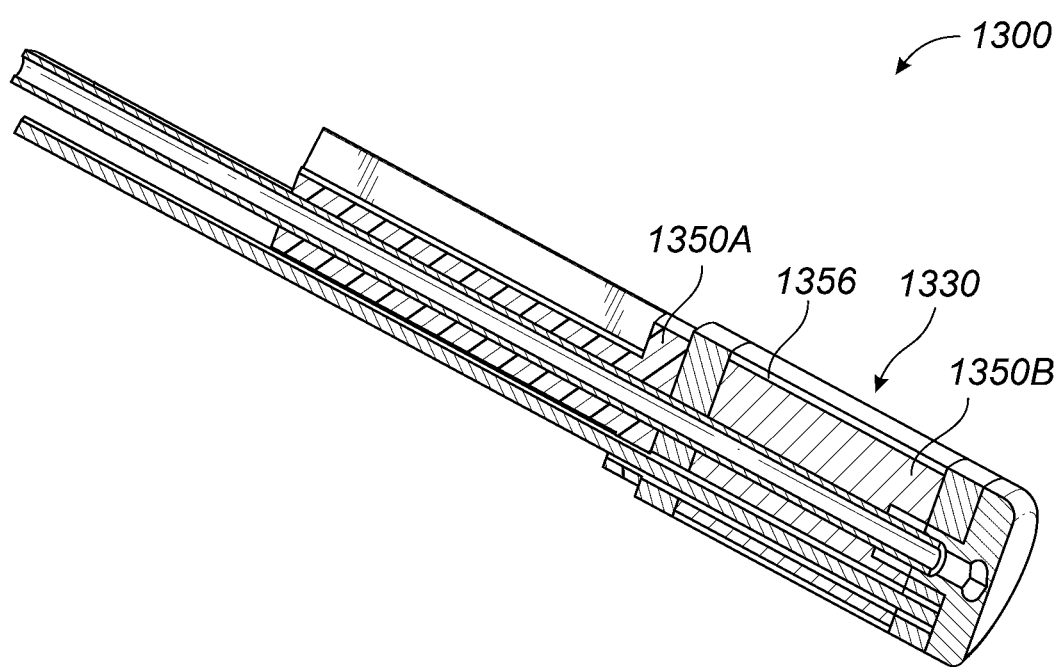
FIG. 12 illustrates a cross-sectional view of an ablation system's catheter comprising an electrode and heat shunt network to facilitate the transfer of heat to an irrigation conduit during use, according to one embodiment.

Another embodiment of an ablation system 1300 comprising one or more heat transfer (e.g., heat shunt) components or features 1350A, 1350B that facilitate the overall heat transfer of the electrode or other ablation member during use is illustrated in FIG. 12. As shown, heat transfer (e.g., shunting) between one or more heat transfer members 1350B located along an interior of an electrode or other ablation member 1330 can be facilitated and otherwise enhanced by eliminating air gaps or other similar spaces between the electrode and the heat transfer members. For example, in the illustrated embodiment, one or more layers 1356 of an electrically conductive material (e.g., platinum, gold, other metals or alloys, etc.) have been positioned between the interior of the electrode 1330 and the exterior of the heat transfer member 1350B. Such layer(s) 1356 can be continuously or intermittently applied between the electrode (or another type of ablation member or energy delivery member) and the adjacent heat transfer member(s), including, but not limited to, heat shunting member(s). Further, such layer(s) 1356 can be applied using one or more methods or procedures, such as, for example, sputtering, other plating techniques and/or the like. Such layer(s) 1356 can be used in any of the embodiments disclosed herein or variations thereof.

Figure 13:
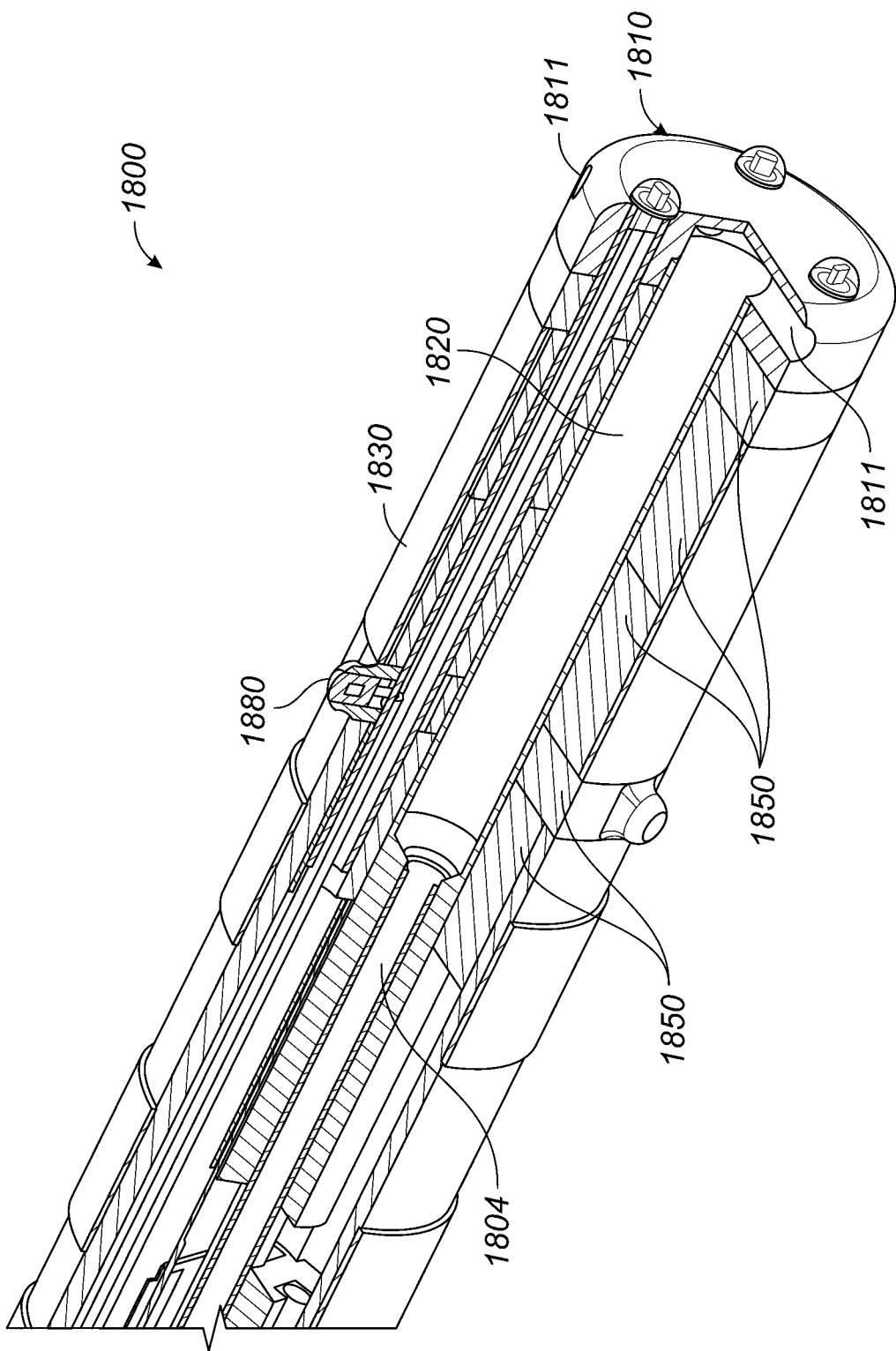
FIG. 13 illustrates a partial cross-sectional perspective view of one embodiment of an ablation system's catheter comprising an open irrigation cooling system.

FIG. 13 illustrates a distal portion of a catheter or other medical instrument of an ablation system 1800 comprising one or more heat transfer members 1850 (e.g., heat shunt members) that facilitate the efficient transfer of heat generated by the electrode or other energy delivery member 1830. As shown in FIG. 13, the heat shunt members 1850 are positioned immediately adjacent (e.g., within an interior of) the electrode 1830. Accordingly, as discussed in greater detail herein, heat generated by the electrode or other energy delivery member 1830 can be transferred via the one or more heat shunt members 1850. As discussed above, the heat shunt members advantageously comprise favorable thermal diffusivity properties to quickly transfer heat while not retaining heat. Thus, the likelihood of localized hot spots (e.g., along the distal and/or proximal ends of the electrode) can be prevented or reduced. In addition, the heat dissipation or removal (e.g., away from the electrode) can be more easily and/or quickly realized using the heat shunt members 1850.

As discussed herein, for example, the heat shunt members 1850 can include industrial diamond (e.g., chemical vapor deposition industrial diamond), Graphene, silica or other carbon-based materials with favorable thermal diffusivity properties and/or the like. In some embodiments, the heat shunt members 1850 comprise a combination of two, three or more materials and/or portions, components or members. In some embodiments, the thermal diffusivity of the material(s) included in the heat shunt members and/or of the overall heat shunting network or assembly (e.g., when viewed as a unitary member or structure) is greater than 1.5 cm$^2$/sec (e.g., 1.5-2, 2-2.5, 2.5-3, 3-4, 4-5, 5-6, 6-7, 7-8, 8-9, 9-10, 10-11, 11-12, 12-13, 13-14, 14-15, 15-20 cm$^2$/sec, values between the foregoing ranges, greater than 20 cm$^2$/sec).

The heat shunt members 1850 (e.g., fins, rings, blocks, etc.) can be in direct or indirect contact with the electrode or other energy delivery member 1830. Regardless of whether direct physical contact is made between the electrode and one or more of the heat transfer shunt 1850, the heat shunt members 1850 can be advantageously in thermal communication with the electrode, thereby facilitating the heat dissipation and/or heat transfer properties of the catheter or other medical instrument. In some embodiments, for example, one or more intermediate layers, coatings, members and/or other components are positioned between the electrode (or other energy delivery member) and the heat shunt members, as desired or required.

With continued reference to FIG. 13, as discussed with other embodiment herein, a catheter or other medical instrument of the ablation system 1800 comprises an open irrigation system configured to deliver a cooling fluid (e.g., saline) to and through the distal end of the catheter or other medical instrument. Such an open irrigation system can help remove heat from the electrode or other energy delivery member during use. In some embodiments, the heat shunting network and the favorable thermal diffusivity properties it possesses can help to quickly and efficiently transfer heat from the electrode and/or the tissue being treated to an irrigation conduit or passage 1804 or chamber 1820 during use. For example, as depicted in FIG. 13, an irrigation conduit or passage 1804 extends through an interior of the catheter and is in fluid communication with one or more outlet ports 1811 along the distal member 1810 of the catheter. However, as discussed in greater detail herein, enhanced heat shunt members can be incorporated into the design of a catheter or other medical instrument without the use of an open irrigation system and/or without an active fluid cooling system, as desired or required. In some embodiments, the flow of irrigation fluid (e.g., saline) through the irrigation conduit or chamber of the catheter or other medical instrument can be modified to vary the heat shunting that occurs through the heat shunting network. For example, in some embodiments, due to the favorable heat transfer properties of the heat shunting network and its ability to not retain heat, the flow rate of irrigation fluid through a catheter can be maintained below 5 ml/min (e.g., 1-2, 2-3, 3-4, 4-5 ml/min, flow rates between the foregoing ranges, less than 1 ml/min, etc.). In one embodiment, the flow rate of irrigation fluid through a catheter is maintained at approximately 1 ml/min. In other embodiments, the flow rate of irrigation fluid passing through the catheter can be between 5 and 15 ml/min (e.g., 5-6, 6-7, 7-8, 8-9, 9-10, 11-12, 12-13, 13-14, 14-15 ml/min, flow rates between the foregoing rates, etc.) or greater than 15 ml/min (e.g., 15-16, 16-17, 17-18, 18-19, 19-20 ml/min, flow rates between the foregoing rates, etc.), as desired or required. In some embodiments, such irrigation flow rates are significantly less than would otherwise be required if non-heat shunting members (e.g., metals, alloys, thermally-conductive polymers, other traditional heat transferring members, etc.) were being used to transfer heat away from the electrode and/or the tissue between treated. For example, the required flow rate of the irrigation fluid passing through an interior of a catheter that has a heat shunting member in accordance with the various embodiments disclosed herein or variations thereof, can be decreased by 20% to 90% (e.g., 20-25, 25-30, 30-35, 35-40, 40-45, 45-50, 50-55, 55-60, 60-65, 65-70, 70-75, 75-80, 80-85, 85-90%, percentages between the foregoing ranges, etc.), as compared to systems that use traditional heat transferring members or no heat transferring members at all (e.g., assuming the same amount of heating is produced at the electrode, the same anatomical location is being treated and other parameters are the same). For example, in some commercially available RF ablation systems, an irrigation flow rate of about 30 ml/min (e.g., 25-35 ml/min) is typically required to accomplish a desired level of heat transfer way from the electrode. As noted above, in some arrangements, the systems disclosed herein that utilize a heat shunting network can utilize a irrigation flow rate of about 10 ml/min or lower to effectively shunt the heat away from the electrode. Thus, in such embodiments, the irrigation flow rate can be reduced by at least 60% to 70% relative to traditional and other commercially available systems.

Thus, as noted in greater detail herein, the use of heat shunting materials to shunt heat away from the electrode and/or the adjacent tissue can also reduce the amount of irrigation fluid that is being discharged into the subject's blood stream in an open irrigation system. Since the discharge of irrigation fluid into the subject is not desirable, the use of heat shunting in an ablation catheter can provide additional benefits to an ablation procedure. For example, in some arrangements, discharging excessive saline or other cooling fluid into the heart, blood vessel and/or other targeted region of the subject can bring about negative physiological consequences to the subject (e.g., heart failure).

As noted above, the use of heat shunting components at or near the electrode can also provide one or more additional benefits and advantages. For example, a significantly lower irrigation flow rate is required to effectively remove heat away from the electrode and the surrounding tissue using heat shunting components (e.g., vis-à-vis traditional heat transferring components and members), the irrigation fluid in such systems is less likely to negatively impact any temperature sensors (e.g., sensor 1880 in FIG. 13) that are located along or near the outside of the distal end of a catheter, allowing more accurate temperature measurements. This is particularly relevant for systems, such as those disclosed herein, where temperature sensors are configured to detect the temperature of adjacent tissue of a subject (e.g., not the temperature of the electrode or another component or portion of the treatment system). Thus, the lower volume of fluid being discharged at or in the vicinity of the sensors (e.g., compared to systems that do not use heat shunting, systems that include traditional heat transfer components, systems that rely primarily or strictly on heat transfer between the electrode (and/or tissue) and blood passing adjacent the electrode (and/or tissue), other open-irrigation systems, etc.) can increase the accuracy of the temperature measurements obtained by the sensors located at or near the distal end of a catheter or other medical instrument.

Also, since the irrigation fluid can be delivered at a lower flow rate which is characterized by a laminar flow profile (e.g., as opposed to a turbulent flow profile that may be required when the irrigation flow rate is higher), any disruptive fluid dynamic effects resulting from an otherwise higher flow rate can be advantageously avoided or at least reduced. Thus, the laminar flow of fluid (and/or in conjunction with the significantly lower flow rate of the fluid relative to higher flow systems) can help with the accuracy of the temperature measurements by the sensors located near the electrode, the tissue being treated and/or any other location along the distal end of the catheter or other medical instrument.

Further, since heat shunting components positioned along or near the electrode are so effective in transferring heat away from the electrode and/or the adjacent tissue of the subject being treated without retaining the heat being transferred, the need to have a longer electrode and/or larger heat transferring members or portions can be advantageously eliminated. For example, traditional systems that utilize one or more heat transferring members (as opposed and in contrast to heat shunting members) or systems that do not use any heat transferring members or components at all rely on the heat transfer between the electrode and the surrounding environment (e.g., blood that flows past the electrode, irrigation fluid passing through an interior of the catheter, etc.) to attempt to cool the electrode. As a result, the length, size and/or other dimensions of the electrode or traditional heat transferring members needs to be increased. This is done to increase the surface area for improved heat transfer between the electrode and/or the heat transferring members and the fluid that will provide the heat transfer (e.g., blood, irrigation fluid, etc.). However, in various embodiments disclosed herein, it is advantageously not necessary to provide such enlarged surface areas for the electrode and/or the heat shunting components or other members of the heat shunting network. Accordingly, the electrode can be sized based on the intended ablation/heating and/or mapping (e.g., high-resolution) properties without the need to oversize based on heat transfer capacity. Such oversizing can negatively impact the safety and efficacy of a lesion formation procedure.

Therefore, as discussed herein, in some embodiments, the size of the heat shunting members can be advantageously reduced (e.g., as compared to the size of heat transferring members in traditional systems). Heat generated during a treatment procedure can be efficiently and rapidly transferred away from electrode and/or the tissue being treated via the heat shunting network without the fear of such network retaining the heat being transferred. In some embodiments, the heat can be shunted to irrigation fluid passing through an interior of the catheter or other medical instrument. In other embodiments, heat can be transferred to surrounding bodily fluid of the subject (e.g., blood) via heat shunting members that are positioned along an exterior of the catheter or other medical instrument, either in addition or in lieu of heat shunting to an irrigation fluid.

According to some embodiments, the total length (e.g., along a longitudinal direction) of the heat shunting members that extend to the exterior of the catheter or other medical instrument (such as, e.g., in the configurations depicted in FIGS. 13 to 17B) can be 1 to 3 mm (e.g., 1-1.5, 1.5-2, 2-2.5, 2.5-3 mm, lengths between the foregoing values, etc.). As noted above, despite such a relatively short exposure length, the heat shunting members can effectively transfer heat away from the electrode and/or the tissue being ablated without retaining heat.

According to some embodiments, the total length (e.g., along a longitudinal direction) of the heat shunting members that extend along an interior of the catheter or other medical instrument (such as, e.g., in the configurations depicted in FIGS. 13 to 17B) can be 1 to 30 mm (e.g., 1-2, 2-3, 3-4, 4-5, 5-6, 6-7, 7-8, 8-9, 9-10, 10-11, 11-12, 12-13, 13-14, 14-15, 15-20, 20-25, 25-30 mm, lengths between the foregoing values, etc.). As noted above, despite such a relatively short overall length, the heat shunting members can effectively transfer heat away from the electrode and/or the tissue being ablated to fluid passing through the irrigation channel of the catheter or other medical instrument without retaining heat.

According to some embodiments, the total length (e.g., along a longitudinal direction) of the heat shunting members that extend along an interior of the catheter or other medical instrument plus the electrode (such as, e.g., in the configurations depicted in FIGS. 13 to 17B) can be 1 to 30 mm (e.g., 1-2, 2-3, 3-4, 4-5, 5-6, 6-7, 7-8, 8-9, 9-10, 10-11, 11-12, 12-13, 13-14, 14-15, 15-20, 20-25, 25-30 mm, lengths between the foregoing values, etc.). As noted above, despite such a relatively short overall length, the heat shunting members can effectively transfer heat away from the electrode and/or the tissue being ablated to fluid passing through the irrigation channel of the catheter or other medical instrument without retaining heat.

As illustrated in FIG. 13, an interior of the distal end of the catheter or other medical instrument can comprise a cooling chamber or region 1820 that is in fluid communication with the irrigation conduit or passage 1804. As shown, according to some embodiments, the cooling chamber 1820 includes a diameter or cross-sectional dimension that is greater than the diameter or cross-sectional dimension of the fluid conduit or passage 1804. For example, in some arrangements, the diameter or other cross-sectional dimension of the cooling chamber or region 1820 is approximately 1 to 3 times (e.g., 1 to 1.1, 1.1 to 1.2, 1.2 to 1.3, 1.3 to 1.4, 1.4 to 1.5, 1.5 to 1.6, 1.6 to 1.7, 1.7 to 1.8, 1.8 to 1.9, 1.9 to 2.0, 2.0 to 2.1, 2.1 to 2.2, 2.2 to 2.3, 2.3 to 2.4, 2.4 to 2.5, 2.5 to 2.6, 2.6 to 2.7, 2.7 to 2.8, 2.8 to 2.9, 2.9 to 3, values between the foregoing, etc.) the diameter or cross-section dimension of the fluid conduit or passage 1804, as desired or required. In other embodiments, the diameter or other cross-sectional dimension of the cooling chamber or region 1820 is approximately greater than 3 times the diameter or cross-section dimension of the fluid conduit or passage 1804, as desired or required (e.g., 3 to 3.5, 3.5 to 4, 4 to 5, values between the foregoing, greater than 5, etc.). In other embodiments, the diameter or cross-section dimension of the cooling chamber or region 1820 is similar or identical to that of the fluid conduit or passage 1804 (or smaller than that of the fluid conduit or passage), as desired or required.

Figure 14:
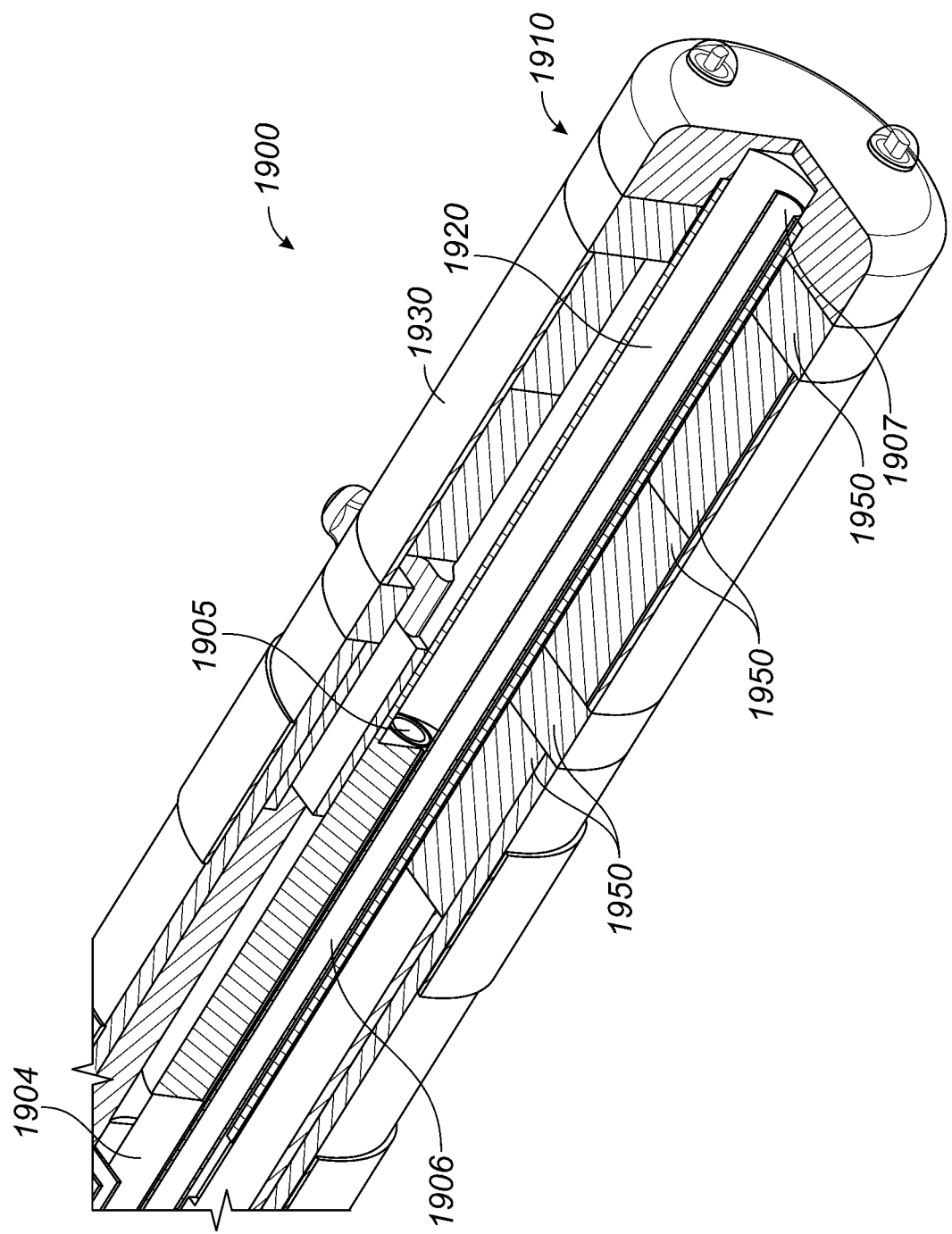
FIG. 14 illustrates a partial cross-sectional perspective view of one embodiment of an ablation system's catheter comprising a closed irrigation cooling system.

FIG. 14 illustrates a distal end of a catheter or other medical instrument of another embodiment of an ablation system 1900. As shown, the catheter comprises one or more energy delivery members 1930 (e.g., a split-tip composite RF electrode, another type of electrode, another type of ablation member, etc.) along its distal end 1910. Like in FIG. 13, the depicted arrangement comprises an active cooling system using one or more fluid conduits or passages that extend at least partially through the interior of the catheter or other medical instrument.

With continued reference to FIG. 14, the catheter or medical instrument of the ablation system 1900 includes a closed irrigation system (e.g., non-open irrigation system) in which cooling fluid (e.g., saline) is circulated at least partially through an interior of the catheter (e.g., to and/or near the location of the electrode or other energy delivery member) to transfer heat away from such electrode or other energy delivery member. As shown, the system can include two separate conduits or passages 1904, 1906 extending at least partially through the interior of the catheter or other medical instrument configured for placement within and/or adjacent targeted tissue of a subject. In some embodiments, one fluid conduit or passage 1904 is configured to deliver fluid (e.g., saline) to the distal end of the catheter or instrument (e.g., adjacent the electrode, ablation member or other energy delivery member), while a separate conduit or passage 1906 is configured to return the cooling fluid delivered to or near the distal end of the catheter or other medical instrument proximally. In other embodiments, more than one passage or conduit delivers fluid to the distal end and/or more than one passage or fluid returns fluid from the distal end, as desired or required.

In the embodiment of FIG. 14, the fluid delivery conduit or passage 1904 is in fluid communication with a cooling chamber or region 1920 that extends within an interior of the electrode or other energy delivery member 1930. In the depicted arrangement, the outlet 1905 of the fluid delivery conduit or passage 1904 is located at a location proximal to the distal end or inlet 1907 of the fluid return conduit or passage 1906. Thus, in the illustrated embodiment, the cooling chamber or region 1920 generally extends between the outlet 1905 of the fluid delivery conduit or passage 1904 and the inlet 1907 of the fluid return conduit or passage 1906. However, in other embodiments, the length, orientation, location and/or other details of the cooling chamber or portion 1920 can vary, as desired or required. Further, in some embodiments, a catheter or other medical instrument can include a closed fluid cooling system (e.g., wherein cooling fluid is circulated through the catheter or medical instrument) without the inclusion of a separate cooling chamber or portion. Regardless of the exact orientation of the various fluid delivery and/or return lines (e.g., passages, conduits, etc.) of the catheter or medical instrument in a closed-loop fluid cooling system, fluid is simply circulated through at least a portion of the catheter or other medical instrument (e.g., adjacent and/or in the vicinity of the electrode or energy delivery member being energized) to selectively and advantageously transfer heat away from the electrode or energy delivery member. Thus, in such embodiments, the various fluid conduits or passages are in thermal communication with the electrode or other energy delivery member.

In some embodiments, it is advantageous to transfer heat away from the electrode (or other energy delivery member) of an ablation system, and thus, the targeted tissue of the subject, without expelling or discharging cooling fluid (e.g., saline) into the subject. For example, in some arrangements, discharging saline or other cooling fluid into the heart, blood vessel and/or other targeted region of the subject can bring about negative physiological consequences to the subject (e.g., heart failure). Thus, in some embodiments, it is preferred to treat a subject with an ablation system that includes a catheter or other medical instrument with a closed fluid cooling system or without an active fluid cooling system altogether.

As with the embodiment of FIG. 14 (and/or other embodiments disclosed herein), the depicted catheter includes one or more heat shunt members 1950 that are in thermal communication with the electrode, ablation member or other energy delivery member 1930 of the system 1900. As discussed above, the heat shunt members 1950 can include industrial diamond, Graphene, silica, other carbon-based materials with favorable thermal diffusivity properties and/or the like. In some embodiments, the thermal diffusivity of the material(s) included in the heat shunt members and/or of the overall heat shunt network or assembly (e.g., when viewed as a unitary member or structure) is greater than 1.5 $cm^2$/sec (e.g., 1.5-2, 2-2.5, 2.5-3, 3-4, 4-5, 5-6, 6-7, 7-8, 8-9, 9-10, 10-11, 11-12, 12-13, 13-14, 14-15, 15-20 $cm^2$/sec, values between the foregoing ranges, greater than 20 $cm^2$/sec).

Figure 15:
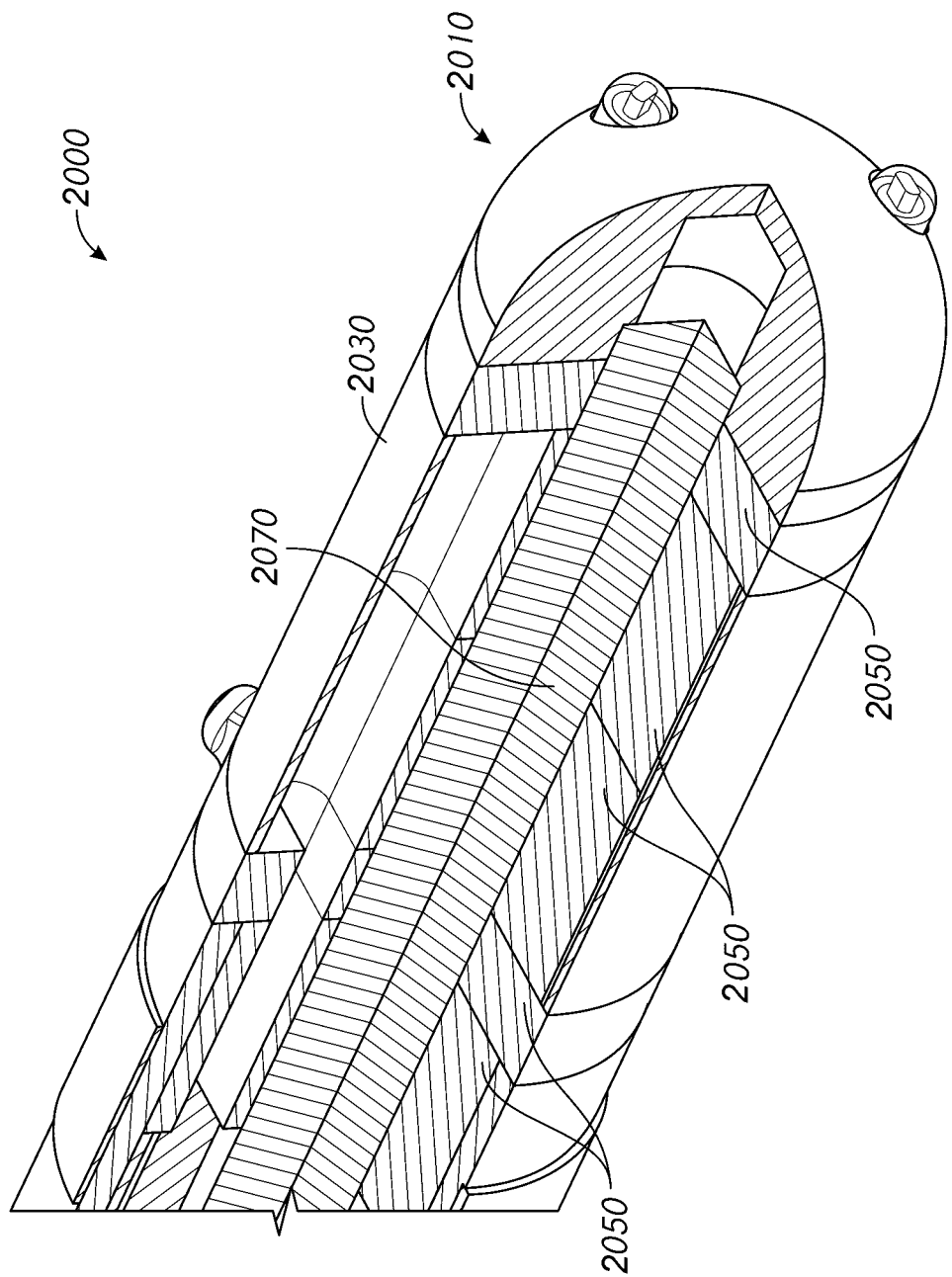
FIG. 15 illustrates a partial cross-sectional perspective view of another embodiment of an ablation system's catheter.

FIG. 15 illustrates yet another embodiment of a catheter or other medical instrument of an ablation system 2000 can includes one or more heat transfer members 2050 (e.g., heat shunt members) along and/or near its distal end 2010. Unlike the arrangements of FIGS. 13 and 14 discussed herein, the depicted embodiment does not include an active fluid cooling system. In other words, the catheter or other medical instrument does not comprise any fluid conduits or passages. Instead, in some embodiments, as illustrated in FIG. 15, the distal end of the catheter comprises one or more interior members (e.g., interior structural members) 2070 along its interior. Such interior members 2070 can include a member or material having favorable thermal diffusivity characteristics. In some embodiments, the interior member 2070 comprises identical or similar thermal diffusivity characteristics or properties as the heat shunt members 2050, such as, for example, industrial diamond or Graphene. In some embodiments, the thermal diffusivity of the material(s) included in the interior member 2070 and/or of the overall heat shunt network or assembly (e.g., when viewed as a unitary member or structure) is greater than 1.5 $cm^2$/sec (e.g., 1.5-2, 2-2.5, 2.5-3, 3-4, 4-5, 5-6, 6-7, 7-8, 8-9, 9-10, 10-11, 11-12, 12-13, 13-14, 14-15, 15-20 $cm^2$/sec, values between the foregoing ranges, greater than 20 $cm^2$/sec). However, in other embodiments, the interior member(s) do not include high heat shunting materials and/or members. In other embodiments, however, the interior member 2070 does not include materials or members similar to those as the heat shunt members 2050. For example, in some arrangements, the interior member(s) 2070 can include one or more components or members that comprise material(s) having a thermal diffusivity less than 1 $cm^2$/sec.

With continued reference to the embodiment of FIG. 15, the volume along the distal end of the catheter or medical instrument includes a structural member that at least partially occupies said volume. This is in contrast to other embodiments disclosed herein, wherein at least a portion of the distal end of the catheter or medical instrument includes a cavity (e.g., a cooling chamber) that is configured to receive cooling fluid (e.g., saline) when such cooling fluid is delivered and/or circulated through the catheter or medical instrument.

In embodiments such as the one illustrated in FIG. 15, wherein no active fluid cooling is incorporated into the design of the catheter or other medical instrument of the ablation system 2000, heat generated by and/or at the electrode (or other energy delivery member) 2030 can be more evenly dissipated along the distal end of the catheter or medical instrument as a result of the heat dissipation properties of the heat transfer members 2050, including, without limitation, heat shunt members, (and/or the interior member 2070, to the extent that the interior member 2070 also comprises favorable heat shunting properties, e.g., materials having favorable thermal diffusivity characteristics). Thus, the heat shunt members 2050 can help dissipate heat away from the electrode or other energy delivery member (e.g., either via direct or indirect thermal contact with the electrode or other energy delivery member) to reduce the likelihood of any localized hotspots (e.g., along the distal and/or proximal ends of the electrode or other energy delivery member). Accordingly, heat can be more evenly distributed with the assistance of the heat shunt member 2050 along a greater volume, area and/or portion of the catheter. As discussed above, the use of heat shunting members can quickly and efficiently transfer heat away from the electrode and the tissue being treated during use. The use of materials that comprises favorable thermal diffusivity properties can accomplish the relatively rapid heat transfer without the negative effect of heat retention (e.g., which may otherwise cause charring, thrombus formation and/or other heat-related problems).

Further, in some embodiments, the flow of blood or other natural bodily fluids of the subject in which the catheter or medical instrument is positioned can facilitate with the removal of heat away from the electrode or other energy delivery member. For example, the continuous flow of blood adjacent the exterior of the catheter during use can help with the removal of heat away from the distal end of the catheter. Such heat transfer can be further enhanced or otherwise improved by the presence of one or more heat shunt members that are in thermal communication with the exterior of the catheter. For example, in some arrangements, such as shown in FIG. 15, one or more heat shunt members 2050 can extend to the exterior of the catheter or other medical instrument. Thus, as blood (and/or other bodily fluids) moves past the catheter or other medical instrument when the catheter or medical instrument is inserted within the subject during use, heat can be advantageously transferred through the heat shunt members 2050 to the blood and/or other bodily fluids moving adjacent the catheter. Again, the use of heat shunt materials with favorable thermal diffusivity characteristics will ensure that heat is not retained within such materials, thereby creating a safer ablation system and treatment procedure.

Figure 16A:
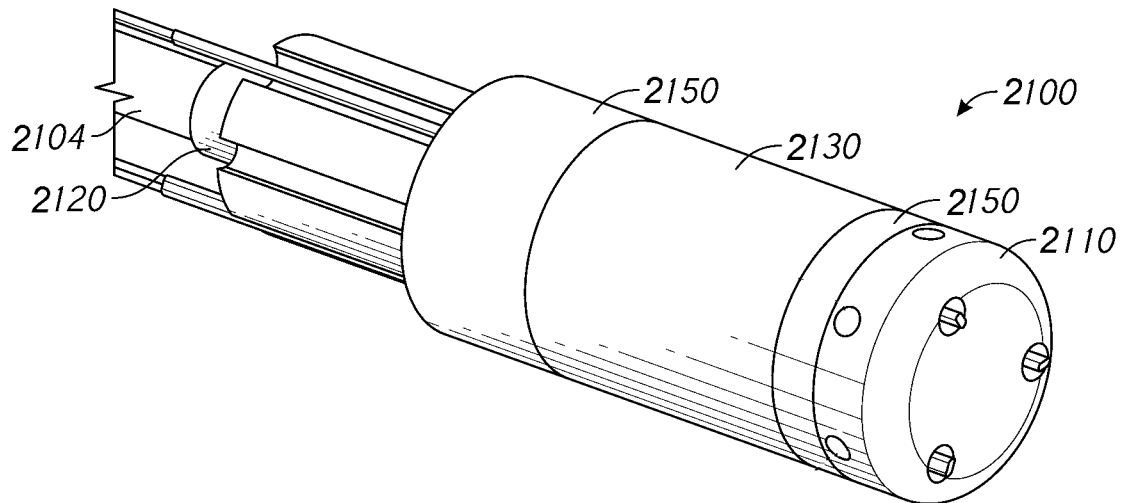
FIG. 16A illustrates a side perspective view of a distal end of one embodiment of a composite (e.g., split-tip) RF ablation system comprising heat transfer (e.g. heat shunt) members.
Figure 16B:
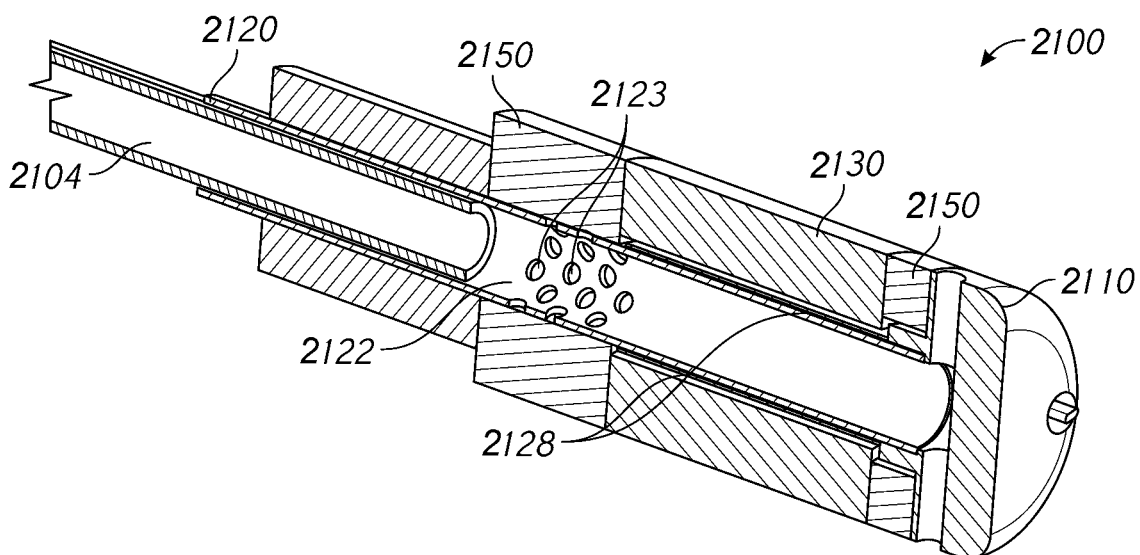
FIG. 16B illustrates a partial cross-sectional perspective view of the system of FIG. 16A.

FIGS. 16A and 16B illustrate another embodiment of a catheter or other medical instrument of an ablation system 2100 that includes one or more heat transfer members 2050 (e.g., heat shunt members) along and/or near its distal end. Unlike other embodiments disclosed herein, the illustrated system includes a proximal electrode or electrode portion 2130 that extends deeper into the interior of the catheter. For example, as depicted in the side cross-sectional view of FIG. 16B, the proximal electrode 2130 can extend to or near the outside of the irrigation channel 2120. As discussed herein, the irrigation channel 2120 can comprise one or more metals, alloys and/or other rigid and/or semi-rigid materials, such as, for example, stainless steel.

With continued reference to FIGS. 16A and 16B, the proximal electrode or proximal electrode portion 2130 can be part of a composite (e.g., split-tip) electrode system, in accordance with the various composite embodiments disclosed herein. Thus, in some embodiments, in order for the split tip electrode configuration to operate properly, the distal electrode 2110 is electrically isolated from the proximal electrode 2130. In the illustrated configuration, since the proximal electrode 2130 extends to or near the metallic (and thus, electrically conductive) irrigation tube 2120, at least one electrically insulative layer, coating, member, portion, barrier and/or the like 2128 can be advantageously positioned between the electrode 2130 and the irrigation tube 2120. In some embodiments, for example, the electrically insulative member 2128 comprises one or more layers of polyimide, other polymeric material and/or another electrically insulative material, as desired or required. Such an electrically-insulative layer and/or other member 2128 can take the place of diamond and/or another electrically-insulative heat shunting member that may otherwise be positioned around the irrigation tube 2120 to electrically isolate the distal electrode 2110 from the proximal electrode 2130.

According to any of the embodiments disclosed herein, the proximal and/or the distal electrodes 2130, 2110 can comprise one or more metals and/or alloys. For example, the electrodes can include platinum, stainless steel and/or any other biocompatible metal and/or alloy. Thus, in some embodiments, the thicker proximal electrode 2130 that extends to or near the irrigation tube 2120 can be referred to as a "slug," e.g., "a platinum slug." As discussed, in such arrangements, the need for an internal diamond and/or other heat shunting member can be eliminated. Instead, in such embodiments, as depicted in FIG. 16B, the proximal and distal ends of the "slug" or thicker proximal electrode 2130 can be placed in thermal communication with one or more heat shunting members (e.g., diamond) to help shunt heat away from the electrode 2130 and/or the tissue of the subject being treated. Thus, in some embodiments, the proximal and/or the distal faces of the proximal electrode or slug 2130 can be placed in good thermal contact with adjacent heat shunting members, as desired or required.

With continued reference to FIG. 16B, according to some embodiments, at least a portion 2222 of the irrigation tube 2120 is perforated and/or has one or more openings 2123. In some embodiments, such openings 2123 can place an irrigation fluid carried within the interior of the irrigation channel 2120 in direct physical and thermal communication with an adjacent heat shunting member (e.g., diamond, Graphene, silica, etc.) to quickly and efficiently transfer heat away from the electrode and/or tissue being treated. In some embodiments, the direct physical and/or thermal communication between the irrigation fluid and the shunting member helps provide improved heat transfer to the irrigation fluid (e.g., saline) passing through the interior of the irrigation channel 2120. In the illustrated embodiment, the openings 2123 along the perforated portion 2222 are generally circular in shape and evenly distributed relative to each other (e.g., comprise a generally even distribution or spacing relative to each other). However, in other arrangements, the size, shape, spacing and/or other characteristics of the openings 2123 along the perforated or direct contact region 2122 of the channel 2120 can vary, as desired or required. For example, in some embodiments, the openings 2123 can be oval, polygonal (e.g., square or rectangular, triangular, pentagonal, hexagonal, octagonal, etc.), irregular and/or the like. In some embodiments, the openings are slotted or elongated.

Regardless of their exact shape, size, orientation, spacing and/or other details, the openings 2123 that comprise the perforated or direct contact region 2122 of the channel 2120 can provide direct contact between the irrigation fluid and the adjacent diamond (and/or another heat shunting member) 1150 for 30% to 70% (e.g., 30-35, 35-40, 40-45, 45-50, 50-55, 55-60, 60-65, 65-70%, percentages between the foregoing ranges, etc.) of the surface area of the perforated or direct contact region 2122 of the channel 2120. In other embodiments, the openings 2123 that comprise the perforated or direct contact region 2122 of the channel 2120 can provide direct contact between the irrigation fluid and the adjacent diamond (and/or another heat shunting member) 2150 for less than 30% (e.g., 1-5, 5-10, 10-15, 15-20, 20-25, 25-30%, percentages between the foregoing ranges, less than 1%, etc.) or greater than 70% (e.g., 70-75, 75-80, 80-85, 85-90, 90-95, 95-99%, percentages between the foregoing ranges, greater than 99%, etc.) of the surface area of the perforated or direct contact region 2122 of the channel 2120, as desired or required. Such a perforated or direct contact region 2122 can be incorporated into any of the embodiments disclosed herein. In addition, any of the embodiments disclosed herein, including, without limitation, the system of FIGS. 16A and 16B, can include more than one perforated or direct contact region 2122. For example, the embodiment of FIGS. 16A and 16B can include a second perforated or direct contact region along the distal end of the proximal slug or electrode 2130 and/or along any other portion adjacent a heat shunting member.

As illustrated in FIG. 16B, the distal end of an irrigation tube (e.g., a flexible polyurethane or other polymeric conduit) 2104 that is in fluid communication with the irrigation channel 2120 that extends through the distal end of the catheter or other medical instrument can be positioned at least partially within an interior of such a channel 2120. Such a configuration can be incorporated into any of the embodiments disclosed herein or variations thereof. In some embodiments, the distal portion of the irrigation tube 2104 can be sized, shaped and/or otherwise configured to press-fit within an interior of the distal channel 2120. However, in some embodiments, one or more other attachment devices or methods, such as, for example, adhesives, heat bonding, fasteners, etc., can be used to help secure the irrigation tube 2104 to the irrigation channel 2120, as desired or required.

Figure 16C:
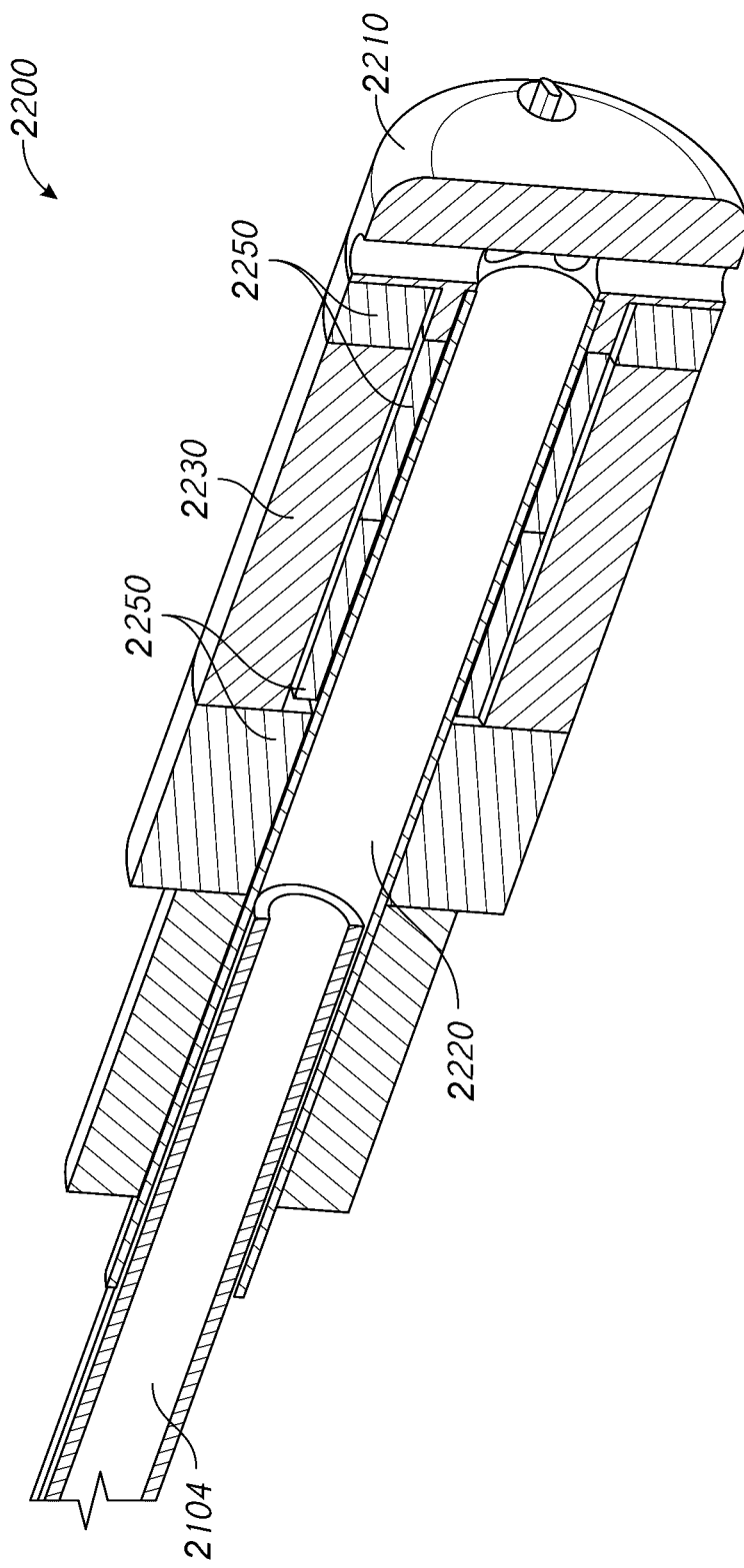
FIG. 16C illustrates a partial cross-sectional perspective view of another embodiment of an ablation system comprising a composite electrode and heat transfer (e.g. heat shunt) members.

Another embodiment of a distal end of a catheter or other medical instrument 2200 comprising proximal and distal electrodes 2230, 2210 and heat shunting characteristics is illustrated in FIG. 16C. As shown, the proximal electrode or slug 2230 extends toward the interior of the catheter (e.g., to or near the irrigation channel 2104, 2220). However, the depicted electrode 2230 is generally thinner than (e.g., does not extend as far as) the embodiment of FIGS. 16A and 16B. In the illustrated embodiment, one or more heating shunting members (e.g., diamond, Graphene, silica, etc.) with favorable thermal diffusivity characteristics are positioned between the interior of the proximal electrode or slug 2230 and the irrigation channel 2220. Thus, is such an arrangement, not only can heat generated at or along the electrode 2230 and/or the tissue of the subject being treated be more quickly and efficiently transferred away from the electrode and/or tissue, but the diamond or other electrically-insulating heat shunting member or network 2250 provides the necessary electrical insulation between the metallic (e.g., stainless steel) irrigation channel 2220 and the proximal electrode or slug 2230. As noted herein, such electrical isolation is helpful with a composite (e.g., split-tip) design.

Figure 17A:
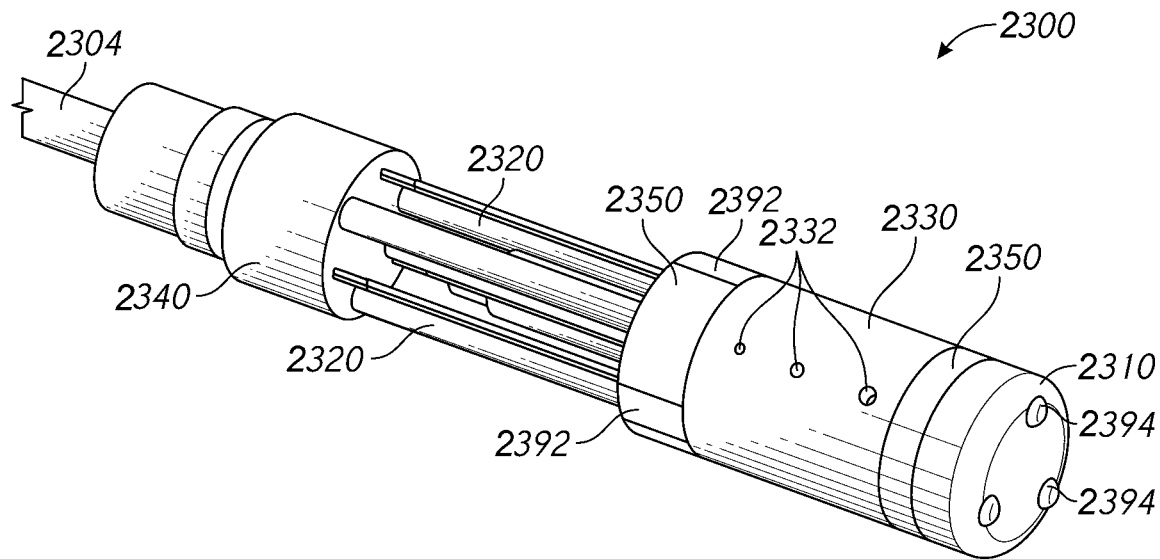
FIG. 17A illustrates a side perspective view of a distal end of one embodiment of a composite (e.g., split-tip) RF ablation system comprising heat transfer (e.g. heat shunt) members and fluid outlets extending through a proximal electrode or slug.
Figure 17B:
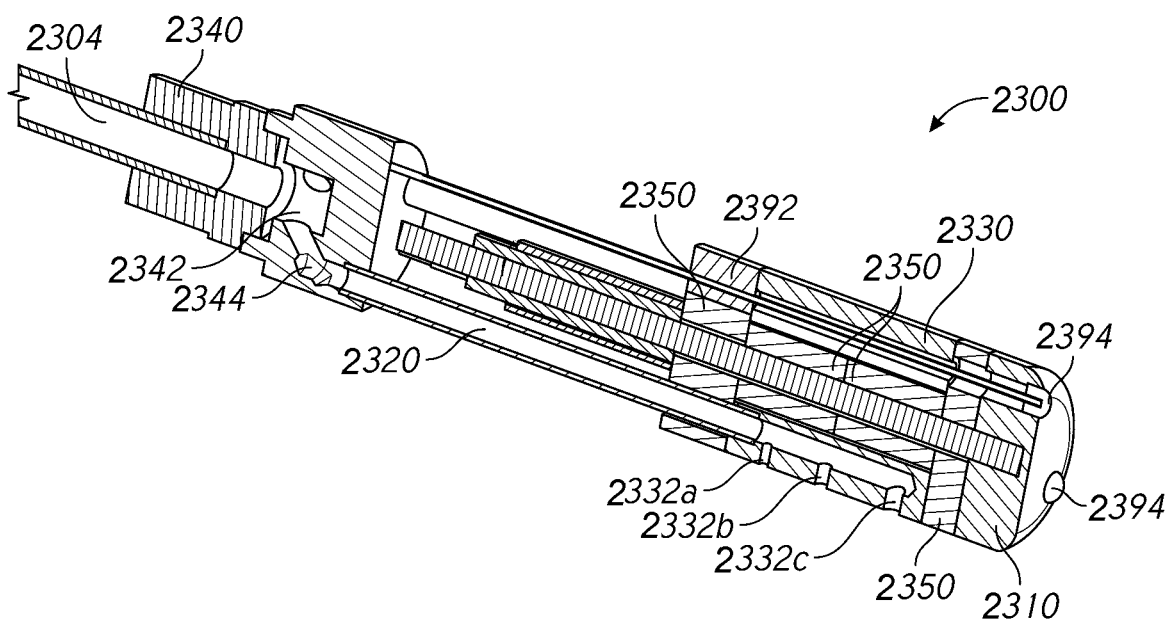
FIG. 17B illustrates a partial cross-sectional perspective view of the system of FIG. 17A.

A distal portion 2300 of another embodiment of an ablation system is illustrated in FIGS. 17A and 17B. As shown, the system comprises a composite (e.g., split-tip) design, with a proximal electrode or slug 2330 and a distal electrode 2310. Further, the catheter or other medical instrument includes one or more heat transfer members 2350, including, without limitation, a heat shunt network (e.g., comprising diamond, Graphene, silica and/or other materials with favorable thermal diffusivity properties). According to some embodiments, as depicted in the illustrated arrangement, the heat shunt network 2350 can include rings that extend to the exterior of the catheter or instrument and/or one or more interior members that are positioned within (e.g., underneath) the proximal electrode 2330, as desired or required. In addition, as with other embodiments disclosed herein, one or more temperature sensors 2392, 2394 can be provide along one or more portions of the system (e.g., along or near the distal electrode 2310, along or near the proximal heat shunt member, along or near the proximal electrode 2330, etc.) to help detect the temperature of tissue being treated. As discussed in greater detail in such temperature sensors (e.g., thermocouples) can also be used to detect the orientation of the tip, to determine whether (and/or to what extent) contact is being made between the tip and tissue and/or the like.

With continued reference to the embodiment of FIGS. 17A and 17B, the catheter or other medical instrument can include a proximal coupling or member 2340. As shown, such a coupling or member 2340 is configured to connect to and be placed in fluid communication with an irrigation conduit (e.g., polyurethane, other polymeric or other flexible conduit, etc.) 2304. For example, in the illustrated embodiment, the distal end of the irrigation conduit 2304 is sized, shaped and otherwise configured to be inserted within a proximal end (e.g., recess) of the coupling 2340. In some embodiments, the irrigation conduit 2304 is press-fit within the recess of the coupling 2340. In other arrangements, however, one or more other attachment devices or methods can be used to secure the conduit 2304 to the coupling 2340 (e.g., adhesive, weld, fasteners, etc.), either in lieu or in addition to a press-fit connection, as desired or required. Regardless of the exact mechanism of securement between the irrigation conduit 2304 and the coupling 2340, fluid passing through the conduit 2304 can enter into a manifold 2342 of the coupling 2340. In some embodiments, the manifold 2342 can divide the irrigation fluid flow into two or more pathways 2344. However, in some embodiments, the coupling 2340 does not have a manifold. For example, irrigation fluid entering the coupling 2340 can be routed only along a single fluid pathway, as desired or required.

In the embodiment of FIGS. 17A and 17B, the manifold (or other flow dividing feature, device or component) 2342 of the coupling 2340 separates the irrigation flow into three different fluid pathways. As shown, each such fluid pathway can be placed in fluid communication with a separate fluid conduit or sub-conduit 2320. In some embodiments, such fluid conduits 2320 are equally spaced apart (e.g., radially) relative to the centerline of the catheter or other medical instrument. For example, the conduits 2320 can be spaced apart at or approximately at 120 degrees relative to each other. As shown, the conduits 2320 extend, at least partially, through the proximal heat shunt member 2350 and the proximal slug or electrode 2330. However, in other embodiments, the orientation, spacing and/or other details of the manifold 2342, 2344 and/or the fluid conduits 2320 can vary. In addition, the number of fluid conduits 2320 originating from the manifold system can be greater than 3 (e.g., 4, 5, 6, 7, greater than 7, etc.) or less than 3 (e.g., 1, 2), as desired or required.

In some embodiments in which the system comprises an open-irrigation system, as illustrated in the longitudinal cross-sectional view of FIG. 17B, one or more irrigation fluid outlets 2332a, 2332b, 2332c can be provided along one or more of the fluid conduits 2320. As shown, such fluid outlets 2332 can provided within the proximal electrode 2330. However, in other embodiments, such outlets 2332 can be included within one or more other portions of the system (e.g., a heat shunt member 2350, the distal electrode 2310, etc.), either in lieu of or in addition to the proximal electrode 2330. Such a configuration (e.g., one including a manifold and/or openings through the proximal electrode) can be incorporated into any of the ablation system embodiments disclosed herein. As with other irrigation system arrangements disclosed herein, heat can be shunted (e.g., from the electrode, the tissue being treated, one or more other portions of the system, etc.) to the irrigation fluid passing through the conduits and/or fluid outlets to help quickly and efficiently dissipate (e.g., shunt) heat from the system during use. In some embodiments, as illustrated in FIGS. 17A and 17B, the relative size, shape and/or other configuration of two or more of the fluid outlets 2332 can vary. For example, in some arrangements, in order to better balance the fluid hydraulics of fluid passing through each conduit 2320 (e.g., to better balance the flow rate passing through each outlet 2332), the proximal fluid outlets can be smaller than one or more of the distal fluid outlets. However, in other embodiments, two or more (e.g., most or all) of the fluid outlets 2332 include the identical shape, size and/or other properties.

In some embodiments, the orientation of the fluid outlets can be skewed relative to the radial direction of the catheter or other medical instrument in which they are located. Such a skewing or offset can occur for any fluid outlets located along the distal end of the catheter or other medical instrument (e.g., fluid outlets located along the distal electrode as shown in FIGS. 13, 16A and 16B and 16C, fluid outlets located along the proximal electrode as shown in FIGS. 17A and 17B, etc.). The extent to which the outlets are skewed or offset (e.g., relative to the radial direction of the catheter or medical instrument, relative to a direction perpendicular to the longitudinal centerline of the catheter or medical instrument) can vary, as desired or required. By way of example, the fluid openings can be skewed or offset relative to the radial direction by 0 to 60 degrees (e.g., 0-5, 5-10, 10-15, 15-20, 20-25, 25-30, 30-35, 35-40, 40-45, 45-50, 50-55, 55-60 degrees, angles between the foregoing ranges, etc.). In some embodiments, the fluid openings are skewed or offset relative to the radial direction by more than 60 degrees (e.g., 60-65, 65-70, 70-75 degrees, angles between the foregoing ranges, greater than 70 degrees, etc.), as desired or required.

According to some embodiments, fluid outlets or openings located along or near the distal electrode are skewed or offset distally (e.g., in a direction distal to the location of the corresponding fluid outlet or opening). In some embodiments, fluid outlets or openings located along or near the proximal electrode are skewed or offset proximally (e.g., in a direction proximal to the location of the corresponding fluid outlet or opening). Thus, in some embodiments, irrigation fluid exiting at or near the distal electrodes is delivered in a direction distal to the corresponding fluid outlet(s), and irrigation fluid exiting at or near the proximal electrodes is delivered in a direction proximal to the corresponding fluid outlet(s). In some embodiments, such a configuration can assist with cooling hot spots that may otherwise be created along or near the electrode. Such a configuration could also help dilute the blood in those areas to help reduce the chance of thrombus and/or coagulation formation.

Multiple Temperature Sensors

According to some embodiments, a medical instrument (e.g., ablation catheter) can include multiple temperature-measurement devices (e.g., thermocouples, thermistors, other temperature sensors) spaced axially at different locations along a distal portion of the medical instrument. The axial spacing advantageously facilitates measurement of a meaningful spatial temperature gradient. Each of the temperature-measurement devices may be isolated from each of the other temperature-measurement devices to provide independent temperature measurements. The temperature-measurement devices may be thermally and/or electrically insulated or isolated from one or more energy delivery members (e.g., radiofrequency electrodes) so as not to directly measure the temperature of the energy delivery member(s), thereby facilitating temperature measurements that are isolated from the thermal effects of the energy delivery member(s). The medical instrument may comprise a first plurality (e.g., set, array, group) of temperature-measurement devices (e.g., sensors) positioned at or adjacent a distal tip, or terminus, of the medical instrument (e.g., within a distal electrode portion of a high-resolution combination electrode assembly, or composite electrode assembly). The first plurality of temperature-measurement devices may be spaced apart (e.g., circumferentially, radially) around the medical instrument along a first cross-sectional plane of the medical instrument, in an equidistant manner or non-equidistant manner. In one embodiment, the first plurality of temperature-measurement devices is positioned symmetrically around a longitudinal axis of the distal end of the medical instrument. The medical instrument may also comprise a second plurality of temperature-measurement devices (e.g., sensors) spaced proximally from the first plurality of temperature-measurement devices along a second cross-sectional plane of the medical instrument that is proximal of the first cross-sectional plane, thereby allowing for temperature measurements to be obtained at multiple spaced-apart locations. In some embodiments, the second plurality of temperature-measurement devices is positioned adjacent to a proximal end (e.g., edge) of an electrode or other energy delivery member (if the medical instrument (e.g., ablation catheter) comprises a single electrode or other energy delivery member) or of the proximal-most electrode or other energy delivery member (if the medical instrument comprises multiple electrode members or other energy delivery members).

The temperature measurements obtained from the temperature-measurement devices (e.g., sensors) may advantageously be used to determine, among other things, an orientation of the distal tip of the medical instrument with respect to a tissue surface, an estimated temperature of a peak temperature zone of a lesion formed by the medical instrument (e.g., ablation catheter), and/or an estimated location of the peak temperature zone of the lesion. In some embodiments, the determinations made using the temperature sensors or other temperature-measurement devices can be used to adjust treatment parameters (e.g., target temperature, power, duration, orientation) so as to prevent char or thrombus if used in a blood vessel and/or to control lesion parameters (e.g., depth, width, location of peak temperature zone, peak temperature), thus providing more reliable and safer treatment (e.g., ablation) procedures. Accordingly, upon implementation of a control scheme that regulates the delivery of power or other parameters to an energy delivery member (e.g., RF electrode, microwave emitter, ultrasound transducer, cryogenic emitter, other emitter, etc.) located along the distal end of a medical apparatus (e.g., catheter, probe, etc.), the target level of treatment can be accomplished without negatively impacting (e.g., overheating, over-treating, etc.) the subject's tissue (e.g., within and/or adjacent a treatment volume).

The term peak temperature, as used herein, can include either a peak or high temperature (e.g., a positive peak temperature) or a trough or low temperature (e.g., negative peak temperature). As a result, determination of the peak temperature (e.g., maximum or minimum temperature or other extreme temperature) within targeted tissue can result in a safer, more efficient and more efficacious treatment procedure. In some embodiments, when, for example, cryoablation is performed, the systems, devices and/or methods disclosed herein can be used to determine the trough or lowest temperature point, within the treatment (e.g., ablation) volume. In some embodiments, technologies that cool tissue face similar clinical challenges of controlling the tissue temperature within an efficacious and safe temperature range. Consequently, the various embodiments disclosed herein can be used with technologies that either cool or heat targeted tissue.

Several embodiments of the invention are particularly advantageous because they include one, several or all of the following benefits: (i) reduction in proximal edge heating, (ii) reduced likelihood of char or thrombus formation, (iii) feedback that may be used to adjust ablation procedures in real time, (iv) noninvasive temperature measurements, (v) determination of electrode-tissue orientation within a short time after initiation of energy delivery; (vi) safer and more reliable ablation procedures; and (vii) tissue temperature monitoring and feedback during irrigated or non-irrigated ablation.

For any of the embodiments disclosed herein, a catheter or other minimally-invasive medical instrument can be delivered to the target anatomical location of a subject (e.g., atrium, pulmonary veins, other cardiac location, renal artery, other vessel or lumen, etc.) using one or more imaging technologies. Accordingly, any of the ablation systems disclosed herein can be configured to be used with (e.g., separately from or at least partially integrated with) an imaging device or system, such as, for example, fluoroscopy technologies, intracardiac echocardiography ("ICE") technologies and/or the like. In some embodiments, energy delivery is substituted with fluid delivery (e.g., hot fluid, cryogenic fluid, chemical agents) to accomplish treatment.

Figure 18A:
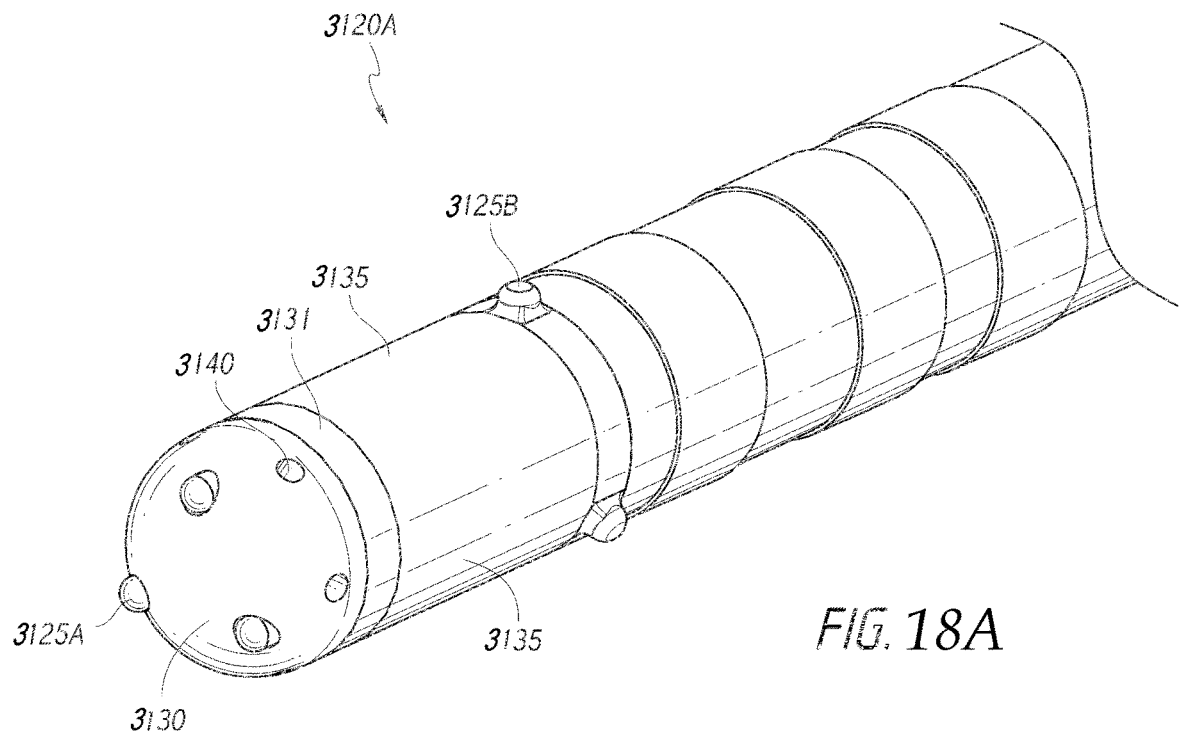
FIG. 18A illustrates a perspective view of a distal portion of an open-irrigated ablation catheter having multiple temperature-measurement devices, according to one embodiment.

FIG. 18A illustrates a perspective view of a distal portion of an open-irrigated ablation catheter 3120A comprising multiple temperature-measurement devices 3125, according to one embodiment. As shown, the embodiment of the ablation catheter 3120A of FIG. 18A is an open-irrigated catheter comprising a high-resolution combination electrode assembly, or composite (e.g., split-tip) electrode design. The composite electrode design comprises a dome- or hemispherical-shaped distal tip electrode member 3130, an insulation gap 3131 and a proximal electrode member 3135. The ablation catheter 3120A comprises multiple irrigation ports 3140 and a thermal transfer member 3145 (e.g., heat shunt member).

The temperature-measurement devices 3125 comprise a first (e.g., distal) group of temperature-measurement devices 3125A positioned in recesses or apertures formed in the distal electrode member 3130 and a second (e.g., proximal) group of temperature-measurement devices 3125B positioned in slots, notches or openings formed in the thermal transfer member 3145 proximate or adjacent the proximal edge of the proximal electrode member 3135. The temperature-measurement devices 3125 may comprise thermocouples, thermistors, fluoroptic sensors, resistive temperature sensors and/or other temperature sensors. In various embodiments, the thermocouples comprise nickel alloy, platinum/rhodium alloy, tungsten/rhenium alloy, gold/iron alloy, noble metal alloy, platinum/molybdenum alloy, iridium/rhodium alloy, pure noble metal, Type K, Type T, Type E, Type J, Type M, Type N, Type B, Type R, Type S, Type C, Type D, Type G, and/or Type P thermocouples. A reference thermocouple may be positioned at any location along the catheter 3120A (e.g., in a handle or within a shaft or elongate member of the catheter 3120A). In one embodiment, the reference thermocouple is thermally insulated and/or electrically isolated from the electrode member(s). The electrode member(s) may be substituted with other energy delivery members.

In some embodiments, the temperature-measurement devices are thermally insulated from the electrode members or portions 3130, 3135 so as to isolate the temperature measurements from the thermal effects of the electrode members (e.g., to facilitate measurement of surrounding temperature, such as tissue temperature, instead of measuring temperature of the electrode members). As shown, the temperature-measurement devices 3125 may protrude or extend outward from an outer surface of the ablation catheter 3120A. In some embodiments, the temperature-measurement devices 3125 may protrude up to about 1 mm away from the outer surface (e.g., from about 0.1 mm to about 0.5 mm, from about 0.5 mm to about 1 mm, from about 0.6 mm to about 0.8 mm, from about 0.75 mm to about 1 mm, or overlapping ranges thereof). The dome shape of the distal tip electrode member 3130 and/or the outward protrusion or extension of the temperature-measurement devices 3125 may advantageously allow the temperature-measurement devices to be buried deeper into tissue and away from effects of the open irrigation provided by irrigation ports 3140, in accordance with several embodiments. The proximal group of temperature-measurement devices and the distal group of temperature-measurement devices may protrude the same amount or different amounts (as a group and/or individually within each group). In other embodiments, the temperature-measurement devices 3125 are flush or embedded within the outer surface (e.g., 0.0 mm, −0.1 mm, −0.2 mm, −0.3 mm, −0.4 mm, −0.5 mm from the outer surface) of an elongate body of the medical instrument. In some embodiments, the distal temperature-measurement devices 3125A protrude or extend distally from a distal outer surface of the distal electrode member and the proximal temperature-measurement devices 3125B are flush within a lateral outer surface of an elongate body of the ablation catheter 3120A.

Figure 18B:
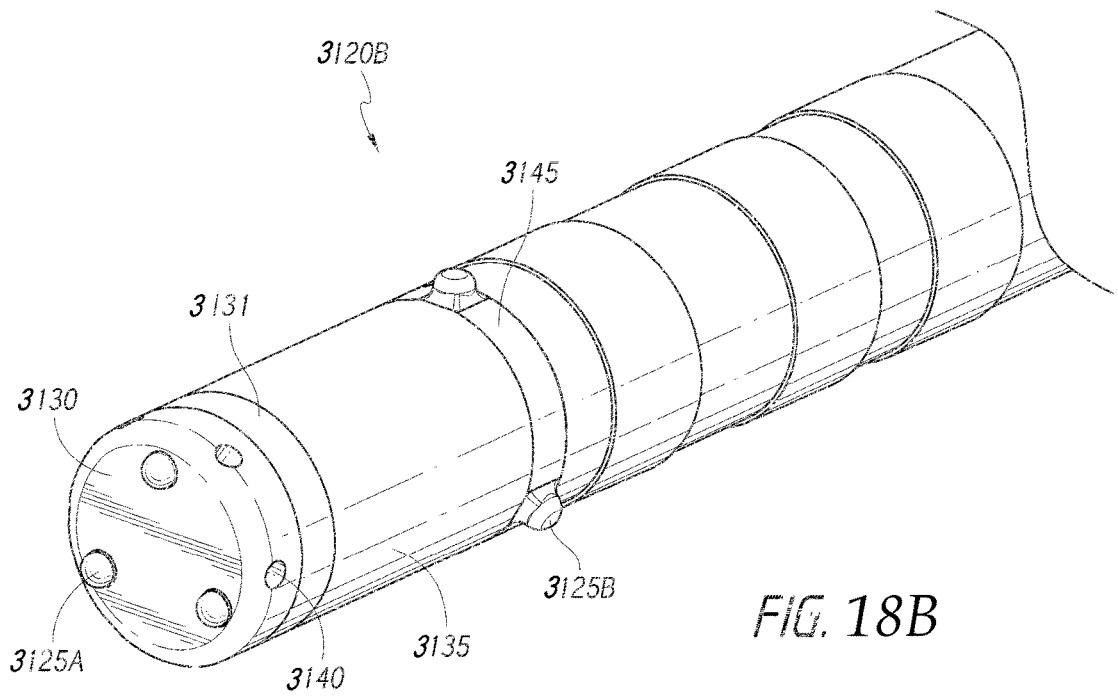
FIGS. 18B and 18C illustrate a perspective view and a cross-sectional view, respectively, of a distal portion of an open-irrigated ablation catheter having multiple temperature-measurement devices, according to another embodiment.
Figure 18C:
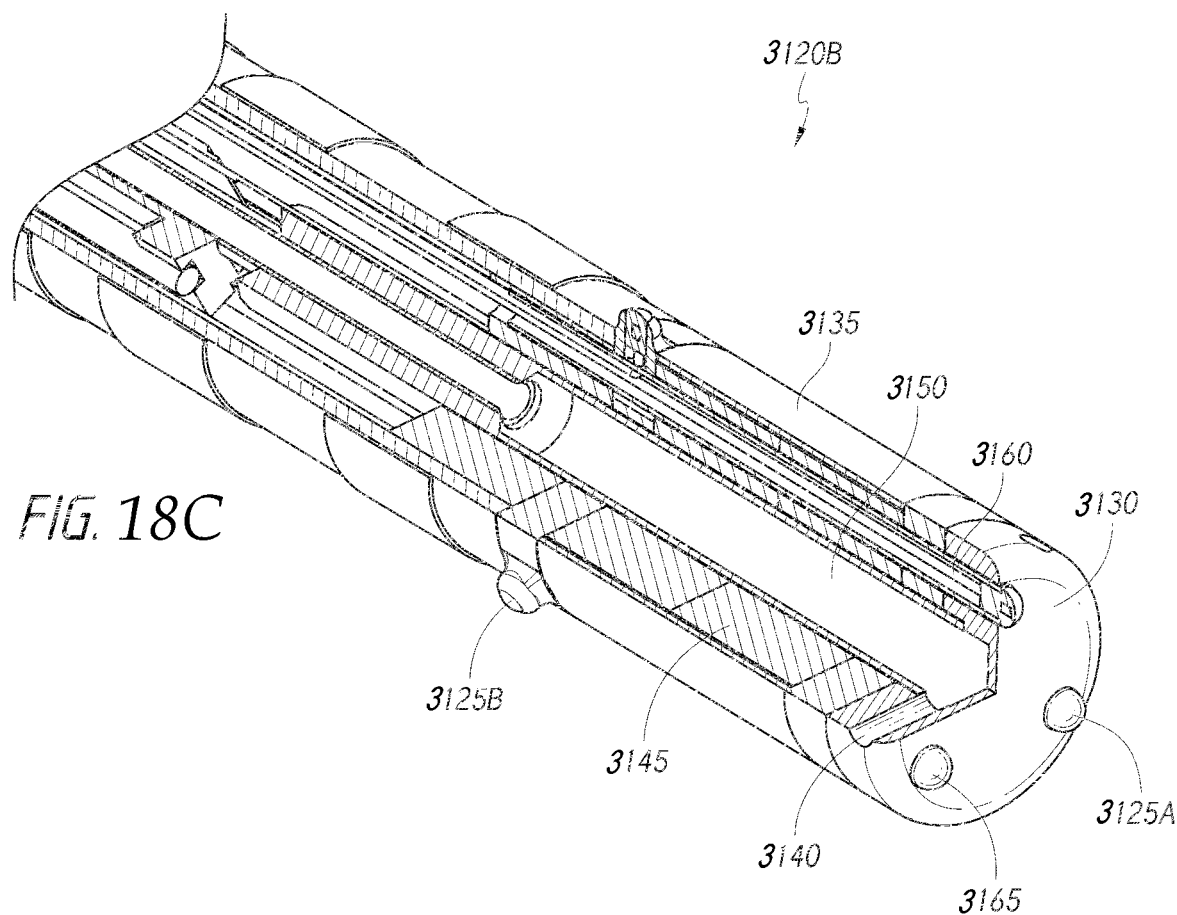
Figure 18D:
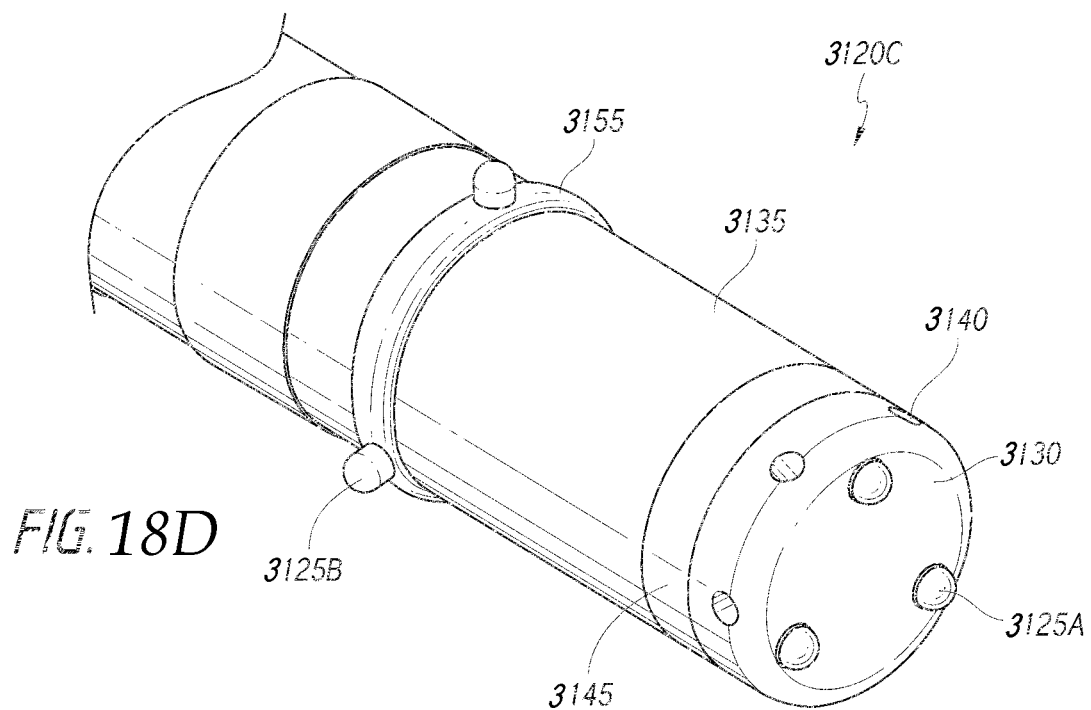
FIG. 18D illustrates a perspective view of a distal portion of an ablation catheter having multiple temperature-measurement devices, according to another embodiment.

With reference to FIG. 18D, a portion of the ablation catheter 3120C where at least some of the temperature-measurement devices 3125 are positioned may have a larger outer diameter or other outer cross-sectional dimension than adjacent portions of the ablation catheter 3120C so as to facilitate deeper burying of at least some of the temperature-measurement devices within tissue and to further isolate the temperature measurements from the thermal effects of the electrode members or fluid (e.g., saline or blood). As shown in FIG. 18D, the portion of the ablation catheter 3120C comprising the proximal group of temperature-measurement devices 3125B comprises a bulge, ring or ridge 3155 having a larger outer diameter than adjacent portions.

In some embodiments, the temperature-measurement devices 3125 are adapted to be advanced outward and retracted inward. For example, the temperature-measurement devices 3125 may be in a retracted position (within the outer surface or slightly protruding outward) during insertion of the ablation catheter and movement to the treatment location to reduce the outer profile and facilitate insertion to the treatment location and may be advanced outward when at the treatment location. The features described above in connection with ablation catheter 3120C of FIG. 18D may be employed with any of the other ablation catheters described herein.

Returning to FIG. 18A, the proximal and distal groups of temperature-measurement devices 3125 may each comprise or consist of two, three, four, five, six, or more than six temperature-measurement devices. In the illustrated embodiment, the proximal and distal groups of temperature-measurement devices 3125 each consist of three temperature-measurement devices, which may provide a balance between volumetric coverage and reduced number of components. The number of temperature-measurement devices 3125 may be selected to balance accuracy, complexity, volumetric coverage, variation in tip to tissue apposition, cost, number of components, and/or size constraints. As shown in FIG. 18A, the temperature-measurement devices 3125 may be equally spaced apart around a circumference of the ablation catheter 3120A or spaced an equal number of degrees apart from each other (e.g., symmetrically) about a central longitudinal axis extending from a proximal end to a distal end of the ablation catheter. For example, when three temperature-measurement devices are used, they may be spaced about 120 degrees apart and when four temperature-measurement devices are used, they may be spaced about 90 degrees apart. In other embodiments, the temperature-measurement devices 3125 are not spaced apart equally.

As shown in the embodiment of FIG. 18A, the temperature-measurement devices 3125 of each group may be positioned along the same cross-sectional plane (e.g., are co-planar) of the ablation catheter 3120A. For example, the distal temperature-measurement devices 3125A may be positioned to extend the same distance outward from the dome-shaped surface and the proximal temperature-measurement devices 3125B may each be spaced the same distance from the distal tip of the ablation catheter 3120A. As shown in the embodiment of FIG. 18A, the distal temperature-measurement devices 3125A extend from a distal outer surface of the distal electrode member in an axial direction that is parallel or substantially parallel with a central longitudinal axis of the distal portion of the ablation catheter 3120A and the proximal temperature-measurement devices 3125B extend radially outward from the outer surface of the ablation catheter 3120A. In other embodiments, the distal temperature-measurement devices 3125A may not be positioned in or on the distal outer surface of the distal terminus but may be positioned on a lateral surface to extend radially outward (similar to the illustrated proximal temperature-measurement devices 3125B). In some embodiments, the temperature-measurement devices 3125 are not spaced apart in two separated groups of co-planar temperature-measurement devices within each group but are otherwise spatially distributed.

As shown in the embodiment of FIG. 18A, the distal temperature-measurement devices 3125A may be positioned distal of the insulation gap 3131 and/or of the irrigation ports 3140 and the proximal temperature-measurement devices 3125B may be positioned proximal to the proximal edge of the proximal electrode member 3135 within the thermal transfer member 3145. In other embodiments, the proximal temperature-measurement devices 3125B may be positioned distal to the proximal edge of the proximal electrode member 3135 (e.g., within recesses or apertures formed within the proximal electrode member 3135 similar to the recesses or apertures formed in the distal tip electrode member illustrated in FIG. 18A). In other embodiments, the distal temperature-measurement devices 3125A and/or the proximal temperature-measurement devices 3125B may be positioned at other locations along the length of the ablation catheter 3120A. In some embodiments, each distal temperature-measurement device 3125A is axially aligned with one of the proximal temperature-measurement devices 3125B and the spacing between the distal temperature-measurement devices 3125A and the proximal temperature-measurement devices is uniform or substantially uniform.

The irrigation ports 3140 may be spaced apart (equidistant or otherwise) around a circumference of the shaft of the ablation catheter 3120A. The irrigation ports 3140 are in communication with a fluid source, such as a fluid source provided by the irrigation fluid system 70 of FIG. 1. The irrigation ports facilitate open irrigation and provide cooling to the electrode members 3130, 3135 and any blood surrounding the electrode members 3130, 3135. In some embodiments, the ablation catheter 3120A comprises three, four, five, six, seven, eight or more than eight exit ports 3140. In various embodiments, the exit ports 3140 are spaced between 0.005 and 0.015 inches from the proximal edge of the distal electrode member 3130 so as to provide improved cooling of the thermal transfer member 3145 at the tissue interface; however, other spacing can be used as desired and/or required. In other embodiments, the exit ports 3140 are spaced apart linearly and/or circumferentially along the proximal electrode member 3135 (as shown, for example, in FIG. 18E).

FIGS. 18B and 18C illustrate a perspective view and a cross-sectional view, respectively, of a distal portion of an open-irrigated ablation catheter 3120B having multiple temperature-measurement devices, according to another embodiment. The ablation catheter 3120B may include any or all of the structural components, elements and features of the ablation catheter 3120A described above and ablation catheter 3120A may include any or all of the structural components, elements and features described in connection with FIGS. 18B and 18C. The ablation catheter 3120B comprises a flat tip electrode member 3130 instead of a dome-shaped tip electrode member as shown in FIG. 18A. In other words, the distal outer surface is planar or flat instead of rounded or hemispherical. In accordance with several embodiments, the distal temperature-measurement devices 3125A are positioned in or on the flat or planar surface and not on a curved, toroidal or radiused surface of the distal tip electrode member connecting the distal outer surface and a lateral outer surface of the distal tip electrode member.

As best shown in FIG. 18C, the thermal transfer member 3145 is in thermal contact with one or both of the electrode members 3130, 3135. The thermal transfer member 3145 can extend to, near or beyond the proximal end of the proximal electrode member 3135. In some embodiments, the thermal transfer member 3145 terminates at or near the proximal end of the proximal electrode member 3135. However, in other arrangements (as shown in FIG. 18C), the thermal transfer member 3145 extends beyond the proximal end of the proximal electrode member 3135. In yet other embodiments, the thermal transfer member 3145 terminates distal of the proximal end (e.g., edge) of the proximal electrode member 3135. The thermal transfer member 3145 may extend from the proximal surface of the tip electrode member 3130 to a location beyond the proximal end of the proximal electrode member 3135. Embodiments wherein the thermal transfer member 3145 extends beyond the proximal end of the proximal electrode member 3135 may provide increased shunting of proximal edge heating effects caused by the increased amount of current concentration at the proximal edge by reducing the heat at the proximal edge through conductive cooling. In some embodiments, at least a portion of the thermal transfer member 3145 is in direct contact with the tissue (e.g., within insulation gap 3131) and can remove or dissipate heat directly from the targeted tissue being heated.

The thermal transfer member 3145 can comprise one or more materials that include favorable heat transfer properties. For example, in some embodiments, the thermal conductivity of the material(s) included in the thermal transfer member is greater than 300 W/m/° C. (e.g., 300-350, 350-400, 400-450, 450-500, 500-600, 600-700 W/m/° C., ranges between the foregoing, greater than 700 W/m/° C., etc.). Possible materials with favorable thermal conductivity properties include, but are not limited to, copper, brass, beryllium, other metals and/or alloys, aluminal ceramics, other ceramics, industrial diamond and/or other metallic and/or non-metallic materials.

According to certain embodiments where the heat transfer members comprise heat shunting members, the thermal diffusivity of the material(s) included in the heat shunt members and/or of the overall heat shunt assembly (e.g., when viewed as a unitary member or structure) is greater than 1.5 cm$^2$/sec (e.g., 1.5-2, 2-2.5, 2.5-3, 3-4, 4-5, 5-6, 6-7, 7-8, 8-9, 9-0, 10-11, 11-12, 12-13, 13-14, 14-15, 15-20 $cm^2/sec$, values between the foregoing ranges, greater than 20 $cm^2/sec$). Thermal diffusivity measures the ability of a material to conduct thermal energy relative to its ability to store thermal energy. Thus, even though a material can be efficient as transferring heat (e.g., can have a relatively high thermal conductivity), it may not have favorable thermal diffusivity properties, because of its heat storage properties. Heat shunting, unlike heat transferring, requires the use of materials that possess high thermal conductance properties (e.g., to quickly transfer heat through a mass or volume) and a low heat capacity (e.g., to not store heat). Possible materials with favorable thermal diffusivity, and thus favorable heat shunting properties, include, but are not limited to, industrial diamond, graphene, silica alloys, ceramics, other carbon-based materials and/or other metallic and/or non-metallic materials. In various embodiments, the material used for the heat transfer (e.g., diamond) provides increased visibility of the catheter tip using ICE imaging or other imaging techniques.

The use of materials with favorable thermal diffusivity properties can help ensure that heat can be efficiently transferred away from the electrode and/or the adjacent tissue during a treatment procedure. In contrast, materials that have favorable thermal conductivity properties, but not favorable thermal diffusivity properties, such as, for example, copper, other metals or alloys, thermally conductive polypropylene or other polymers, etc., will tend to retain heat. As a result, the use of such materials that store heat may cause the temperature along the electrode and/or the tissue being treated to be maintained at an undesirably elevated level (e.g., over 75 degrees C.) especially over the course of a relatively long ablation procedure, which may result in charring, thrombus formation and/or other heat-related problems.

Industrial diamond and other materials with the requisite thermal diffusivity properties for use in a thermal shunting network, as disclosed in the various embodiments herein, comprise favorable thermal conduction characteristics. Such favorable thermal conduction aspects emanate from a relatively high thermal conductance value and the manner in which the heat shunt members of a network are arranged with respect to each other within the tip and with respect to the tissue. For example, in some embodiments, as radiofrequency energy is emitted from the tip and the ohmic heating within the tissue generates heat, the exposed distal most shunt member (e.g., located 0.5 mm from the distal most end of the tip) can actively extract heat from the lesion site. The thermal energy can advantageously transfer through the shunting network in a relatively rapid manner and dissipate through the shunt residing beneath the radiofrequency electrode surface the heat shunt network, through a proximal shunt member and/or into the ambient surroundings. Heat that is shunting through an interior shunt member can be quickly transferred to an irrigation conduit extending through an interior of the catheter or other medical instrument. In other embodiments, heat generated by an ablation procedure can be shunted through both proximal and distal shunt members (e.g., shunt members that are exposed to an exterior of the catheter or other medical instrument, such as shown in many of the embodiments herein).

Further, as noted above, the materials with favorable thermal diffusivity properties for use in a heat shunt network not only have the requisite thermal conductivity properties but also have sufficiently low heat capacity values. This helps ensure that the thermal energy is dissipated very quickly from the tip to tissue interface as well as the hot spots on the electrode, without heat retention in the heat shunting network. The thermal conduction constitutes the primary heat dissipation mechanism that ensures quick and efficient cooling of the tissue surface and of the radiofrequency electrode surface. Conversely a heat transfer (e.g., with relatively high thermal conductivity characteristics but also relatively high heat capacity characteristics) will store thermal energy. Over the course of a long ablation procedure, such stored heat may exceed 75 degrees Celsius. Under such circumstances, thrombus and/or char formation can undesirably occur.

The thermal convection aspects of the various embodiments disclosed herein two-fold. First, an irrigation lumen of the catheter can absorb thermal energy which is transferred to it through the shunt network. Such thermal energy can then be flushed out of the distal end of the electrode tip via the irrigation ports. In closed irrigation systems, however, such thermal energy can be transferred back to a proximal end of the catheter where it can be removed. Second, the exposed shunt surfaces along an exterior of the catheter or other medical instrument can further assist with the dissipation of heat from the electrode and/or the tissue being treated. For example, such heat dissipation can be accomplished via the inherent convective cooling aspects of the blood flowing over the surfaces of the electrode.

Accordingly, the use of materials in a heat shunting network with favorable thermal diffusivity properties, such as industrial diamond, can help ensure that heat is quickly and efficiently transferred away from the electrode and treated tissue, while maintaining the heat shunting network cool (e.g., due to its low heat capacity properties). This can create a safer ablation catheter and related treatment method, as potentially dangerous heat will not be introduced into the procedure via the heat shunting network itself.

In some embodiments, the heat shunt members disclosed herein draw out heat from the tissue being ablated and shunt it into the irrigation channel. Similarly, heat is drawn away from the potential hot spots that form at the edges of electrodes and are shunted through the heat shunt network into the irrigation channel. From the irrigation channel, via convective cooling, heat can be advantageously released into the blood stream and dissipated away. In closed irrigation systems, heat can be removed from the system without expelling irrigation fluid into the subject.

According to some embodiments, the various heat shunting systems disclosed herein rely on heat conduction as the primary cooling mechanism. Therefore, such embodiments do not require a vast majority of the heat shunting network to extend to an external surface of the catheter or other medical instrument (e.g., for direct exposure to blood flow). In fact, in some embodiments, the entire shunt network can reside within an interior of the catheter tip (i.e., with no portion of the heat shut network extending to an exterior of the catheter or other medical instrument). Further, the various embodiments disclosed herein do not require electrical isolation of the heat shunts from the electrode member or from the irrigation channel.

As shown in FIG. 18C, the thermal transfer member 3145 is also in thermal contact with a heat exchange chamber (e.g., irrigation conduit) 3150 extending along an interior lumen of the ablation catheter 3120B. For any of the embodiments disclosed herein, at least a portion of a thermal transfer member (e.g., heat shunt member) that is in thermal communication with the heat exchange chamber 3150 extends to an exterior surface of the catheter, adjacent to (and, in some embodiments, in physical and/or thermal contact with) one or more electrodes or other energy delivery members. Such a configuration, can further enhance the cooling of the electrode(s) or other energy delivery member(s) when the system is activated, especially at or near the proximal end of the electrode(s) or energy delivery member(s), where heat may otherwise tend to be more concentrated (e.g., relative to other portions of the electrode or other energy delivery member). According to some embodiments, thermal conductive grease and/or any other thermally conductive material (e.g., thermally-conductive liquid or other fluid, layer, member, coating and/or portion) can be used to place the thermal transfer member 3145 in thermal communication with the heat exchange chamber (e.g., irrigation conduit) 3150, as desired or required. In such embodiments, such a thermally conductive material places the electrode members 3130, 3135 in thermal communication, at least partially, with the irrigation conduit 3150.

The irrigation conduit(s) 3150 can be part of an open irrigation system, in which fluid exits through the exit ports or openings 3140 along the distal end of the catheter (e.g., at or near the electrode member 3130) to cool the electrode members and/or the adjacent targeted tissue. In various embodiments, the irrigation conduit 3150 comprises one or more metallic and/or other favorable heat transfer (e.g., heat shunting) materials (e.g., copper, stainless steel, other metals or alloys, ceramics, polymeric and/or other materials with relatively favorable heat transfer properties, etc.). The irrigation conduit 3150 can extend beyond the proximal end of the proximal electrode member 3135 and into the proximal portion of the thermal transfer member 3145. The inner wall of the irrigation conduit 3150 may comprise a biocompatible material (such as stainless steel) that forms a strong weld or bond between the irrigation conduit 3150 and the material of the electrode member(s).

In some embodiments, the ablation catheters 3120 only comprise irrigation exit openings 3140 along a distal end of the catheter (e.g., along a distal end of the distal electrode member 3130). In some embodiments, the system does not comprise any irrigation openings along the thermal transfer member 3145.

The thermal transfer member 3145 may advantageously facilitate thermal conduction away from the electrode members 3130, 3135, thereby further cooling the electrode members 3130, 3135 and reducing the likelihood of char or thrombus formation if the electrode members are in contact with blood. The thermal transfer member 3145 may provide enhanced cooling of the electrode members 3130, 3135 by facilitating convective heat transfer in connection with the irrigation conduit 3150 in addition to thermal conduction.

Heat transfer (e.g., heat shunting) between the thermal transfer member 3145 and the electrode members 3130, 3135 can be facilitated and otherwise enhanced by eliminating air gaps or other similar spaces between the electrode members and the thermal transfer member. For example, one or more layers of an electrically conductive material (e.g., platinum, gold, other metals or alloys, etc.) may be positioned between the interior of the electrode member and the exterior of the thermal transfer member 3145. Such layer(s) can be continuously or intermittently applied between the electrode member (or another type of ablation member) and the adjacent thermal transfer member. Further, such layer(s) can be applied using one or more methods or procedures, such as, for example, sputtering, other plating techniques and/or the like. Such layer(s) can be used in any of the embodiments disclosed herein or variations thereof. In addition, the use of a heat shunting network specifically can help transfer heat away from the tissue being treated by the electrode member(s) without itself absorbing heat.

In some embodiments, the ablation catheter 3120 comprises multiple thermal transfer members 3145 (e.g., heat shunt disks or members). For example, according to some embodiments, such additional heat transfer members may be positioned proximal of thermal transfer member 3145 and may comprise one or more fins, pins and/or other members that are in thermal communication with the irrigation conduit 3150 extending through an interior of the ablation catheter. Accordingly, as with the thermal transfer members 3145 positioned in contact with the electrode members 3130, 3135 heat can be transferred and thus removed or dissipated, from other energy delivery members or electrodes, the adjacent portions of the catheter and/or the adjacent tissue of the subject via these additional heat transfer members (e.g., heat shunting members). In other embodiments, ablation catheters do not comprise any thermal transfer members.

In some embodiments, for any of the ablation catheters disclosed herein or variations thereof, one or more of the thermal transfer members (e.g., heat shunting members) that facilitate the heat transfer to a heat exchange chamber (e.g., irrigation conduit) of the catheter are in direct contact with the electrode members and/or the heat exchange chamber. However, in other embodiments, one or more of the thermal transfer members do not contact the electrode members and/or the irrigation conduit. Thus, in such embodiments, the thermal transfer members are in thermal communication with the electrode members or single electrode and/or irrigation conduit, but not in physical contact with such components. For example, in some embodiments, one or more intermediate components, layers, coatings and/or other members are positioned between a thermal transfer member (e.g., heat shunting member) and the electrode (or other ablation member) and/or the irrigation conduit. In some embodiments, irrigation is not used at all due to the efficiency of the thermal transfer members. For example, where multiple levels or stacks of thermal transfers are used, the heat may be dissipated over a larger area along the length of the ablation catheter. Additional details regarding function and features of thermal transfer members (e.g., heat shunting members) are provided herein. The features of the various embodiments disclosed therein (e.g., of thermal shunt systems and members) may be implemented in any of the embodiments of the medical instruments (e.g., ablation catheters) disclosed herein.

Figure 18E:
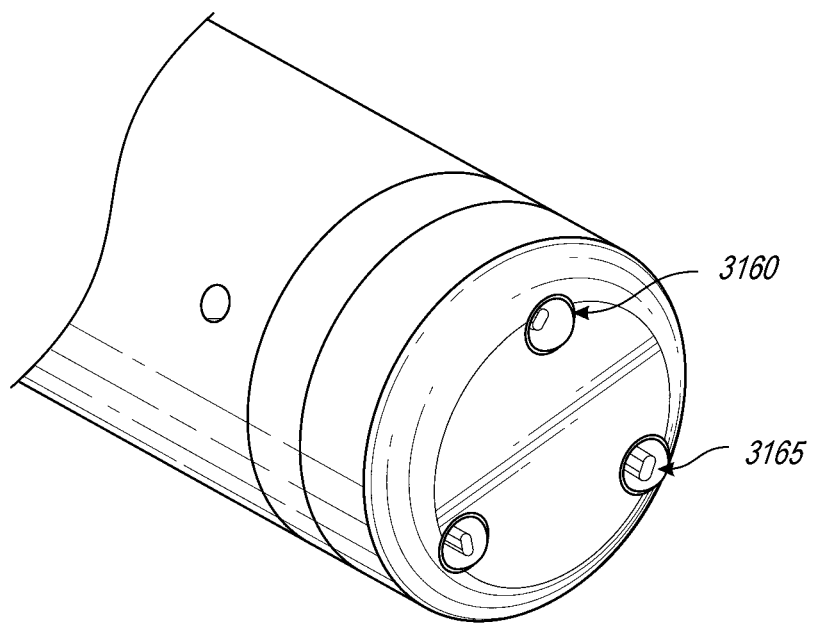
FIGS. 18E and 18F illustrate a perspective view and a cross-sectional view, respectively, of a distal portion of an ablation catheter showing isolation of the distal temperature-measurement devices from an electrode tip, according to one embodiment.
Figure 18F:
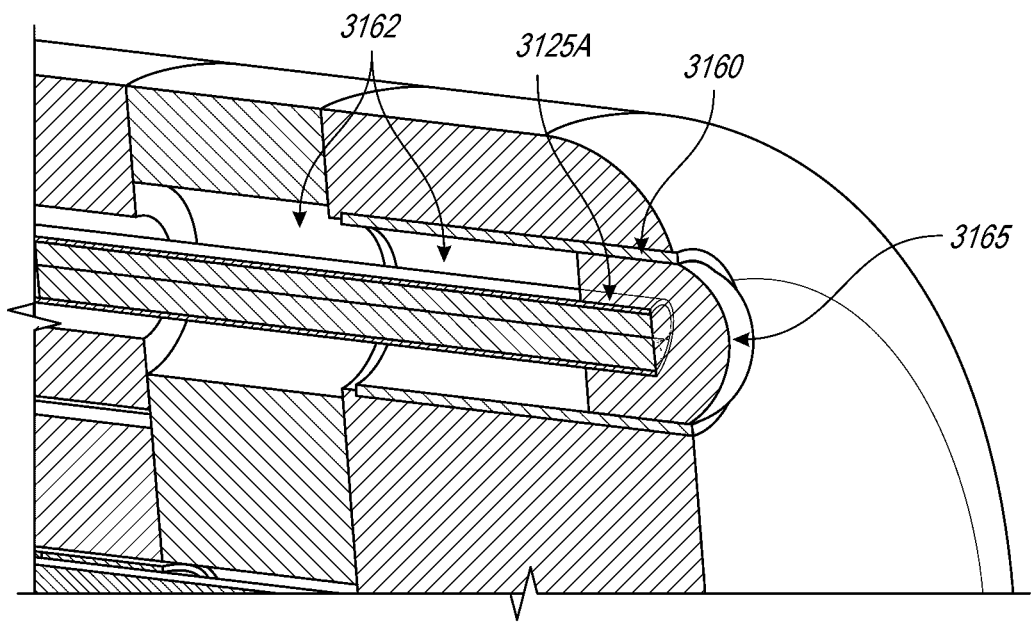

As best shown in FIGS. 18C, 18E and 18F, the temperature-measurement devices 3125 are thermally insulated from the electrode members 3130, 3135 by tubing 3160 and/or air gaps. In some embodiments, the tubing 3160 extends along an entire length (and beyond in some embodiments) of the electrode members 3130, 3135 such that no portion of the electrode member is in contact with the temperature-measurement devices 3125, thereby isolating the temperature measurements from the thermal effects of the electrode members. The outer tubing 3160 of the temperature-measurement devices may comprise an insulating material having low thermal conductivity (e.g., polyimide, ULTEM™, polystyrene or other materials having a thermal conductivity of less than about 0.5 W/m/° K). The tubing 3160 is substantially filled with air or another gas having very low thermal conductivity. The distal tip 3165 of the temperature-measurement device (e.g., the portion where the temperature is sensed) may comprise an epoxy polymer covering or casing filled with a highly conductive medium (e.g., nanotubes comprised of graphene, carbon or other highly thermally conductive materials or films) to increase thermal conduction at a head of the temperature-measurement device where temperature is measured. In some embodiments, the distal tip 3165 comprises an epoxy cap having a thermal conductivity that is at least 1.0 W/m/° K. The epoxy may comprise metallic paste (e.g., containing aluminum oxide) to provide the enhanced thermal conductivity. In some embodiments, the distal tip 3165 or cap creates an isothermal condition around the temperature-measurement device 3125 that is close to the actual temperature of tissue in contact with the temperature-measurement device. Because the distal tip 3165 of each temperature-measurement device 3125 is isolated from thermal conductive contact with the electrode member(s), it retains this isothermal condition, thereby preventing or reducing the likelihood of dissipation by the thermal mass of the electrode member(s). FIGS. 18E and 18F illustrate a perspective view and a cross-sectional view, respectively, of a distal portion of an ablation catheter showing isolation of the distal temperature-measurement devices from an electrode tip, according to one embodiment. As shown, the distal temperature measurement devices 3125A may be surrounded by air gaps or pockets 3162 and/or insulation. The outer tubing 3160 may comprise an insulation sleeve that extends along the entire length, or at least a portion of the length, of the distal electrode member 3130. The sleeve may extend beyond the distal electrode member 3130 or even to or beyond the proximal electrode member 3135.

The electrode member(s) (e.g., the distal electrode member 3130) can be electrically coupled to an energy delivery module (e.g., energy delivery module 40 of FIG. 1). As discussed herein, the energy delivery module 40 can comprise one or more components or features, such as, for example, an energy generation device 42 that is configured to selectively energize and/or otherwise activate the energy delivery members (e.g., RF electrodes), one or more input/output devices or components, one or more processors (e.g., one or more processing devices or control units) that are configured to regulate one or more aspects of the treatment system, a memory and/or the like. Further, such a module can be configured to be operated manually or automatically, as desired or required.

The temperature-measurement devices 3125 can be coupled to one or more conductors (e.g., wires, cables, etc.) that extend along the length of the ablation catheter 3120 and communicate the temperature signals back to at least one processing device (e.g., processor 46 of FIG. 1) for determining temperature measurements for each of the temperature-measurement devices, as will be discussed in greater detail below.

According to some embodiments, the relative length of the different electrodes or electrode members 3130, 3135 can vary. For example, the length of the proximal electrode member 3135 can be between 1 to 20 times (e.g., 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, values between the foregoing ranges, etc.) the length of the distal electrode member 3130, as desired or required. In yet other embodiments, the lengths of the distal and proximal electrode members 3130, 3135 are about equal. In some embodiments, the distal electrode member 3130 is longer than the proximal electrode member 3135 (e.g., by 1 to 20 times, such as, for example, 1-2, 2-3, 3-4, 4-5, 5-6, 6-7, 7-8, 8-9, 9-10, 10-11, 11-12, 12-13, 13-14, 14-15, 15-16, 16-17, 17-18, 18-19, 19-20, values between the foregoing ranges, etc.).

In some embodiments, the distal electrode member 3130 is 0.5 mm long. In other embodiments, the distal electrode member 3130 is between 0.1 mm and 1 mm long (e.g., 0.1-0.2, 0.2-0.3, 0.3-0.4, 0.4-0.5, 0.5-0.6, 0.6-0.7, 0-0.8, 0.7-0.8, 0.8-0.9, 0.9-1 mm, values between the foregoing ranges, etc.). In other embodiments, the distal electrode member 3130 is greater than 1 mm in length, as desired or required. In some embodiments, the proximal electrode member 3135 is 2 to 4 mm long (e.g., 2-2.5, 2.5-3, 3-3.5, 3.5-4 mm, lengths between the foregoing, etc.). However, in other embodiments, the proximal electrode member 3135 is greater than 4 mm (e.g., 4-5, 5-6, 6-7, 7-8, 8-9, 9-10 mm, greater than 10 mm, etc.) or smaller than 1 mm (e.g., 0.1-0.5 0.5-1, 1-1.5, 1.5-2 mm, lengths between the foregoing ranges, etc.), as desired or required. In embodiments where the split electrodes are located on catheter shafts, the length of the electrode members can be 1 to 5 mm (e.g., 1-2, 2-3, 3-4, 4-5 mm, lengths between the foregoing, etc.). However, in other embodiments, the electrode members can be longer than 5 mm (e.g., 5-6, 6-7, 7-8, 8-9, 9-10, 10-15, 15-20 mm, lengths between the foregoing, lengths greater than 20 mm, etc.), as desired or required.

The electrode member(s) may be energized using one or more conductors (e.g., wires, cables, etc.). For example, in some arrangements, the exterior of the irrigation conduit 3150 comprises and/or is otherwise coated with one or more electrically conductive materials (e.g., copper, other metal, etc.). Thus, the conductor can be placed in contact with such a conductive surface or portion of the irrigation conduit 3150 to electrically couple the electrode member(s) to an energy delivery module. However, one or more other devices and/or methods of placing the electrode member(s) in electrical communication with an energy delivery module can be used. For example, one or more wires, cables and/or other conductors can directly or indirectly couple to the electrode member(s), without the use of the irrigation conduit.

The use of a composite tip (e.g., split tip) design can permit a user to simultaneously ablate or otherwise thermally treat targeted tissue and map (e.g., using high-resolution mapping) in a single configuration. Thus, such systems can advantageously permit precise high-resolution mapping (e.g., to confirm that a desired level of treatment occurred) during a procedure. In some embodiments, the composite tip (e.g., split tip) design that includes two electrode members or electrode portions 3130, 3135 can be used to record a high-resolution bipolar electrogram. For such purposes, the two electrodes or electrode portions can be connected to the inputs of an electrophysiology (EP) recorder. In some embodiments, a relatively small separation distance (e.g., gap G) between the electrode members or electrode portions 3130, 3135 enables high-resolution mapping. According to some arrangements, the composite-tip electrode embodiments disclosed herein are configured to provide localized high-resolution electrograms (e.g., electrograms having a highly increased local specificity as a result of the separation of the two electrode portions and a high thermal diffusivity of the material of the separator, such as industrial diamond). The increased local specificity may cause the electrograms to be more responsive to electrophysiological changes in underlying cardiac tissue or other tissue so that effects that RF energy delivery has on cardiac tissue or other tissue may be seen more rapidly and more accurately on the high-resolution electrograms.

In some embodiments, a medical instrument (e.g., a catheter) 3120 can include three or more electrode members or electrode portions (e.g., separated by gaps), as desired or required. According to some embodiments, regardless of how many electrodes or electrode portions are positioned along a catheter tip, the electrode members or electrode portions 3130, 3135 are radiofrequency electrodes and comprise one or more metals, such as, for example, stainless steel, platinum, platinum-iridium, gold, gold-plated alloys and/or the like.

According to some embodiments, the electrode members or electrode portions 3130, 3135 are spaced apart from each other (e.g., longitudinally or axially) using the gap (e.g., an electrically insulating gap) 3131. In some embodiments, the length of the gap 3131 (or the separation distance between adjacent electrode members or electrode portions) is 0.5 mm. In other embodiments, the gap or separation distance is greater or smaller than 0.5 mm, such as, for example, 0.1-1 mm (e.g., 0.1-0.2, 0.2-0.3, 0.3-0.4, 0.4-0.5, 0.5-0.6, 0.6-0.7, 0.7-0.8, 0.8-0.9, 0.9-1.0 mm, values between the foregoing ranges, less than 0.1 mm, greater than 1 mm, etc.), as desired or required.

According to some embodiments, a separator is positioned within the gap 3131 between the adjacent electrode members or electrode portions 3130, 3135. The separator can comprise one or more electrically insulating materials, such as, for example, Teflon, polyetheretherketone (PEEK), diamond, epoxy, polyetherimide resins (e.g., ULTEM™), ceramic materials, polyimide and the like. As shown in FIGS. 18A-18C and 19A-19C, the separator may comprise a portion of the thermal transfer member 3145 extending within the gap 3131.

As noted above with respect to the gap 3131 separating the adjacent electrode members or electrode portions, the insulating separator can be 0.5 mm long. In other embodiments, the length of the separator can be greater or smaller than 0.5 mm (e.g., 0.1-0.2, 0.2-0.3, 0.3-0.4, 0.4-0.5, 0.5-0.6, 0.6-0.7, 0.7-0.8, 0.8-0.9, 0.9-1.0 mm, values between the foregoing ranges, less than 0.1 mm, greater than 1 mm, etc.), as desired or required.

According to some embodiments, to ablate or otherwise heat or treat targeted tissue of a subject successfully with the split tip electrode design, such as the ones depicted in FIGS. 18A-18C and 19A-19C, the two electrode members or electrode portions 3130, 3135 are electrically coupled to each other at the RF frequency. Thus, the two electrode members or electrode portions can advantageously function as a single longer electrode at the RF frequency. Additional details regarding function and features of a composite (e.g., split tip) electrode design are provided herein.

Figure 19A:
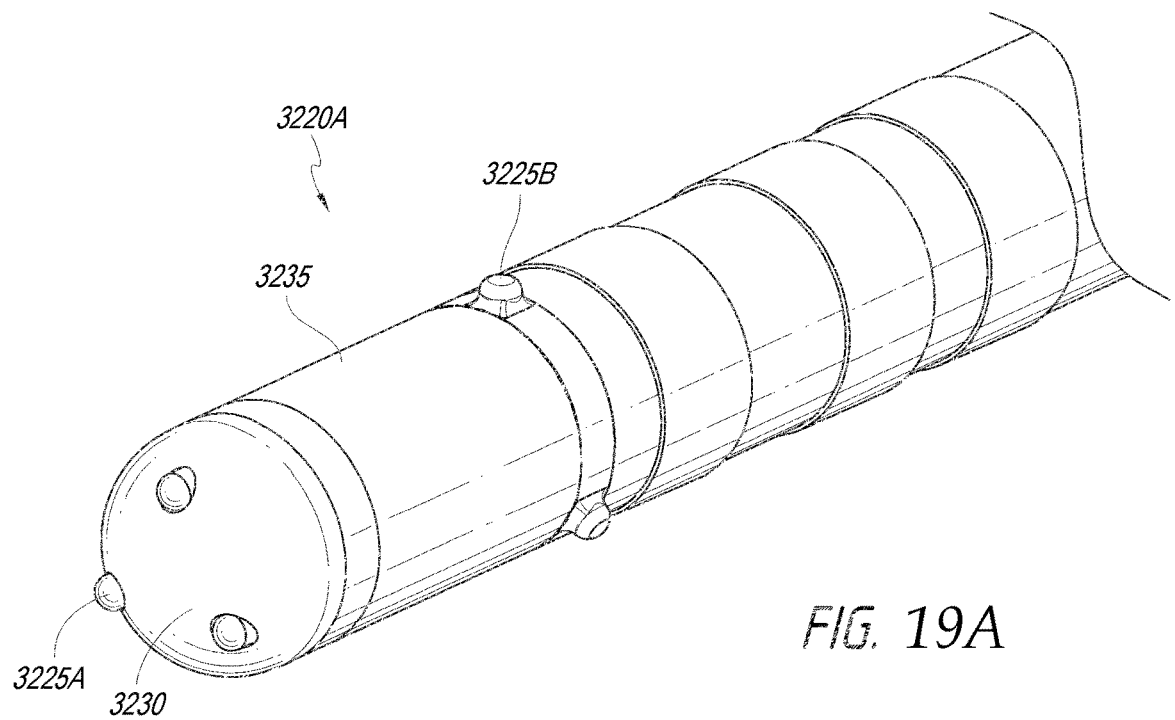
FIG. 19A illustrates a perspective view of a distal portion of a closed-irrigation ablation catheter having multiple temperature-measurement devices, according to one embodiment.
Figure 19B:
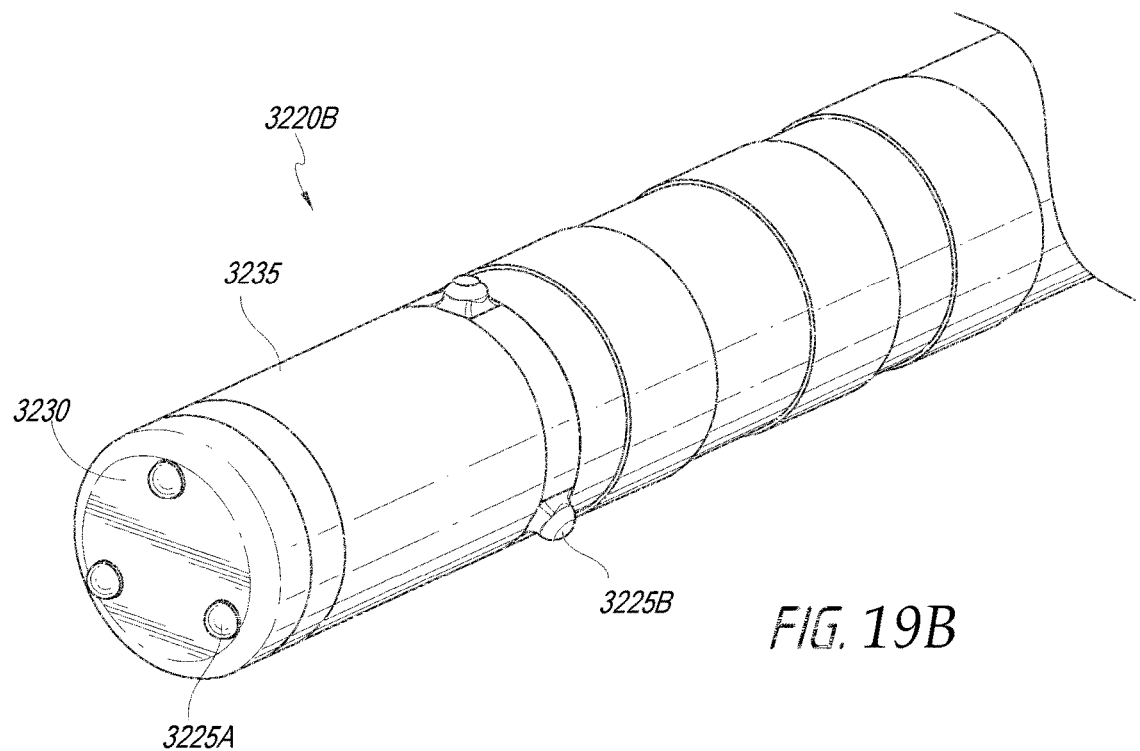
FIGS. 19B and 19C illustrate a perspective view and a cross-sectional view, respectively, of a distal portion of a closed-irrigation ablation catheter having multiple temperature-measurement devices, according to another embodiment.
Figure 19C:
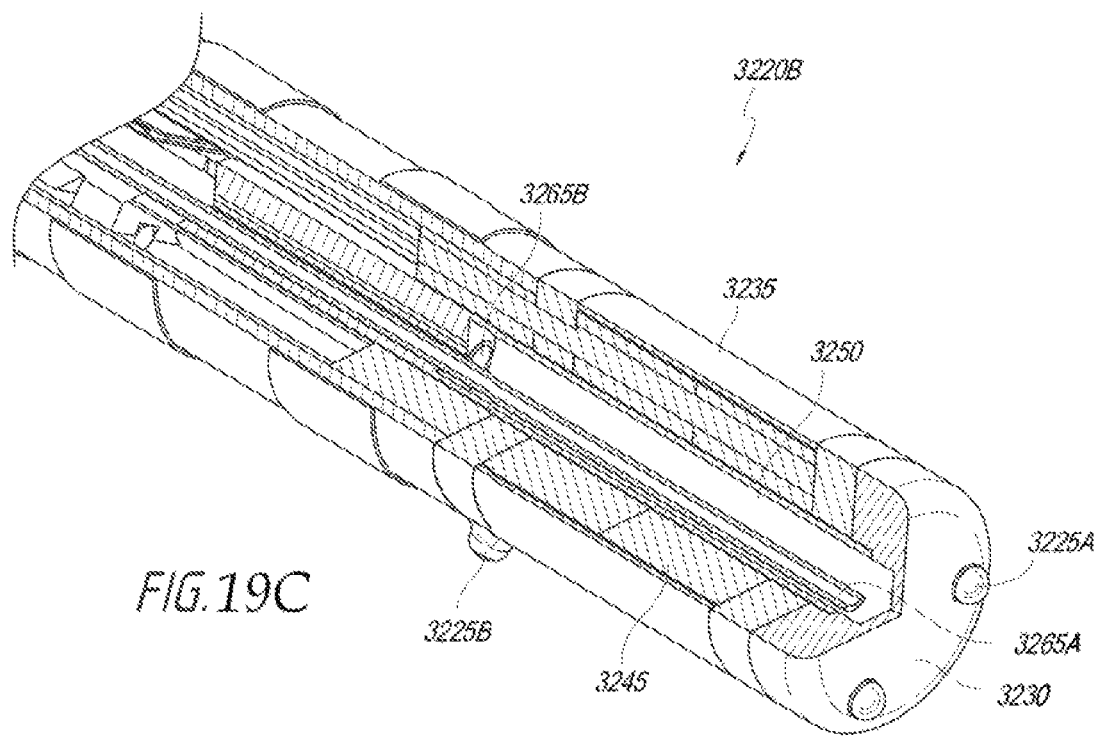

FIGS. 19A-19C illustrate a distal portion of closed-irrigation ablation catheters 3220 having multiple temperature-measurement devices 3225, according to various embodiments. The embodiment of the ablation catheter 3220A of FIG. 19A comprises a dome-shaped tip electrode member 3230 similar to the ablation catheter 3120A of FIG. 18A. The embodiment of the ablation catheter 3220B of FIGS. 19B and 19C comprises a flat tip electrode member similar to the ablation catheter 3120B of FIGS. 18B and 18C. The ablation catheters 3220A and 3220B include similar components and features as those described above in connection with FIGS. 18A-18C. For example, temperature-measurement devices 3225 correspond to temperature-measurement devices 3125, electrode members 3230, 3235 correspond to electrode members 3130, 3135, thermal transfer member 3245 corresponds to thermal transfer member 3145 and irrigation conduit 3250 corresponds to irrigation conduit 3150. Accordingly, these features will not be described again in connection with FIGS. 19A-19C. The ablation catheter 3220 does not include irrigation ports because it operates as a closed irrigation device.

The ablation catheter 3220 comprises two lumens 3265 within the irrigation conduit 3250, an inlet lumen (e.g., fluid delivery channel) 3265A and an outlet lumen (e.g., return channel) 3265B. As illustrated in the cross-sectional view of FIG. 19C, the outlet of the inlet lumen 3265A and the inlet of the outlet lumen 3265B terminate at spaced-apart locations within the irrigation conduit 3250. The outlet of the inlet lumen 3265A terminates within the distal electrode member 3230 or adjacent to a proximal end surface of the distal electrode member 3230. The inlet of the outlet lumen terminates proximal to the proximal end of the proximal electrode member 3235. The offset spacing of the distal ends of the lumens 3265 advantageously induces turbulence, vortexing or other circulating fluid motions or paths within the irrigation conduit, thereby facilitating enhanced cooling by circulating the fluid to constantly refresh or exchange the fluid in contact with the thermal transfer member 3245 and/or electrode members.

Figure 19D:
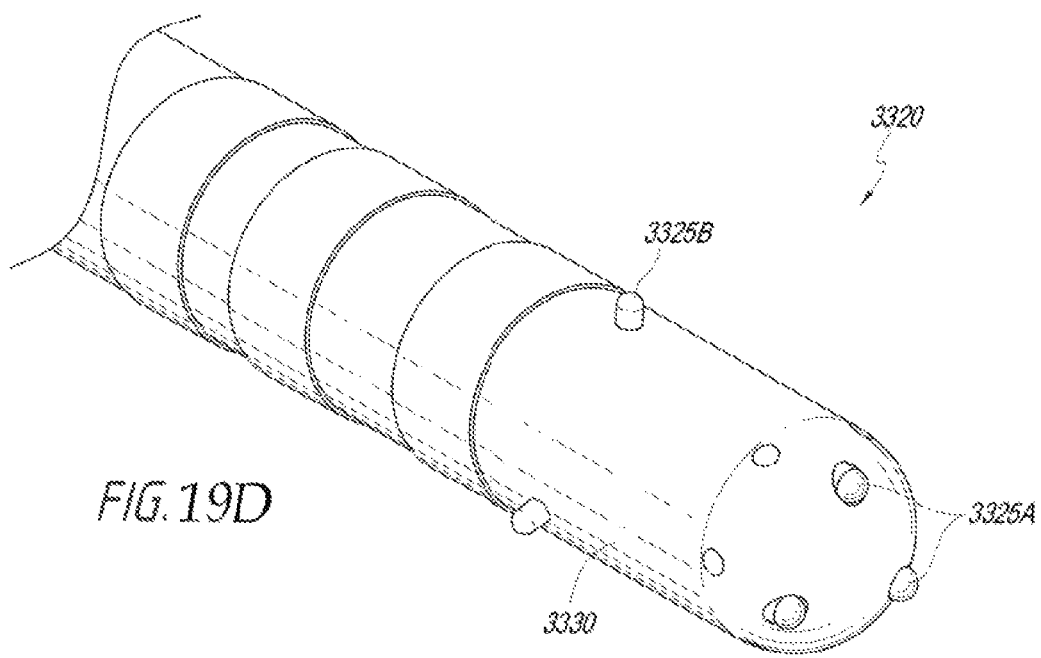
FIG. 19D illustrates a perspective view of a distal portion of an open-irrigated ablation catheter comprising a non-split-tip or other non-composite design according to one embodiment.

In accordance with several embodiments, ablation catheters having multiple temperature-measurement devices do not require a composite (e.g., split-tip) electrode design and/or thermal transfer members. FIG. 19D illustrates a perspective view of a distal portion of an open-irrigated ablation catheter 3320 that does not include a composite electrode design or a thermal transfer member. The ablation catheter 3320 comprises a first (e.g., distal) plurality of temperature-measurement devices 3325A and a second (e.g., proximal) plurality of temperature-measurement devices 3325B. The temperature-measurement devices 3325 comprise similar features, properties, materials, elements and functions as the temperature-measurement devices 3125, 3225 (FIGS. 18A-19C). The ablation catheter 3320 may comprise or consist of a single unitary tip electrode 3330. The tip electrode 3330 may comprise apertures, slots, grooves, bores or openings for the temperature-measurement devices 3325 at their respective spaced-apart locations. As shown in FIG. 19D, the proximal temperature-measurement devices 3325B are positioned distal but adjacent to the proximal edge of the tip electrode 3330. The proximal temperature-measurement devices 3325B could be positioned within 1 mm of the proximal edge (e.g., within 0.9, 0.8, 0.7, 0.6, 0.5, 0.4, 0.3, 0.2, 0.1 mm proximal or distal of the proximal edge, depending on the length of the tip electrode 3330). In other embodiments, the proximal temperature-measurement devices 3325B are positioned proximal of the proximal edge of the tip electrode 3330 and within the same distance as described above of distal placement. In various embodiments, the temperature-measurement devices are positioned at or near the proximal and distal edges of the electrode or composite (e.g., split-tip) electrode assembly because those locations tend to be the hottest. Based on manufacturing tolerances, these temperature measurement devices may be embedded at the proximal or distal edge of the tip electrode 3330. Accordingly, positioning of the temperature-measurement devices at or near these locations may facilitate prevention, or reduced likelihood, of overheating or char or thrombus formation. Additionally, such temperature-measurement device placement offers the ability to monitor tissue temperature during irrigated ablation.

In some embodiments, epoxy comprising a conductive medium (such as graphene or other carbon nanotubes) may be blended in to the distal tubing (typically formed of plastic) of the ablation catheter shaft and the distal tubing of the ablation catheter itself may function as a thermal transfer. In some embodiments, the addition of the conductive epoxy could increase the thermal conductivity of the distal tubing by 2-3 times or more. These conductive tubing features and other features described in connection with FIG. 19D may be used in connection with the ablation catheters 3120, 3220 as well.

In certain embodiments, the heat shunt members included along the distal end of the catheter or other medical instrument are maintained within an interior of such a catheter or medical instrument. In some embodiments, this is accomplished by providing one or more layers or coatings partially or completely along the exterior or outer surfaces of heat shunt portions. Such layers or coatings can be electrically insulative. Further, in some arrangements, such layers or coatings can be both electrically-insulative and thermally-insulative, as desired or required. However, in other embodiments, the layers or coatings can be electrically insulative but not thermally insulative. As used herein, electrically insulative means having an electrical resistivity in excess of 1000 Ω·cm. Further, as used herein, thermally conductive means having a thermal conductivity greater than 0.5 W/cm-K at 20° C.

Embodiments that include such layers or coatings along one or more shunting portions or members (e.g., to maintain shunting portions or members along an interior of a catheter or other medical instrument) can provide several benefits and advantages to the resulting devices and systems, as well as the resulting methods of use and treatment. For example, the coating(s) or layer(s) can: (i) improve the conductive cooling effects of the irrigation fluid (which, in turn, can permit irrigation flow rates and the resultant volume of fluid infused into the patient to be significantly decreased; in some embodiments, lower irrigation rates result in better temperature measurement accuracy, as temperature sensors are less likely to be flooded by the irrigation fluid), (ii) improve manufacturing and operational aspects of the catheter or other medical instrument (e.g., can compensate for the effects of the superficial layer of the heat shunt portions becoming electrically conductive as a result of the cutting process, thereby providing more flexibility to the manufacture of the heat shunt portions while still maintaining a consistent outer surface for the catheter or other medical instrument), (iii) provide additional protection against the formation of hot spots or localized heating at or near the proximal ends of the proximal electrode during use and/or the like.

According to some embodiments, as discussed in greater detail herein, the primary heat shunting mechanism of catheters that include heat shunting networks occurs via the cooling action of (e.g., via conductive heat transfer to) the irrigation fluid running within an interior of the catheter or other medical instrument. In some embodiments, the conductive cooling capacity of room-temperature (e.g., around 27° C.) irrigation fluid flowing through the heat shunting network (e.g., the diamond or other heat shunting network that is in thermal contact with the irrigation passage extending through the distal portion of the catheter or other medical instrument) is greater than that of the convective cooling provided by the blood flow over the external surface of the heat shunting network. This occurs, in part, because the temperature of blood (e.g., which is around 37° C.) is notably higher than the temperature of irrigation fluid. Also, this may occur, because the heat transport velocity of the blood may be inferior to that provided by the irrigation fluid (e.g. the blood flow velocity is low in certain regions of the heart, for example in parts of the atria or under valve leaflets). Thus, by thermally insulating the external surfaces of heat shunting portions or members (e.g., diamond), the conductive cooling effects of the irrigation fluid (e.g., via heat transfer to the irrigation fluid) can be augmented. In some embodiments, this can help to significantly decrease the irrigation flow rates and the resultant volume of fluid infused into the patient. Low irrigation flow rates can result in improved temperature sensing accuracy, as the temperature sensors associated with electrodes are less likely to be flooded by the irrigation fluid (e.g., the volume of required irrigation fluid is reduced).

In some embodiments, when industrial diamond or other heat shunting members or portions are cut in preparation for incorporation into a catheter, the resulting superficial portion (e.g., outer surface or layer, portions immediately adjacent (e.g., within 0.1 mm) the outer surface or layer, etc.) can become at least partially electrically conductive (e.g., especially vis-à-vis the electrical properties of the uncut diamond or other heat shunting material). For example, in some arrangements, the electrical conductivity of industrial diamond or other heat shunting material that is cut or otherwise prepared can increase by 1% to 100% (e.g., 1-5, 5-10, 10-20, 20-50, 50-100, 25-75, 20-100%, values and ranges between the foregoing), or more that 100% (e.g., 100-150, 150-200, 200-300%, more than 300%, etc.), relative to uncut or otherwise undisturbed or unprepared material. As a result, in some embodiments, such a superficial portion (e.g., surface, layer or area) can present problems during operation of the catheter or other medical instrument into which it is incorporated if it is exposed to the exterior of the catheter or medical instrument. For example, the electrical conductivity of the superficial portion (e.g., surface, layer or area) of diamond or other heat shunting material can cause electrical short-circuiting of the two electrodes (or electrode portions) included in the catheter or medical instrument. Accordingly, providing an electrically non-conductive layer or coating along the exterior surfaces of certain heat shunting portions, as discussed herein, can provide operational benefits to the manufacturing and performance of the resulting catheter or medical instrument. This, in turn, may result in out-of-speciation performance of system features such as tissue contact sensing, impedance measurements, energy delivery and/or the like. Thus, in some embodiments, all or the majority of the heat shunting members or portions included in a catheter or other medical instrument are not exposed to the exterior of the catheter or medical instrument. In some configurations, none of the diamond or other heat shunting network is exposed to the exterior of the catheter or other medical instrument. In other embodiments, 70-100% (e.g., 70-75, 75-80, 80-85, 85-90, 90-95, 95-100%, percentages between the foregoing ranges, etc.), 50-70%, or less than 50% of an outer surface area of the heat shunting is covered or coated with a layer or coating.

Figure 20:
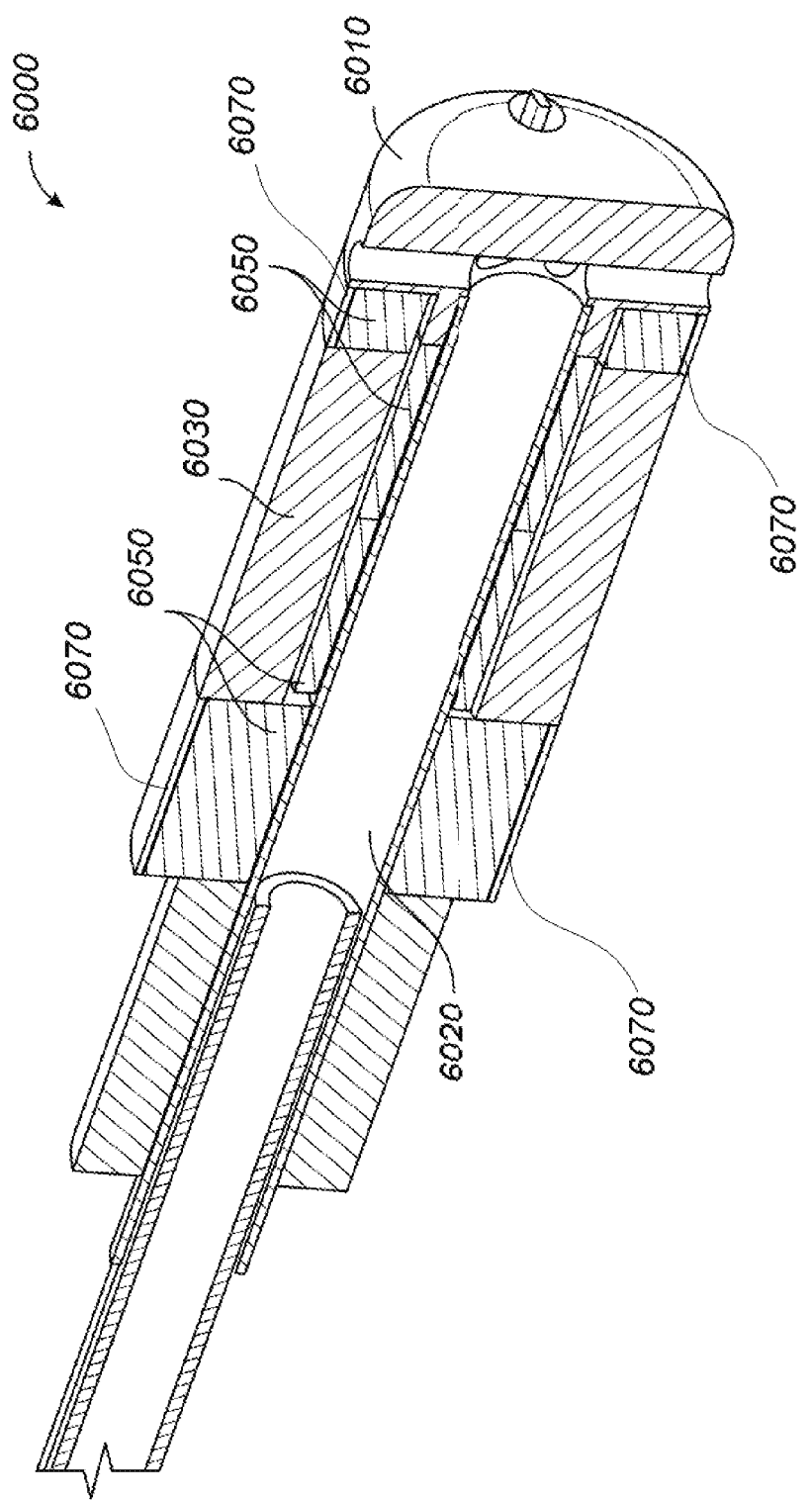
FIG. 20 illustrates a cross-sectional perspective view of one embodiment of a catheter comprising a layer or coating along an exterior of heat shunting members or portions.

As illustrated in FIG. 20, one or more thermally-insulating layers or coatings 6070 can be placed around the exterior of the heat shunt portions 6050 that are exposed to the outside of the catheter or other medical instrument 6000. The layer or coating 6070 can include one or more thermally insulative materials (e.g., thermoset polymers, polyimide, PEEK, polyester, polyethylene, polyurethane, pebax, nylon, hydratable polymers, other polymers, etc.). In some embodiments, such materials have a thermal conductivity of less than 0.001 W/cm*K (e.g., 0.0001-0.001, 0.001-0.0025, 0.0025-0.001 W/cm*K, less than 0.0001 W/cm*K, etc.). The thickness of such a layer or coating 6070 can be about 50 μm (2 mils) or less. For example, in some embodiments, the thickness of the layer or coating 6070 is 1-50 μm (e.g., 1-5, 5-10, 10-20, 20-30, 30-40, 40-50 μm, values between the foregoing ranges, etc.) or less than 1 μm (e.g., 0.01-0.5, 0.5-0.75, 0.75-1 μm, values between the foregoing ranges, etc.). In other embodiments, however, the thickness of the layer or coating 6070 is greater than 50 μm, such as, for example, 50-100 (e.g., 50-55, 55-60, 60-65, 65-70, 70-75, 75-80, 80-85, 85-90, 90-95, 95-100, values between the foregoing ranges), 100-200 (e.g., 100-110, 110-120, 120-130, 130-140, 140-150, 150-160, 160-170, 170-180, 180-190, 190-200, values between the foregoing ranges), 200-300, 300-400, 400-500, 500-1000, 1000-5000 μm, greater than 5000 μm.

In any embodiments where the heat shunting portions include a coating or layer, such a coating or layer can be a single or unitary coating or layer. However, in other embodiments, more than one layer or coating can be positioned along the exterior of one or more heat shunting members or portions, as desired or required. For example, in some arrangements, the coating or layer 6070 can include two or more (e.g., 2, 3, 4, 5, more than 5) separate coatings or layers. Such separate coatings or layers can be positioned along the catheter 6000 either individually or as a single member, as desired or required by the particular technologies used to secure such coatings or layers along the desired surfaces of the heat shunting members or portions.

The coating or layer 6070 can be positioned along the exterior of the heat shunt portions using a variety of technologies, such as, for example, glues or other adhesives, press-fit methods, dip molding, other molding technologies and/or the like. As noted above, depending on the specific methods and/or technologies used, the coating or layer 6070 can include two or more separate coatings or layers, which may be positioned along heat shunt members or portions separately or as a single coating or layer, as desired or required. Further, the coating or layer 6070 can be positioned along heat shunt members directly or indirectly. For example, in some embodiments, the coating or layer 6070 directly contacts and is secured directly to an adjacent surface of a heat shunt member or portion. However, in other embodiments, the coating or layer 6070 does not contact or is not secured directly to an adjacent surface of a heat shunt member or portion. In such arrangements, for instance, one or more intermediate layers, coatings, structures (e.g., air gaps) or other members can be positioned between a heat shunt member or portion and the coating or layer 6070.

As noted herein, the various embodiments of a catheter or other medical instrument can include an irrigation channel that is responsible for the majority of heat transfer away from the electrode(s) or electrode portion(s) positioned along a distal end of the catheter or medical instrument. In embodiments that comprise diamond and/or other heat shunting materials and/or configurations, heat can be transferred to irrigation fluid (e.g., flowing through an irrigation channel) via the heat shunting network. As discussed in greater detail herein, such a heat shunting network facilitates heat transfer away from the source (e.g., electrodes) without itself retaining heat or retaining very little heat. Relatedly, heat is transferred away from potential hot spots that form at the edges of electrodes and are shunted through the heat shunt network into the irrigation channel. From the irrigation channel, via convective cooling, heat can be advantageously released into the blood stream and dissipated. In closed irrigation systems, heat can be removed from the system without expelling irrigation fluid into the subject. The layer(s) and/or coating(s) discussed above can be incorporated into any catheter or other medical instrument device or system disclosed herein or equivalent thereof.

Figure 21A:
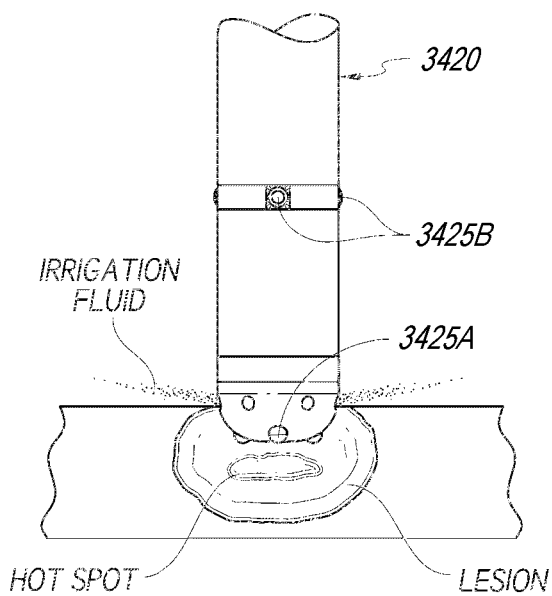
FIG. 21A schematically illustrates a distal portion of an open-irrigated ablation catheter in contact with tissue to be ablated in a perpendicular orientation and a lesion formed using the ablation catheter, according to one embodiment.
Figure 21B:
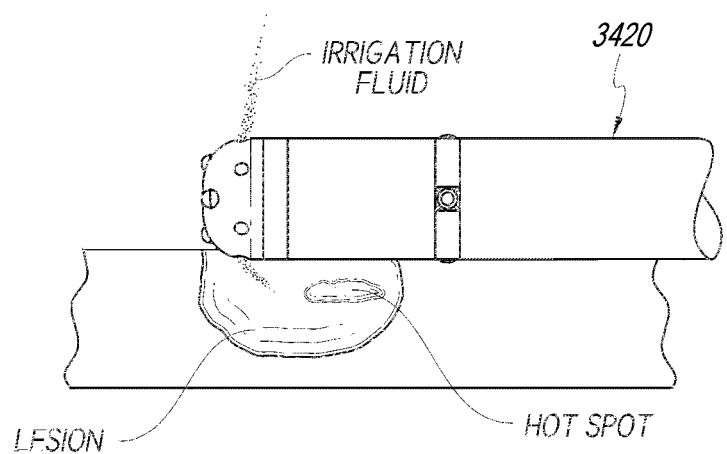
FIG. 21B schematically illustrates a distal portion of an open-irrigated ablation catheter in contact with tissue to be ablated in a parallel orientation and a lesion formed using the ablation catheter, according to one embodiment.

FIGS. 21A and 21B schematically illustrate a distal portion of an open-irrigated ablation catheter 3420 in perpendicular contact and parallel contact, respectively, with tissue and formation of thermal lesions by delivering energy to the tissue using the ablation catheter 3420. In accordance with several embodiments, the ablation catheters having multiple temperature-measurement devices described herein advantageously facilitate determination of, among other things: an orientation of the distal tip of the ablation catheter with respect to the tissue (e.g., electrode-tissue orientation), an estimated peak temperature within the thermal lesion, and/or a location of the peak temperature zone within the thermal lesion.

As mentioned above, the temperature-measurement devices 3425 may send or transmit signals to at least one processing device (e.g., processor 46 of FIG. 1). The processing device may be programmed to execute instructions stored on one or more computer-readable storage media to determine temperature measurements for each of the temperature-measurement devices 3425 and to compare the determined temperature measurements with each other to determine an orientation of the distal tip of the ablation catheter with respect to the tissue (e.g., electrode-tissue orientation) based, at least in part, on the comparisons. Additional details regarding the comparisons are provided below in connection with the discussion of FIGS. 23D-23F. The processing device may select (e.g., determine) an orientation from one of three orientations (e.g., parallel, perpendicular, or angled (e.g., skewed or oblique) orientations).

For example, the differences in the spreads of the temperature measurement profiles or values between the proximal temperature-measurement devices and the distal temperature-measurement devices may be used to determine orientation. As one example, if the temperature measurements received from the distal temperature-measurement devices are all greater (e.g., hotter) than the temperature measurements received from the proximal temperature-measurement devices, then the processor may determine that the orientation is perpendicular. If the temperature measurements received from at least one proximal temperature-measurement device and at least one corresponding distal temperature-measurement device are similar, then the processor may determine that the orientation is parallel.

As other examples, for embodiments using three temperature-measurement devices, if two of three proximal temperature-measurement devices generate much lower (and generally equal) temperature measurements than the third proximal-temperature measurement device, then the processing device may determine that the orientation is parallel. For embodiments using three temperature-measurement devices, if the temperature measurements received from a first proximal temperature-measurement device are appreciably greater than temperature measurements from a second proximal temperature-measurement device and if the temperature measurements received from the second proximal temperature-measurement device are appreciably greater than temperature measurements received from a third proximal temperature-measurement device, then the processing device may determine that the orientation is neither parallel nor perpendicular but skewed at an angle (e.g., oblique orientation). Additional details regarding orientation determination are provided below in connection with the discussion of FIGS. 23C-23E. In some embodiments, orientation may be confirmed using fluoroscopic imaging, ICE imaging or other imaging methods or techniques. Orientation may also be confirmed using a tissue mapping system, such as a three-dimensional cardiac mapping system.

In some embodiments, the determined orientation may be output on a display (e.g., a graphical user interface) for visibility by a user (e.g., clinical professional). The output may comprise one or more graphical images indicative of an orientation and/or alphanumeric information indicative of the orientation (e.g., a letter, word, phrase or number). Additional details regarding output will be described in connection with FIGS. 23F-1, 23F-2 and 23F-3. The processing device may apply correction factors to the temperature measurements received from the temperature-measurement devices based on the determined orientation in order to generate more accurate estimates of a peak temperature of the thermal lesion. For example, if a perpendicular orientation is determined, then a correction factor or function corresponding to the distal temperature-measurement devices may be applied to determine the estimated peak temperature.

The processing device may comprise a temperature acquisition module and a temperature processing module, in some embodiments. The temperature acquisition module may be configured to receive as input temperature signals (e.g., analog signals) generated by each of the temperature-measurement devices. The input signals may be continuously received at prescribed time periods or points in time. The temperature acquisition module may be configured to covert analog signals into digital signals. The temperature processing module may receive the digital signals output from the temperature acquisition module and apply correction factors or functions to them to estimate a hottest tissue temperature, a peak temperature or a peak temperature in a thermal lesion created in the vicinity of the electrode or other energy delivery member(s). The temperature processing module may compute a composite temperature from the temperature-measurement devices (e.g., thermocouples) based on the following equation:

$$Tcomp(t) = k(t) * f(TC1(t), TC2(t), \ldots, TCn(t));$$

where Tcomp is the composite temperature, k is the k function or correction or adjustment function, f is a function of the thermocouple readings TCi, i=1 to n. The k function may comprise a function over time or a constant value. For example, a k function may be defined as follows:

$$k(t) = e^{(-t/\tau)} + k_{final} * (1 - e^{(-t/\tau)});$$

where τ is a time constant representative of the tissue time constant and $k_{final}$ is a final value of k, as per a correction factor or function, such as described in connection with FIG. 22A below.

The temperature processing module may also be configured to determine an orientation of a distal tip of a medical instrument with respect to tissue, as described above. The processing device may further comprise an output module and a feedback/monitoring module. The output module may be configured to generate output for display on a display, such as the various outputs described herein. The feedback/monitoring modules may be configured to compare measured temperature values against a predetermined setpoint temperature or maximum temperature and to initiate action (e.g., an alert to cause a user to adjust power or other ablation parameters or automatic reduction in power level or termination of energy delivery (which may be temporary until the temperature decreases below the setpoint temperature). In various embodiments, the setpoint, or maximum, temperature is between 50 and 90 degrees Celsius (e.g., 50, 55, 60, 65, 70, 75, 80, 85 degrees Celsius). In some embodiments, an algorithm identifies which temperature-measurement device (e.g., thermocouple) is currently recording the highest temperature and selects that thermocouple to control the power delivery required to reach and maintain the setpoint temperature or other target temperature. As the tip electrode moves with respect to tissue and different temperature-measurement devices come in greater or lesser contact with tissue, the processor or processing device may automatically select whichever temperature-measurement device is reading the highest temperature to control the power delivery.

In accordance with several embodiments, there is a proportional relationship between the temperature gradient determined by the temperature-measurement devices and the peak temperature of the lesion. From this relationship, a function or correction factor is generated or applied based on numerical modeling (e.g., finite element method modeling techniques) and/or measurements stored in a look-up table to adjust or correct from the thermal gradient identified by the temperature-measurement devices to determine the peak temperature. The thermal gradient of an open-irrigated lesion is such that the lesion surface is a little bit cooled and the peak temperature zone is deeper. The further the temperature-measurement devices can be buried into tissue, the better or more accurate the proportional relationship may be between the thermal gradient determined by the temperature-measurement devices and the peak temperature. For example, the thermal gradient can be estimated as:

$$\Delta T/\Delta d = (T_{distal} - T_{proximal})/TC\_\text{separation distance}$$

In other words, the temperature spatial gradient is estimated as the difference in temperature between the distal and proximal temperature-measurement devices divided by the distance between the distal and proximal temperature-measurement devices. The peak tissue temperature (where peak can be a hill or a valley) can then be estimated as:

$$T_{peak} = \Delta T/\Delta d * T_{peak\_dist} + T_{distal}$$

The processing device may also determine an estimated location of the peak temperature zone of the thermal lesion based, at least in part, on the determined orientation and/or the temperature measurements. For example, for a perpendicular orientation, the peak temperature location may be determined to be horizontally centered in the thermal lesion. In some embodiments, the processor may be configured to output information indicative of the peak temperature location on a display (e.g., a graphical user interface). The information may include textual information and/or one or more graphical images.

Figure 22A:
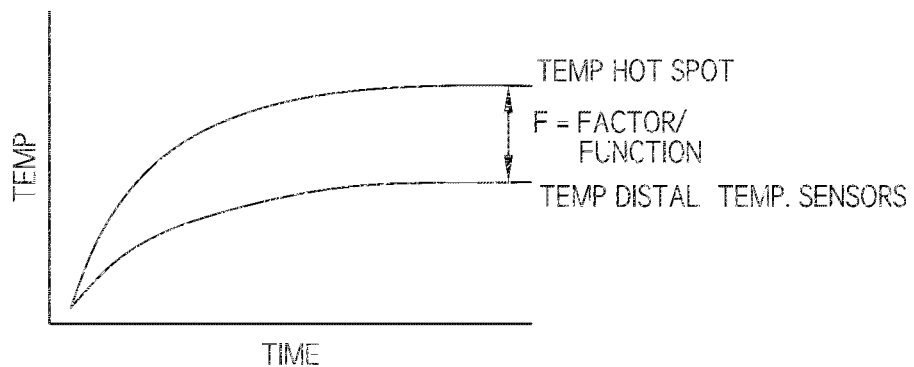
FIG. 22A is a graph illustrating that temperature of a lesion peak may be correlated to the temperature of the temperature-measurement devices by a correction factor or function, according to one embodiment.
Figure 22B:
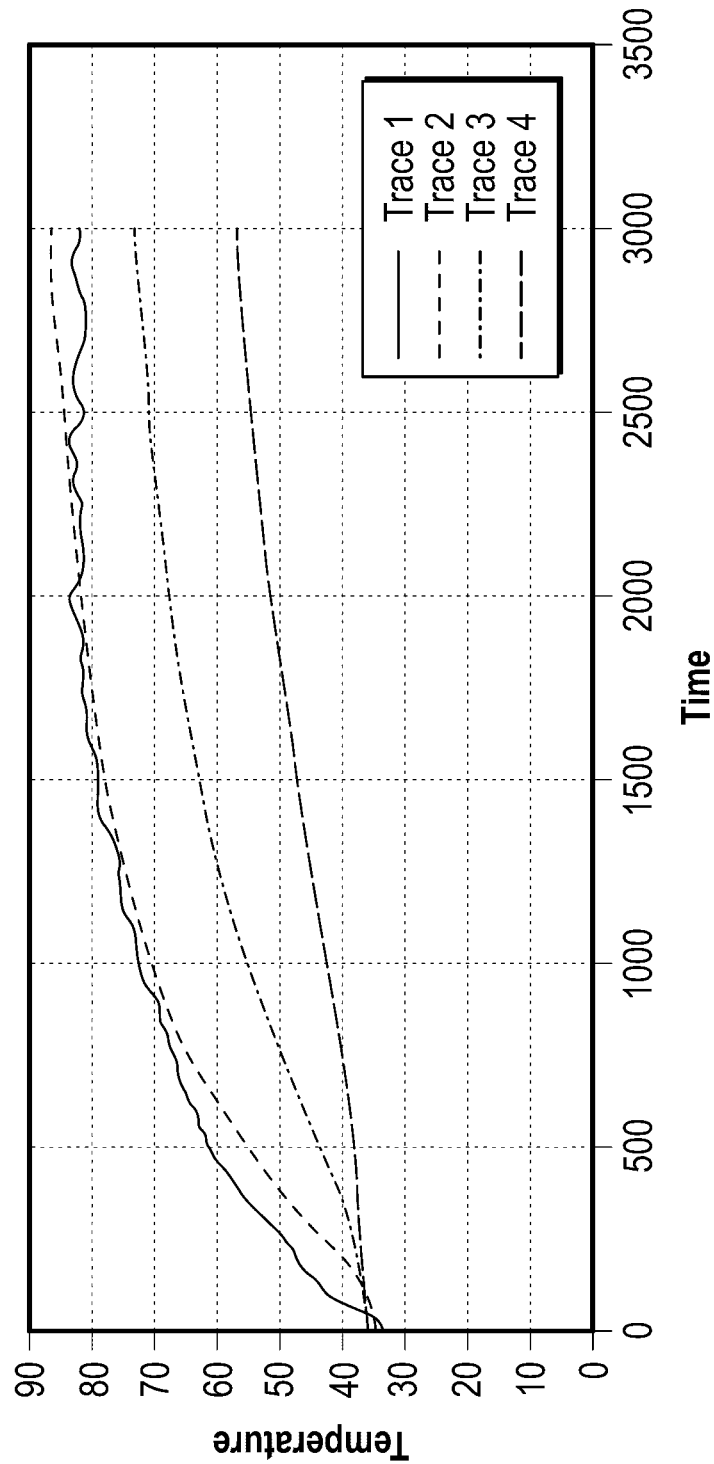
FIG. 22B is a plot showing an estimated peak temperature determined by an embodiment of an ablation catheter having multiple temperature-measurement devices compared against actual tissue measurements at various depths within a tissue.

FIG. 22A is a graph illustrating that temperature measurements obtained from the temperature-measurement devices may be used to determine a peak temperature by applying one or more analytical correction factors or functions to the temperature measurements (e.g., using numerical modeling approximations or look-up tables). As shown in FIG. 22A, a single correction factor or function (k) may be applied to each of the distal temperature-measurement devices to determine the peak temperature. In some embodiments, different correction factors or functions may be applied to each individual temperature-measurement device or to subsets of the groups of temperature-measurement devices depending on a determined orientation or on a comparison of the temperature measurements obtained by the temperature-measurement devices, thereby providing increased accuracy of peak temperature and peak temperature zone location. The increased accuracy of peak temperature and peak temperature zone location may advantageously result in safer and more reliable ablation procedures because the ablation parameters may be adjusted based on feedback received by the processing unit from the temperature-measurement devices. In accordance with several embodiments, peak temperatures at a depth beneath the tissue surface are accurately estimated without requiring microwave radiometry. With reference to FIG. 22A, the peak tissue temperature can be estimated as follows:

$$T_{peak}(t) = e^{(-t/\tau)} + k*(1-e^{(-t/\tau)})*\max(TCi(t));$$

where i spans the range of temperature-measurement devices, with max(TCi(t)) representing the maximum temperature reading of the temperature-measurement devices at time t. For example, FIG. 22B shows an implementation of the above formula. Trace 1 shows the estimated peak tissue temperature ($T_{peak}$) at a constant k value of 1.8 and a t value of 1, whereas Traces 2, 3 and 4 show the actual tissue temperatures measured at 1 mm, 3 mm and 5 mm, respectively, from the tissue surface using tissue-embedded infrared probes. As seen, the estimated peak tissue temperature ($T_{peak}$) of Trace 1 tracks well the actual peak tissue temperature measured at 1 mm depth (Trace 2).

In another embodiment, a predictive model-based approach utilizing the bioheat equation may be utilized to estimate peak tissue temperature. A recursive algorithm for determining the temperature T at a time point n, at a single point in a volume during treatment (e.g., RF ablation) may be defined as follows:

$$T_n = \frac{\frac{\rho \cdot C}{dt} \cdot T_{n-1} + W_e \cdot C \cdot T_a + P \cdot N}{\frac{\rho \cdot C}{dt} + W_e \cdot C}$$

where $T_n$ is the current temperature, $T_{n-1}$ is the previous temperature, t is time, p is the tissue density, C is the specific heat of tissue, $T_a$ is the core arterial temperature, $W_e$ is an effective perfusion rate, and P·N provides an estimate of the volumetric power deposited in tissue. The above equation can be formulated at various spatial locations, including the temperature-measurement device location(s) as well as the location of peak temperature (e.g., hot spot). By utilizing this model at different locations, along with calibration to determine the model parameters, mapping techniques can be utilized to predict the temperature at one spatial location using measurement data from the other spatial location.

In some embodiments, the processing device is configured to output the peak temperature or other output indicative of the peak temperature on a display (e.g., a graphical user interface). The output may comprise alphanumeric information (e.g., the temperature in degrees), one or more graphical images, and/or a color indication. In some embodiments, the processor may generate an output configured to terminate energy delivery if the determined peak temperature is above a threshold or maximum temperature. The output may comprise a signal configured to cause automatic termination of energy delivery or may comprise an alert (audible and/or visual) to cause a user to manually terminate energy delivery.

In various embodiments, ablation parameters may be adjusted based on temperature measurements received from the temperature-measurement devices. The ablation parameters may comprise, among other things, duration of ablation, power modulation, contact force, target or setpoint temperature, a maximum temperature. For example, the processor 46 (FIG. 1) may be configured to send control signals to the energy delivery module 40 based on the temperature measurements (and other measurements or estimations derived or otherwise determined therefrom) received from the plurality of distributed temperature-measurement devices.

In one embodiment, the energy delivery module 40 (FIG. 1) may be set to run in a temperature control mode, wherein radiofrequency energy of a certain power level is delivered and a maximum temperature is identified which cannot be exceeded. Each of the temperature-measurement devices may be monitored (either simultaneously or via toggled queries) on a periodic or continuous basis. If the maximum temperature is reached or exceeded, as determined by temperature measurements received from any of the temperature-measurement devices of the ablation catheters described herein, control signals may be sent to the energy delivery module to adjust ablation parameters (e.g., reduction in power level) to reduce the temperature or to terminate energy delivery (temporarily or otherwise) until the temperature is reduced below the maximum temperature. The adjustments may be effected for example by a proportional-integral-derivative controller (PID controller) of the energy delivery module 40. In another embodiment, the energy delivery module 40 may be set to run in a power control mode, in which a certain level of power is applied continuously and the temperature measurements received from each of the temperature-measurement devices are monitored to make sure a maximum temperature is not exceeded. In some embodiments, a temperature-controlled mode comprises specifying a setpoint temperature (e.g., 70 degrees Celsius, 75 degrees Celsius, 80 degrees Celsius, and then adjusting power or other parameters to maintain temperature at, below or near the setpoint temperature, as determined from the temperature measurements received from each of the temperature-measurement devices. As the tip electrode moves with respect to tissue and different temperature-measurement devices come in greater or lesser contact with tissue, a processor or processing device of the energy delivery module may automatically select whichever temperature-measurement device is reading the highest temperature to control the power delivery.

Table 1 below shows examples of ablation parameters used in various test ablation procedures using an embodiment of an ablation catheter described herein.

TABLE 1

| Orientation | Blood flow (cm/s) | Irrigation (ml/min) | Power (W) | Max Tissue Temp (° C.) | Lesion width (mm) | Lesion depth (mm) | Impedance (Ohms) |
|---|---|---|---|---|---|---|---|
| Parallel | 0.5 | 15 | 13.3 | 91.7 | 9.8 | 5.2 | 85 |
| Parallel | 25 | 15 | 15.8 | 94.9 | 9.2 | 5.4 | 85 |
| Parallel | 0.5 | 0 | 8.6 | 98.8 | 11.2 | 4.7 | 85 |
| Parallel | 25 | 0 | 14.9 | 94.8 | 10.0 | 5.3 | 85 |
| Perpend. | 0.5 | 15 | 16.8 | 99.4 | 11 | 5.6 | 83 |
| Perpend. | 25 | 15 | 18.1 | 99.9 | 10.3 | 5.8 | 83 |
| Perpend. | 0.5 | 0 | 10.4 | 97.9 | 10.3 | 4.8 | 83 |
| Perpend. | 25 | 0 | 16.9 | 95.7 | 9.3 | 5.3 | 83 |

As can be seen from the data in Table 1, the maximum tissue temperature and lesion sizes remained relatively constant with or without irrigation and/or with or without significant blood flow by modulating the power. The multivariant or multiple temperature-measurement device system according to embodiments of this invention ensures appropriate tissue ablation under different electrode-tissue orientations. As explained above, the electrode-tissue orientation can be determined based on readings from the multiple distributed temperature-measurement devices. If both proximal and distal temperatures become dominant, then the electrode orientation may be estimated or indicated to be parallel to tissue. Similarly, when the distal temperatures are dominant, then the electrode orientation may be inferred, estimated and/or indicated to be perpendicular to tissue. Combinations of proximal and distal dominant temperatures may provide indications for oblique electrode orientations. FIG. 23A illustrates a plot of temperature data from the multiple temperature-measurement devices (e.g., thermocouples) that are indicative of a perpendicular orientation and FIG. 23B illustrates a plot of temperature data from the multiple temperature-measurement devices (e.g., thermocouples) that are indicative of an oblique orientation.

In accordance with several embodiments, a treatment system comprises a medical instrument (e.g., an ablation catheter), at least one processor, and an energy source (e.g., an ablation source such as a radiofrequency generator). The medical instrument comprises or consists essentially of an elongate body having a proximal end and a distal end, an energy delivery member (e.g., a high-resolution combination electrode assembly comprised of a proximal electrode portion and a distal electrode portion spaced apart from the proximal electrode portion) positioned along the distal end of the elongate body, and a plurality of distributed temperature-measurement devices (e.g., thermocouples or other temperature sensors) carried by or positioned along or within the elongate body or a portion of the energy delivery member. In some embodiments, the distributed temperature-measurement devices comprise a distal plurality of temperature-measurement devices positioned at the distal end of the elongate body (e.g., along a distal surface of the energy delivery member) and a proximal plurality of temperature-measurement devices positioned along the elongate body and spaced apart proximally of the distal plurality of temperature-measurement devices, as described and illustrated in connection with certain embodiments of the ablation catheters herein. In one embodiment, the proximal plurality of temperature-measurement devices consists of three co-planar temperature-measurement devices spaced equally apart around a circumference of the elongate body and the distal plurality of temperature-measurement devices consists of three co-planar temperature-measurement devices spaced apart symmetrically or equally around a central longitudinal axis extending through the distal end of the elongate body. The energy delivery member may be configured to contact tissue of a subject and to deliver energy generated by the energy source to the tissue. In some embodiments, the energy is sufficient to at least partially ablate the tissue. The energy source of the embodiment of the system may be configured to provide the energy to the energy delivery member through one or more conductors (e.g., wires, cables, etc.) extending from the energy source to the energy delivery member. In several embodiments, the energy is radiofrequency energy.

The at least one processor of the embodiment of the treatment system (e.g., ablation system) may be programmed or otherwise configured (e.g., by execution of instructions stored on a non-transitory computer-readable storage medium) to receive signals from each of the temperature-measurement devices indicative of temperature and determine an orientation, or alignment, of the distal end of the elongate body (e.g., electrode-tissue orientation) of the ablation catheter with respect to the tissue (e.g., orientation, or alignment, of the outer distal surface of the electrode or other energy delivery member with a target surface) based on the received signals. In accordance with several embodiments, multiple separate processing devices are used in parallel to simultaneously perform portions of the processes described herein so as to increase processing speeds. Each of the separate processing devices may be controlled by a main processing device or control unit that receives output from each of the separate processing devices.

In accordance with several embodiments, determination of orientation at neighboring treatment sites facilitates increased likelihood or confirmation of treatment efficacy (e.g., continuous lesion formation without gaps). For example, if it is determined that the ablation catheter was in a perpendicular orientation at two adjacent ablation sites, there may be an increased probability that the lesion profiles do not overlap and the clinical professional may decide to perform another ablation between the two adjacent ablation sites to increase the likelihood of continuous lesion formation without gaps. In accordance with several embodiments, determination of orientation is performed during delivery of energy (e.g., radiofrequency energy). In instances where determination of orientation is performed during energy delivery, it can be particularly advantageous to determine orientation early on in the energy delivery process (e.g., within a few seconds after initiation of energy delivery) so as to provide increased confidence that a particular lesion profile or pattern (e.g., volume, shape or zone) was formed by the energy delivery. For example, parallel orientations may form shallower but longer or wider lesion profiles, perpendicular orientations may form deeper but narrower lesion profiles and oblique orientations may form lesion profiles somewhere in between the parallel and perpendicular orientations. In some embodiments, a particular orientation may be targeted by a clinical professional and the orientation determination can confirm to the clinical professional that the targeted orientation has been achieved. In some instances, a clinical professional may decide to terminate energy delivery if the targeted orientation is not achieved, to adjust parameters of the energy delivery based on the determined orientation, or to perform an additional treatment at a treatment site close to the current treatment site to increase the likelihood of continuous lesion formation without gaps.

FIG. 23C illustrates an embodiment of a process 23000 for determining orientation of a distal end of a medical instrument (e.g., ablation catheter) with respect to target tissue (e.g., vessel surface or cardiac tissue surface) while energy (e.g., radiofrequency energy) is being applied to the target tissue by the medical instrument. The process 23000 may be executed by one or more processors communicatively coupled with the medical instrument (e.g., via wires or cables or via wireless communication such as via Bluetooth or a wireless network) upon execution of instructions stored on one or more computer-readable media (e.g., non-transitory, non-volatile memory or storage devices). The process 23000 may advantageously result in orientation, or alignment, determination in a very short amount of time following initiation of treatment (e.g., within less than fifteen seconds, within less than ten seconds, within less than eight seconds, within less than five seconds, within less than three seconds, within less than two seconds following initiation of energy delivery, in the first 40% of total treatment duration, in the first 30% of total treatment duration, in the first 25% of total treatment duration, in the first 20% of total treatment duration, in the first 15% of total treatment duration, in the first 10% of total treatment duration, in the first 5% of total treatment duration). Treatment times (e.g., ablation durations) may be very short (e.g., less than 30 seconds); accordingly, if orientation determination is not made quickly, the orientation determination may not be performed until the treatment is either over or substantially complete and the determined orientation at that time may not accurately reflect the orientation during the majority of the treatment because the orientation of the ablation catheter or other medical instrument may change during the treatment (e.g., due to movement of tissue caused by contraction and relaxation of muscle tissue, patient or operator movement, and/or respiration).

The process 23000 begins upon initiation of treatment (e.g., ablative energy delivery) and includes three phases: an initial phase, a temperature rise phase, and a steady state phase. In the initial phase, the at least one processor obtains temperature measurements from a plurality of temperature-measurement devices distributed along the length of an elongate body of the medical instrument for a first time period (Block 23005). Obtaining the temperature measurements may comprise receiving signals indicative of temperature and determining temperature measurement values based on the received signals (which may be performed, for example, by a temperature processing module executed by the at least one processor, such as described above). The first time period can start upon initiation of treatment (e.g., energy delivery) by the medical instrument and may continue for a first time duration (e.g., between 1 and 5 seconds, between 1 and 2 seconds, between 1 and 3 seconds, between 2 and 4 seconds, between 3 and 5 seconds, 1 second, 1.5 seconds, 2 seconds, 2.5 seconds, 3 seconds, 3.5 seconds, 4 seconds, 4.5 seconds, 5 seconds, overlapping ranges thereof or any value within the ranges). In some embodiments, the temperature measurements are obtained at a plurality of time points, or measurement points (e.g., at regular intervals within the first time duration of the initial phase or at multiple irregular intervals or non-periodic points of time within the first time duration of the initial phase). The first time duration may be varied as desired and/or required for optimization. Measurements can be obtained and recorded at any desired frequency (e.g., every 1 ms, every 5 ms, every 10 ms, every 50 ms, or every 100 ms). At Block 23010, a starting temperature is determined for each temperature-measurement device (e.g., thermocouple or thermistor) based on the temperature measurements obtained during the first time period. Each temperature-measurement device may be associated with a channel that can be tracked and plotted (and output on a display for viewing). In some embodiments, the starting temperature is determined by averaging the temperature measurements obtained during the first time period. Any of the configurations or arrangements of the temperature-measurement devices described herein may be used. For example, the temperature-measurement devices may include a distal plurality of temperature-measurement devices and a proximal plurality of temperature-measurement devices spaced proximal to the distal plurality of temperature-measurement devices as discussed herein.

After determining a starting temperature, the process 23000 proceeds to the temperature rise phase. The temperature rise phase corresponds to the time during which the temperature measurements are increasing as a result of tissue heating caused by the application of energy (e.g., RF energy) to the tissue. In the temperature rise phase, temperature measurements are continuously obtained from each of the temperature-measurement devices and recorded (Block 23015). Obtaining the temperature measurements may comprise receiving signals indicative of temperature and determining temperature measurement values based on the received signals. Again, the frequency of the temperature measurements may vary as desired and/or required for optimization. In some embodiments, the temperature measurements are obtained at a plurality of time points, or measurement points (e.g., at regular intervals within a time period of the temperature rise phase or at multiple irregular intervals or non-periodic points of time within the time period of the temperature rise phase). For example, temperature measurements may be obtained every 0.1 seconds, every 0.5 seconds, every second, etc. The temperature rise phase may continue for a second time period (e.g., from one second to thirty seconds after initiation of energy delivery, from one second to twenty seconds after initiation of energy delivery, from one second to eighteen seconds after initiation of energy delivery, from five seconds to eighteen seconds after initiation of energy delivery, from three seconds to thirteen seconds after initiation of energy delivery, from five seconds to ten seconds after initiation of energy delivery, overlapping ranges thereof or any value within the ranges).

At every measurement point in time during the temperature rise phase, a characteristic of a temperature response is determined (e.g., computed or calculated by the at least one processor or computing device) for each temperature-measurement device (or each channel associated with a respective temperature-measurement device) based on the obtained temperature measurements (Block 23020). In some embodiments, the characteristic is a rate of change of temperature (e.g., how fast temperature measurement values obtained by the temperature-measurement devices increase over time). As another example, the characteristic may be a temperature rise value that is computed for each temperature-measurement device (or each channel associated with a respective temperature-measurement device) by subtracting the starting temperature value from a current temperature value (for example, Tn–Ts). In some embodiments, a moving average is applied over time to remove "noise" or fluctuations in temperature measurement values and the starting temperature value is subtracted from the moving average to determine the temperature rise value. The moving average window may nominally be 1 second, but may be varied to address variation in the temperature-measurement response such as cardiac and respiratory artifacts (e.g., 0.1 seconds, 0.5 seconds, 1 second, 1.5 seconds, 2 seconds, 2.5 seconds, 3 seconds, 3.5 seconds, 4 seconds, 4.5 seconds, 5 seconds, or any value between 0.1 seconds and 5 seconds). A rate of change may be determined by dividing the temperature rise value by the time duration between the current time and the start time. For example, at second n there is a measured temperature value Tn between second n−1 and second n. The starting temperature value may be subtracted from Tn and then divided by n to get the rate of change at second n.

At Block 23025, the one or more processing devices (e.g., upon execution of a temperature processing module) determine an orientation, or alignment, of the distal end of the medical instrument based on one or more orientation criteria (e.g., thresholds, tests or conditions) that rely on the determined characteristic for at least two of the temperature-measurement devices. The orientation determination may be performed at each measurement point, or point in time in which a measurement is obtained or determined, thereby advantageously indicating if the orientation changes during the treatment procedure (e.g., as a result of patient or operator movement or other perturbations). The determination of the orientation may include performing different comparisons between the characteristics of the temperature responses (e.g., temperature rise values or rates of change) between two or more of the temperature-measurement devices. For example, comparisons may be performed at each of the time points, or measurement points, between the characteristics of the proximal temperature-measurement devices and the distal temperature-measurement devices (such as average of the temperature rise values or rates of change of the proximal temperature-measurement devices compared with the average of the temperature rise values or rates of change of the distal temperature-measurement devices, or the minimum of the temperature rise values or rates of change of the distal temperature-measurement devices compared with the maximum of the temperature rise values or rates of change of the proximal temperature-measurement devices, or the maximum of the temperature rise values or rates of change of the distal temperature-measurement devices compared with the minimum of the temperature rise values or rates of change of the proximal temperature-measurement devices). As one example, if the average proximal temperature rise or rate of change is greater than the average distal temperature rise or rate of change by a certain factor N, where N can be any real number, the one or more processing devices may determine that the orientation is oblique. In accordance with several embodiments, by determining orientation based on comparisons of characteristics of a temperature response (e.g. rate of change or rise value or rise time comparisons) instead of on comparisons of temperature measurement values themselves or the spread of the temperature-measurement values once they have reached a steady state, accurate determinations of orientation can be made much more quickly after initiation of energy delivery.

The orientation criteria may be determined based on empirical data and may be stored in a look-up table or in memory. In some embodiments, the orientation criteria include time-dependent thresholds in addition to or instead of static thresholds or conditions. For example, the maximum proximal temperature rise or rate of change can be subtracted from the minimum distal temperature rise or rate of change and this value can be compared to a time-dependent threshold as follows: $DRmin-PRmax <= A*(t-B)+C$, where DRmin is the smallest temperature rise value of the distal temperature-measurement devices and PRmax is the largest temperature rise value of the proximal temperature-measurement devices and A, B and C are constants determined by empirical data and define how the threshold changes as a function of time. The orientation criteria for a respective orientation option may include multiple criteria of which one, some or all must be satisfied for that orientation option to be selected. Multiple criteria may be used to account for different alignments or orientations caused by anatomical variations in the temperature rise phase. For example, for an oblique orientation it may be possible in one instance that a distal electrode member (or one or more temperature-measurement devices along the distal electrode member) of the electrode is in contact with tissue while a proximal electrode member (or one or more temperature-measurement devices spaced proximal to the distal electrode member) is not in contact with tissue whereas in another instance the distal electrode member (or one or more temperature-measurement devices along the distal electrode member) is not in contact with tissue while a proximal electrode member (or one or more temperature-measurement devices spaced proximal to the distal electrode member) is in contact with tissue. Both of these instances (which may be caused by anatomical variations) may have quite different temperature response characteristics but should both be determined to be oblique orientations in accordance with several embodiments. In addition, in a parallel orientation, it is possible that only one proximal temperature-measurement device is in contact with tissue (and therefore generating higher temperature measurements) while two distal temperature-measurement devices are in contact with tissue (and therefore generating higher temperature measurements). If only average value comparisons are made, an improper orientation may be determined by the at least one processing device. Accordingly, different orientation criteria may be needed to account for the variance in possible orientations (and accordingly variance in temperature response characteristics) for a single orientation option.

The orientation may be determined from one of two possible orientation options (e.g., parallel or perpendicular) or one of three orientation options (e.g., oblique, parallel or perpendicular). The definition of oblique, parallel and perpendicular may be adjusted as desired and/or required for usability and/or performance factors. In accordance with several embodiments involving three orientation options, a parallel orientation may be considered to be from 0 to 20 degrees (or 160 to 180 degrees), an oblique orientation may be considered to be from 20 degrees to 80 degrees (or 120 to 160 degrees) and a perpendicular orientation may be considered to be from 80 to 120 degrees (assuming a 0 or 180 degree rotation (between the medical instrument and tissue) to be perfectly parallel and a 90 degree rotation to be perfectly perpendicular). In embodiments involving three orientation options, the determination of orientation proceeds with first determining whether one or more orientation criteria of a first orientation are satisfied. If the one or more orientation criteria for the first orientation are satisfied, the one or more processing devices optionally generate an output indicative of the first orientation at Block 23030. If the one or more orientation criteria of the first orientation are not met, then the one or more processing devices determine whether one or more orientation criteria of a second orientation are met. If the one or more orientation criteria for the second orientation are satisfied, the one or more processing devices optionally generate an output indicative of the second orientation at Block 23030. If the one or more orientation criteria of the second orientation are not met, then the one or more processing devices determining that the orientation must be the third orientation by default since there are only three orientation options and the one or more processing devices optionally generate an output indicative of the third orientation at Block 23030. If only two orientation options are available, if the criteria associated with the first orientation are not satisfied, then the second orientation is selected by default. The orientation criteria may vary depending on the order in which the orientation options are tested. If multiple criteria are associated with a particular orientation being tested, the tests may be performed in parallel by separate processors to speed up the orientation determination process 23000.

As one example, the process 23000 may first test for an oblique orientation in the temperature rise phase. The oblique orientation criteria may include tests that involve comparing the average temperature rise or rate of temperature change of distal temperature-measurement devices and the proximal temperature devices (e.g., that the proximal average temperature rise or rate of temperature change is greater than or equal to the distal average temperature rise or rate of temperature change by a predetermined factor) and/or comparing the minimum temperature rise or rate of temperature change of the distal temperature-measurement devices with the maximum temperature rise or rate of temperature change of the proximal temperature-measurement devices (e.g., that the difference is less than or equal to a predetermined amount, which may be determined using a time-dependent equation, such as $A^*(t-B)+C$, where A, B and C are constants and t is time in seconds). If the oblique orientation criteria (which may be one criterion or a combination of multiple criteria) are satisfied, then an oblique orientation is determined. Otherwise, the process 23000 may proceed to test for a parallel orientation. The parallel orientation criteria may include tests that involve comparing the average temperature rise or rate of temperature change of distal temperature-measurement devices and the proximal temperature devices (e.g., that the absolute value of the difference between the two averages divided by the proximal average temperature rise or rate of temperature change is less than or equal to a predetermined amount) and/or comparing a maximum temperature rise or rate of temperature change of the distal and proximal temperature-measurement devices (e.g., that the difference between the maximum values is less than or equal to a predetermined amount, which may be determined using a time-dependent equation, such as $A^*(t-B)+C$, where A, B and C are constants and t is time in seconds). If the parallel orientation criteria (which may be one criterion or a combination of multiple criteria) are satisfied, then a parallel orientation is determined. Otherwise, the process 23000 may determine that the orientation is perpendicular.

After the second period of time has elapsed, the process 23000 proceeds to a steady state phase, corresponding to a third time period in which the temperature measurement values (or the profiles of the channels plotted on a graph) have reached a steady state such that the temperature measurement values (e.g., peak temperature measurement values) do not change or fluctuate by a significant amount (e.g., less than 20%, less than 15%, less than 10%, less than 5%, less than 4%, less than 3%, less than 2%) between measurement points, or points in time in which measurement values are obtained. In accordance with several embodiments, because the temperature measurement values are not normally changing significantly in the steady state phase, orientation, or alignment, determinations do not need to be made based on time-dependent conditions or on characteristics of temperature response such as rate of change or temperature rise values. Accordingly, in the steady state phase, the orientation determinations are made using a different set of orientation criteria than the orientation criteria used in the temperature rise phase. While the temperature measurement values are nominally not changing significantly, the orientation determinations in the steady state phase may be designed to react to deviations and changes in temperature due to, for example, patient or operator movement or other perturbations. Again, the orientation criteria for the steady state phase are different for each orientation option and may vary depending on the order in which the orientation options are tested.

At Block 23035, temperature measurements (e.g., values) are continuously obtained at periodic intervals (e.g., plurality of time points, or measurement points) from each of the distributed temperature-measurement devices during the third time period. Similar to the temperature rise phase, a moving average may be applied to each of the temperature-measurement device channels; however, the averaging window may be different for the steady-state phase as a result of the deviation or fluctuation in temperature measurement values being low in the steady-state phase. For example, the averaging window may be longer in the steady-state phase than in the temperature rise phase. The averaging window may nominally be 5 seconds, but may be varied depending on the type of instrument utilized and the therapy being provided (e.g., any value between 0.5 and 10 seconds, such as 0.5 seconds, 1 second, 1.5 seconds, 2 seconds, 2.5 seconds, 3 seconds, 3.5 seconds, 4 seconds, 4.5 seconds, 5 seconds, 5.5 seconds, 6 seconds, 6.5 seconds, 7 seconds, 7.5 seconds, 8 seconds, 8.5 seconds, 9 seconds, 9.5 seconds, 10 seconds). Orientation of the distal end of the medical instrument (e.g., electrode tissue orientation) is continuously determined at each measurement point during the third time period based on the steady-state phase orientation criteria, which are different than the temperature rise phase orientation criteria (Block 23040). By continuously determining orientation at each time measurement point, a more accurate estimation of the lesion profile formed by the treatment at that particular target site may be obtained and further treatment may be adjusted accordingly, if desired or required. In accordance with several embodiments, the orientation criteria in the steady state phase only comprise static thresholds or conditions and not time-dependent thresholds or conditions. For example, the orientation criteria may compare one or more of: a maximum of the temperature values of the distal temperature-measurement devices or channels with the maximum of the temperature values of the proximal temperature-measurement devices or channels, a minimum of the temperature values of the distal temperature-measurement-devices or channels with the maximum of the temperature values of the proximal temperature-measurement devices or channels or a maximum of the temperature values of the distal temperature-measurement devices or channels with the minimum of the distal temperature values of the proximal temperature-measurement devices or channels.

The orientation criteria for the steady state phase may be based on empirical data and stored in a look-up table or memory. The orientation criteria for a respective orientation option in the steady state phase may include multiple criteria of which one, some or all must be satisfied for that orientation option to be selected. As for the temperature rise phase, multiple criteria may be used to account for different alignments or orientations caused by anatomical variations in the steady state phase. For example, for an oblique orientation it may be possible in one instance that a distal electrode member (or one or more temperature-measurement devices along the distal electrode member) of the electrode is in contact with tissue while a proximal electrode member (or one or more temperature-measurement devices spaced proximal to the distal electrode member) is not in contact with tissue whereas in another instance the distal electrode member (or one or more temperature-measurement devices along the distal electrode member) is not in contact with tissue while a proximal electrode member (or one or more temperature-measurement devices spaced proximal to the distal electrode member) is in contact with tissue. Both of these instances (which may be caused by anatomical variations) may have quite different temperature-measurement values or temperature response characteristics but should both be determined to be oblique orientations in the steady state phase in accordance with several embodiments. Accordingly, different orientation criteria may be needed to account for the variance in possible orientations (and accordingly variance in temperature measurement values or temperature response characteristics) for a single orientation option.

Similar to the temperature rise phase, the determination of orientation in the steady state phase can proceed with first determining whether orientation criteria of a first orientation are met. If the criteria for the first orientation are not met, then the process proceeds with determining whether criteria of a second orientation are met. If the criteria are not met for the second orientation, then the process may determine that the orientation is the third orientation. At Block 23045, the one or more processing devices optionally generate an output indicative of the determined orientation. The steady state phase continues until the application of energy is terminated. In other embodiments, the temperature measurements obtained in the steady state phase may not be obtained at periodic intervals. In some embodiments, the process 23000 does not include the steady state phase and the process 23000 ends before Block 23035.

As one example of an orientation determination operation at Block 23040, the first orientation to be tested in the steady state phase is the oblique orientation. The oblique orientation may include one or more of the following: comparing the average temperature measurement values of the distal temperature-measurement devices and the proximal temperature devices (e.g., that the difference is less than a predetermined amount), comparing the maximum distal temperature measurement value and the maximum proximal temperature measurement value (e.g., the difference is less than a predetermined amount), comparing the minimum temperature measurement value of the distal temperature-measurement devices and the maximum temperature measurement value of the proximal temperature devices, comparing the middle temperature measurement value of the distal temperature-measurement devices and the maximum temperature measurement value of the proximal temperature devices, comparing the minimum temperature measurement value of the proximal temperature-measurement devices and the maximum temperature measurement value of the distal temperature devices, and comparing the middle (or median) temperature measurement value of the proximal temperature-measurement devices and the maximum temperature measurement value of the distal temperature devices. One, some or all of the criterial may need to be satisfied to have the oblique orientation be determined as the current orientation. If the oblique orientation criteria (which may be one criterion or a combination of multiple criteria) are satisfied, then an oblique orientation is determined. Otherwise, the process 23000 may proceed to test for a parallel orientation. The parallel orientation criteria may include tests that involve comparing the average temperature measurement value of the distal temperature-measurement devices and the proximal temperature devices (e.g., that the difference between the two averages is within a predetermined range) and/or comparing a maximum temperature measurement value of the distal and proximal temperature-measurement devices (e.g., that the difference between the maximum values is within a predetermined range). If the parallel orientation criteria (which may be one criterion or a combination of multiple criteria) are satisfied, then a parallel orientation is determined. Otherwise, the process 23000 may determine that the orientation is perpendicular.

Another example of an orientation determination operation at Block 23040, the process 23000 may first test for a perpendicular orientation in the steady state phase. The perpendicular orientation criteria may include tests that involve any one or more of the following: comparing the maximum temperature measurement values of the distal temperature-measurement devices and the proximal temperature devices (e.g., that the maximum distal temperature measurement value is greater than the maximum proximal temperature measurement value by a predetermined temperature value), comparing the minimum temperature measurement value of the distal temperature-measurement devices with the maximum temperature measurement value of the proximal temperature-measurement devices (e.g., that the difference is greater than a predetermined temperature value), comparing the maximum and median temperature values of the distal temperature-measurement devices with the maximum and minimum temperature measurement values of the distal temperature-measurement devices (e.g., determining that the difference between the maximum and middle temperature measurement values of the distal temperature-measurement devices is less than the difference between the maximum and minimum temperature measurement values of the distal temperature-measurement devices by a predetermined amount), or comparing the maximum and minimum temperature measurement values of the distal temperature-measurement devices with the maximum temperature measurement values of the distal and proximal temperature-measurement devices (e.g., that the difference between the maximum and minimum temperature measurement values of the distal temperature-measurement devices is less than the difference between the maximum temperature measurement values of the distal and proximal temperature-measurement devices). If the perpendicular orientation criteria (which may be one criterion or a combination of multiple criteria) are satisfied, then a perpendicular orientation is determined. Otherwise, the process 23000 may proceed to test for a parallel orientation. The parallel orientation criteria may include tests that involve determining whether the difference between the maximum temperature measurement values of the distal and proximal temperature-measurement devices is within a predetermined range and/or whether the difference between the average measurement values of the distal and proximal temperature-measurement devices is within a predetermined range. If the parallel orientation criteria (which may be one criterion or a combination of multiple criteria) are satisfied, then a parallel orientation is determined. Otherwise, the process 23000 may determine that the orientation is oblique.

FIGS. 23D and 23E illustrate two example embodiments of processes 23050, 23075 for determining an orientation of a distal end of a medical instrument with respect to a target region (e.g., cardiac tissue or a vessel wall). Each of the processes 23050, 23075 starts with determining or specifying orientation criteria (e.g., thresholds or conditions for at least two of the orientation options (Blocks 23055, 23080). As discussed previously, the orientation criteria may include static and/or time dependent thresholds or conditions. The orientation criteria may have been stored in memory or a look-up table prior to initiation of the process and simply accessed or may be determined in real-time. The processes 23050, 23075 may be performed in either the temperature rise phase or the steady state phase.

Process 23050 starts with determining whether one or more orientation criteria for the oblique orientation are satisfied. The criteria may include one criterion or multiple criteria. If multiple criteria, either one or all of the criteria may need to be satisfied. If the criteria for the oblique orientation are satisfied, then an output indicative of an oblique orientation is generated at Block 23060. If the criteria for the oblique orientation are not satisfied, then the process 23050 proceeds to determine whether one or more orientation criteria for the parallel orientation are satisfied. If the criteria for the parallel orientation are satisfied, then an output indicative of a parallel orientation is generated at Block 23065. If the criteria for the parallel orientation are not satisfied, then an output indicative of a perpendicular orientation is generated at Block 23070 by default. The process 23075 is similar to process 23050 except that the order of orientations is changed such that a test is first performed for the perpendicular orientation (with an output being generated at Block 23085 indicative of a perpendicular orientation if the respective orientation criteria are satisfied) instead of for the oblique orientation and the default orientation is the oblique orientation instead of the perpendicular orientation (with an output being generated at Block 23095 indicative of an oblique orientation if the orientation criteria for the perpendicular and parallel orientations are not satisfied). As with process 23050, an output indicative of a parallel orientation is generated at Block 23090 if the orientation criteria for a parallel orientation are satisfied. The orientations may be tested in any order. For example, a parallel orientation may be tested for first instead of an oblique orientation or perpendicular orientation as shown in FIGS. 23D and 23E, respectively. In accordance with several embodiments, an oblique orientation is tested first because it is the most likely orientation and therefore testing for the oblique orientation first may reduce determination time.

In some embodiments, the processor is configured to cause the output indicative of a particular orientation that is generated by the processes 23050 and 23075 to a display. The output may comprise textual information (such as a word, phrase, letter or number). In some embodiments, the display comprises a graphical user interface and the output comprises one or more graphical images indicative of the determined orientation. The orientation determination processes are performed at each time point or measurement point and the output is continuously updated based on the current orientation determination, thereby advantageously indicating if an orientation is changed during a treatment procedure, which may indicate a possible deviation from an expected lesion profile.

FIGS. 23F-1, 23F-2 and 23F-3 illustrate various embodiments of output on a graphical user interface (for example, of a display on a radiofrequency generator or a computing device communicatively coupled to the one or more processors of the energy delivery system). As illustrated, the output may include three radio buttons 23105, each having a label 23110 identifying one of the orientation options (e.g., perpendicular, oblique and parallel). In some embodiments, the radio button corresponding to the determined orientation may be marked or differentiated from the other radio buttons (e.g., have a lit up appearance as illustrated by the rays emanating from one of the radio buttons in FIG. 23F). The marking may comprise a filling in of the respective radio button, highlighting of the respective radio button or changing of a color of the respective radio button. In one embodiment, the radio buttons may appear as LEDs and the LED corresponding to the determined orientation may be changed to a green color or otherwise "lit up" to signal the determined orientation. The output may also include a graphical image 23115 of an electrode icon or the distal end of the medical instrument in the determined orientation. As shown, the output may also include a graphical image of an arrow oriented according to the determined orientation. FIG. 23F-1 illustrates an example output when a parallel orientation is determined, FIG. 23F-2 illustrates an example output when an oblique orientation is determined and FIG. 23F-3 illustrates an example output when a perpendicular orientation is determined. The radio buttons may be replaced with checkboxes or other visual indicators.

Contact Sensing

According to some embodiments, various implementations of electrodes (e.g., radiofrequency or RF electrodes) that can be used for high-resolution mapping and radiofrequency ablation are disclosed herein. For example, as discussed in greater detail herein, an ablation or other energy delivery system can comprise a high-resolution, or combination electrode, design, wherein the energy delivery member (e.g., radiofrequency electrode, laser electrode, microwave transmitting electrode) comprises two or more separate electrodes or electrode members or portions. As also discussed herein, in some embodiments, such separate electrodes or electrode portions can be advantageously electrically coupled to each other (e.g., to collectively create the desired heating or ablation of targeted tissue). In various embodiments, the combination electrode, or composite (e.g., split-tip), design may be leveraged to determine whether or not one or more portions of the electrodes or other energy delivery members are in contact with tissue (e.g., endocardial tissue) and/or whether or not contacted tissue has been ablated (e.g., to determine whether the tissue is viable or not).

Several embodiments of the invention are particularly advantageous because they include one, several or all of the following benefits: (i) confirmation of actual tissue contact that is easily ascertainable; (ii) confirmation of contact with ablated vs. unablated (viable) tissue that is easily ascertainable; (iii) low cost, as the invention does not require any specialized sensor; (iv) does not require use of radiometry; (v) provides multiple forms of output or feedback to a user; (vi) provides output to a user without requiring the user to be watching a display; and/or (vii) provides safer and more reliable ablation procedures.

With reference to FIG. 1, according to some embodiments, the delivery module 40 includes a processor 46 (e.g., a processing or control device) that is configured to regulate one or more aspects of the treatment system 10. The delivery module 40 can also comprise a memory unit or other storage device 48 (e.g., non-transitory computer readable medium) that can be used to store operational parameters and/or other data related to the operation of the system 10. In some embodiments, the processor 46 comprises or is in communication with a contact sensing and/or a tissue type detection module or subsystem. The contact sensing subsystem or module may be configured to determine whether or not the energy delivery member(s) 30 of the medical instrument 20 are in contact with tissue (e.g., contact sufficient to provide effective energy delivery). The tissue type detection module or subsystem may be configured to determine whether the tissue in contact with the one or more energy delivery member(s) 30 has been ablated or otherwise treated. In some embodiments, the system 10 comprises a contact sensing subsystem 50. The contact sensing subsystem 50 may be communicatively coupled to the processor 46 and/or comprises a separate controller or processor and memory or other storage media. The contact sensing subsystem 50 may perform both contact sensing and tissue type determination functions. The contact sensing subsystem 50 may be a discrete, standalone sub-component of the system (as shown schematically in FIG. 1) or may be integrated into the energy delivery module 40 or the medical instrument 20. Additional details regarding a contact sensing subsystem are provided below.

In some embodiments, the processor 46 is configured to automatically regulate the delivery of energy from the energy generation device 42 to the energy delivery member 30 of the medical instrument 20 based on one or more operational schemes. For example, energy provided to the energy delivery member 30 (and thus, the amount of heat transferred to or from the targeted tissue) can be regulated based on, among other things, the detected temperature of the tissue being treated, whether the tissue is determined to have been ablated, or whether the energy delivery member 30 is determined to be in contact (e.g., "sufficient" contact, or contact above a threshold level) with the tissue to be treated.

Figure 24:
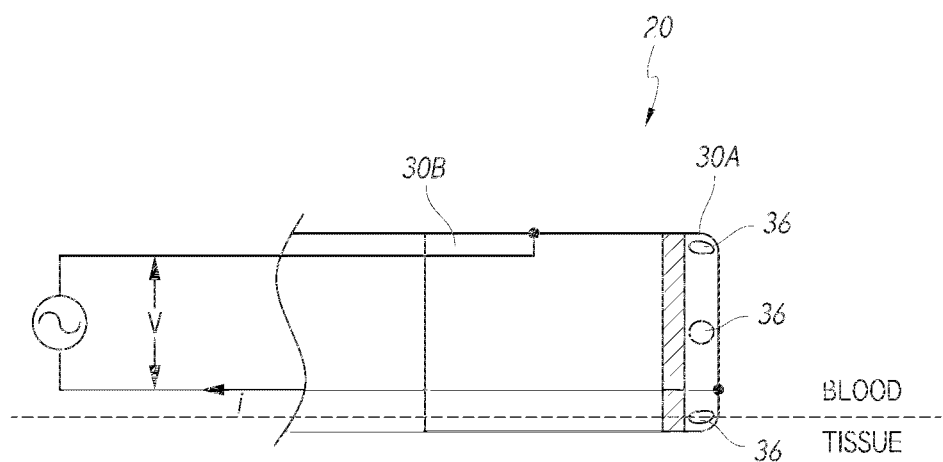
FIG. 24 schematically illustrates one embodiment of variable frequency being applied to the high-resolution tip, or composite, electrode design of FIG. 2 to determine whether the tip electrode is in contact with tissue.

With reference to FIG. 24, the distal electrode 30A may be energized using one or more conductors (e.g., wires, cables, etc.). For example, in some arrangements, the exterior of an irrigation tube comprises and/or is otherwise coated with one or more electrically conductive materials (e.g., copper, other metal, etc.). Thus, the one or more conductors can be placed in contact with such a conductive surface or portion of the irrigation tube to electrically couple the electrode or electrode portion 30A to an energy delivery module (e.g., energy delivery module 40 of FIG. 1). However, one or more other devices and/or methods of placing the electrode or electrode portion 30A in electrical communication with an energy delivery module can be used. For example, one or more wires, cables and/or other conductors can directly or indirectly couple to the electrodes, without the use of the irrigation tube. The energy delivery module may be configured to deliver electromagnetic energy at frequencies useful for determining contact (e.g., between 5 kHz and 1000 kHz).

FIG. 24 schematically illustrates one embodiment of a combination, or composite (e.g., split-tip), electrode assembly that can be used to perform contact sensing or determination by measuring the bipolar impedance between the separated electrodes or electrode portions 30A, 30B at different frequencies. Resistance values may be determined from voltage and current based on Ohm's Law: Voltage=Current*Resistance, or V=IR. Accordingly, resistance equals voltage divided by current. Similarly, if the impedance between the electrodes is complex, the complex voltage and current may be measured and impedance (Z) determined by V_complex=I_complex*Z_complex. In this case, both magnitude and phase information for the impedance can be determined as a function of frequencies. The different frequencies may be applied to the composite (e.g., split-tip) electrode assembly by an energy delivery module (e.g., by energy generation device 42 of energy delivery module 40 of FIG. 1) or a contact sensing subsystem (such as contact sensing subsystem 50 of system 10 of FIG. 1). Because the voltage and current values may be known or measured, the resistance and/or complex impedance values can be determined from the voltage and current values using Ohm's Law. Thus, the impedance values may be calculated based on measured voltage and/or current values in accordance with several embodiments rather than directly obtaining impedance measurements.

Figure 25A:
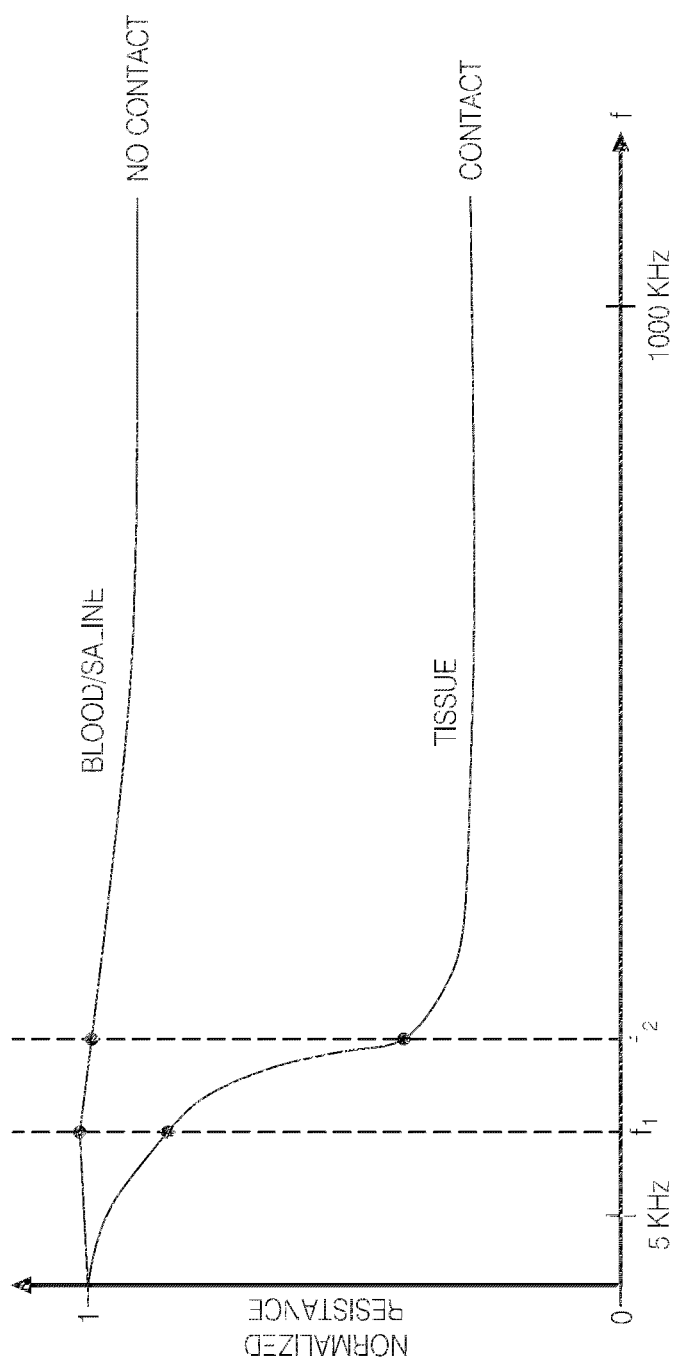
FIG. 25A is a plot showing normalized resistance of blood/saline and tissue across a range of frequencies.

FIG. 25A is a plot showing resistance, or magnitude impedance, values of blood (or a blood/saline combination) and of cardiac tissue across a range of frequencies (5 kHz to 1000 kHz). The impedance values are normalized by dividing the measured impedance magnitude by the maximum impedance magnitude value. As can be seen, the normalized impedance of blood (or a blood/saline combination) does not vary significantly across the entire range of frequencies. However, the normalized impedance of cardiac tissue does vary significantly over the range of frequencies, forming a roughly "s-shaped" curve.

In one embodiment, resistance or impedance measurements can be obtained at two, three, four, five, six or more than six different discrete frequencies within a certain range of frequencies. In several embodiments, the range of frequencies may span the range of frequencies used to ablate or otherwise heat targeted tissue. For example, resistance or impedance measurements may be obtained at two different frequencies $f_1$ and $f_2$ within the range of frequencies, where $f_2$ is greater than $f_1$. Frequency $f_1$ may also be below the ablation frequency range and $f_2$ may be above the ablation frequency range. In other embodiments, $f_1$ and/or $f_2$ can be in the range of ablation frequencies. In one embodiment, $f_1$ is 20 kHz and $f_2$ is 800 kHz. In various embodiments, $f_1$ is between 10 kHz and 100 kHz and $f_2$ is between 400 kHz and 1000 kHz. By comparing the impedance magnitude values obtained at the different frequencies, a processing device (e.g., a contact sensing subsystem or module coupled to or executable by processor 46 of FIG. 1) can determine whether or not the electrode portion 30A is in contact with issue (e.g., cardiac tissue) upon execution of specific program (machine-readable) instructions stored on a non-transitory computer-readable storage medium. The processing device is adapted to communicate with and execute modules (for example, a contact sensing module) for processing data, wherein the modules are stored in a memory. The modules may comprise software in the form of an algorithm or machine-readable instructions.

For example, if the ratio r of an impedance magnitude value obtained at the higher frequency $f_2$ to the impedance magnitude value obtained at the lower frequency $f_1$ is smaller than a predetermined threshold, the processing device may determine that the electrode portion 30A is in contact with cardiac tissue or other target region (e.g., upon execution of specific program instructions stored on a non-transitory computer-readable storage medium). However, if the ratio r of an impedance magnitude value obtained at the higher frequency $f_2$ to the impedance magnitude value obtained at the lower frequency $f_1$ is greater than a predetermined threshold, the processing device may determine that the electrode portion 30A is not in contact with cardiac tissue but instead is in contact with blood or a blood/saline combination. The contact determinations may be represented as follows:

$$\frac{r_{f2}}{r_{f1}} < \text{threshold} = \text{CONTACT}$$

$$\frac{r_{f2}}{r_{f1}} > \text{threshold} = \text{NO\_CONTACT}$$

In various embodiments, the predetermined threshold has a value between 0.2 and less than 1 (e.g., between 0.2 and 0.99, between 0.3 and 0.95, between 0.4 and 0.9, between 0.5 and 0.9 or overlapping ranges thereof).

Figure 25B:
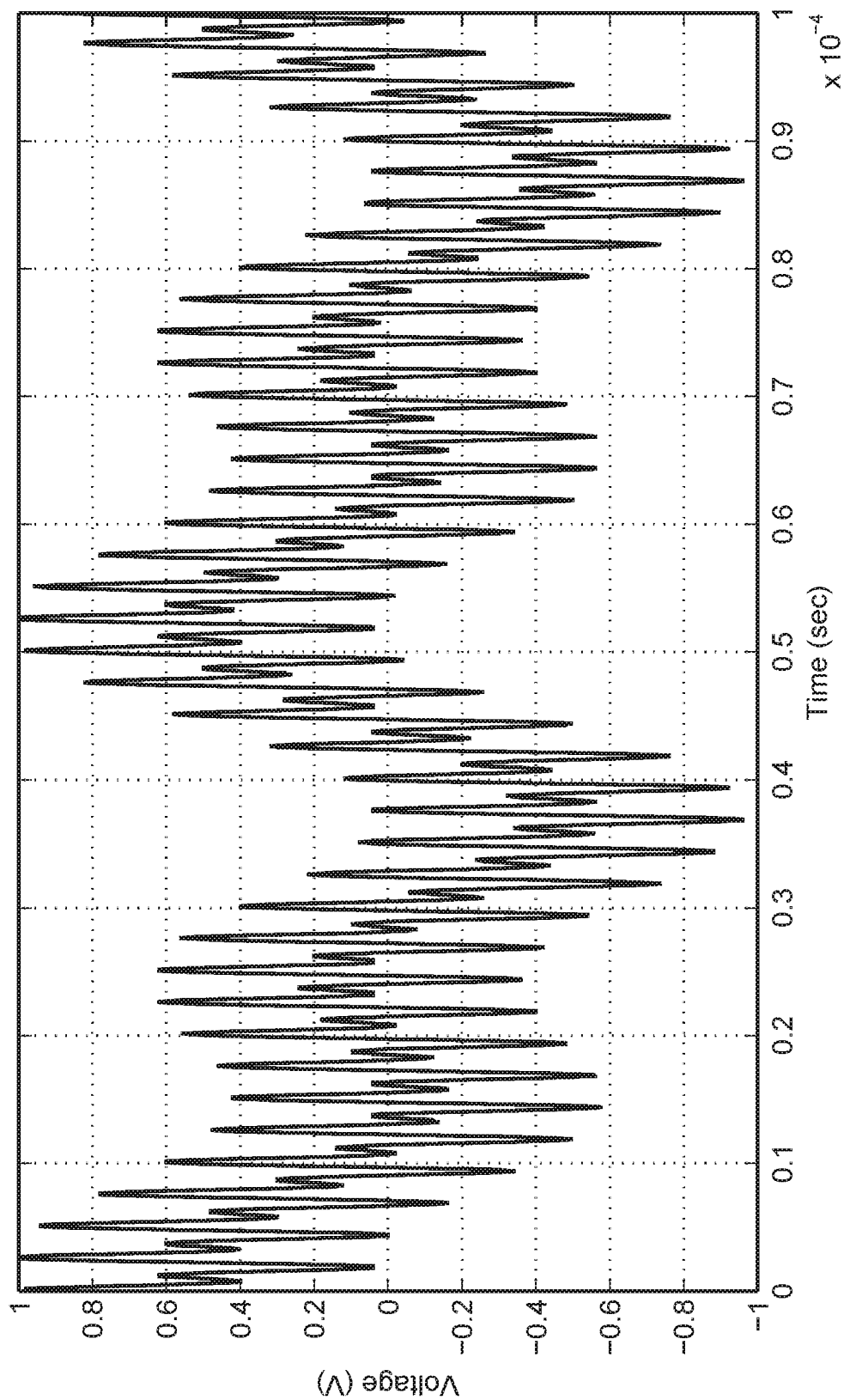
FIG. 25B is a plot of a four tone waveform utilized for impedance measurements.
Figure 25C:
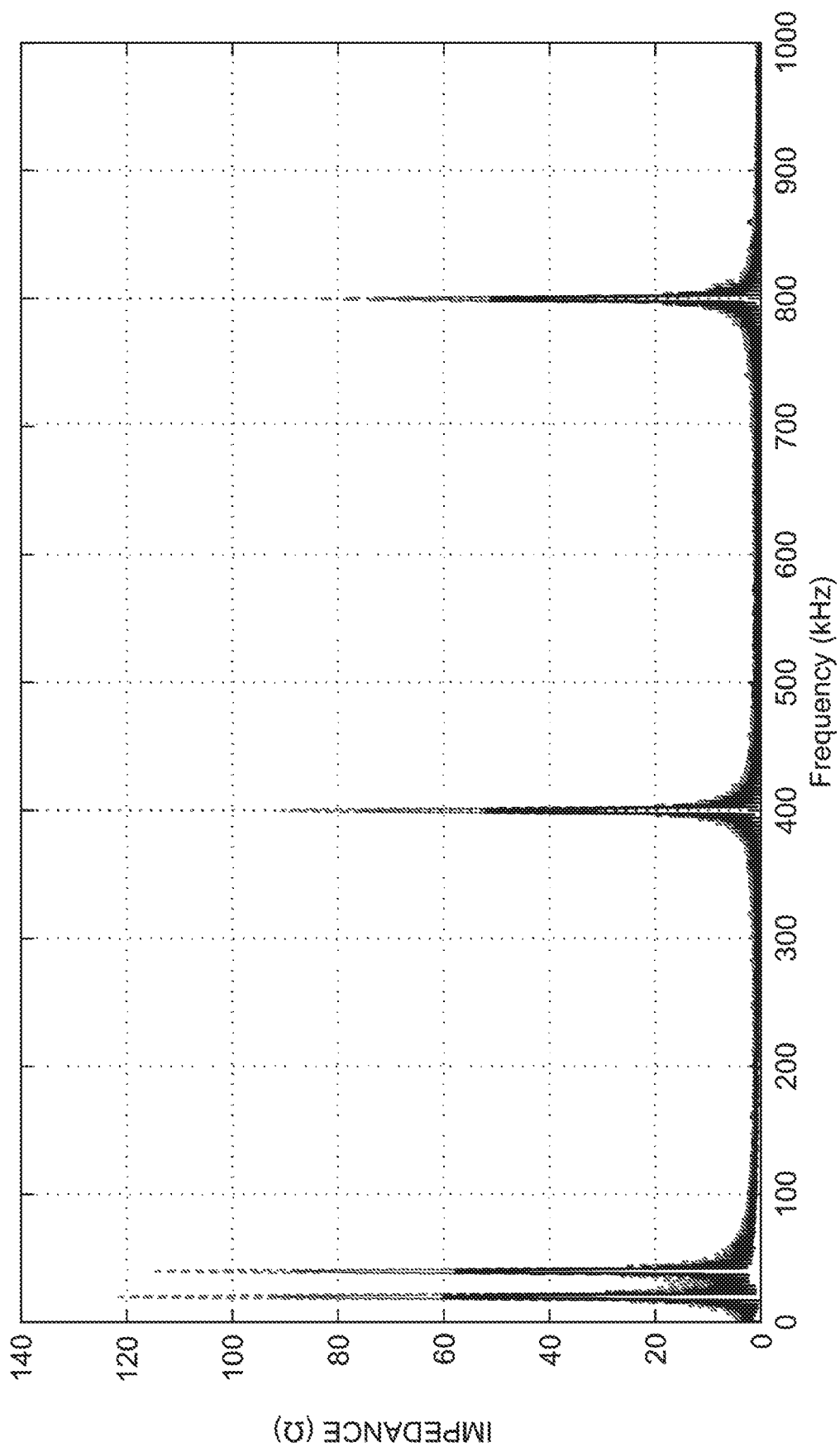
FIG. 25C is a plot of impedance vs. frequency, with tones at four frequencies.
Figure 25D:
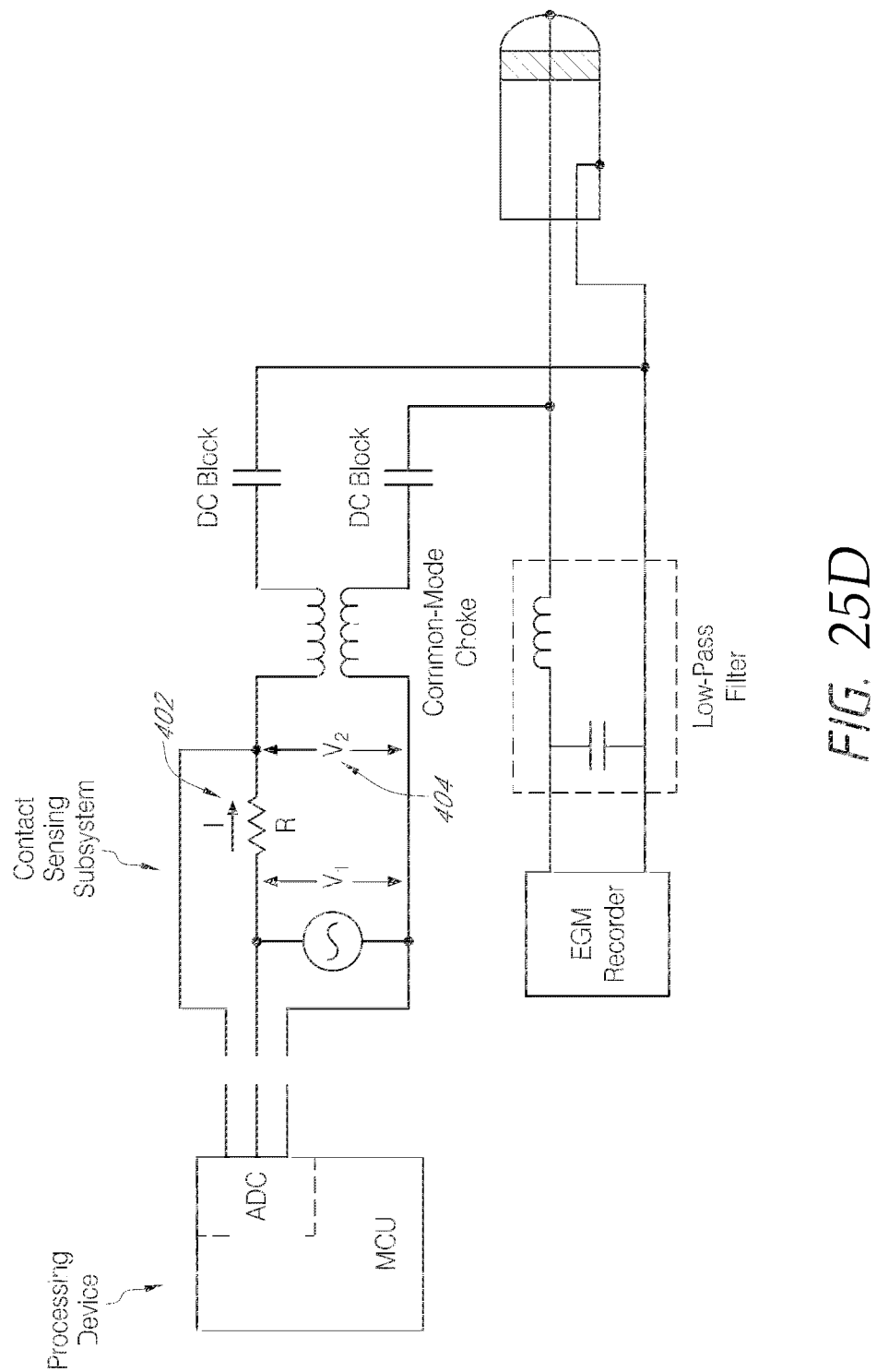
FIG. 25D schematically illustrates one embodiment of a contact sensing subsystem configured to perform contact sensing functions while simultaneously conducting electrogram (EGM) measurements, in accordance with one embodiment.

In various embodiments, resistance or impedance measurements are periodically or continuously obtained at the different frequencies (e.g., two, three, four or more different frequencies) by utilizing a source voltage or current waveform that is a multi-tone signal including the frequencies of interest, as shown in FIG. 25B. The multi-tone signal or waveform may be sampled in the time-domain and then transformed to the frequency domain to extract the resistance or impedance at the frequencies of interest, as shown in FIG. 25C. In some embodiments, measurements or determinations indicative of contact may be obtained in the time domain instead of the frequency domain. Signals or waveforms having different frequencies may be used. In accordance with several embodiments, performing the contact sensing operations is designed to have little or no effect on the electrogram (EGM) functionality of the combination, or composite (e.g., split-tip), electrode assembly. For example, common mode chokes and DC blocking circuits may be utilized in the path of the impedance measurement circuitry as shown in FIG. 25D. The circuitry may also include a reference resistor R to limit the maximum current flow to the patient, as well as dual voltage sampling points V1 and V2 to enhance the accuracy of the impedance measurements. Additionally, a low-pass filter circuit (with, for example, a cut-off frequency of 7 kHz) may be utilized in the path of the EGM recording system, as shown in FIG. 4D. In several embodiments, all or portions of the circuitry shown in FIG. 25D are used in a contact sensing subsystem, such as contact sensing subsystem 50 of FIG. 1 or contact sensing subsystem 4650 of FIG. 27. The frequencies used for contact sensing may be at least greater than five times, at least greater than six times, at least greater than seven times, at least greater than eight times, at least greater than nine times, at least greater than ten times the EGM recording or mapping frequencies. The contact sensing subsystem may be controlled by a processing device including, for example, an analog-to-digital converter (ADC) and a microcontroller (MCU). The processing device may be integral with the processing device 46 of FIG. 1 or may be a separate, stand-alone processing device. If a separate processing device is used, the separate processing device may be communicatively coupled to the processing device 46 of FIG. 1.

Figure 26A:
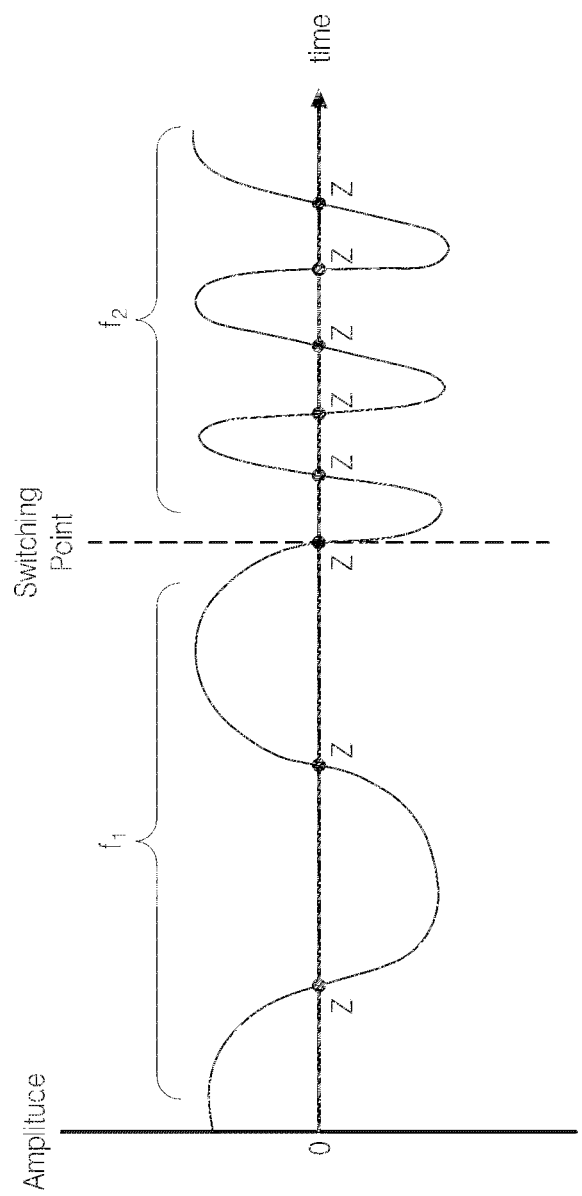
FIG. 26A illustrates zero crossings of a frequency spectrum and is used to illustrate that switching between frequencies may be designed to occur at the zero crossings to avoid interference at EGM frequencies.

In various embodiments, resistance or impedance measurements (e.g., total impedance or component parts of complex impedance) are periodically or continuously obtained at the different frequencies (e.g., two or three different frequencies) by switching between the different frequencies. In accordance with several embodiments, performing the contact sensing operations may be designed to have little or no effect on the electrogram (EGM) functionality of the combination electrode, or composite (e.g., split-tip), assembly. Accordingly, switching between the different frequencies may advantageously be synched to zero crossings of an AC signal waveform, as illustrated in FIG. 26A. In some embodiments, if the frequency switching does not occur at zero crossings, artifacts may be induced in the electrograms, thereby degrading the quality of the electrograms. In some embodiments, impedance measurements (e.g., bipolar impedance measurements) are obtained at multiple frequencies simultaneously. In other embodiments, impedance measurements are obtained at multiple frequencies sequentially.

In another embodiment, contact sensing or determination is performed by obtaining resistance or impedance measurements across a full range of frequencies from an $f_{min}$ to an $f_{max}$ (e.g., 5 kHz to 1 MHz, 10 kHz to 100 kHz, 10 kHz to 1 MHz). In such embodiments, the variation in the frequency response, or the impedance measurements over the range of frequencies, is indicative of whether the electrode portion 30A is in contact with tissue (e.g., cardiac tissue) or not.

The impedance measurements may be applied to a model. For example, a frequency response function r(f) may be created and fit to a polynomial or other fitting function. The function may take the form, for example, of:

$$r(f)=a\cdot f^3+b\cdot f^2+c\cdot f+d$$

where a, b, c and d are the terms for the polynomial function that match the response of r(f) to measured data. Thresholds may then be set on the polynomial terms to determine whether or not the electrode is in contact with tissue. For example, a large d term may indicate a large impedance indicative of tissue contact. Similarly, a large c term may indicate a large slope in the impedance which is also indicative of tissue contact. The higher-order terms may be utilized to reveal other subtle differences in the impedance response that indicate tissue contact.

Figure 26B:
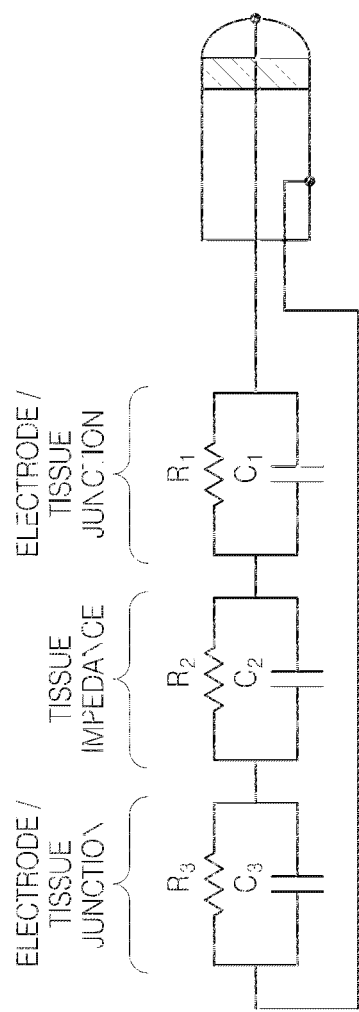
FIG. 26B schematically illustrates one embodiment of a circuit model to describe the behavior of the impedance of tissue or blood or blood/saline combination, as measured across two electrodes or electrode portions.

In some embodiments, a circuit model such as that shown in FIG. 26B is used to determine the frequency response function r(f). The model may comprise resistors and capacitors that predict the response of tissue and the tissue to electrode interfaces. In this approach, the R and C values may be determined that best fit the measured data and thresholds may be utilized based on the R and C values to determine whether or not the electrode is in contact with tissue. For example a small value of capacitance (C2) may indicate a condition of tissue contact, while a large value may indicate no contact. Other circuit configurations are also possible to model the behavior of the electrode impedance as desired and/or required.

Figure 26C:
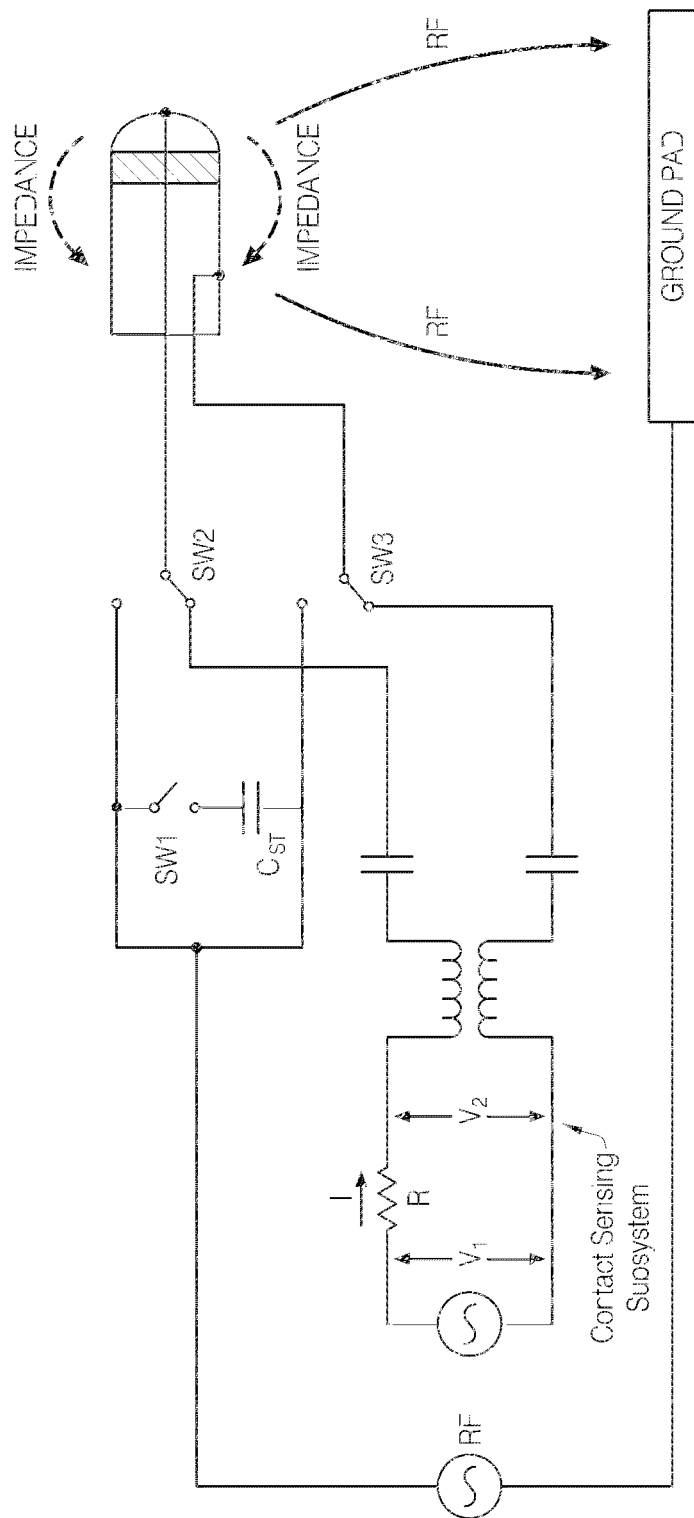
FIG. 26C schematically illustrates one embodiment of a circuit configured to switch between contact sensing circuitry in standby mode and radiofrequency energy delivery circuitry in treatment mode, in accordance with one embodiment.

In some embodiments, the contact sensing or contact determination assessments are performed prior to initiation of ablative energy delivery and not performed during energy delivery. In this case, switching may be utilized to separate the contact impedance measurement circuitry from the ablative energy, as shown in FIG. 26C. In this implementation, a switch SW1 is opened to disconnect the composite (e.g., split-tip) capacitor ($C_{ST}$) and allow measurement of impedance in the higher frequency ranges where $C_{ST}$ might present a short circuit (or low impedance in parallel with the measurement). At the same time, switches SW2 and SW3 are set to connect to the impedance measurement circuitry, or contact sensing subsystem. As shown in FIG. 26C, the impedance measurement circuit, or contact sensing subsystem, is the same as that shown in FIG. 25D. When ablations are to be performed, SW2 and SW3 connect the tip electrodes to the ablative energy source (e.g., RF generator labeled as RF in FIG. 26C) and disconnect the impedance measurement circuit. SW1 is also switched in order to connect the composite (e.g., split-tip) capacitor $C_{ST}$, thereby allowing the pair of electrodes to be electrically connected via a low impedance path. In one embodiment, the split-tip capacitor $C_{ST}$ comprises a 100 nF capacitor that introduces a series impedance lower than about 4Ω at 460 kHz, which, according to some arrangements, is a target frequency for radiofrequency ablation. As FIG. 26C also shows, the ablation current path is from both electrodes to a common ground pad. The impedance measurement path is between the two electrodes, although other current paths for the impedance measurement are also possible. In one embodiment, the switch is a relay such as an electromechanical relay. In other embodiments, other types of switches (e.g., solid-state, MEMS, etc.) are utilized.

In some embodiments, the contact sensing or contact determination assessments described above may be performed while ablative energy or power (e.g., ablative radiofrequency energy or power) is being delivered because the frequencies being used for contact sensing are outside of the range (either above or below, or both) of the ablation frequency(ies).

Figure 27:
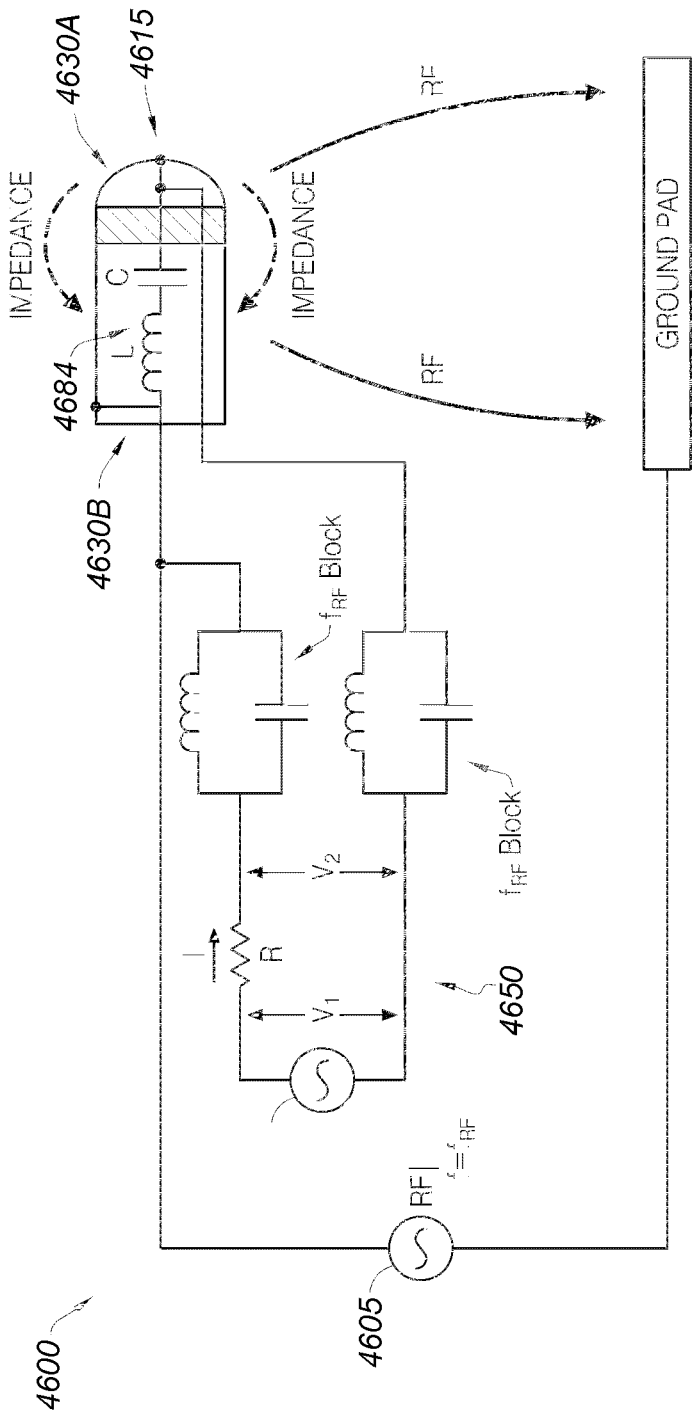
FIG. 27 schematically illustrates one embodiment of a circuit configured to perform contact sensing functions while radiofrequency energy is being delivered, in accordance with one embodiment.

FIG. 27 schematically illustrates a system 4600 comprising a high-resolution, combination electrode, or composite (e.g., split-tip), electrode catheter, the system being configured to perform ablation procedures and contact sensing or determination procedures simultaneously. The high resolution (e.g., composite or split-tip) electrode assembly 4615 may comprise two electrodes or two electrode members or portions 4630A, 4630B separated by a gap. A separator is positioned within the gap G, between the electrodes or electrode portions 4630A, 4630B. The composite electrode assembly 4615 may comprise any of the features of the high resolution (e.g., composite or split-tip) electrode assemblies described above in connection with FIG. 2 and/or as otherwise disclosed herein. An energy delivery module (not shown, such as energy delivery module 40 of FIG. 1) or other signal source 4605 may be configured to generate, deliver and/or apply signals in an ablative range (e.g., radiofrequency energy 200 kHz-800 kHz, and nominally 460 kHz) while a contact sensing subsystem 4650 (such as the contact sensing subsystem shown in FIG. 25D) delivers low-power signal(s) 4607 (such as excitation signals) in a different frequency range (e.g., between 5 kHz and 1000 kHz) to be used to perform the contact sensing or determination assessments to a composite electrode assembly 4615. The low-power signal(s) 4607 may comprise a multi-tone signal or waveform or separate signals having different frequencies. The contact sensing subsystem 4650 may comprise the elements shown in FIG. 25D, as well as notch filter circuits to block the ablation frequency (e.g., a 460 kHz notch filter if a 460 kHz ablation frequency is used). In this configuration, a filter 4684 is utilized to separate the contact sensing frequencies and the ablation frequency(ies).

The filter 4684 may comprise, for example, an LC circuit element, or one or more capacitors without an inductor. The elements and values of the components of the filter 4684 may be selected to center the minimum impedance at the center frequency of the ablative frequencies delivered by the energy delivery module to effect ablation of targeted tissue. In some embodiments, the filtering element 4684 comprises a single capacitor that electrically couples the two electrodes or electrode portions 4630A, 4630B when radiofrequency current is applied to the system. In one embodiment, the capacitor comprises a 100 nF capacitor that introduces a series impedance lower than about 4Ω at 460 kHz, which, according to some arrangements, is a target frequency for ablation (e.g., RF ablation). However, in other embodiments, the capacitance of the capacitor(s) or other band-pass filtering elements that are incorporated into the system can be greater or less than 100 nF, for example, 5 nF to 300 nF, according to the operating ablation frequency, as desired or required. In this case, the contact sensing impedance frequencies would all be below the ablation frequency range; however, in other implementations, at least some of the contact sensing impedance frequencies are within or above the ablation frequency range.

Figure 28:
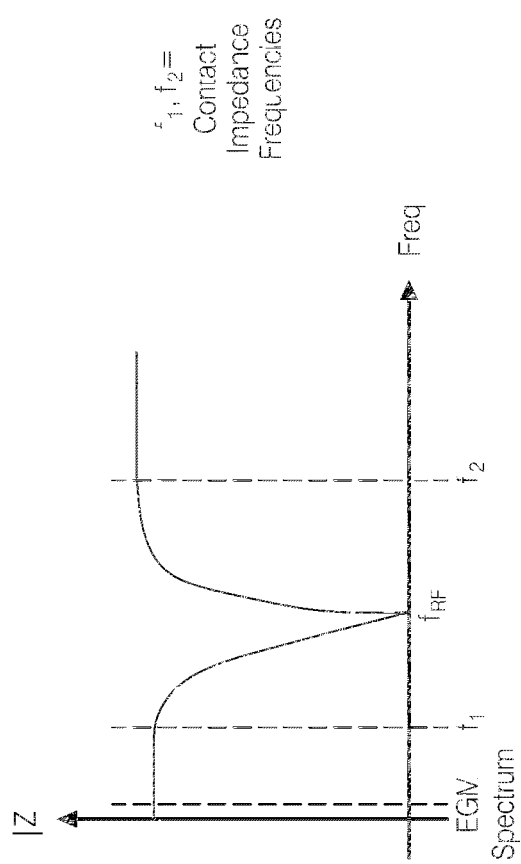
FIG. 28 is a plot of impedance of an LC circuit element across a range of frequencies.

FIG. 28 illustrates a plot of impedance of an LC circuit element comprising the filter 4684, for example. As shown, the minimum impedance is centered at the center frequency of the ablative RF frequencies (460 kHz as one example) and the impedance is high at the frequencies in the EGM spectrum so as not to affect EGM signals or the contact sensing measurements. Additionally, the contact impedance measurements are performed at frequencies that exist above and/or below the RF frequency (and above the EGM spectrum). For example, two frequencies $f_1$ and $f_2$ may be utilized where $f_1$=20 kHz and $f_2$=800 kHz. At these frequencies, the LC circuit would have a large impedance in parallel with the electrodes, thereby allowing the impedance to be measured. In one embodiment, the inductor L has an inductance value of 240 pH and the capacitor C has a capacitance value of 5 nF. However, in other embodiments, the inductor L can range from 30 μH to 1000 μH (e.g., 30 to 200 pH, 200 to 300 pH, 250 to 500 pH, 300 to 600 pH, 400 to 800 pH, 500 to 1000 pH, or overlapping ranges thereof) and the capacitor C can range from 0.12 nF to 3.3 μF (e.g., 0.12 to 0.90 nF, 0.50 to 1.50 nF, 1 nF to 3 nF, 3 nF to 10 nF, 5 nF to 100 nF, 100 nF to 1 μF, 500 nF to 2 μF, 1 μF to 3.3 μF, or overlapping ranges thereof). In various embodiments, $f_1$ is between 10 kHz and 100 kHz and $f_2$ is between 400 kHz and 1000 kHz.

Figure 29:
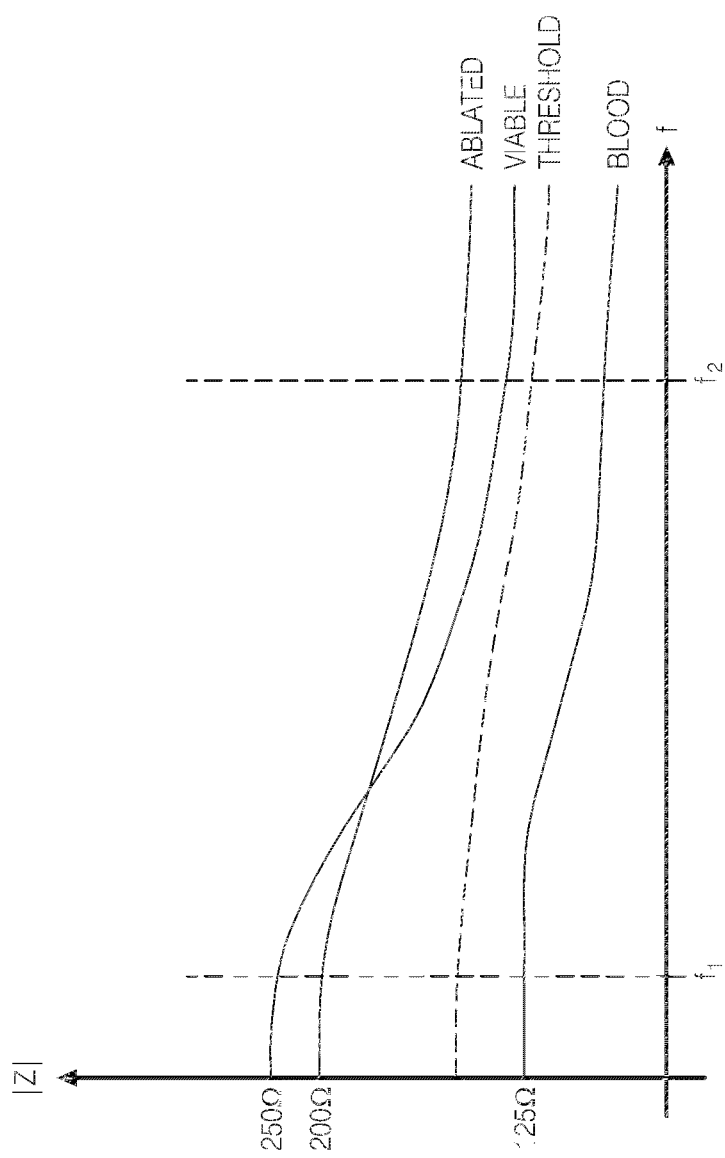
FIG. 29 is a plot showing resistance, or impedance magnitude, values of ablated tissue, viable tissue and blood across a range of frequencies.

In accordance with several embodiments, the same hardware and implementation as used for contact sensing may be used to determine tissue type (e.g., viable tissue vs. ablated tissue), so as to confirm whether ablation has been successful or not. FIG. 29 is a plot illustrating resistance, or impedance magnitude, values for ablated tissue, viable tissue and blood across a range of frequencies. As can be seen, the resistance of ablated tissue starts at a high resistance value (200Ω) and remains substantially flat or stable, decreasing slightly over the range of frequencies. The resistance of blood starts at a lower resistance (125Ω) and also remains substantially flat or stable, decreasing slightly over the range of frequencies. The resistance of viable tissue, however, starts at a high resistance value (250Ω) and significantly decreases across the range of frequencies, roughly forming an "s-shaped" curve. The reason for the different resistance responses between ablated and viable tissue is due, at least partially, to the fact that the viable cells (e.g., cardiac cells) are surrounded by a membrane that acts as a high-pass capacitor, blocking low-frequency signals and allowing the higher-frequency signals to pass, whereas the cells of the ablated tissue no longer have such membranes as a result of being ablated. The reason for the substantially flat response for blood resistance is that most of the blood is comprised of plasma, which is more or less just electrolytes having low impedance. The red blood cells do provide some variance, because they have similar membranes acting as capacitors as the viable cardiac cells. However, because the red blood cells constitute such a small percentage of the blood composition, the effect of the red blood cells is not substantial.

Similar to the contact sensing assessments described above, resistance, or impedance magnitude, values may be obtained at two or more frequencies (e.g., 20 kHz and 800 kHz) and the values may be compared to each other to determine a ratio. In some embodiments, if the ratio of the impedance magnitude value at the higher frequency $f_2$ to the impedance magnitude value at the lower frequency $f_1$ is less than a threshold, then the processing device (e.g., processing device 4624, which may execute a tissue type determination module for processing data, wherein the module is stored in memory and comprises algorithms or machine-readable instructions) determines that the contacted tissue is viable tissue and if the ratio of the impedance magnitude value at the higher frequency $f_2$ to the impedance magnitude value at the lower frequency $f_1$ is greater than a threshold, then the processing device 4624 determines that the contacted tissue is ablated tissue. In various embodiments, the predetermined threshold has a value between 0.5 and 0.8 (e.g., 0.50, 0.55, 0.60, 0.65, 0.70, 0.75, 0.80).

In some embodiments, a combination of impedance magnitude differences and differences in the ratio of impedance magnitudes at frequencies $f_2$ and $f_1$ are utilized to determine both contact state (e.g., contact vs. in blood) as well as tissue type (e.g., viable tissue vs. ablated tissue). In some embodiments, contact state and tissue type determinations are not performed during energy delivery or other treatment procedures. In other embodiments, contact state and/or tissue type determinations are performed during energy delivery or other treatment procedures using filters and/or other signal processing techniques and mechanisms to separate out the different frequency signals.

Figure 30:
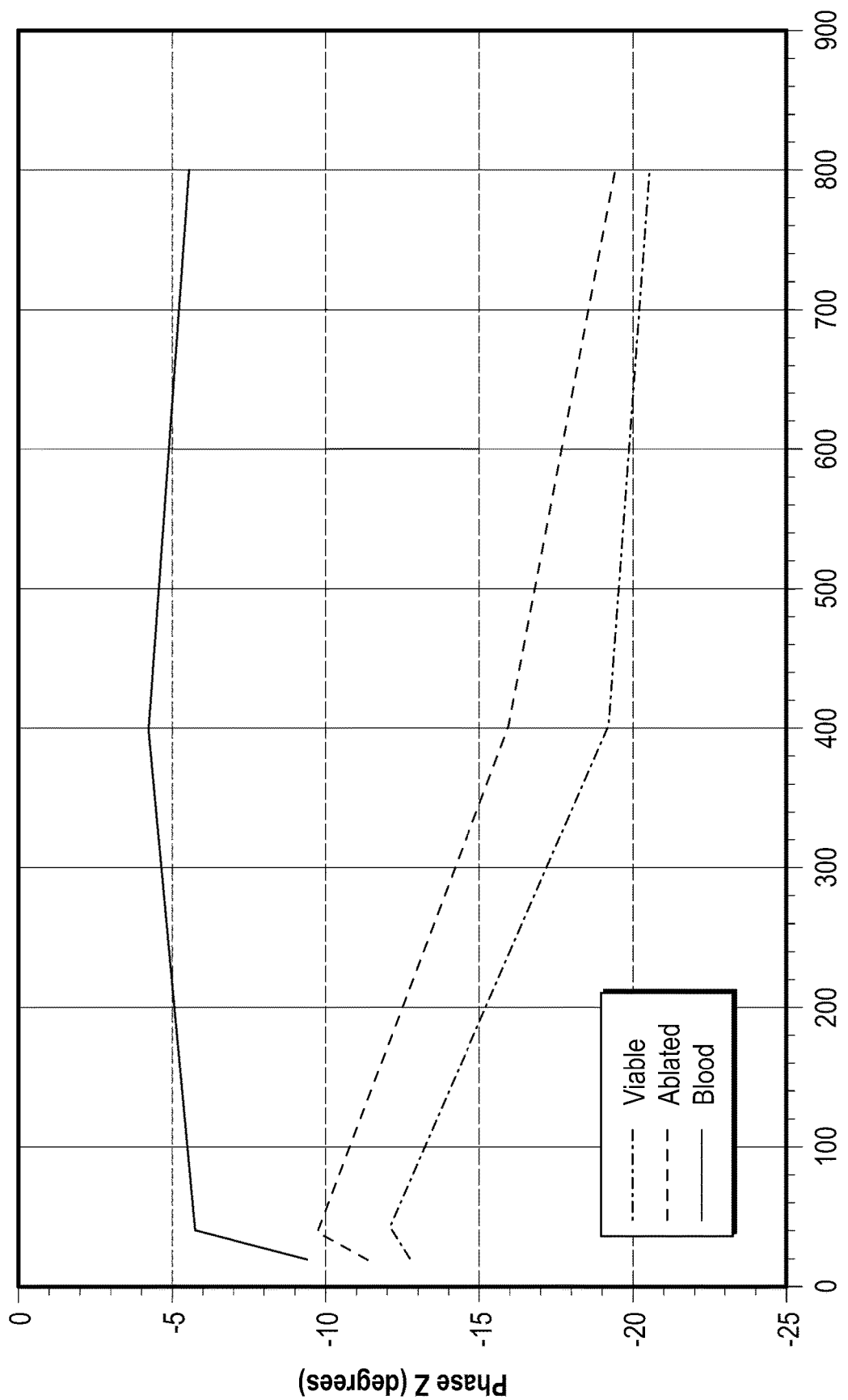
FIG. 30 is a plot showing the phase of impedance values of ablated tissue, viable tissue and blood across a range of frequencies.

In addition to the impedance magnitude, the same hardware and implementation used for contact sensing (e.g., contact sensing subsystem 50, 4650) may be utilized to compute the phase of the impedance (e.g., complex impedance) across electrode portions. In one embodiment, the phase of the impedance may be added to algorithms for determining different contact states (e.g., contact vs. in blood) as well as different tissue states (e.g., viable tissue vs. ablated tissue). FIG. 30 shows an example of the phase of the impedance across electrode portions versus frequency for viable tissue, ablated tissue and blood. The phase tends to be larger (closer to 0 degrees) for blood and smaller for viable (unablated) tissue. For ablated tissue the phase may be in between blood and viable tissue. In one embodiment, a negative phase shift at a single frequency indicates contact with tissue (either viable or ablated). A larger negative phase shift may indicate contact with viable tissue. In one embodiment, a phase of less than −10 degrees at 800 kHz indicates contact with tissue (either viable or ablated). In one embodiment, a phase of less than −20.5 degrees at 800 kHz indicates contact with viable tissue. In other embodiments, the phase at other frequencies or combinations of frequencies are utilized to determine contact state and tissue type. In some embodiments, the impedance magnitude and phase are utilized together as vector quantities, and differences in the vectors for different frequencies are utilized to determine contact state and tissue type.

Figure 31:
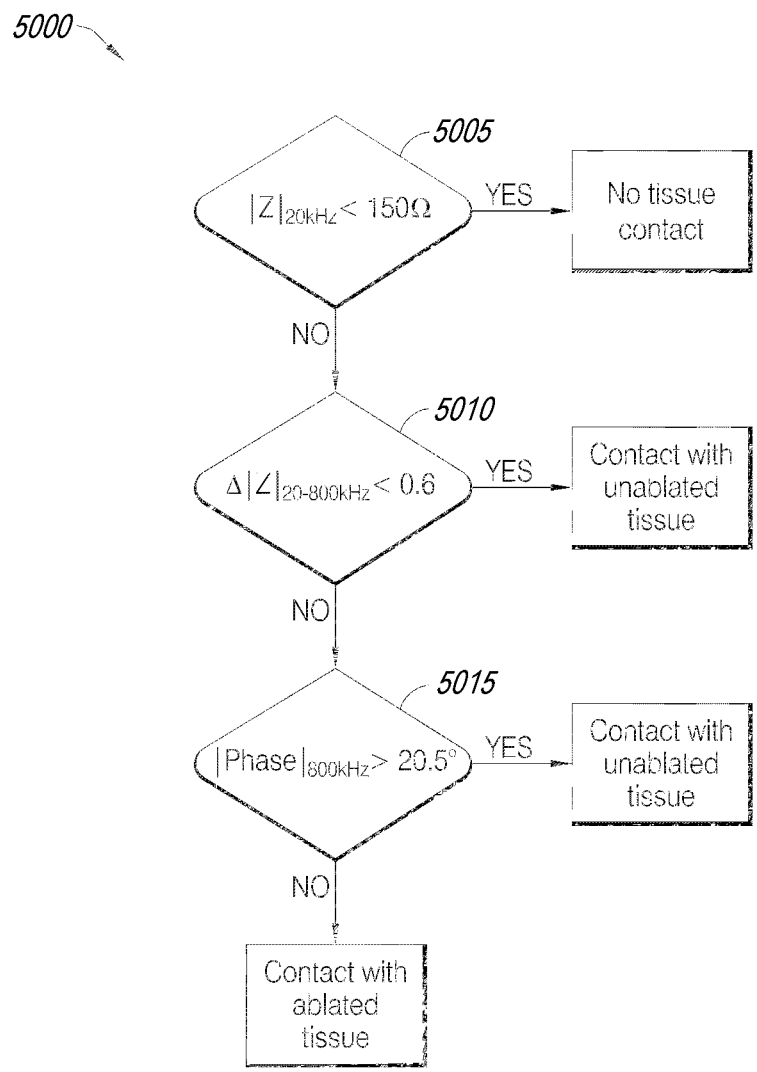
FIG. 31 illustrates one embodiment of a sensing algorithm that utilizes impedance magnitude, ratio of impedance magnitude at two frequencies, and impedance phase data to determine contact state as well as tissue state.

In some embodiments, a combination of impedance magnitude differences, differences in the ratio of impedance magnitude values at frequencies $f_2$ and $f_1$, and differences in the phase of the impedance are utilized together to determine both contact state (e.g., contact vs. in blood) as well as tissue type (e.g., viable tissue vs. ablated tissue). In one embodiment, the determination process 5000 illustrated in FIG. 31 is utilized to determine both contact state as well as tissue type. In this embodiment, an impedance magnitude threshold of 150Ω at 20 kHz is utilized to delineate between no contact and tissue contact (with a larger value indicating contact) at block 5005. Once contact is determined at block 5005, the ratio of the impedance magnitude at $f_2$=800 kHz and $f_1$=20 kHz is computed at block 5010, with a value of less than 0.6 indicating contact with unablated, or viable, tissue. If the aforementioned ratio is greater than 0.6, then the impedance phase at 800 kHz is utilized at block 5015, and an (absolute) value greater than 20.5 degrees indicates contact with ablated tissue. An (absolute) value of less than 20.5 degrees indicates contact with unablated, or viable, tissue.

In some embodiments, the contact sensing subsystem 50 or system 10 (e.g., a processing device thereof) analyzes the time-domain response to the waveform described in FIG. 25B, or to an equivalent waveform. In accordance with several embodiments, contact sensing or tissue type determinations are based on processing the response to a signal applied to a pair of electrodes or electrode portions (for example electrode pair 4630A, 4630B), the signal either including multiple frequencies or several frequencies applied sequentially. In some embodiments, processing device 4624 may process the response in time domain or frequency domain. For example, given that blood is mostly resistive, with little capacitive characteristics, it is expected that time-domain features such as rise or fall times, lag or lead times, or delays between applied signal 4402 (e.g., I in FIG. 25D) and processed response 4404 (e.g., V2 in FIG. 25D) will exhibit low values. Conversely, if the electrode pair 4630A, 4630B of FIG. 27 is in contact with tissue, given that tissue exhibits increased capacitive characteristics, it is expected that time-domain features such as rise or fall times, lag or lead times, or delays between applied signal 4402 (e.g., I in FIG. 25D) and processed response 4404 (e.g., V2 in FIG. 25D) will exhibit higher values. An algorithm that processes parameters such as, but not limited to, rise or fall times, lag or lead times, or delays between applied signal 4402 and processed response 4404 may indicate or declare contact with tissue when the parameters exceed a threshold, or, conversely, it may indicate or declare no contact with tissue when the parameters have values below a threshold. For example, assuming the signal 4402 is represented by a sinusoidal current of 800 kHz frequency, the algorithm could declare contact with tissue if the response 4404 lags by more than 0.035 μs. Conversely, the algorithm could declare lack of tissue contact if the response 4404 lags by less than 0.035 μs. Similarly, if the frequency of signal 4402 were 400 kHz, the algorithm may decide:

no tissue contact, when the lag time is less than 0.07 ρs;
contact with ablated tissue, when the lag time is between 0.07 ρs and 0.13 ρs;
contact with viable or unablated tissue, when the lag time is greater than 0.13 ρs.

The decision thresholds or criteria depend on the waveform of signal 4402. Thresholds or decision criteria for other types of waveforms may also be derived or determined.

In some embodiments, multiple inputs may be combined by a contact sensing or contact indication module or subsystem executable by a processor (e.g., processor of the contact sensing subsystems 50, 4650) to create a contact function that may be used to provide an indication of contact vs. no contact, an indication of the amount of contact (e.g., qualitative or quantitative indication of the level of contact, contact state or contact force), and/or an indication of tissue type (e.g., ablated vs. viable (non-ablated) tissue). For example, a combination of (i) impedance magnitude at a first frequency $f_1$, (ii) the ratio of impedance magnitudes at two frequencies $f_2$ and $f_1$ (defined as the slope) or the delta, or change, in impedance magnitudes at the two frequencies, and/or (iii) the phase of the complex impedance at the second frequency $f_2$ are utilized together to create a contact function that is indicative of contact state (e.g., tissue contact vs. in blood). Alternatively, instead of slope, a derivative of impedance with respect to frequency may be used. In accordance with several embodiments, the impedance measurements or values comprise bipolar impedance measurements between the pair of electrode members.

In one embodiment, a minimum threshold $|Z|_{min}$ is defined for the impedance magnitude at $f_1$, and a maximum threshold $|Z|_{max}$ is defined for the impedance at $f_1$. The impedance magnitude measured by the contact sensing subsystem 50, 650 at $f_1$ can be normalized such that the impedance magnitude is 0 if the measured result is equal to $|Z|_{min}$ or below, and the impedance magnitude is 1 if the measured result is equal to $|Z|_{max}$ or above. Results in-between $|Z|_{min}$ and $|Z|_{max}$ may be linearly mapped to a value between 0 and 1. Similarly, a minimum threshold $S_{min}$ and a maximum threshold $S_{max}$ may be defined for the slope (ratio of impedance magnitude between $f_2$ and $f_1$). If a derivative of impedance with respect to frequency is used, then similar minimum and maximum thresholds may be defined. The slope measured by the contact sensing subsystem 50 may be normalized such that the slope is 0 if the measured result is equal to or above $S_{min}$ and the slope is 1 if the measured result is equal to or below $S_{max}$. Results in between $S_{min}$ and $S_{max}$ may be linearly mapped to a value between 0 and 1. A minimum threshold $P_{min}$ and a maximum threshold $P_{max}$ may also be defined for the phase of the complex impedance at $f_2$. The phase measured by the contact sensing subsystem 50 at $f_2$ may be normalized such that the phase is 0 if the measured result is equal to or greater than $P_{min}$ and 1 if the measured result is equal to or less than $P_{max}$.

In accordance with several embodiments, the resulting three normalized terms for magnitude, slope and phase are combined utilizing a weighting factor for each. The sum of the weighting factors may be equal to 1 such that the resulting addition of the three terms is a contact indicator that goes from a zero to 1 scale. The weighted contact function (CF) can thus be described by the below equation:

$$CF = WF1 \frac{|Z|_{f1} - |Z|_{min}}{|Z|_{max} - |Z|_{min}} + WF2 \frac{S - S_{min}}{S_{max} - S_{min}} + WF3 \frac{P_{f2} - P_{min}}{P_{max} - P_{min}}$$

where $|Z|_{f1}$ is the measured impedance magnitude at a first frequency $f_1$, clipped to a minimum value of $|Z|_{min}$ and a maximum value of $|Z|_{max}$ as described above; S is the ratio of the impedance magnitude at a second frequency $f_2$ to the magnitude at $f_1$, clipped to a minimum value of $S_{min}$ and a maximum value of $S_{max}$ as described above; and $P_{f2}$ is the phase of the impedance at frequency $f_2$, clipped to a minimum value of $P_{min}$ and a maximum value of $P_{max}$ as described above. The weighting factors WF1, WF2 and WF3 may be applied to the magnitude, slope and phase measurements, respectively. As previously stated, the weighting factors WF1+WF2+WF3 may sum to 1, such that the output of the contact function always provides a value ranging from 0 to 1. Alternatively, values greater than 1 may be allowed to facilitate generation of alerts to a user about circumstances when more tissue-electrode contact may become unsafe for patients. Such alerts may be helpful in preventing application of unsafe levels of contact force. For example, CF values in the range of 1 to 1.25 may be flagged as a "contact alert" and may cause the contact sensing subsystem to generate an alert for display or other output to a user. The alert may be visual, tactile, and/or audible. The weighting factors may vary based on catheter design, connection cables, physical patient parameters, and/or the like. The weighting factors may be stored in memory and may be adjusted or modified (e.g., offset) depending on various parameters. In some embodiments, the weighting factors may be adjusted based on initial impedance measurements and/or patient parameter measurements.

The contact function described above can be optimized (e.g., enhanced or improved) to provide a reliable indicator of the amount of contact with tissue (e.g., cardiac tissue, such as atrial tissue or ventricular tissue). The optimization may be achieved by defining minimum thresholds $Z_{min}$, $S_{min}$ and $P_{min}$ that correspond with no to minimal tissue contact, as well as thresholds $Z_{max}$, $S_{max}$ and $P_{max}$ that correspond with maximal tissue contact. Weighting terms may also be optimized (e.g., enhanced or improved) for robust responsiveness to contact. In some embodiments, windowed averaging or other smoothing techniques may be applied to the contact function to reduce measurement noise.

As one example, at a frequency $f_1$=46 kHz and $f_2$=800 kHz, the values $Z_{min}$=115 ohms, $Z_{max}$=175 ohms, $S_{min}$=0.9, $S_{max}$=0.8, $P_{min}$=−5.1 degrees, $P_{max}$=−9 degrees, WF1=0.75, WF2=0.15, and WF3=0.1 are desirable (e.g., optimal) for representing the amount of tissue contact (e.g., for cardiac tissue of the atria or ventricles). In other embodiments, $Z_{min}$ may range from 90 ohms to 140 ohms (e.g., 90 ohms to 100 ohms, 95 ohms to 115 ohms, 100 ohms to 120 ohms, 110 ohms to 130 ohms, 115 ohms to 130 ohms, 130 ohms to 140 ohms, overlapping ranges thereof, or any value between 90 ohms and 140 ohms), $Z_{max}$ may range from 150 ohms up to 320 ohms (e.g., 150 ohms to 180 ohms, 160 ohms to 195 ohms, 180 ohms to 240 ohms, 200 ohms to 250 ohms, 225 ohms to 260 ohms, 240 ohms to 300 ohms, 250 ohms to 280 ohms, 270 ohms to 320 ohms, overlapping ranges thereof, or any value between 150 ohms and 320 ohms), $S_{min}$ may range from 0.95 to 0.80 (e.g., 0.95 to 0.90, 0.90 to 0.85, 0.85 to 0.80, overlapping ranges thereof, or any value between 0.95 and 0.80), $S_{max}$ may range from 0.85 to 0.45 (e.g., 0.85 to 0.75, 0.80 to 0.70, 0.75 to 0.65, 0.70 to 0.60, 0.65 to 0.55, 0.60 to 0.50, 0.55 to 0.45, overlapping ranges thereof, or any value between 0.85 and 0.45), $P_{min}$ may range from 0 to −10 degrees (e.g., 0, −1, −2, −3, −4, −5, −6, −7, −8, −9, −10 or any combinations of ranges between, such as 0 to −5, −2 to −6, −4 to −8, −5 to −10), and $P_{max}$ may range from −5 to −25 degrees (e.g., −5 to −10, −7.5 to −15, −10 to −20, −15 to −25, overlapping ranges thereof or any value between −5 and −25 degrees). The weighting factors WF1, WF2 and WF3 may cover the range from 0 to 1. In some embodiments, values above or below the ranges provided may be used as desired and/or required. Appropriate values for these parameters may be dependent on the electrode geometry and frequencies $f_1$ and $f_2$ used for the measurements. Changes in the electrode geometry, physical patient parameters, connection cables, and frequencies may require different ranges for the above values.

In some treatment procedures, contact impedance measurements or calculations (e.g., magnitude |Z|, slope S and/or phase P components of bipolar contact impedance) may "drift" over time as liquid is infused into a patient prior to or during a treatment procedure. Examples of liquid introduced during preparation for a treatment procedure or during a procedure include, for example, saline, anesthetic drugs such as propofol, blood thinners such as heparin, or other physiological liquids. The liquids can be introduced through the treatment device (e.g., ablation catheter) itself (e.g., saline through irrigation ports) and/or through IV infusion (IV fluid bags, tubing and syringes) or other delivery mechanisms. The introduction of liquids over time may affect the resistivity and/or impedance of the blood over time, which, in turn, can affect contact impedance measurements or calculations determined by a contact sensing subsystem or module based on electrical measurements (e.g., voltage and current measurements or direct impedance measurements) between a pair of contact sensing electrodes (e.g., between the pair of electrode members or portions of a composite tip (e.g., high-resolution or combination electrode) assembly as described herein) over time. This drift over time due to changes in the blood resistivity and/or impedance can affect the accuracy or reliability of the contact function or contact index determination (e.g., indicator of quality of contact, level of contact or contact state) over time if not accounted, or compensated, for. For example, electrophysiological saline is conductive and so as more saline is introduced into the vasculature, the patient's blood is diluted and the resistivity of the blood drops, causing a drift in the contact impedance measurements or calculations over time. As a result, corrections to the contact functions or algorithms may be desired to account, or compensate, for the drift, thereby improving the accuracy of the contact function or contact index determinations or algorithms. For example, without compensation, the drift may result in contact indication determinations (which may be determined based on static threshold values) that can substantially vary even though the level of contact (e.g., contact force) remains steady, thereby providing inaccurate or unreliable contact level indication or assessment output and misleading a clinician as to the actual contact level.

Infusion rates are generally not constant or linear over time. Accordingly, look-up tables or set formulas based on flow rate and time duration may not be used as reliably, in accordance with several embodiments. Changes in blood resistivity could also be affected by factors other than introduction of liquid and the techniques described herein to counteract the drift due to introduction of liquid could also be used to account for changes in blood resistivity due to other factors, such as patient's body temperature, fluctuation in metabolic rates, etc.

In some embodiments, the thresholds in the contact functions or algorithms, such as the thresholds $|Z|_{max}$, $|Z|_{min}$, $S_{max}$, $S_{min}$, $P_{max}$, $P_{min}$ in the weighted contact function provided above, can advantageously be changed or adjusted from constant values to values that change based on one or more reference measurements. For example, if the contact impedance measurements are being measured between a distal and proximal RF electrode member of a high-resolution, or combination, electrode assembly (such as a split-tip electrode assembly) as described herein (which are likely in contact with target tissue such as cardiac tissue), a second set of reference measurements may be obtained between a different pair of reference electrodes that are in the blood pool but are not expected to be in contact with tissue (or at least not in constant contact with tissue). In accordance with several embodiments, impedance measurements or values determined from the pair of reference electrodes when in blood change proportionally or substantially proportionally to the impedance measurements or values determined between the contact sensing electrodes when in blood or in contact with tissue (e.g., electrode portions of a composite tip, or combination electrode, assembly). The impedance values determined from the reference electrodes do not have to be the same in an absolute sense as the impedance values of the contact sensing electrodes. A correction factor, or scaling value, can be applied as long as the drift for the reference electrodes proportionally or substantially proportionally tracks, or is otherwise indicative of, the drift for the contact sensing electrodes. In some implementations, the drift between the impedance values of the reference electrodes and the drift of the impedance values of the contact sensing electrodes is within ±20% (e.g., within 20%, within 15%, within 10%, within 5%). In some embodiments, the pair of reference electrodes may be positioned adjacent or proximate a target treatment site (e.g., ablation site) but not in contact with tissue. In other embodiments, the pair of reference electrodes are not positioned adjacent the target treatment site. In some embodiments, the pair of reference electrodes are not positioned external to the patient and are not within the medical instrument such that they cannot be exposed to blood.

Figure 41A:
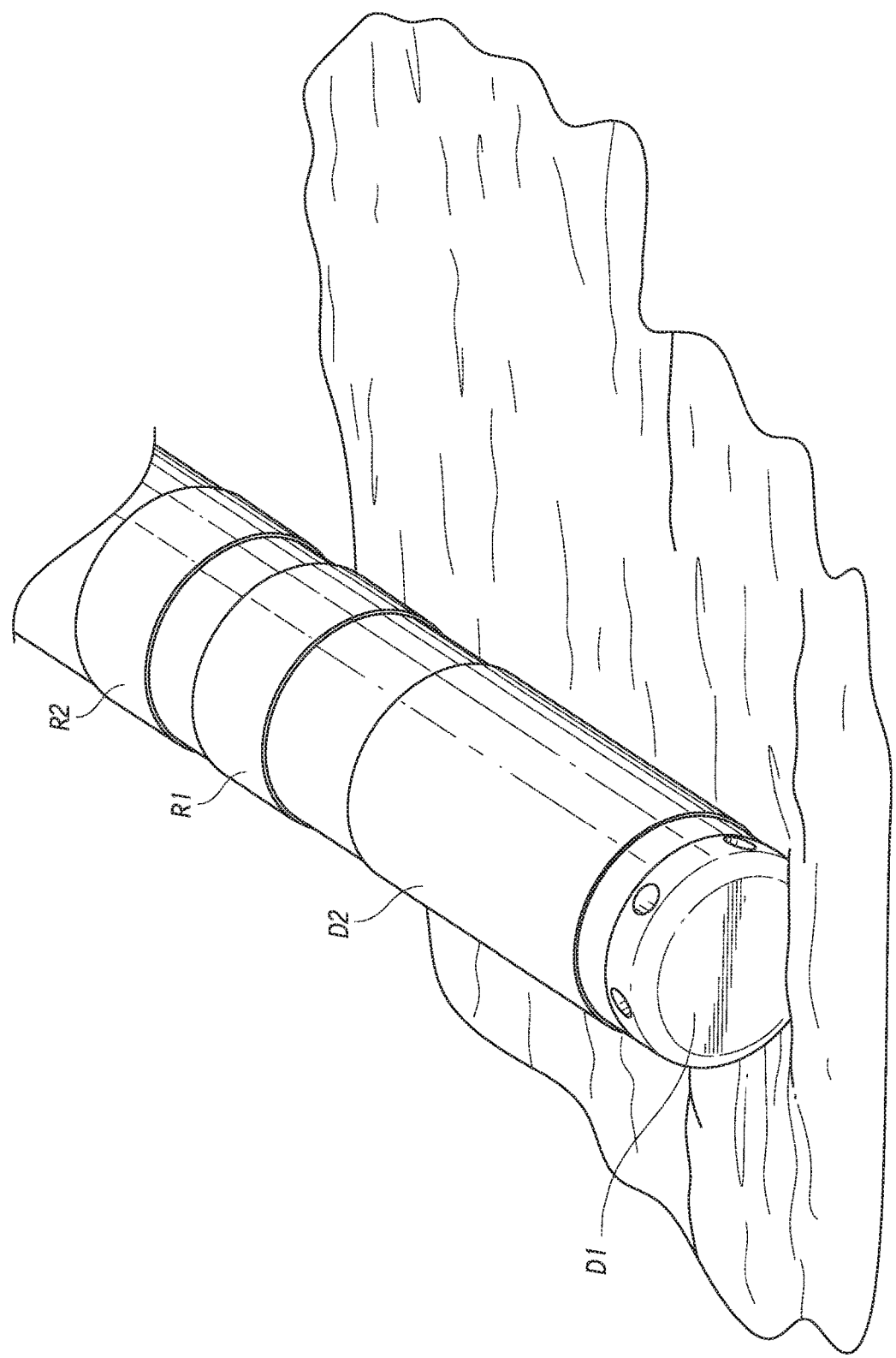
FIG. 41A illustrates an embodiment of an ablation catheter in which a first set of electrodes at a distal tip of the ablation catheter is in contact with tissue and a second set of electrodes spaced proximal of the first set of electrodes is not in contact with tissue.

FIG. 41A illustrates an ablation catheter having a composite tip (e.g., high-resolution, or combination) electrode assembly comprised of a distal electrode member D1 and a proximal electrode member D2 separated by a gap distance, as well as a distal ring electrode R1 and a proximal ring electrode R2 that are positioned at a distance along the ablation catheter proximal to the proximal electrode member D2 and that are separated from each other by a separation distance. In various embodiments, the separation distance between R1 and R2 (the distance between a proximal edge of R1 and a distal edge of R2) is between 0.5 mm and 3.5 mm (e.g., between 0.5 mm and 1.5 mm, between 1.0 and 3.0 mm, between 1.5 and 2.5 mm, between 2.0 and 3.5 mm, overlapping ranges thereof or any value within the recited ranges, including but not limited to 0.5 mm, 1.0 mm, 1.5 mm, 2.0 mm, 2.5 mm, 2.5 mm, 3.0 mm, and 3.5 mm). The separation distance between R1 and R2 (or other set of reference electrodes) may be the same as the gap distance between D1 and D2 (or other set of contact sensing electrodes) may be different than the gap distance between D1 and D2. The distance between the proximal edge of D2 and the distal edge of R1 may range from 1 mm to 10 mm (e.g., from 1.0 mm to 2.0 mm, from 2.0 to 3.0 mm, from 3.0 to 5.0 mm, from 4.0 to 8.0 mm, from 5.0 to 10.0 mm, overlapping ranges thereof, or any value within the recited ranges, including but not limited to 1.0 mm, 1.5 mm, 2.0 mm, 2.5 mm, 3.0 mm, 3.5 mm, 4.0 mm, 4.5 mm, and 5.0 mm.

In some embodiments, the ring electrodes R1, R2 are used for mapping or other functions in addition to being used for reference measurements. The ring electrodes R1, R2, which are spaced proximal from the distal tip of the ablation catheter, tend not to be in contact with tissue (or at least are not in continuous contact with tissue) and instead are in the blood/liquid mixture within a chamber, cavity, space or vessel of the heart, other organ or within vasculature adjacent to (e.g., proximate or close to) the target tissue being treated. Accordingly, the measurements obtained by the ring electrodes R1, R2 can serve as effective reference measurements that can be used to track changes in the impedance of blood as saline or other liquids are infused over time (and thus be used to adjust impedance measurements or calculations (e.g., magnitude, slope, and/or phase) that are used in qualitative contact assessment functions or algorithms), thereby improving the accuracy and/or reliability of the qualitative contact assessment functions or algorithms. In some embodiments, reference measurements can be obtained over a period of time and a minimum measurement value can be selected as the reference measurement in order to account for possible instances over the period of time when one or both of the ring electrodes are in contact with tissue (e.g., when the ablation catheter is in a parallel or substantially parallel orientation). The ablation catheter can include any of the structures or features described herein (e.g., filtering element and/or spacing between the D1 and D2 electrode members to facilitate high resolution mapping and ablative RF energy delivery, plurality of distributed temperature-measurement devices or sensors, thermal shunting structures, irrigation outlets, etc.).

Figure 41B:
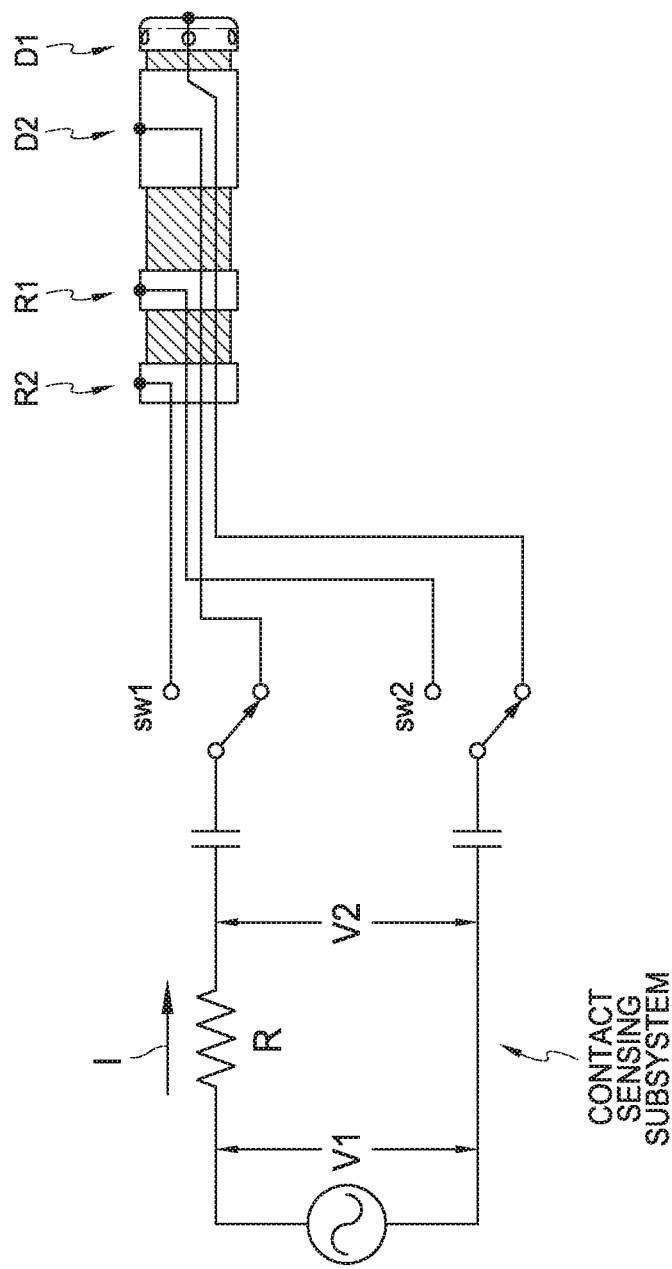
FIG. 41B schematically illustrates an embodiment of a circuit connection between the electrode members of the ablation catheter of FIG. 41A and a contact sensing subsystem or module of an energy delivery system.

FIG. 41B schematically illustrates an embodiment of a circuit connection between the electrode members D1, D2 of the high resolution, or combination, electrode assembly and the ring electrodes R1, R2 of the ablation catheter of FIG. 41A and a contact sensing system or module, such as described herein. The contact sensing system or module may be housed, embodied or stored in a standalone component or within the energy delivery module 40 (e.g., RF generator) or within the ablation catheter itself. As shown in FIG. 41B, the circuit can include switches SW1, SW2 to switch, or toggle, the connection to the contact sensing system or module between the ring electrodes R1, R2 for reference measurements and the electrode members D1, D2. Other alternative connection implementations may be used as desired and/or required.

As one example when a pair of proximal ring electrodes are used to obtain reference impedance measurements, a correction may be applied to the $|Z|_{max}$ threshold as follows:

$$|Z|_{max\_adj} = |Z|_{max} * (1 - A*(Z_{R1R2\_initial} - Z_{R1R2\_current})),$$

where $|Z|_{max}$ is a baseline threshold that is valid when there is no infusion of saline or other liquids, $Z_{R1R2\_initial}$ is an initial baseline impedance value determined from one or more electrical measurements between the ring electrodes R1 and R2, $Z_{R1R2\_current}$ is a current impedance value determined from one or more electrical measurements between the ring electrodes R1 and R2, and A is a scaling factor.

A similar concept can be applied to the $|Z|_{min}$ threshold:

$$|Z|_{min\_adj} = Z_{min} * (1 - B*(Z_{R1R2\_initial} - Z_{R1R2\_current})),$$

where $Z_{min}$ is the baseline threshold that is valid when there is no infusion of saline, $Z_{R1R2\_initial}$ and $Z_{R1R2\_current}$ are the same as previously described above, and B is a scaling factor.

An example of how this correction, or compensation, can be effected by the contact sensing subsystem or module (e.g., upon execution of specific program instructions stored in memory by one or more processors) is presented below with respect to an example bench test in which salinity level was adjusted over time. For simplicity, only the magnitude portion of the contact function, denoted CF1, will be described. However, the same concept can also be utilized to compensate for drift in the slope or the phase response as liquid is infused into a patient.

Table 2 below shows the response of $|Z|_{f1}$ and CF1 vs Salinity Level for a realistic bench test with 5 g of contact force on cardiac tissue:

TABLE 2

Response of CF1 as Salinity Level increases, constant force of 5 g applied.

| Salinity Level | $|Z|_{f1}$ | CF1 |
|---|---|---|
| 1 | 224 | 2.8 |
| 2 | 218 | 2.6 |
| 3 | 210 | 2.3 |
| 4 | 200 | 1.9 |

| Contact Parameters: | |
|---|---|
| Zmax | 230 |
| Zmin | 150 |

As can be seen in Table 2, as the salinity level increases past the baseline (salinity level 1) the magnitude $|Z|_{f1}$ begins to drop and CF1 begins to decrease—indicating reduced contact despite the contact force being held constant at 5 g.

Table 3 below illustrates how the drift correction might be applied to account for this effect caused by changes in salinity level (which may occur due to introduction of liquid over time).

TABLE 3

Response of CF1 and CF1_adj with drift correction.

| Salinity Level | $Z_{R1R2\_current}$ | $|Z|_{f1}$ | Zmax_adj | Zmin_adj | CF1 | CF1_adj | Contact Parameters: | | Drift Adjustment Parameters: | |
|---|---|---|---|---|---|---|---|---|---|---|
| 1 | 152 | 224 | 230.0 | 150.0 | 2.8 | 2.8 | Zmax | 230 | A | 0.004 |
| 2 | 143 | 218 | 221.7 | 141.9 | 2.6 | 2.9 | Zmin | 150 | B | 0.006 |
| 3 | 133 | 210 | 212.5 | 132.9 | 2.3 | 2.9 | | | | |
| 4 | 126 | 200 | 206.1 | 126.6 | 1.9 | 2.8 | | | | |

$Z_{R1R2\_initial}$  152

In this embodiment, the reference measurement $Z_{R1R2\_current}$ is utilized with the technique described above to compute $|Z|_{max\_adj}$ and $|Z|_{min\_adj}$. In this embodiment, $|Z|_{max\_adj}$ is calculated as $Z_{max}*(1-A*(Z_{R1R2\_initial}-Z_{R1R2\_current}))$ and $|Z|_{min\_adj}$ is calculated as $Z_{min}*(1-B*(Z_{R1R2\_initial}-Z_{R1R2\_current}))$. These values for $|Z|_{max\_adj}$ and $|Z|_{min\_adj}$ can then be utilized to compute a drift-corrected value for CF1, denoted as CF1_adj. As shown in Table 3, the response of CF1_adj remains consistent as the salinity level increases over time.

The above technique is an example of how drift correction can be applied to impedance magnitude measurements or calculations as liquid is infused into a patient over time. The same concept can also be utilized to compensate for drift in the slope or the phase response as liquid is infused into a patient over time. In order to correct the slope or phase response, the magnitude measurement between the ring electrodes R1 and R2 can be used in the same way described above. Additionally, the slope or phase response measured or calculated across the ring electrodes R1 and R2 may be utilized to create a drift correction.

In accordance with several embodiments, instead of using the ring electrodes R1 and R2 for the reference measurements, the electrode members D1 and D2 of the high resolution, or combination, electrode assembly can periodically be pulled into a non-contact position to conduct a reference measurement. Other combinations of pairs of electrodes other than two ring electrodes on the ablation catheter could be used to obtain reference measurements (e.g., R1 and D2, R1 and D1, R2 and D1 or R2 and D2). Reference measurements could also be obtained from other measurement devices or sources, as desired and/or required. For example, reference measurements could be obtained from a separate device other than the ablation catheter, such as a diagnostic catheter, a mapping catheter, a coronary sinus catheter, and/or the like. The same drift correction approach, or technique, described above when using the ring electrodes for the reference measurement can be similarly applied for reference measurements obtained by the electrode members D1 and D2 of the high resolution, or combination, electrode assembly or from any other electrodes or other measurement devices or sources. The drift correction techniques described herein can be applied to contact sensing measurements or values obtained or determined by any pair of electrodes or electrode portions or other contact assessment members using reference measurements or values obtained or determined by another pair of electrodes or electrode portions or other contact assessment members. The pairs of electrodes or electrode portions may be substituted with single members or with more than two members (e.g., three, four, five, six members). For example, although a two-electrode impedance measurement technique was described, three- or four-electrode impedance measurement techniques may be applied with equivalent results.

A method of correcting for drift in contact impedance measurements or calculations (e.g., magnitude, slope, and/or phase components of bipolar contact impedance measurements or calculations) comprises determining at least one reference impedance value that can be used to adjust corresponding threshold impedance component values of a contact quality assessment function (e.g., the contact functions described herein) over time. For example, the at least one reference impedance value can be determined from electrical measurements obtained using a pair of electrodes that are not likely to be in contact with tissue but are likely to be in contact with the blood/liquid mixture adjacent the electrodes or electrode portions being used to obtain contact impedance measurements for use in a contact quality assessment function or contact indication algorithm (such as those described herein), thereby providing a baseline that can be used to adjust contact impedance component measurements to increase the accuracy and/or reliability of the contact quality assessment function or contact indication algorithm. In some embodiments, at least one reference impedance value can be obtained for each threshold impedance component (e.g., magnitude at a first frequency, slope between magnitude at the first frequency and magnitude at a second frequency, and phase at the second frequency) of the contact quality assessment function or contact indication algorithm. The method may further include adjusting the threshold impedance component values based on the reference measurement(s). The adjustment may be performed continuously over time or at predefined time intervals (e.g., every tenth of a second, every half-second, every second, every two seconds, every three seconds, every four seconds, every five seconds, every ten seconds, every fifteen seconds, every twenty seconds).

The method may also include using the adjusted threshold impedance component values in the contact quality assessment function or contact indication algorithm instead of the actual measured threshold impedance component values by electrodes or electrode portions in contact with tissue. The method may be automatically performed by a contact sensing subsystem or module (which may comprise, for example, program instructions stored on a non-transitory computer-readable medium executable by one or more processing devices and/or may comprise hardware devices, such as one or more microprocessors or central processing units, memory (RAM or ROM), integrated circuit components, analog circuit components, digital circuit components and/or mixed-signal circuits) without transparency to a clinical professional.

In some embodiments, a contact function, or contact criterion, can be determined based, at least in part, on an if-then case conditional criterion. One example if-then case criterion is reproduced here: CC=IF($|Z_{MAG}| \geq Z_{THR1}$, Best, IF(AND($Z_{THR1} \geq |Z_{MAG}|$, $|Z_{MAG}| \geq Z_{THR2}$), Good, IF(AND ($Z_{THR2} \geq |Z_{MAG}|$, $|Z_{MAG}| \geq Z_{THR3}$), Medium, IF(AND ($Z_{THR3} \geq |Z_{MAG}|$, $|Z_{MAG}| \geq Z_{THR4}$), Low, No_Contact))))+IF ($|Z_{MAG}| \geq Z_{THR1}$, 0, IF(AND(SLOPE$\leq S_{THR1}$), Good, IF(AND($S_{THR1} \leq$SLOPE, SLOPE$\leq S_{THR2}$), Medium, IF(AND($S_{THR2} \leq$SLOPE, SLOPE$\leq S_{THR3}$), Low, No_Contact))))+IF($|Z_{MAG}| \geq Z_{THR1}$, 0, IF(AND(PHASE$\leq P_{THR1}$), Good, IF(AND($P_{THR1} \leq$PHASE, PHASE$\leq P_{THR2}$), Medium, IF(AND($P_{THR2} \leq$PHASE, PHASE$\leq P_{THR3}$), Low, No_—Contact))))

Figure 32:
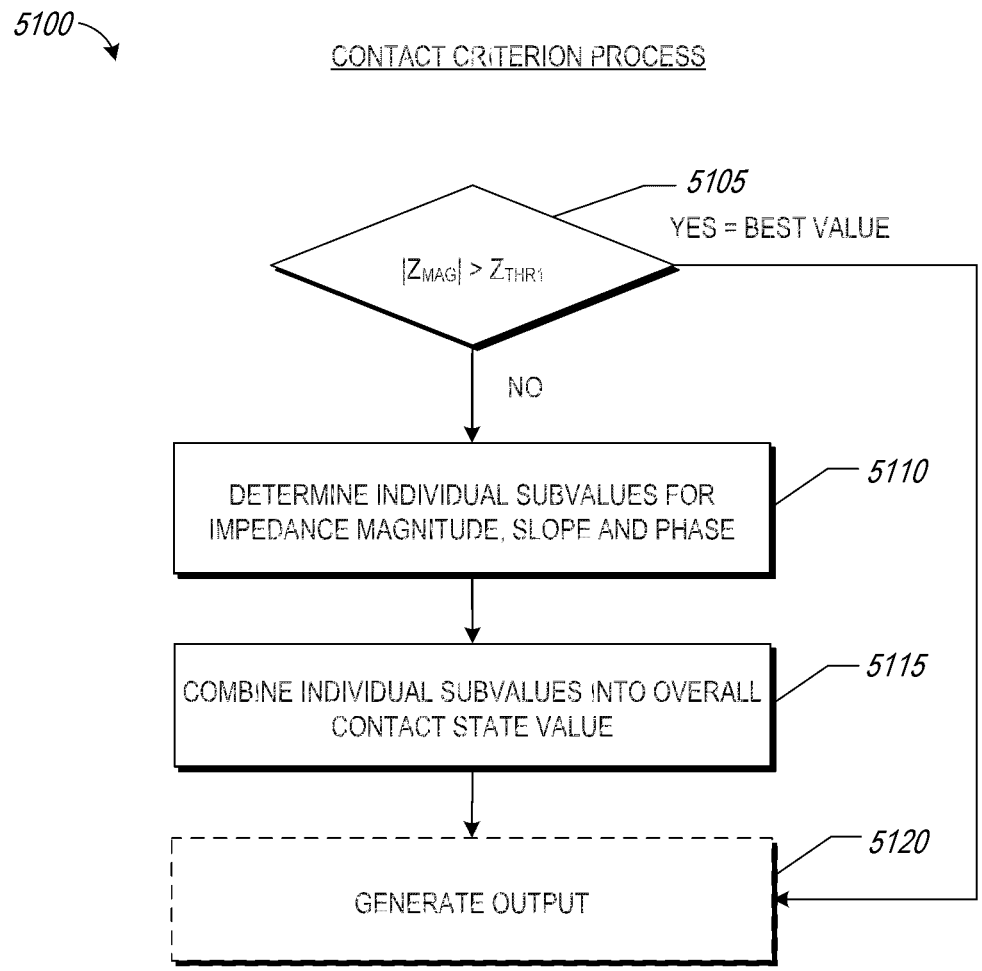
FIG. 32 illustrates an embodiment of a contact criterion process.

FIG. 32 illustrates an embodiment of a contact criterion process 5100 corresponding to the above if-then case conditional criterion. The contact criterion process 5100 may be executed by a processor upon execution of instructions stored in memory or a non-transitory computer-readable storage medium. At decision block 5105, a measured or calculated impedance magnitude value (e.g., based on direct impedance measurements or based on voltage and/or current measurements obtained by a combination electrode assembly comprising two electrode portions) is compared to a predetermined threshold impedance. If the measured or calculated impedance magnitude value $|Z_{MAG}|$ is greater than a first threshold $Z_{THR1}$ (e.g., 350Ω), then the Contact Criterion (CC) is assigned a "best" or highest value. If, however, the measured or calculated impedance magnitude value $|Z_{MAG}|$ is less than the threshold $Z_{THR1}$, then the process 5100 proceeds to block 5110, where individual subvalues for impedance magnitude, slope and phase are determined. At block 5115, the individual subvalues are combined (for example summed) into an overall value indicative of contact state. In some embodiments, the combination is a sum of a weighted combination, as described above.

The process 5100 may optionally generate output at block 5120. For example, if at decision block 5105, the measured or calculated impedance magnitude value $|Z_{MAG}|$ is greater than the first threshold $Z_{THR1}$, the process can generate an alert to a user that further manipulation of the catheter or other medical instrument may not further improve tissue contact, but may instead compromise patient safety. For example, if the user pushes too hard on the catheter or other medical instrument, the additional pressure may achieve little improvement in tissue contact but may increase the risk of tissue perforation (e.g., heart wall perforation). The output may comprise a qualitative or quantitative output as described in further detail herein (for example in connection with FIG. 33).

FIG. 32A illustrates an embodiment of the individual subvalue subprocess 5110 of process 5100 performed when the measured or calculated impedance magnitude value $|Z_{MAG}|$ is less than the first threshold $Z_{THR1}$. The Contact Criterion (CC) overall value may be calculated by bracketing the impedance magnitude ($|Z_{MAG}|$), the slope (S) and the phase (P) into intervals corresponding to good, medium, low and no contact levels. Subvalues corresponding to either good, medium, low or not contact are determined for each of the impedance magnitude, slope and phase components depending on comparisons to various predetermined threshold values. The subvalues may be combined to determine an overall contact state value. In the example case conditional criterion above, the CC is a sum of the individual values received by each of the three parameters ($|Z_{MAG}|$, S, P) according to their corresponding level of contact (e.g., good, medium, low or no contact). For example, if Good=3, Medium=2, Low=1 and No_Contact=0 then the overall CC could be between 0-2 for no or low contact, between 3-4 for poor contact, between 5-6 for medium contact and 7-9 for good contact. In one embodiment, when $|Z_{MAG}|$ exceeds the first threshold $Z_{THR1}$, then CC=10, as an indication that a "best," or "optimal" level of tissue contact was achieved. Other intervals or numbers can be used as desired.

In some embodiments, more than two frequencies are used (e.g., three or four frequencies) for tissue contact or tissue type detection. Although the computations described above were presented using impedance magnitude, slope and phase, other characteristics of the complex impedance may be used in other embodiments. For example, analyses of the real and imaginary components of impedance may be used. Analyses of admittance parameters or scattering parameters may also be used. In some embodiments, direct analyses of the voltages and currents described in FIGS. 25A-27 (e.g., processing of voltage or current magnitudes, frequency changes or relative phase) may be used. Analyses of voltages or currents may be performed in time domain or frequency domain. Impedance measurements, or values, may be calculated based on voltage and current measurements or may be directly measured. For example, phase measurements may comprise a difference in phase between measured voltage and measured current or may be actual impedance phase measurements.

In some embodiments, the contact indicator or contact function is associated with output via an input/output interface or device. The output may be presented for display on a graphical user interface or display device communicatively coupled to the contact sensing subsystem 50 (FIG. 1). The output may be qualitative (e.g., comparative level of contact as represented by a color, scale or gauge) and/or quantitative (e.g., represented by graphs, scrolling waveforms or numerical values) as shown in FIG. 33.

Figure 33:
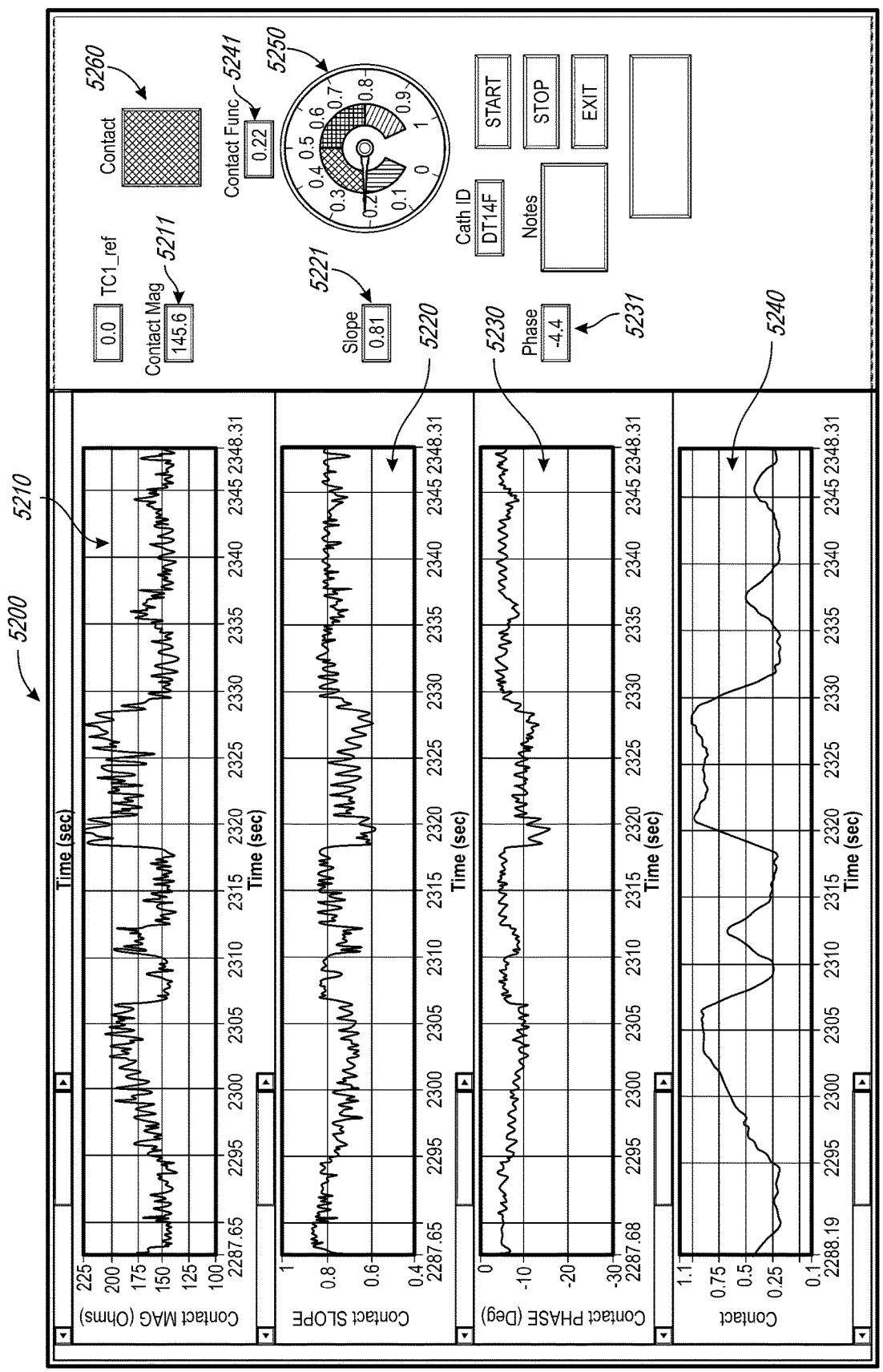
FIG. 33 illustrates an embodiment of a graphical user interface of a display of output indicative of tissue contact by a high resolution combination electrode device.

FIG. 33 illustrates an embodiment of a screen display 5200 of a graphical user interface of a display device communicatively coupled to the contact sensing subsystem 50 (FIG. 1). The screen display 5200 includes a graph or waveform 5210 illustrating impedance magnitude at frequency $f_1$ over time, as well as a box 5211 indicating the real-time numerical value of the impedance magnitude. The screen display 5100 also includes a graph or waveform 5220 of slope (from $f_2$ to $f_1$) over time, as well as a box 5221 indicating the real-time numerical value of the slope. The screen display 5200 further includes a graph or waveform 5230 illustrating phase at frequency $f_2$ over time, as well as a box 5231 indicating the real-time numerical value of the phase. The three measurements (magnitude, slope and phase) are combined into a contact function as described above and may be represented as a contact function or indicator over time, as displayed on graph or waveform 5240. The real-time or instantaneous numerical value of the contact function may also be displayed (Box 5241).

In some embodiments, as shown in FIG. 33, the contact function or indicator may be represented as a virtual gauge 5250 that provides a qualitative assessment (either alone or in addition to a quantitative assessment) of contact state or level of contact in a manner that is easily discernable by a clinician. The gauge 5250 may be segmented into, for example, four segments, or regions, that represent different classifications or characterizations of contact quality or contact state. For example, a first segment (e.g., from contact function values of 0 to 0.25) may be red in color and represent no contact, a second segment (e.g., from contact function values of 0.25 to 0.5) may be orange in color and represent "light" contact, a third segment (e.g., from contact function values of 0.5 to 0.75) may be yellow in color and represent "medium" or "moderate" contact, and a fourth segment (e.g., from contact function values of 0.75 to 1) may be green in color and represent "good", or "firm", contact. In other embodiments, fewer than four segments or more than four segments may be used (e.g., two segments, three segments, five segments, six segments). In one embodiment, three segments are provided, one segment for no contact or poor contact, one segment for moderate contact and one segment for good, or firm, contact. The segments may be divided equally or otherwise as desired and/or required. Other colors, patterns, graduations and/or other visual indicators may be used as desired. Additionally, a "contact alert" color or gauge graduation may be provided to alert the user about engaging the catheter or other medical instrument with too much force (e.g., contact function values greater than 1). The gauge 5250 may include a pointer member that is used to indicate the real-time or instantaneous value of the contact function on the gauge 5250.

In some embodiments, a qualitative indicator 5260 indicates whether or not contact is sufficient to begin a treatment (e.g., ablation) procedure, the level of contact, tissue type, and/or whether contact is greater than desired for safety. The qualitative indicator 5260 may provide a binary indication (e.g., sufficient contact vs. insufficient contact, contact or no contact, ablated tissue or viable tissue) or a multi-level qualitative indication, such as that provided by the gauge 5250. In one embodiment, the qualitative indicator 5260 displays the color on the gauge 5250 corresponding to the current contact function value. Other types of indicators, such as horizontal or vertical bars, other meters, beacons, color-shifting indicators or other types of indicators may also be utilized with the contact function to convey contact quality to the user. Indicators may include one or more light-emitting diodes (LEDs) adapted to be activated upon contact (or a sufficient level of contact) or loss of contact. The LEDs may be different colors, with each color representing a different level of contact (e.g., red for no contact, orange for poor contact, yellow for medium contact and green for good contact). The LED(s) may be positioned on the catheter handle, on a display or patient monitor, or any other separate device communicatively coupled to the system.

In one embodiment involving delivery of radiofrequency energy using a radiofrequency ablation catheter having a plurality of temperature-measurement devices (such as the ablation catheters and temperature-measurement devices described herein), the criterion for detecting a loss of tissue contact during delivery of radiofrequency energy may be implemented as:

$$\Delta T_i/\Delta t < -\text{Threshold1} \qquad \text{(Condition 1)}$$

or $$\Delta T_{comp}/\Delta P < \text{Threshold2} \qquad \text{(Condition 2)}$$

where $\Delta T_i$ is the change in the temperature of any of the plurality of temperature-measurement devices (e.g., sensors, thermocouples, thermistors) positioned along the catheter or other medical instrument; $\Delta t$ is the interval of time over which the temperature change is measured; $\Delta T_{comp}$ is the change in the maximum of the temperatures of the temperature-measurement devices and $\Delta P$ is the change in applied power.

Condition 1 may signal that the temperature measurements obtained by the temperature-measurement devices have dropped rapidly in a short period of time, which may be indicative of a loss of contact or an insufficient or inadequate level of contact. For example, if $\Delta T_i$ is $-10$ degrees Celsius over a $\Delta t$ of 1 second and Threshold1 is $-5$ degrees Celsius/second, then the contact loss condition is met (because $-10$ degrees Celsius/second $<-5$ Celsius/second).

Condition 2 may signal that the temperature of the temperature-measurement devices is not increasing even though sufficient power is being applied, which may be indicative of a loss of contact or an insufficient or inadequate level of contact. For example, if $\Delta T_{comp}$=5 degrees Celsius and $\Delta P$=30 Watts and if Threshold2 is 1 degree Celsius/Watt, then the contact loss condition is met (because 5 degrees Celsius/30 Watts<1 degree Celsius/Watt).

Electrical measurements (for example, impedance measurements, such as impedance magnitude, impedance phase and/or or slope between impedance magnitudes at different frequencies) obtained by contact detection subsystem or module (which may be, for example, within energy delivery module 40, such as a radiofrequency generator unit, or may be a separate, standalone component) may be affected by hardware components in a network parameter circuit (for example, impedance circuit) or network positioned between the contact detection subsystem or module and the electrodes D1, D2 of a high-resolution electrode assembly, or split-tip electrode assembly, of an ablation catheter or other treatment device. For example, different types (for example, brands, lengths, materials) of cables or wires may have different network parameters and/or other parameters that affect electrical measurements (for example, voltage, current and/or impedance measurements) differently or coiling of the cables or wires can affect electrical measurements. In addition, in some implementations, a catheter interface unit may be connected at some point along the network parameter circuit (or may reside in the electrical path) between the contact detection subsystem or module (for example, contact detection subsystem module) and the electrodes or electrode portions D1, D2 of a high-resolution electrode assembly, or split-tip electrode assembly, of an energy delivery catheter or other treatment device. The catheter interface unit may or may not comprise filters adapted for filtering signals having various frequencies (for example, low-pass filters, band-pass filters, high-pass filters implemented in hardware or software). As one example, the catheter interface unit may comprise a hardware module or unit adapted for facilitating the connection of both a radiofrequency generator and an electroanatomical mapping system to a high resolution mapping and energy delivery catheter having multiple electrode portions or members (devices (such as the ablation catheters or other energy delivery and temperature-measurement devices described herein) is connected at some point along the network parameter circuit (for example, impedance measurement circuit) or otherwise resides in the electrical path of the separated-apart electrode members. The presence or absence of a catheter interface unit or other hardware module or unit, or differences in the network parameters of cables, generators, or wires used may cause variations in the network parameters (for example, scattering parameters or electrical parameters such as impedance measurements depending directly or from voltage and current measurements) or may result in network parameters (for example, electrical measurements or values such as impedance measurements or values) that do not accurately reflect the actual network parameter value (for example, impedance) between two electrodes of a high-resolution electrode assembly, thereby resulting in less accurate and/or inconsistent contact indication values. Accordingly, the lack of accuracy or consistency may adversely affect treatment outcomes or parameters and could have detrimental consequences related to safety and/or efficacy. Thus, several embodiments are disclosed herein to improve the accuracy and consistency of the network parameter values (for example, electrical measurements such as impedance magnitude, slope or phase values or voltage or current measurement values) obtained by an ablation system comprising a combination electrode assembly (for example, high-resolution, or split-tip, electrode arrangement of spaced-apart electrode members or portions).

In accordance with several embodiments, systems and methods for de-embedding, removing, or compensating for the effects caused by variations in cables, generators, wires and/or any other component of an ablation system (and/or components operatively coupled to an ablation system) or by the presence or absence of a catheter interface unit or other hardware component in an energy delivery and mapping system are provided. In some embodiments, the systems and methods disclosed herein advantageously result in contact indication values that are based on network parameter values (e.g., impedance values) that more closely represent the actual network parameter value (e.g., impedance) across the electrodes of the high resolution electrode assembly. Accordingly, as a result of the compensation or calibration systems and methods described herein, a clinician may be more confident that the contact indication values are accurate and are not affected by variations in the hardware or equipment being used in or connected to the system or network parameter circuit. In some arrangements, the network parameter values (e.g., impedance measurements) obtained by the system using the compensation or calibration embodiments disclosed herein can be within ±10% (e.g., within ±10%, 9%, 8%, 7%, 6%, 5%, 4%, 3%, 2%) of the actual network parameter values (e.g., impedance values) across the electrode members of the combination electrode assembly. For example, the impedance magnitude, the impedance slope (ratio of impedance magnitudes at two frequencies) and phase of the impedance may each individually be measured to within +/−10% or better using this approach. As a result, the contact function or contact indicator can advantageously provide an accurate representation of tissue contact, with an accuracy of +/−10% or greater.

FIG. 34A illustrates a schematic block diagram of an embodiment of a network parameter measurement circuit 5400 (e.g., tissue contact impedance measurement circuit). The network parameter measurement circuit 5400 includes a contact sensing signal source 5405, a load 5410 between two electrodes D1, D2 of a high-resolution electrode assembly at a distal end portion of an ablation catheter, and a chain of multiple two-port networks representative of a generator 5415, catheter interface unit cables 5420A, 5420B, a catheter interface unit 5425, a generator cable 5430 and catheter wires 5435. Because in some arrangements the network parameter values (e.g., scattering parameter or electrical measurement such as voltage, current or impedance measurements) are obtained at the beginning of the chain at the level of the generator 5415, the measured network parameter values (e.g., impedance values obtained directly or from voltage and/or current values) may differ significantly from the actual network parameter values (e.g., impedance values) between the two spaced-apart electrode members D1, D2 due to effects of the components of the network parameter circuit between the signal source 5405 and the electrode members D1, D2. The impedance values may comprise impedance magnitude, slope between impedance magnitude at different frequencies, and/or impedance phase values. For example, detected impedance magnitude at a frequency $f_1$ can be as much as ±25% different than the actual impedance magnitude at a frequency $f_1$. Similarly, a detected slope (ratio of impedance magnitudes at frequencies $f_2$ and $f_1$) can be as much as ±50% different than the actual slope. Additionally, the detected phase may be as much as ±−30 degrees different than the actual phase. As a result of these combined inaccuracies, a contact function (CF) or contact indication values may be as much as −100% or +150% different than the intended contact function or contact indication values, thereby rendering the contact function ineffective in determining tissue contact. In accordance with several embodiments, the compensation or calibration embodiments disclosed herein can advantageously improve the accuracy of the contact function or contact indication values.

The network parameters of each of the multi-port (e.g., two-port) networks in the network parameter measurement circuit 5400 can be obtained (e.g., measured) and utilized to convert the measured network parameter value (e.g., scattering parameter or electrical parameter such as impedance) to a corrected (actual) value (e.g., impedance value). In some embodiments, a two-port network analyzer is used to directly measure the scattering parameters (S-parameters) at the input and output of each of the two-port networks. In other embodiments, multiple components of the network parameter measurement circuit 5400 can be combined into groups of components and measured together. The network parameters of the individual components or groups of components can be combined to determine an aggregate effect of the chain of two-port networks on the network parameter value(s). In some implementations, the scattering parameters of at least some of the components may be hard-coded into a software program (e.g., using an average value based on a few measurement samples) so as to reduce the number of measurements to be taken or obtained.

According to one implementation, S-parameter matrices for each of the two-port networks or groups of two-port networks can be transformed to an overall transmission matrix. The overall transmission matrix may then be transformed back into S-parameters (or some other parameters) to generate an S-parameter (or another type of) matrix for the total network. The S-parameters from the total S-parameter matrix can then be used to de-embed, calibrate or compensate for the S-parameters from the measured input reflection coefficient to result in a corrected (actual) reflection coefficient. The actual reflection coefficient may then be converted into a corrected impedance value that is more closely indicative of the actual impedance between the two electrode portions D1, D2 of a high-resolution electrode assembly. In several embodiments, the corrected impedance values are used as the inputs for the Contact Function (CF) or other contact indication or level of contact assessment algorithm or function, as described above. For example, the corrected impedance values can be used to determine the Z, S and P values in the weighted contact function (CF) described above.

The effects of the hardware components of the network parameter measurement circuit (e.g., impedance measurement circuit) 5400 can be compensated for, de-embedded from, or calibrated so as to reduce or remove the effects of the hardware components or differences in the hardware components of a particular system (e.g., impedance measurement circuit) setup prior to first use; however, the components of the network parameter circuit may differ across different procedures as different hardware components (e.g., generators, cables, catheters and/or the like) are used or as a catheter interface unit or other hardware component to facilitate electroanatomical mapping is plugged in or removed, thereby resulting in inconsistency if not compensated for. In some embodiments, the total system S-parameter matrix may only be updated when the connections within the network parameter measurement circuit 5400 change (e.g., when a catheter interface is plugged in or removed from the electrical path, when a cable is switched, etc.).

In some embodiments, instead of requiring a manual de-embedding of the effects on impedance of certain circuit components when connections change (which can be time-consuming and result in increased likelihood of user error), the network parameters of a subset of the various components (e.g., the generator 5415, the catheter interface unit cables 5420A, 5420B and the catheter interface unit 5425) are automatically measured to enable the effects of these elements to be de-embedded from the network parameters (e.g., scattering parameters or impedance measurements) or otherwise compensated for or calibrated. FIG. 34B illustrates an embodiment of a circuit 5450 that can be used to automatically de-embed or compensate for the effects of certain hardware components in the network parameter circuit 5400. In one embodiment, the auto-calibration circuit 5450 is positioned at a distal end of the catheter interface unit cable before the generator cable 5430 and catheter wires 5435. The circuit 5450 may advantageously provide the ability to disconnect the electrode members D1, D2 of the high-resolution electrode assembly from the generator cable 5430 and catheter 5435 and to connect a known load between D1 and D2.

In this embodiment, the auto-calibration circuit 5450 can assume that the network parameters of the generator cable 5430 and catheter wire 5435 components are known and can be assumed to be constant. However, if the generator cable 5430 and/or catheter wires 5435 are determined to vary significantly from part to part, the circuit 5450 could be implemented at the distal end of the generator cable 5430, in the catheter tip or at any other location, as desired or required. In some embodiments, the known load of the auto-calibration circuit 5450 includes a calibration resistor $R_{cal}$ and a calibration capacitor $C_{cal}$. Switches may be used to connect $R_{cal}$ as the load, $C_{cal}$ as the load and both $R_{cal}$ and $C_{cal}$ in parallel as the load. Other elements (such as inductors, combinations of resistors, inductors and/or capacitors, or shorts or open circuits can be utilized as the known load). As shown in FIG. 34B, the combined network parameters of the generator 5415, catheter interface unit cables 5420A, 5420B and the catheter interface unit 5425 are represented as a single combined network (Network 1).

In this embodiment, the network parameters (for example S-parameters) of Network 1 are measured directly using the network parameter circuit and an S-parameter matrix is created from the network parameters. Each of the elements in the S-parameter matrix is a complex number and is frequency dependent. The S-parameters may be measured at multiple different frequencies (e.g., 3 different frequencies in the kHz range, such as a first frequency from 5-20 kHz a second frequency from 25-100 kHz and a third frequency from 500-1000 kHz). In one embodiment, the complex impedance is measured with the resistor $R_{cal}$ connected and the capacitor $C_{cal}$ disconnected, with the capacitor $C_{cal}$ connected and the resistor $R_{cal}$ disconnected and with both the resistor $R_{cal}$ and the capacitor $C_{cal}$ connected in parallel. The relationship between the measured complex impedance, the S-parameters of Network 1 and the known load can be expressed as three equations, which can then be used to solve for the S-parameters of Network 1. Once the S-parameters are characterized, they can be combined (e.g., using a transmission matrix approach) with the known network parameters of the generator cable 5430 and catheter wires 5435 to provide corrected (actual) impedance measurements at the distal end portion of the catheter (e.g., across two spaced-apart electrode portions of a combination electrode assembly).

The automatic calibration techniques and systems described herein advantageously allow for increased confidence in the contact indication values regardless of the generator, cables, catheter or other equipment being used and regardless of whether a hardware component to facilitate simultaneous electroanatomical mapping (e.g., a catheter interface unit) is connected. The various measurements may be performed automatically upon execution of instructions stored on a computer-readable storage medium executed by a processor or may be performed manually.

Figure 34C:
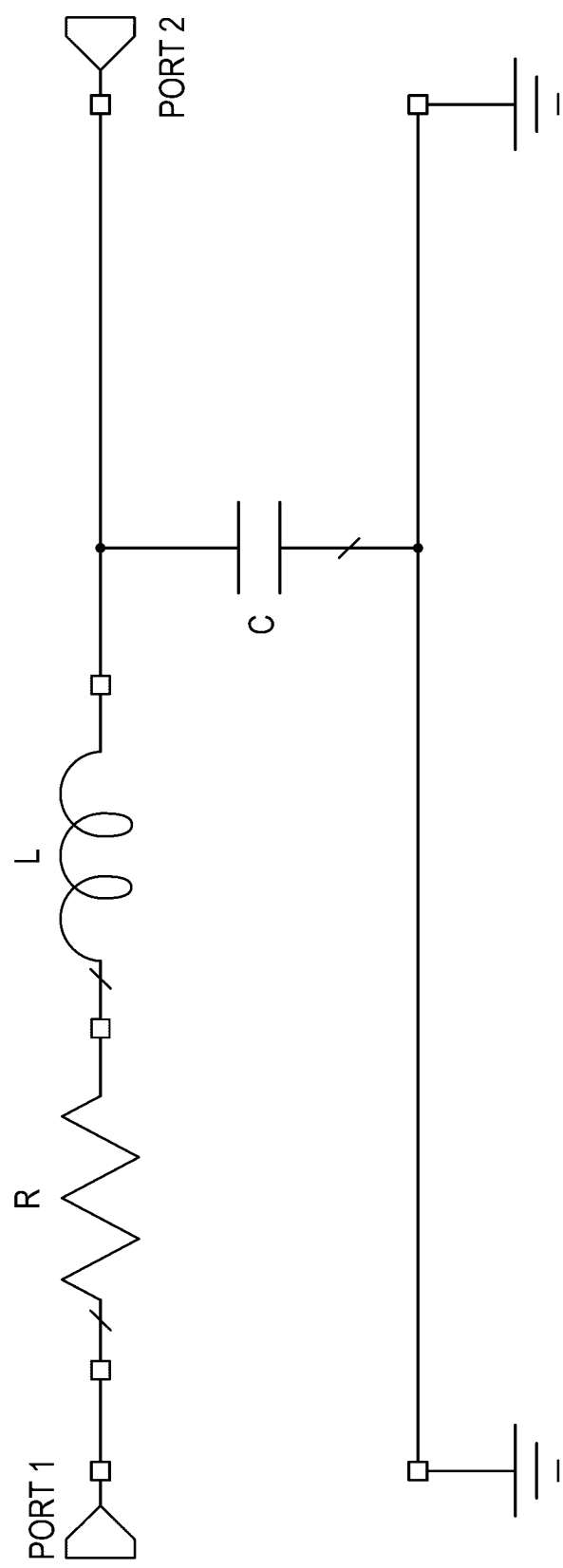
FIG. 34C illustrates a schematic representation of one embodiment of an equivalent circuit model for a hardware component present in an impedance measurement circuit.

The automatic calibration systems and methods described herein may also be implemented using an equivalent circuit model for one or more hardware components of the system (e.g., the generator circuitry, cable and catheter wiring). In such implementations, the equivalent circuit model comprises one or more resistors, one or more capacitors and/or one or more inductors that approximate an actual response of the one or more hardware components being represented. As one example, a generator cable component 5430 can be represented by a transmission-line equivalent RLC model as shown in FIG. 34C, where the measurement of the impedance $Z_{meas}$ would be performed at Port 1 with the actual (corrected) impedance $Z_{act}$ desired being at Port 2. In this example, if the impedance measurement circuit is measuring an impedance $Z_{meas}$, the actual impedance measurement $Z_{act}$ can be extracted by using circuit analysis techniques. The equation relating the two impedances is given by:

$$Z_{meas} = R + j\omega L + \frac{Z_{act}}{1 + j\omega C \cdot Z_{act}}$$

The actual values for R, L and C may be extracted from network parameter measurements. For example if we measure the impedance (Z) parameters of this network, we can derive the following relationships:

$$Z_{11} = \left.\frac{V_1}{I_1}\right|_{(I2=0)} = R + j\omega L + \frac{1}{j\omega C}$$

$$Z_{21} = \left.\frac{V_2}{I_1}\right|_{(I2=0)} = \frac{1}{j\omega C}$$

$$Z_{11} - Z_{21} = R + j\omega L$$

where 1 and 2 denote the port numbers of the circuit, and $V_1$, $I_1$, $V_2$ and $I_2$ represent the voltages and currents at each of the respective ports. The values for R, L and C may also be measured utilizing measurement tools (e.g., a multimeter). The equivalent circuit model approach described above is an example of this concept. In other implementations, more complex circuit models may be utilized to represent the various elements of the system.

Figure 35:
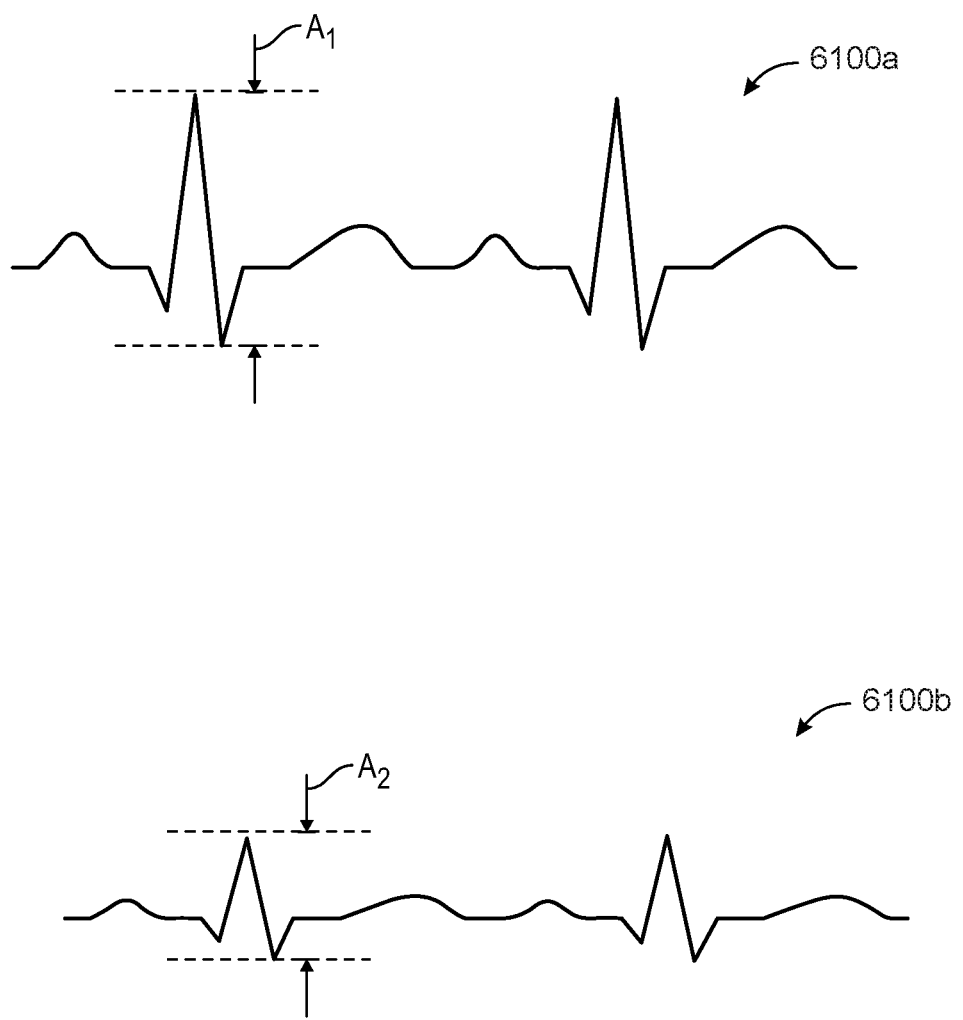
FIG. 35 illustrates embodiments of EKGs obtained from a high-resolution-tip electrode systems disclosed herein configured to detect whether an ablation procedure has been adequately performed.

According to some arrangements, the high-resolution-tip electrode embodiments disclosed herein are configured to provide localized high-resolution electrograms (e.g., electrograms having a highly increased local specificity as a result of the separation of the two electrode portions and a high thermal diffusivity of the material of the separator, such as industrial diamond). The increased local specificity may cause the electrograms to be more responsive to electrophysiological changes in underlying cardiac tissue or other tissue so that effects that RF energy delivery has on cardiac tissue or other tissue may be seen more rapidly and more accurately on the high-resolution electrograms. For example, the electrogram that is obtained using a high-resolution-tip electrode, in accordance with embodiments disclosed herein, can provide electrogram data (e.g., graphical output) 6100a, 6100b as illustrated in FIG. 35. As depicted in FIG. 35, the localized electrograms 6100a, 6100b generated using the high-resolution-tip electrode embodiments disclosed herein include an amplitude A1, A2.

With continued reference to FIG. 35, according to some embodiments, the amplitude of the electrograms 6100a, 6100b obtained using high-resolution-tip electrode systems can be used to determine whether targeted tissue adjacent the high-resolution-tip electrode has been adequately ablated or otherwise treated. For example, according to some configurations, the amplitude A1 of an electrogram 6100a in untreated tissue (e.g., tissue that has not been ablated or otherwise heated, tissue that has not been ablated or otherwise heated to a desired or required threshold, etc.) is greater that the amplitude A2 of an electrogram 6100b that has already been ablated or otherwise treated. In some embodiments, therefore, the amplitude of the electrogram can be measured to determine whether tissue has been treated (e.g., treated to a desired or required level in accordance with a particular treatment protocol). For example, the electrogram amplitude A1 of untreated tissue in a subject can be recorded and used as a baseline. Future electrogram amplitude measurements can be obtained and compared against such a baseline amplitude in an effort to determine whether tissue has been ablated or otherwise treated to an adequate or desired degree.

In some embodiments, a comparison is made between such a baseline amplitude (A1) relative to an electrogram amplitude (A2) at a tissue location being tested or evaluated. A ratio of A1 to A2 can be used to provide a quantitative measure for assessing the likelihood that ablation has been completed. In some arrangements, if the ratio (i.e., A1/A2) is above a certain minimum threshold, then the user can be informed that the tissue where the A2 amplitude was obtained has been properly ablated. For example, in some embodiments, adequate ablation or treatment can be confirmed when the A1/A2 ratio is greater than 1.5 (e.g., 1.5-1.6, 1.6-1.7, 1.7-1.8, 1.8-1.9, 1.9-2.0, 2.0-2.5, 2.5-3.0, values between the foregoing, greater than 3, etc.). However, in other embodiments, confirmation of ablation can be obtained when the ratio of A1/A2 is less than 1.5 (e.g., 1-1.1, 1.1-1.2, 1.2-1.3, 1.3-1.4, 1.4-1.5, values between the foregoing, etc.).

According to some embodiments, data which relate to tissue ablation or other tissue heating or treatment and which are collected, stored, processed and/or otherwise obtained or used by an ablation system can be integrated with data obtained by one or more other devices or systems, such as, for example, a mapping system. As used herein, data is a broad term and includes, without limitation, numerical data, textual data, image data, graphical data, unprocessed data, processed data and the like. As discussed in greater detail herein, such integration of data can be used to advantageously provide useful information to a physician or other user (e.g. via a monitor or other output). For example, certain data can be configured to be displayed in relation to various ablation or other heating points or locations that are visually depicted on a model of the targeted region of a subject's anatomy (e.g., atrium, other chamber or location of the heart, other tissue or organs, etc.). In some embodiments, such a model comprises a three-dimensional rendering or other model of the anatomy that is generated, at least in part, by a mapping system. As used herein, mapping system is a broad term and includes, without limitation, a three-dimensional (3D) electroanatomical navigation system, a rotor mapping system, other types of navigation and/or mapping devices or systems, an imaging device or system and/or the like.

According to some embodiments, a mapping system (e.g., a 3D electroanatomical navigation system, another type of device or system that is configured to generate a model of the anatomical structures surrounding a particular anatomical location, etc.) is configured to receive data and other information regarding an ablation procedure from a separate ablation or tissue treatment device or system (e.g., a catheter-based, RF ablation system, as disclosed herein) and/or any other type of mapping device or system that is configured to facilitate a treatment procedure (e.g., a rotor mapping system, another imaging or mapping device, any other electrophysiology device or system, etc.). In other embodiments, however, the ablation device or system is configured to be integrated with a mapping system and/or one or more other mapping or other devices or system, as desired or required.

In embodiments where the mapping system is separate and distinct from an ablation device or system and/or any other device or system, the mapping system can be configured to integrate with such other devices or systems. For example, in some embodiments, the mapping system (e.g., electroanatomical navigation system) can be designed and otherwise adapted to receive data from a processor of a generator, other energy delivery module and/or any other component of an ablation system. Thus, the mapping system can include one or more processors, ports (e.g., for hardwired connection to and integration with the separate devices/systems), wireless components (e.g., for hardwired connection to and integration with the separate devices/systems), filters, synchronization components or device and/or the like. In some arrangements, the mapping system (e.g., a 3D electroanatomical navigation system) can be configured to work with two or more different ablation devices or systems, as desired or required.

According to some embodiments, any of the ablation devices and systems disclosed herein, or equivalents thereof, can be configured to provide information to a user regarding one or more completed ablations (e.g., ablation occurrences, spots or locations) along the targeted anatomy (e.g., cardiac tissue) of a subject. Such ablation data may include, without limitation, temperature, power, electrode orientation, electrode-tissue contact quality or amount (e.g. contact index or contact force), etc. Such ablation data can be provided via integration into an existing mapping system (e.g., the EnSite™ Velocity™ Cardiac Mapping System by St. Jude Medical, Inc., CARTO® 3 EP System by Biosense Webster, Inc, Rhythmia™ Mapping System by Boston Scientific, Inc., any other electroanatomical navigation system, etc.). For example, in some arrangements, information collected by the ablation system during an ablation procedure can be processed and integrated with mapping data (e.g. graphical output) of a separate 3D electroanatomical navigation system or other mapping system. In some embodiments, the graphical output of the separate mapping system can be configured to create and display a three-dimensional model of the targeted anatomical region (e.g., pulmonary veins, atrium, other chambers of the heart, other organs, etc.), the electrode and catheter itself, the located where an ablation was performed and/or the like. In other embodiments, the combined data are displayed on a monitor that is separate and district from any portion or component of the separate mapping system. For example, the combined model or other graphical or textual representation can be configured to be depicted on a display or output of the ablation system, an altogether separate monitor or output device (e.g., one that is in data communication with the mapping system and/or the ablation system and/or the like).

In arrangements where a mapping system with a graphical user interface or other graphical output (e.g., that determines the 3D location of the catheter or electrode and creates a three-dimensional view of the targeted anatomical region being treated) is separate from a system that receives, processes, stores and otherwise manipulates data regarding the various ablations (e.g., ablation occurrences, points, spots, etc.) created by the an ablation device (e.g., a catheter with a RF electrode), the two systems can be integrated or otherwise coupled to one another via one or more processors or control units. In some embodiments, such processors or control units can be included, at least partially, within the mapping system, within the ablation system, within both systems and/or one or more separate devices or systems, as desired or required.

In some embodiments, the 3D location data, EGM activity data, rotor mapping data, ablation data and/or any other data can be provided in a single, stand-alone system that is configured to provide a graphical output and other mapping data (e.g., EGM activity data, rotor mapping data, etc.), and ablation data within the same user interface. For example, in some arrangements, such a stand-alone system can be configured to provide the graphical output and the ablation data without the need for integration or other manipulation of data. In other words, in some embodiments, such a stand-alone system can be manufactured, assembled or otherwise provided to a user in a ready-to-use design.

Figure 36A:
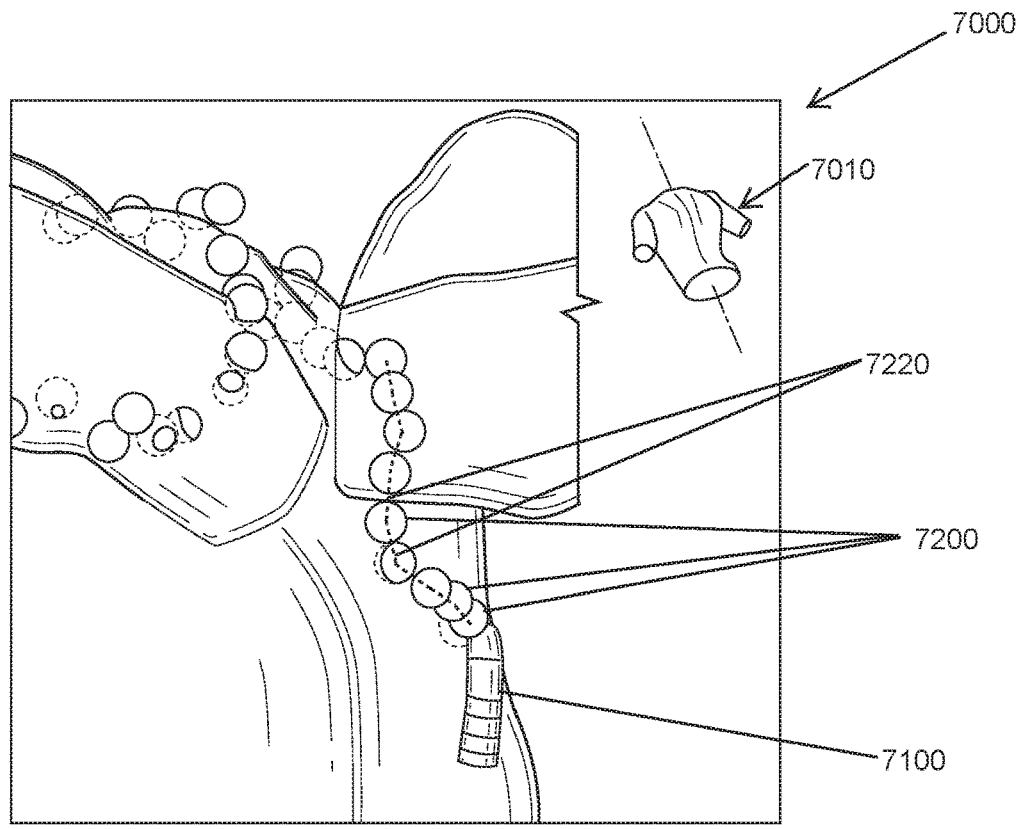
FIGS. 36A and 36B illustrate different embodiments of a graphical representation of a target anatomical area being ablated together with ablation data and/or information.

FIG. 36A illustrates one embodiment of a graphical output 7000 provided to a user via a monitor, another type of display or any other output device. Such a monitor or other output device can be configured to be part of an ablation system. Alternatively, the output device can be separate of an ablation system (e.g., a standalone device) or part of a separate mapping system (e.g., 3D electroanatomical navigation system, other mapping device or system, etc.), another type of imaging or guidance system, etc. In such configurations, the output device can be advantageously configured to operatively couple to an ablation system (e.g., the generator or other energy delivery module, a processor or controller, etc.).

As shown in FIG. 36A, the tip or distal portion of the ablation catheter 7100 can be visible on the display or other output. As also illustrated in this embodiment, the various points along the targeted tissue (e.g., cardiac tissue) that have been ablated can be depicted as circles, dots or any other symbol or design. In some configurations, one or more other symbols or representations other than circles or dots can be used to denote the locations where ablation or heating/treatment has been performed. For example, rectangles (e.g., squares), ovals, triangles, other polygonal shapes (e.g., pentagons, hexagons, etc.), irregular shapes and/or the like can be used, either in addition to or in lieu of circles.

In some embodiments, as illustrated in FIG. 36A, the monitor or other output 7000 can be configured to display the orientation of the body of the subject being treated via a graphical representation 7010 of a torso. Accordingly, the user performing the procedure can better visualize and understand the anatomy that is mapped and indicated on the output.

Any other information or data can also be provided on the output 7000, either in addition to or in lieu of what is depicted in FIG. 36A. For example, in some embodiments, information or data displayed on the output can include, but not limited to, the date, time, duration and/or other temporal information regarding a procedure, the name and/or other information about the subject being treated, the name and/or other information about the physician and/or others conducting or assisting with the procedure, the name of the facility and/or the like, as desired or required.

Figure 36B:
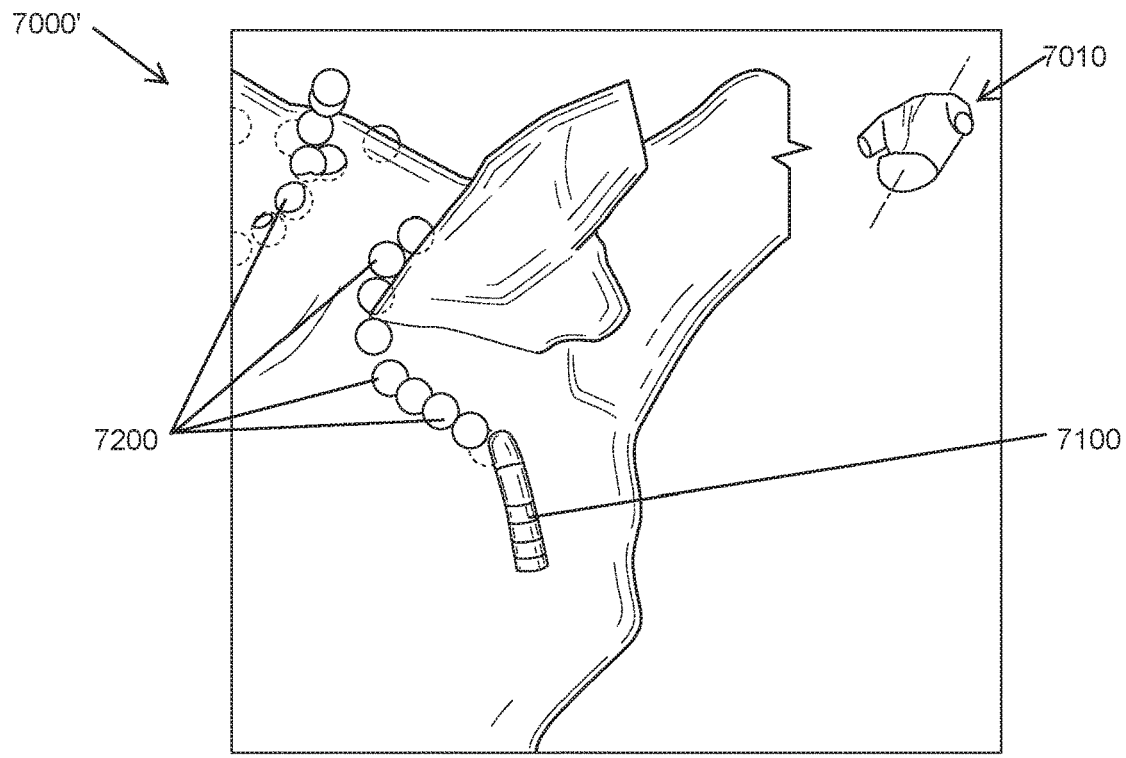

According to some arrangements, as illustrated in FIGS. 36A and 36B, the graphical representation of the ablations 7200 displayed on the monitor or other output 7000 can help ensure that a physician accurately creates a desired ablation or heating/treatment pattern in the targeted anatomy. For example, in some embodiments, the individual ablations form a circular or rounded pattern around one or more pulmonary veins of a subject (e.g., around the ostium of a single pulmonary vein, around the ostia of two adjacent pulmonary veins, along the roofline between adjacent ostia, etc.). In other embodiments, as discussed in greater detail herein, the ablation pattern can be located along at least a portion of a heart chamber (e.g., atrium) to disrupt aberrant pathways along or near the pulmonary veins (e.g., along one or more ostia of the pulmonary veins).

Figure 37A:
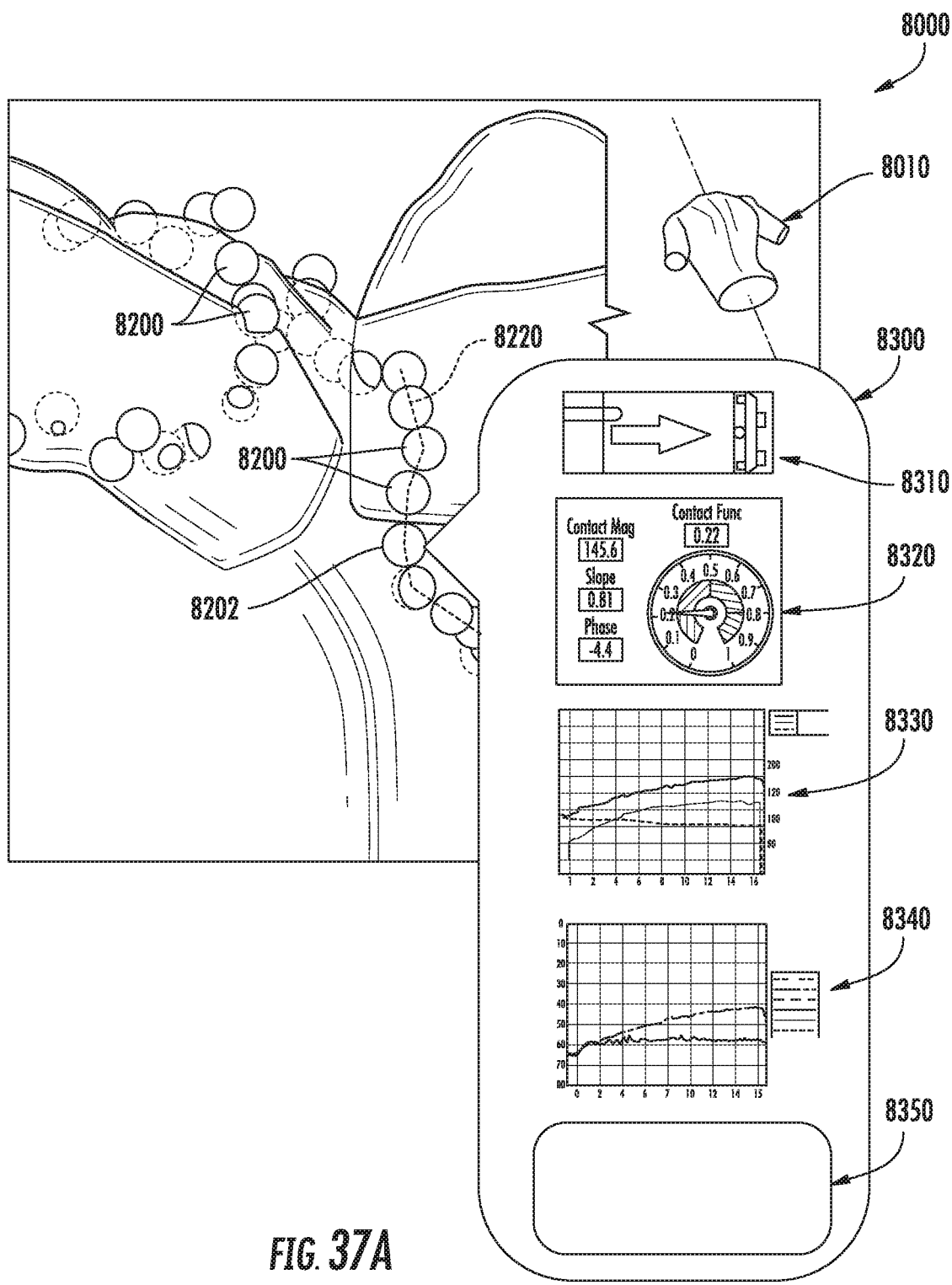
FIG. 37A illustrates one embodiment of a graphical representation that is configured to provide data and/or information regarding specific ablations along targeted portions of a subject's anatomy.

In some embodiments, information related to each ablation (e.g., ablation instance, occurrence, point or location) 7200 of a series of individual ablations included in an ablation procedure can be provided to the user via the monitor other output 7000. By way of example, information can be provided to a user regarding an ablation 7200 when the user identifies a specific point or location. For example, in some embodiments, by manipulating a mouse, a touchpad and/or other device (e.g., the cursor or other pointing feature of such devices) on or near a particular ablation, a user can be provided with information regarding that ablation point or location. In other embodiments, selecting a particular ablation can be done by a user touching a specific portion of a touchscreen with his or her finger. Regardless of how a specific ablation is "selected" or otherwise "activated" by a user, the output (and the corresponding devices and/or systems to which the output are operatively coupled) can be configured to provide certain data and/or other information regarding such a selected ablation. For instance, as illustrated in FIG. 37A, once a user "hovers" over or otherwise selects a particular ablation 8202, a separate window 8300 (e.g., a pop-up or side window) can be displayed on the monitor or other output 8000. Further, according to some arrangements, once the user moves his or her cursor, finger and/or other selection device or feature away from a particular ablation, the separate window 8300 can collapse or otherwise disappear. In some embodiments, the pop-up or separate windows are configured to stay activated or otherwise visible for a particular time period following selection or activation (e.g., for 0.5 to 5 seconds, 5 to 10 seconds, longer than 10 seconds, time periods between the foregoing ranges, etc.), as desired or required. Advantageously, such configurations can permit a user to quickly, easily and conveniently review data and other information regarding the procedure being performed using the ablation system.

In some embodiments, the manner by which ablation data, electrical activity data (e.g., EGM activity data, rotor mapping data, etc.) and/or any other data are synchronized or linked to a specific can vary. For example, in some embodiments, ablation and/or other data can be captured during the time period (during the entire time period, some point in time during the time period, a subset of the time during the time period, etc.) that an ablation is occurring (e.g., during the time period when energy is being delivered from a generator or other energy delivery module to the electrode of the catheter). In some configurations, for example, a physician (and/or another individual assisting with a procedure, e.g., another physician, a technician, a nurse, etc.) is able to commence and terminate such energy delivery via one or more controllers (e.g., foot pedal, a hand-operated controller, etc.).

Therefore, according to some configurations, data from an ablation device or system (e.g., data captured, calculated, stored and/or otherwise processed by a generator or other component of the ablation device or system), data from a separate mapping system (e.g., a device or system used to obtain and process EGM activity data, rotor mapping data, etc.) and/or the like is automatically provided to and synchronized with one or more processors of another mapping system (e.g., a 3D electroanatomical navigation system), as noted herein. Such synchronization and integration can occur simultaneously with the execution of an ablation procedure or once the procedure has been completed, as desired or required.

In other embodiments, however, the synchronization and integration of data between different devices and systems can be performed in other ways, either during or after the execution of an ablation procedure. For example, time logs between the different devices and systems can be aligned to extract the necessary data and other information from the ablation system and/or any other separate system (e.g., a mapping system configured to obtain and process EGM activity data) to "match up" or otherwise assign the necessary data to each ablation that is mapped by the mapping system (e.g., the 3D electroanatomical navigation system).

According to some arrangements, the data and other information provided to a user in the pop-up windows on the display or other output device can be fixed or set by the manufacturer or supplier of the various components of the system (e.g., an integrated mapping/ablation system, a stand-alone 3D electroanatomical navigation system, etc.). However, in other embodiments, the data and information can be customized by the user, as desired or required. Accordingly, a user can choose the data and information that is desired for a particular application or use.

In some embodiments, as illustrated in the embodiment of FIG. 37A, the data and other information provided to the user (e.g., in a pop-up or other separate window 8300) by hovering over or otherwise selecting an ablation 8202 can include, among other things, information (e.g., graphical, textual, etc.) regarding the electrode's orientation relative to targeted tissue 8310, contact information 8320 (e.g., a qualitative or quantitative output relating to the level of contact between the electrode and tissue as described in further detail herein), a graph or waveform illustrating impedance measurements and determinations, slope measurements and determinations, phase measurements and determinations, a contact index or other calculation (e.g., based on various contact measurements such as, for instance, magnitude, slope and/or phase, etc.), temperatures curves/profiles (e.g., of targeted tissue over time), electrogram amplitude reduction charts and/or data (e.g., per the configurations disclosed in FIG. 35) and/or the like, as desired or required.

With continued reference to FIG. 37A, the pop-up or separate window 8300 related to an ablation 8202 includes a chart 8330 that plots tissue temperature (e.g. composite tissue temperature from the various thermocouples or other temperature sensors at or near the electrode), power and impedance over time. As noted in greater detail herein, such information (e.g., whether in graphical or textual form) can be valuable to the physician performing an ablation procedure. For example, the physician can quickly and conveniently hover over various ablations (e.g., ablation instances, points or locations) 8200, 8202 to ensure that ablation of the targeted tissue has occurred according to his or her requirements and desires. In other embodiments, the pop-up or separate window 8300 can include one or more other charts or plots, as desired or required by a particular user or facility. For example, in some embodiments, the window includes a chart of the temperature detected by the various thermocouples or other sensors located at or near the electrode over time (see, for example, FIGS. 22A, 22B, 23A and 23B). In some embodiments, as illustrated in FIG. 37A, the separate window 8300 can include temperature measurements over time for each of the proximal and distal thermocouples (or other temperature sensors) included along the electrode. As shown, the temperature data can be presented in graphical form to allow a practitioner to quickly and easily compare the readings from different thermocouples. Such curves, either alone or together with other data and information provided via the graphical representation of the output device, can ensure that the practitioner maintains well informed during an ablation procedure. For example, such a graph of individual thermocouple trends can permit the practitioner to assess whether desired or adequate contact between the electrode and the targeted tissue is maintained during ablation. In some arrangements, for example, review of the individual thermocouples curves can infer a clinical decision, such as, the quality of tissue contact, whether and when loss of contact or dislodgement occurred and/or the like, as discussed in greater detail herein. Thus, in some configurations, the system can alert a user (e.g., visually, audibly, etc.) of such dislodgement or any other potentially undesirable occurrence. In some embodiments, a separate display region, portion or area 8350 of the window 8300 (and/or any other portion or area) can be provided along the pop-up window 8300 to provide additional data or information to a user, such as, for example, EGM activity data, rotor map data, additional temperature data and/or the like.

In some embodiments, as noted herein, the pop-up or separate window 8300 can be customizable by the user. Thus, for example, a user can choose (and between procedure or over time, modify) the graphical, textual and/or other data and information that is displayed in the pop-up window 8300. In addition, various other features and characteristics related to the pop-up window can be modified. For instance, the hover sensitivity of the system (e.g., how close a cursor, touching motion or other selection method or technique needs to be to an ablation to activate the pop-up window), whether the user needs to click or otherwise manipulate a controller (e.g. mouse button, pressing a touchscreen, etc.) to activate the pop-up window, how long the pop-up window stays activated before disappearing from the monitor or other output device, the size, color and/or other general display features of the graphical and/or textual information provided on the pop-up display (e.g., text font and size, colors, etc.) and/or the like.

As noted in greater detail herein, in some embodiments, the contact function or indicator may be represented as a virtual gauge that provides a qualitative assessment (either alone or in addition to a quantitative assessment) of contact state or level of contact in a manner that is easily discernable by a clinician. Such a gauge can be segmented into, for example, four segments, or regions, that represent different classifications or characterizations of contact quality or contact state. For example, a first segment (e.g., from contact function values of 0 to 0.25) may be red in color and represent no contact, a second segment (e.g., from contact function values of 0.25 to 0.5) may be orange in color and represent "light" contact, a third segment (e.g., from contact function values of 0.5 to 0.75) may be yellow in color and represent "medium" or "moderate" contact, and a fourth segment (e.g., from contact function values of 0.75 to 1) may be green in color and represent "good", or "firm", contact. In other embodiments, fewer than four segments or more than four segments may be used (e.g., two segments, three segments, five segments, six segments). In one embodiment, three segments are provided, one segment for no contact or poor contact, one segment for moderate contact and one segment for good, or firm, contact. The segments may be divided equally or otherwise as desired and/or required. Other colors, patterns, graduations and/or other visual indicators may be used as desired. Additionally, a "contact alert" color or gauge graduation may be provided to alert the user about engaging the catheter or other medical instrument with too much force (e.g., contact function values greater than 1). The gauge may include a pointer member that is used to indicate the real-time or instantaneous value of the contact function on the gauge. Such a gauge and/or other contact data and information can be displayed in the pop-up window 8300. The contact index displayed may be determined using the drift correction techniques described herein based on reference measurements. The reference measurements and the times they were obtained could also be displayed.

Additional data and/or information regarding an ablation can be displayed, either in lieu of or in addition to the foregoing. For example, the data and/or information can comprise, without limitation, information (e.g., graphical, textual, etc.) regarding the electrode's orientation relative to targeted tissue, temperature data (e.g., tissue temperature before, during and/or after ablation, the rate of change of tissue temperature during an ablation procedure, etc.), contact information (e.g., a qualitative or quantitative output relating to the level of contact between the electrode and tissue as described in further detail herein, whether contact with previously ablated or non-ablated tissue has been achieved, etc.), a graph or waveform illustrating impedance measurements and determinations, slope measurements and determinations, phase measurements and determinations, textual measurements of impedance, contact index or other calculations (e.g., based on various contact measurements such as, for instance, magnitude, slope and/or phase, etc.), temperatures curves/profiles (e.g., of targeted tissue over time), electrode orientation during ablation, applied RF power statistics (e.g. maximum and average power), electrogram amplitude reduction charts and/or data, mapping images and/or data, heart rate, blood pressure and other vitals of subject during the specific ablation, and/or the like.

According to some embodiments, the individual ablations depicted on a monitor or other output can be represented by symbols (e.g., circles, rectangles, other shapes, etc.) that are configured to vary in size (e.g., diameter, other cross-sectional dimension, etc.), color and/or in any other visually apparent manner, based on, at least in part, one or more parameters associated with the ablation at the corresponding point or location. By way of example, in some embodiments, the diameter of a first ablation can be larger (e.g., proportionally or non-proportionally) than the diameter of a second ablation when the first ablation is associated with a greater level of tissue ablation (e.g., greater size (e.g., deeper, longer, wider, larger area of impact, etc.), higher temperature of ablated tissue, longer duration of energy application, etc.). In some embodiments, the differences in size (e.g., diameter) of the various ablations are proportional to one or more ablation characteristics, as listed above.

Figure 37B:
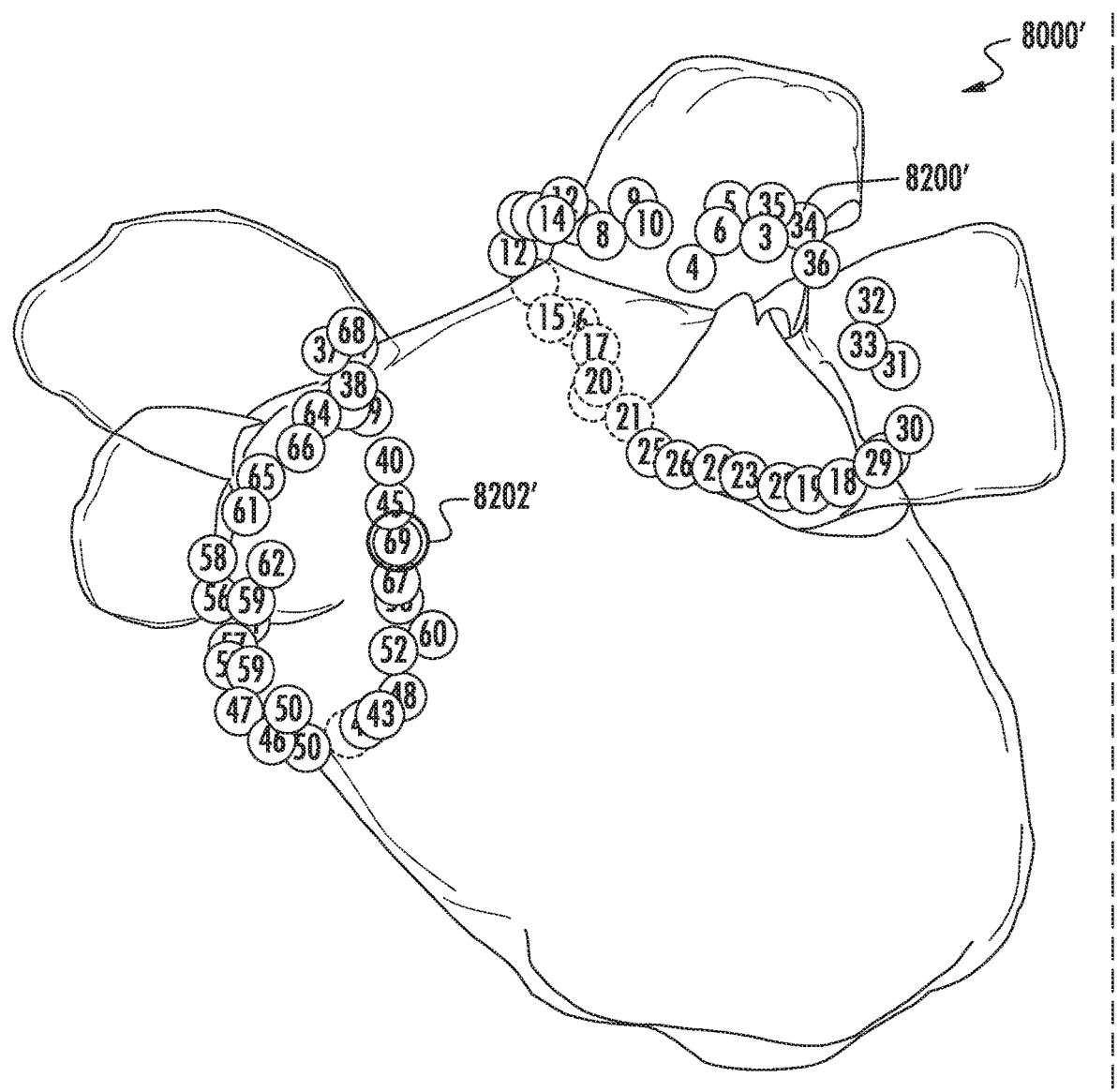
FIG. 37B illustrates another embodiment of a graphical representation that is configured to provide data and/or information regarding specific ablations along targeted portions of a subject's anatomy.
Figure 37B:
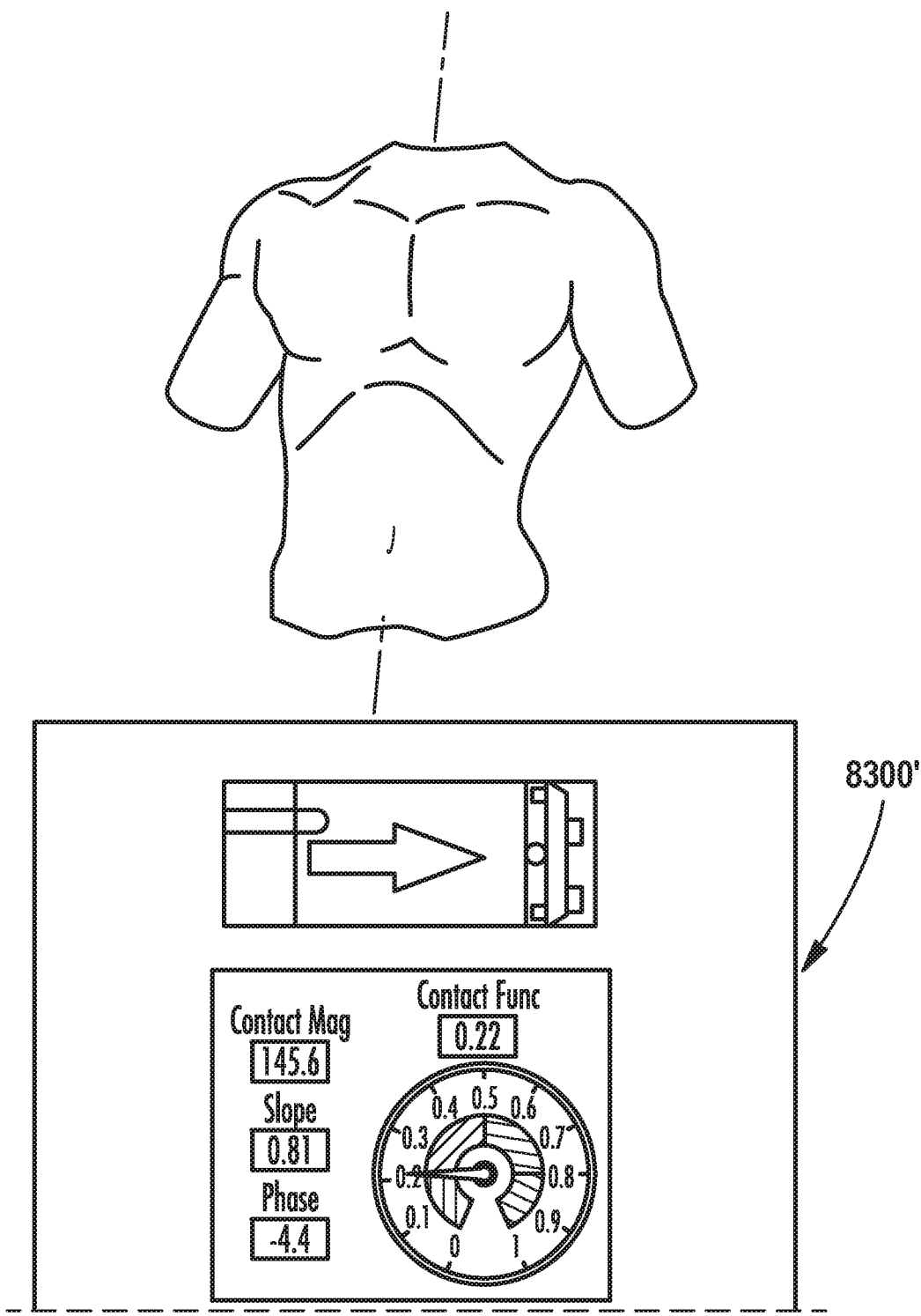
Figure 37B:
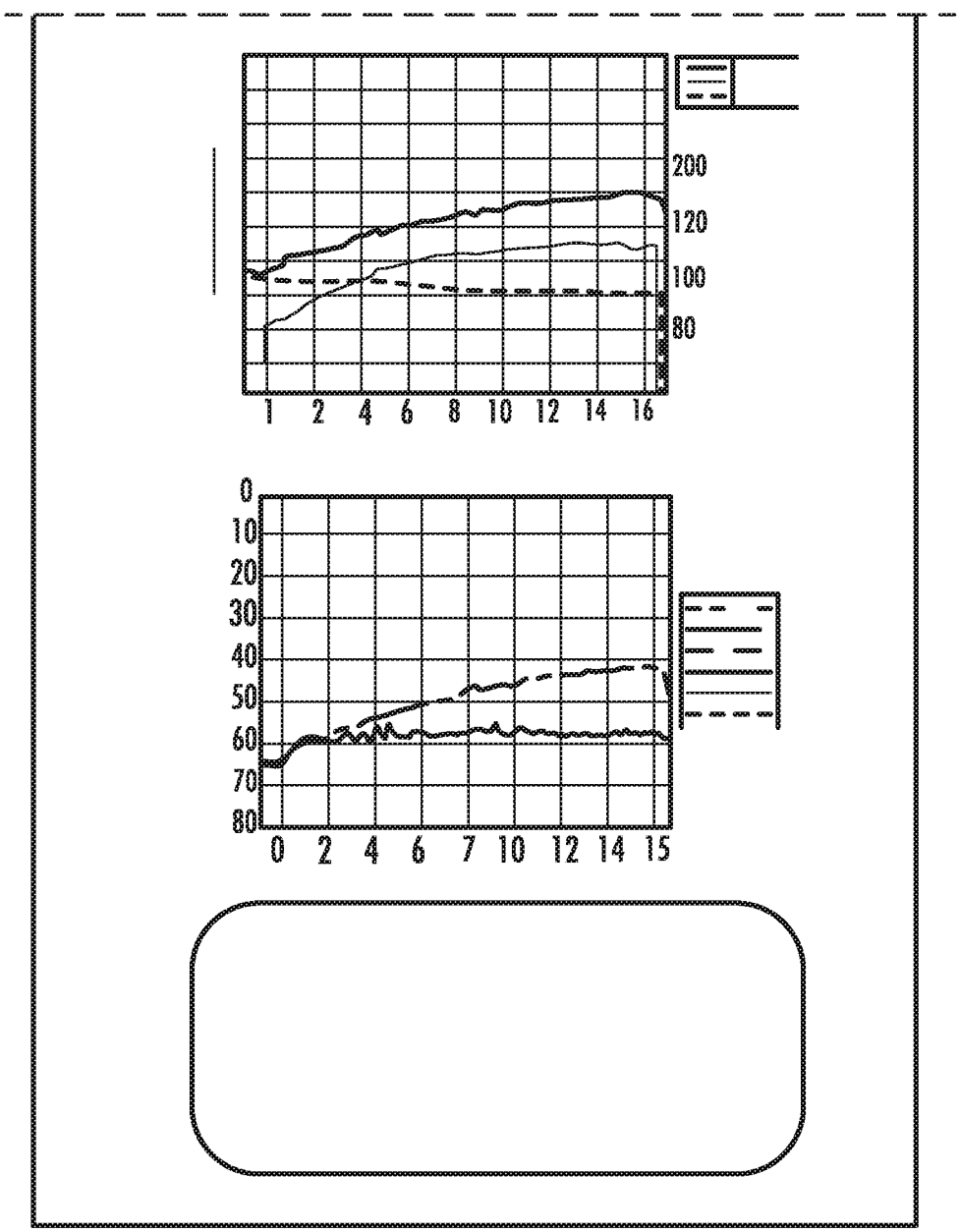

Another embodiment of a representation provided on a monitor or other output device 8000' is illustrated in FIG. 37B. As shown, the targeted anatomical area being treated has been mapped and is depicted in a three-dimensional model. Further, the various ablations 8200' that have been conducted during a procedure can be illustrated relative to the mapped tissue. In the depicted embodiment, such ablations are numbered or otherwise labeled (e.g., sequentially in the order of ablation). However, in other arrangements, the ablations 8200' need not be labeled. As shown in FIG. 37B, in some configurations, information related to the ablations (e.g., orientation, contact data, temperature curves, etc.) can be provided in a window or area 8300' of the graphical representation 8000' that remains on the monitor during an entire treatment procedure. Thus, in some embodiments, unlike the features of the representation discussed above with reference to FIG. 37A, the data and other information relating to the ablations is not provided in a pop-up window. In some embodiments, the data and other information provided in window 8300' pertains to a specific ablation 8202' that the practitioner or other user has selected (e.g. via hovering, depression of a touchscreen and/or any other selection technique).

In some embodiments, as illustrated in FIG. 38, the graphical representation 9000 of the various ablations 9400 depicted on a monitor or other output can include graphical and/or textual data that are configured to be constantly visible (e.g., for a duration of an entire procedure or at least longer than the relatively brief time period of the pop-up window configurations disclosed herein). Such arrangements can be helpful to simultaneously provide to a physician or other reviewer of the monitor or other output of the graphical representation 9000 data and information about two or more (e.g., some or all) ablations of an ablation procedure. Thus, in some embodiments, a physician can conveniently and easily assess (e.g., via a single image, without the need to activate separate pop-up windows or the like) the status of an ablation procedure. Further, in some arrangements, the constantly-presented data and information can assist the physician in identifying potential gaps in lesion formation (e.g., areas of targeted tissue that are non-ablated or under-ablated). As a result, the user can target such tissue areas to ensure a more complete and effective ablation procedure.

With continued reference to FIG. 38, the orientation of the electrode (or other energy delivery member) located along a distal end of a catheter 9100 relative to skin at each ablation can be illustrated in a single graphical representation 9000. As shown, in some arrangements, each ablation 9200 can include (e.g. within it, adjacent to it, etc.) one of three symbols 9400 that indicates whether the electrode was in a parallel, perpendicular or oblique orientation relative to tissue, in accordance with the various determination methods and techniques disclosed herein.

In some embodiments, each ablation 9200 illustrated in a graphical representation 9000 can include an illustrated treatment area 9500 that approximates a zone or area of ablation (e.g., effective ablation, ablation that meets certain threshold requirements, etc.). For example, in some embodiments, such an area 9500 can identify the portion of tissue along each ablation 9200 that was heated above a targeted temperature (e.g., 60 degrees C.) or some other threshold temperature that provides a level of comfort to the physician that sufficient tissue heating was accomplished, as desired or required for a particular procedure or protocol. In some arrangements, the various treatment area representations 9500 can be color coded (e.g., yellow for low heating, orange for medium heating, red for high heating, etc.) to provide more detailed information to the physician. In other embodiments, such color coding can depend on approximated and/or actual tissue temperatures. Thus, the various treatment area representations 9500 associated with each ablation can be color-coded (e.g., different colors, different shades (e.g., gray-scale) or other color property levels, etc.) according to a temperature legend that may also be displayed.

With further attention to FIG. 38, regardless if or how the various treatment area representations 9500 surrounding the ablations 9200 are color-coded or otherwise distinguished, the graphical representation 9000 can be configured to advantageously indicate areas or zones around or along the ablations 9200 where the heating or ablation effects of adjacent ablations are compounded. Alternatively, as described in greater detail herein (e.g., with reference to FIGS. 38 and 39), estimates or determinations of lesion depth, width or volume, may be drawn and displayed as part of a graphical representation or other output. For example, in FIG. 38, such regions or areas 9500 that include the overlapping ablation/heating effects of two or more separate ablations 9200 are illustrated in darker color. Overlapping may be determined or estimated based on lesion depth, width and volume estimates, as explained herein (e.g., with reference to FIGS. 38 and 39). Various other graphical representations, in addition to or lieu of those depicted herein, can be used to conveniently provide useful information to a physician or other user or viewer of such systems about a particular ablation procedure. Thus, as noted above, the physician can better assess the status of a procedure and, if necessary, conduct supplemental, well-targeted ablation to ensure a successful result.

In some embodiments, the graphical representation can be configured to display a pathway of a desired or required ablation pattern. Such a pathway (not illustrated herein) can guide and otherwise assist the physician in following a predictable, safe and efficacious ablation path when conducting an ablation procedure. In certain arrangements, such a desired pathway can be illustrated as a line, points and/or in any other manner that distinguishes it from other elements on the graphical representation 9000, as desired or required.

Figure 39:
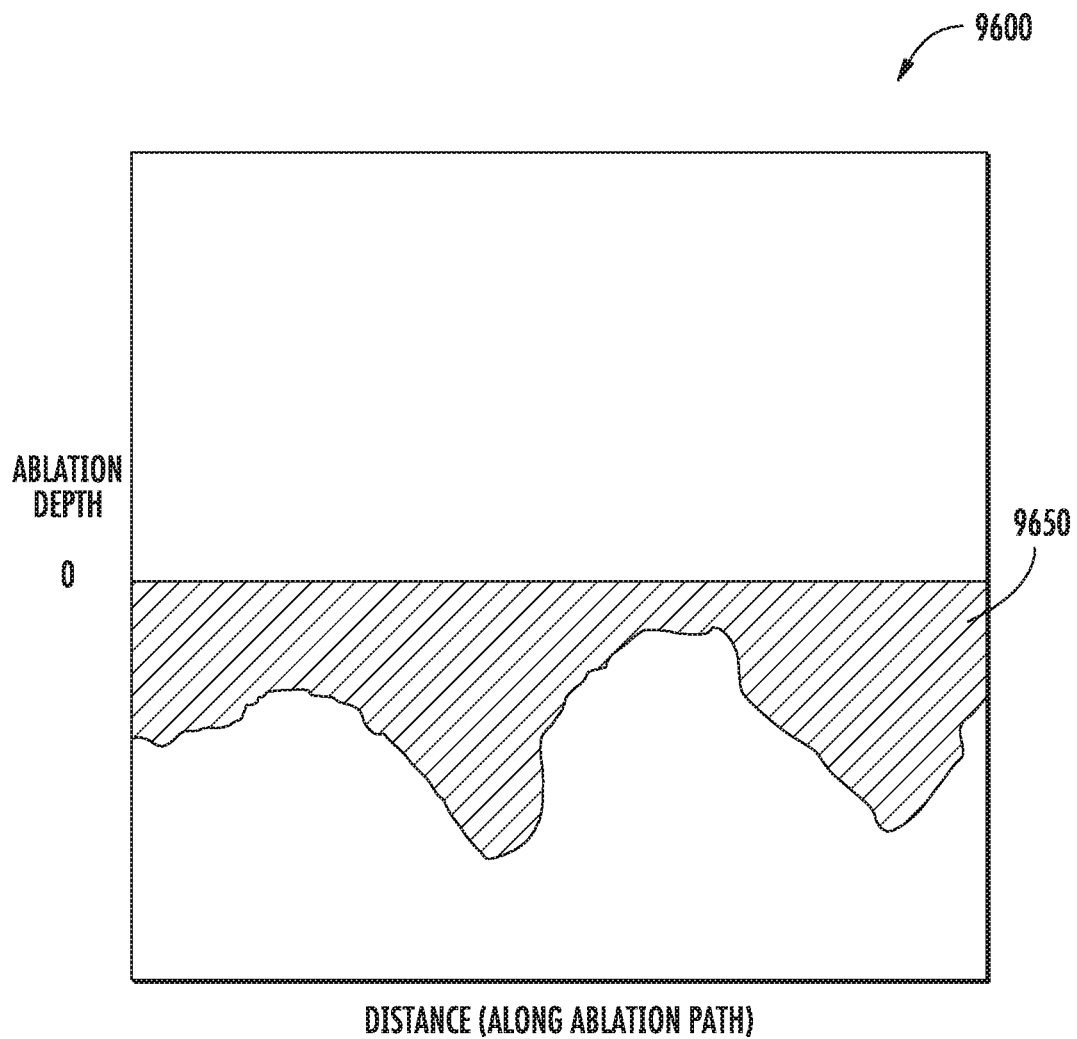

FIG. 39 illustrates a two-dimensional graph of ablation depth over a particular ablation pathway. Such ablation depth data may be derived or estimated from electrode orientation, temperature, power, tissue-contact information and/or any other input. As discussed in Panescu et al., "Three-Dimensional Finite Element Analysis of Current Density and Temperature Distributions During Radio-Frequency Ablation," IEEE Transaction on Biomedical Engineering, Vol. 42, No. 9 (September 1995), pp. 879-889, which is hereby incorporated by reference herein and made part of the present specification, lesion depth and width depend on electrode orientation, temperature and power, among other factors. Accordingly, a graphical representation or other output 9600 can be configured to incorporate such data in order to draw and estimate lesion depth, width or volume profile, as desired or required. For example, in some embodiments, the ablation pathway can include a generally circumferential path around a pair of pulmonary veins within the left atrium of a subject (e.g., around the ostia of such veins). In some arrangements, as known in the art, such an ablation procedure can help disrupt aberrant conduction patterns in subjects with atrial fibrillation or other cardiac arrhythmias. Thus, either in combination with or in lieu of the ablation area approximations (as illustrated in FIG. 38), a system can be configured to determine (e.g., estimate in accordance with various embodiments disclosed herein) the effective ablation or targeted heating depth, width and/or volume along the tissue being treated. As shown in the graphical representation 9600 in FIG. 39, the system can illustrate the ablation depth 9650 as a function of distance along the treatment pathway. Such information can be displayed (e.g., continuously, intermittently (for example, as part of a pop-up window), etc.) together with an overall ablation representation, as shown in FIG. 37A or 37B or FIG. 38. Thus, a physician can be effectively provided with a three-dimensional assessment associated with an ablation procedure, where both areal/spatial extent and depth of ablation (or desired heating) of tissue are graphically represented to him or her during a procedure. In other embodiments, a three-dimensional, volumetric representation of ablated tissue can be provided to the user that graphically combines areal extent and depth into a single integrated image.

As noted herein, regardless of how data and other information related to a particular procedure is processed and displayed to a user, such embodiments can be advantageous in easily and conveniently assessing potential weak or clinically susceptible points or locations in a procedure (e.g., identifying gaps along the tissue being treated). Accordingly, a physician or other user can use this valuable information to ensure that more complete and thorough ablation procedures are consistently performed. As discussed herein, for example, with the assistance of the various configurations disclosed herein, a physician can quickly identify regions of tissue along a desired ablation pathway that may not have been treated to a threshold level. Thus, such tissue regions can be targeted before an ablation procedure is completed to ensure proper and efficacious treatment.

According to some embodiments, the system can be configured to identify and highlight (e.g., automatically) potential or actual gaps (e.g., potentially under-ablated or other susceptible tissue regions) and identify (e.g., graphically, textually, etc.) such regions to the user. For example, in some embodiments, the system can highlight portions of the targeted anatomy that may not have been ablated properly (e.g., regions where the length, width, depth of ablation or heating is insufficient relative to some threshold). Such highlighting can take any desired form, such as, for example, circling or otherwise drawing an outline around such areas, coloring such regions with a different color or other graphical pattern (e.g., cross-hatching) and/or the like.

In some embodiments, the ability of the system to determine and indicate potential, likely or actual lesion gaps (e.g., potentially under-ablated regions of the subject's anatomy being treated) can help ensure that a practitioner is alerted to such locations. Accordingly, the physician can evaluate and determine if any such regions exist, and if necessary (e.g., based on his or her expertise, experience and general approach) conduct additional ablations at various locations before a treatment procedure is completed. This can help ensure that practitioners consistently and reliably complete an ablation procedure that will increase the likelihood of clinical success.

In some embodiments, the mapping system (e.g., a 3D electroanatomical navigation system) can be configured to map a subject's cardiac chamber (e.g., atrium) during a cardiac fibrillation (e.g., atrial fibrillation) treatment. For example, the electroanatomical navigation system or other mapping system can be configured to obtain EGM activity data, rotor mapping data and/or other electrical data. As noted herein such data can be obtained from a mapping system that is also configured to obtain and process data that facilitate the 3D mapping and modeling of a targeted anatomical location (e.g., the left atrium of a subject). Alternatively, such data can be provided to the mapping system (e.g., the electroanatomical navigation system) via a separate mapping device or system that is operatively coupled to the mapping system, as desired or required.

In some embodiments, subjects that indicate for atrial fibrillation exhibit an atrial fibrillation rotor pattern in their atrium that is characteristic of the disease. In some arrangements, electrically mapping the signals being transmitted through a subject's atrium, and thus, more accurately determining a map of the corresponding atrial fibrillation rotor that is cause of the disease, can assist with the subject treatment of the subject. For example, in some embodiments, once the atrial fibrillation rotor is accurately mapped (e.g., using a separate mapping device or system that is either integrated with or operatively coupled to a 3D electroanatomical navigation system), a practitioner can more precisely treat the portions of the atrium that help treat the disease. This can provide several benefits to a subject, including more precise and accurate ablation that increases the likelihood of effective treatment, less trauma to the subject as area or volume of tissue that is ablated can be reduced and/or the like. Thus, in some embodiments, the use of the various embodiments described herein that provide detailed data and other information regarding the status of an ablation procedure can be helpful in ensuring that targeted tissue is properly ablated in view of the corresponding rotor map. This can provide more reliable and efficacious treatment of atrial fibrillation and other cardiac arrhythmias.

Figure 40A:
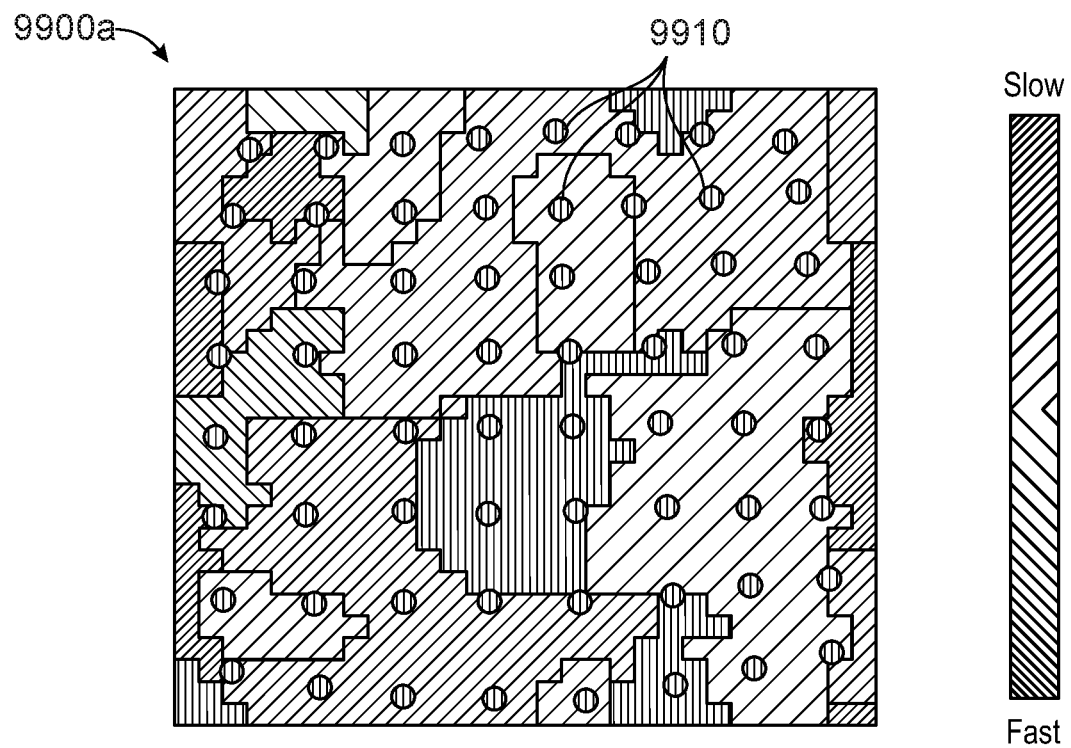
FIGS. 40A and 40B illustrate different embodiments of 3D tissue maps that have been enhanced by high-resolution data obtained.

As illustrated in the example 3D activation map of FIG. 40A, there exist relatively large gaps or spaces between adjacent electrodes of the multi-electrode device or system. As a result, the corresponding 3D map that is generated using only the multi-electrode mapping device or system may be inaccurate and/or incomplete. For example, in some embodiments, there may exist a rotor or other indicia of a cardiac arrhythmia (e.g., atrial fibrillation) or other condition that may not be identified by the fixed-space electrodes of a multi-electrode mapping device or system.

Figure 40B:
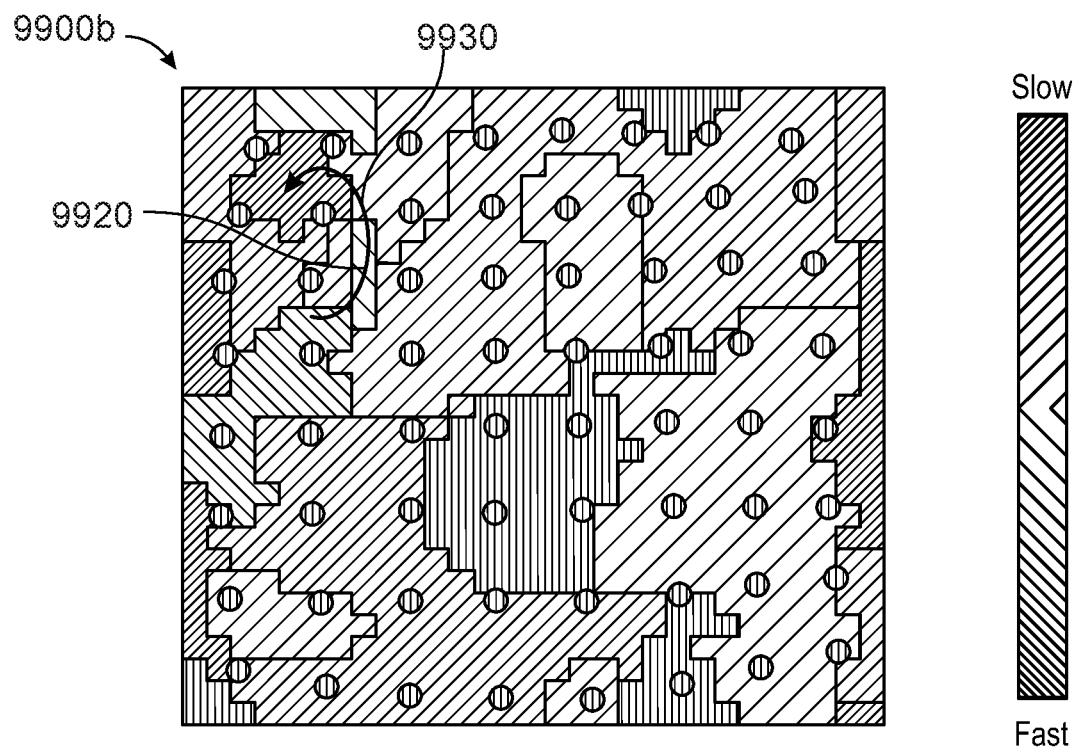

By way of example, FIG. 40B illustrates a region 9920 of the subject's anatomical space that has been mapped using a catheter-based device or system, either alone or in combination with one or more other mapping devices or systems (e.g., a multi-electrode mapping system), in accordance with the various embodiments disclosed herein. The map of FIG. 40B provides additional mapping data between the set, fixed locations of the electrodes in a multi-electrode device or system. Such enhanced mapping systems and related methods (e.g., using high-resolution electrode embodiments disclosed herein) could be used to detect the presence of a rotor 9930 (e.g., wherein a region of the targeted anatomical region exhibits a localized area in which activation of said tissue forms a circular or repetitive pattern). Thus, the presence of a condition can be accurately identified, and subsequently treated, using embodiments of the enhanced mapping devices or systems disclosed herein. As enumerated above, the embodiments disclosed herein can be used to generate many types of enhanced cardiac maps, such as, without limitation: cardiac activation maps, cardiac activity propagation velocity maps, cardiac voltage maps and rotor maps. In accordance with several embodiments, the enhanced mapping system facilitates more focused, localized or concentrated ablation targets and/or may reduce the number of ablations required to treat various conditions.

Accordingly, the ability to generate such enhanced cardiac maps can further enhance the various graphical representations presented herein (e.g., with reference to FIGS. 36A to 39) and can further improve ablation systems and techniques that take advantage of such features. For example, in some embodiments, the identification of a rotor 9930 can be superimposed or otherwise identified on a graphical representation of an ablation map relative to a mapped region of the targeted anatomy, as discussed herein, e.g., with respect to the arrangements of FIGS. 36A to 39. As a result, the physician conducting an ablation procedure can more accurately, reliably and efficaciously target the proper portions of the subject's anatomy in an effort to treat the subject's condition (e.g., atrial fibrillation, other cardiac arrhythmia or ailment, other conduction-related malady, etc.).

In some embodiments, the system comprises one or more of the following: means for tissue modulation (e.g., an ablation or other type of modulation catheter or delivery device), means for generating energy (e.g., a generator or other energy delivery module), means for connecting the means for generating energy to the means for tissue modulation (e.g., an interface or input/output connector or other coupling member), means for performing tissue contact sensing and/or tissue type determination, means for displaying output generated by the means for performing tissue contact sensing and/or tissue type determination, means for determining a level of contact with tissue, means for calibrating network parameter measurements in connection with contact sensing means, etc.

In some embodiments, the system comprises various features that are present as single features (as opposed to multiple features). For example, in one embodiment, the system includes a single ablation catheter with a single high-resolution (e.g., composite, such as split-tip) electrode and one or more temperature sensors (e.g., thermocouples) to help determine the temperature of tissue at a depth. The system may comprise an impedance transformation network. In some embodiments, the system includes a single ablation catheter with a heat shunt network for the transfer of heat away from the electrode and/or tissue being treated. In some embodiments, the system includes a single contact sensing subsystem for determining whether there is and to what extent there is contact between the electrode and targeted tissue of a subject. Multiple features or components are provided in alternate embodiments.

In one embodiment, the system comprises one or more of the following: means for tissue modulation (e.g., an ablation or other type of modulation catheter or delivery device), means for generating energy (e.g., a generator or other energy delivery module), and/or means for connecting the means for generating energy to the means for tissue modulation (e.g., an interface or input/output connector or other coupling member), etc.

In some embodiments, the system comprises one or more of the following: means for tissue modulation (e.g., an ablation or other type of modulation catheter or delivery device), means for measuring tissue temperature at a depth (e.g., using multiple temperature sensors (e.g., thermocouples) that are thermally insulated from the electrode and that are located along two different longitudinal portions of the catheter), means for effectively transferring heat away from the electrode and/or the tissue being treated (e.g., using heat shunting materials and components) and means for determining whether and to what extent there is contact between the electrode and adjacent tissue (e.g., using impedance measurements obtained from a high-resolution electrode that is also configured to ablate the tissue).

In some embodiments, the system comprises one or more of the following: an ablation system consists essentially of a catheter, an ablation member (e.g., a RF electrode, a composite (e.g., split-tip) electrode, another type of high-resolution electrode, etc.), an irrigation conduit extending through an interior of the catheter to or near the ablation member, at least one electrical conductor (e.g., wire, cable, etc.) to selectively activate the ablation member and at least one heat transfer member that places at least a portion of the ablation member (e.g., a proximal portion of the ablation member) in thermal communication with the irrigation conduit, at least one heat shunt member configured to effectively transfer heat away from the electrode and/or tissue being treated, a plurality of temperature sensors (e.g., thermocouples) located along two different longitudinal locations of the catheter, wherein the temperature sensors are thermally isolated from the electrode and configured to detect temperature of tissue at a depth, contact detection subsystem for determining whether and to what extent there is contact between the electrode and adjacent tissue (e.g., using impedance measurements obtained from a high-resolution electrode that is also configured to ablate the tissue), etc.

In the embodiments disclosed above, a heat transfer member is disclosed. Alternatively, a heat retention sink is used instead of or in addition to the heat transfer member in some embodiments.

According to some embodiments, an ablation system consists essentially of a catheter, an ablation member (e.g., a RF electrode, a composite (e.g., split-tip) electrode, another type of high-resolution electrode, etc.), an irrigation conduit extending through an interior of the catheter to or near the ablation member, at least one electrical conductor (e.g., wire, cable, etc.) to selectively activate the ablation member and at least one heat transfer member that places at least a portion of the ablation member (e.g., a proximal portion of the ablation member) in thermal communication with the irrigation conduit, at least one heat shunt member configured to effectively transfer heat away from the electrode and/or tissue being treated and a plurality of temperature sensors (e.g., thermocouples) located along two different longitudinal locations of the catheter, wherein the temperature sensors are thermally isolated from the electrode and configured to detect temperature of tissue at a depth.

Any methods described herein may be embodied in, and partially or fully automated via, software code modules (e.g., in the form of an algorithm or machine readable instructions) stored in a memory or computer-readable medium executed by one or more processors or other computing devices. In embodiments involving multiple processors, the processors may operate in parallel to form a parallel processing system in which a process is split into parts that execute simultaneously on different processors of the ablation system. The methods may be executed on the computing devices in response to execution of software instructions or other executable machine-readable code read from a tangible computer readable medium. A tangible computer readable medium is a data storage device that can store data that is readable by a computer system. Examples of computer readable mediums include read-only memory (e.g., ROM or PROM, EEPROM), random-access memory, other volatile or non-volatile memory devices, CD-ROMs, magnetic tape, flash drives, and optical data storage devices. The modules described herein (for example, the contact detection or sensing modules) may comprise structural hardware elements and/or non-structural software elements stored in memory (for example, algorithms or machine-readable instructions executable by processing or computing devices).

In addition, embodiments may be implemented as computer-executable instructions stored in one or more tangible computer storage media. As will be appreciated by a person of ordinary skill in the art, such computer-executable instructions stored in tangible computer storage media define specific functions to be performed by computer hardware such as computer processors. In general, in such an implementation, the computer-executable instructions are loaded into memory accessible by at least one computer processor (for example, a programmable microprocessor or microcontroller or an application specific integrated circuit). The at least one computer processor then executes the instructions, causing computer hardware to perform the specific functions defined by the computer-executable instructions. As will be appreciated by a person of ordinary skill in the art, computer execution of computer-executable instructions is equivalent to the performance of the same functions by electronic hardware that includes hardware circuits that are hardwired to perform the specific functions. As such, while embodiments illustrated herein are typically implemented as some combination of computer hardware and computer-executable instructions, the embodiments illustrated herein could also be implemented as one or more electronic circuits hardwired to perform the specific functions illustrated herein.

The various systems, devices and/or related methods disclosed herein can be used to at least partially ablate and/or otherwise ablate, heat or otherwise thermally treat one or more portions of a subject's anatomy, including without limitation, cardiac tissue (e.g., myocardium, atrial tissue, ventricular tissue, valves, etc.), a bodily lumen (e.g., vein, artery, airway, esophagus or other digestive tract lumen, urethra and/or other urinary tract vessels or lumens, other lumens, etc.), sphincters, prostate, brain, gall bladder, uterus, other organs, tumors and/or other growths, nerve tissue and/or any other portion of the anatomy. The selective ablation and/or other heating of such anatomical locations can be used to treat one or more diseases or conditions, including, for example, atrial fibrillation (persistent or paraoxysmal), atrial flutter, ventricular tachycardia, mitral valve regurgitation, other cardiac diseases, asthma, chronic obstructive pulmonary disease (COPD), other pulmonary or respiratory diseases, including benign or cancerous lung nodules, hypertension, heart failure, denervation, renal failure, obesity, diabetes, gastroesophageal reflux disease (GERD), other gastroenterological disorders, other nerve-related disease, tumors or other growths, pain and/or any other disease, condition or ailment.

In any of the embodiments disclosed herein, one or more components, including a processor, computer-readable medium or other memory, controllers (e.g., dials, switches, knobs, etc.), contact sensing subsystem, displays (e.g., temperature displays, timers, etc.) and/or the like are incorporated into and/or coupled with (e.g., reversibly or irreversibly) one or more modules of the generator, the irrigation system (e.g., irrigant pump, reservoir, etc.) and/or any other portion of an ablation or other modulation or treatment system.

Although several embodiments and examples are disclosed herein, the present application extends beyond the specifically disclosed embodiments to other alternative embodiments and/or uses of the inventions and modifications and equivalents thereof. It is also contemplated that various combinations or subcombinations of the specific features and aspects of the embodiments may be made and still fall within the scope of the inventions. Accordingly, it should be understood that various features and aspects of the disclosed embodiments can be combine with or substituted for one another in order to form varying modes of the disclosed inventions. The headings used herein are merely provided to enhance readability and are not intended to limit the scope of the embodiments disclosed in a particular section to the features or elements disclosed in that section.

While the embodiments disclosed herein are susceptible to various modifications, and alternative forms, specific examples thereof have been shown in the drawings and are herein described in detail. It should be understood, however, that the inventions are not to be limited to the particular forms or methods disclosed, but, to the contrary, the inventions are to cover all modifications, equivalents, and alternatives falling within the spirit and scope of the various embodiments described and the appended claims. Any methods disclosed herein need not be performed in the order recited. The methods disclosed herein include certain actions taken by a practitioner; however, they can also include any third-party instruction of those actions, either expressly or by implication. For example, actions such as "advancing a catheter" or "delivering energy to an ablation member" include "instructing advancing a catheter" or "instructing delivering energy to an ablation member," respectively. The ranges disclosed herein also encompass any and all overlap, sub-ranges, and combinations thereof. Language such as "up to," "at least," "greater than," "less than," "between," and the like includes the number recited. Numbers preceded by a term such as "about" or "approximately" include the recited numbers. For example, "about 10 mm" includes "10 mm." Terms or phrases preceded by a term such as "substantially" include the recited term or phrase. For example, "substantially parallel" includes "parallel."

What is claimed is:

1. A method of determining an orientation of a distal end of an ablation catheter with respect to a target region, the method comprising:
receiving signals indicative of temperature from a plurality of temperature sensors distributed along the distal end of the ablation catheter at a first plurality of time points in a first period of time;
determining temperature measurement values at each of the first plurality of time points for each of the plurality of temperature sensors;
calculating an initial temperature value for each of the plurality of temperature sensors based on the determined temperature measurement values;
receiving signals indicative of temperature from the plurality of temperature sensors at a second plurality of time points in a second period of time after the first period of time;
determining temperature measurement values at each of the second plurality of time points for each of the plurality of temperature sensors;
calculating a rate of change between the determined temperature values at each of the second plurality of time points and the initial temperature value for each of the plurality of temperature sensors, the calculating including subtracting the initial temperature value from a moving average value and dividing by a time elapsed from the first period of time to the second period of time;
at each time point of the second plurality of time points, determining the orientation of the distal end of the ablation catheter relative to the target region based on a comparison of the calculated rate of change of at least two of the plurality of temperature sensors, which further includes determining whether the calculated rates of change satisfy one or more orientation criteria of a respective orientation, the orientation being determined from one of three orientation options including parallel, perpendicular, and oblique options, and the orientation criteria are different for each of the orientation options.

2. The method of claim 1:
wherein the plurality of temperature sensors comprises a first plurality of temperature sensors positioned at a distal tip of the ablation catheter and a second plurality of temperature sensors positioned at a distance proximal to the first plurality of temperature sensors,
wherein the first plurality of temperature sensors consists of a first three thermocouples spaced apart circumferentially about a longitudinal axis of the ablation catheter,
wherein the second plurality of temperature sensors consists of a second three thermocouples spaced apart circumferentially about the longitudinal axis of the ablation catheter,
wherein the distal end of the ablation catheter further comprises at least one thermal shunt member in thermal communication with at least one energy delivery member and at least one fluid conduit extending at least partially through an interior of the ablation catheter, wherein the at least one thermal shunt member is in thermal communication with the at least one fluid conduit, and
wherein the step of determining the orientation of the distal end of the ablation catheter relative to the target region comprises determining an initial orientation in less than 5 seconds after application of ablative energy by an energy source coupled to the ablation catheter.

3. The method of claim 1, wherein calculating the initial temperature value for each of the plurality of temperature sensors comprises averaging the temperature measurement values determined at each of the first plurality of time points.

4. The method of claim 1, wherein the plurality of temperature sensors comprises a first plurality of temperature sensors positioned at a distal tip of the ablation catheter and a second plurality of temperature sensors positioned at a distance proximal to the first plurality of temperature sensors.

5. The method of claim 1, wherein at least some of the orientation criteria are time-dependent.

6. The method of claim 1, wherein the orientation criteria are empirically determined.

7. A method of determining an orientation of a distal end of an ablation catheter with respect to a target region, the method comprising:
receiving signals indicative of temperature from a plurality of temperature sensors distributed along a distal end of the ablation catheter at a plurality of time points over a period of time;
determining temperature measurement values at each of the plurality of time points for each of the plurality of temperature sensors;
calculating a rate of change between the determined temperature measurement values at each of the plurality of time points and a starting temperature value for each of the plurality of temperature sensors, the calculating including subtracting the starting temperature value from a moving average value and dividing by a time elapsed during the period of time;
at each time point of the plurality of time points, determining the orientation of the distal end of the ablation catheter relative to the target region based on a comparison of the calculated rate of change of at least two of the plurality of temperature sensors which includes determining whether the calculated rates of change satisfy one or more orientation criteria of a respective orientation, the orientation being determined from one of three orientation options including parallel, perpendicular, and oblique options, and the orientation criteria are different for each of the orientation options.

8. The method of claim 7, wherein the plurality of time points each occur after delivery of ablative energy has been initiated by the ablation catheter.

9. The method of claim 7, wherein the step of determining the orientation of the distal end of the ablation catheter comprises determining an initial orientation in less than 5 seconds after application of ablative energy by an energy source coupled to the ablation catheter.

10. The method of claim 7, wherein the plurality of temperature sensors comprises a first plurality of temperature sensors positioned at a distal tip of the ablation catheter and a second plurality of temperature sensors positioned at a distance proximal to the first plurality of temperature sensors.

11. The method of claim 7, wherein at least some of the orientation criteria are time-dependent.

* * * * *